(12) United States Patent
Moyle et al.

(10) Patent No.: US 6,962,795 B1
(45) Date of Patent: Nov. 8, 2005

(54) NEUTROPHIL INHIBITORS

(75) Inventors: Matthew Moyle, Escondido, CA (US);
David L. Foster, Brighton, MA (US);
George P. Vlasuk, Carlsbad, CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 08/151,064

(22) Filed: Nov. 10, 1993

Related U.S. Application Data

(63) Continuation-in-part of application No. 08/060,433, filed on May 11, 1993, now Pat. No. 6,756,211, which is a continuation-in-part of application No. 07/996,972, filed on Dec. 24, 1992, now abandoned, which is a continuation-in-part of application No. 07/881,721, filed on May 11, 1992, now abandoned.

(51) Int. Cl.⁷ .................. C07H 21/04; C12N 15/00; C12N 15/85; C12P 21/00; C07K 14/00
(52) U.S. Cl. .................. 435/69.1; 435/325; 435/358; 435/365; 435/348; 435/252.3; 435/252.8; 435/254.2; 435/254.23; 435/254.21; 435/320.1; 536/23.5; 536/24.31
(58) Field of Search .................. 435/325, 358, 435/365, 348, 252.3, 252.8, 254.2, 254.23, 254.21, 69.1, 320.1, 69.2; 536/24.31; 530/23.5; 514/12

(56) References Cited

U.S. PATENT DOCUMENTS

| | | | | |
|---|---|---|---|---|
| 4,874,743 A | * | 10/1989 | Wallner et al. | 514/12 |
| 4,965,195 A | * | 10/1990 | Namen et al. | 435/69.52 |
| 5,081,019 A | * | 1/1992 | Wallner et al. | 435/69 |

OTHER PUBLICATIONS

Rudinger, J. "Characteristics of the amino acids as components of a peptide hormone sequence", in, Peptide Hormones, University Park Press, Jun. 1976.*
Alberts et al., Molecular Biology of the Cell, Jan. 1994, Garland Publishing, Inc., New York, NY, page(s) 119.*
Bowie et al. Deciphering the message in protein sequences: tolerance to amino acid substitutions. Science, (Mar. 16, 1990) 247 (4948) 1306–10.*
Creighton T.E. Protein Folding. Biochemical Journal (1990) 270, 1–16.*
Principles of Protein Structure, G.E. Schulz, R.H. Schrimer, 1979 Springer–Verlag, pp 14–16.*
Peptide Hormones J.A. Parsons, 1976; Characteristics of the amino acids as components of a peptide hormone J. Rudinger; pp 1–7.*
Bowie et al. "Deciphering the Messag in Protein Sequences: Tolerance to Amino Acid Substitutions" Science vol. 247, No. 4948 pp. 1306–1310.*
Madden, K., "A peptide derived from neutrophil inhibitory factor (NIF) blocks neutrophil adherence to endothelial cells", *Inflammation Research* 46 (1997) 216–223.

* cited by examiner

*Primary Examiner*—David S. Romeo
(74) *Attorney, Agent, or Firm*—Pillsbury Winthrop LLP

(57) ABSTRACT

Compositions enriched for Neutrophil Inhibitory Factor which inhibit neutrophil activity including adhesion to vascular endothelial cells are provided. Also provided are recombinant Neutrophil Inhibitory Factors which also which inhibit neutrophil activity. Such compositions may comprise a glycoprotein isolated from nematodes. These compositions and recombinant Neutrophil Inhibitory Factors are useful in the therapy of conditions which involve abnormal or undesired inflammatory responses.

142 Claims, 36 Drawing Sheets

FIG. 7

TRYPSIN FRAGMENTS:
T-24      Ser Ala Phe Glu Leu Asp Ile Thr Asn Asn Gly Asn Gly Val Leu Met Arg
T-20      Leu Ala Ile Leu Gly Trp Ala Arg
T-22-10   Leu Phe Asp Arg Phe Pro Glu Lys
T-13      Leu Glu Met Asp Cys Glu Ala Glu Lys
T-15-6    Val Gly Thr Pro Cys Gly Asp Cys Ser Asn Tyr Thr Lys

AspN FRAGMENTS:
D-53      Asp Glu Asn Ile Tyr Ile Phe Glu Asn Ser
D-54      Asp Glu Asn Ile Tyr Ile Phe Glu Asn (Glu/his)
D-61      Asp Ile (His/gln) Val Tyr Phe Ile Gly Gln (Arg/gly) (Ala/tyr)
D-67      Asp Phe Ala Pro Arg Ala Ser Lys Met Arg Tyr Leu Glu Tyr
D-83      Asp Tyr Ile Tyr Tyr Gln Leu Tyr Pro (Phe/Ala) Pro Met Ala His Lys Met Arg Tyr Leu
D-85      Asp Xxx Met Gly Leu Gln Phe Leu Xxx Met His Asn Gly Xxx Arg
D-94      Asp Ala Met Arg Leu Gln Phe Leu Ala (Met/gln/asn) Xxx Asn Gly Tyr Xxx Gly
D-96      Asp Ile Ser Asn Phe Ala Asn Leu Ala Trp Asp
D-102     Asp Glu Asn Lys Tyr Ile Phe Glu Asn Ser Asn Asn Ile Ser Glu Ala Ala Leu Lys Ala Met Ile Ser Gly
          Ala Lys Gly Ala Phe Asn LysC FRAGMENTS:
K-34A     Ala Met Ile Ser Trp Ala Lys
K-46B     Xxx Ala Tyr Ala Val Val Asn Leu Pro Leu Gly Glu Ile Ala Pro Glu Ala Ile
K-48      Xxx Phe Tyr Xxx Phe Arg Glu Glu (Leu/ile)
K-50A     Gly Ala Phe Asn Leu Asn Leu Thr Glu Gly Glu Gly Val Leu Tyr Xxx Xxx Asn Xxx Asp Ile Ser Asn
          Phe Ala Asn Leu Ala Trp Asp
K-58A     Xxx Xxx Gly Val Leu Tyr Arg Xxx Xxx Leu Thr Ile Ser Asn Phe Ala Asn Leu Ala

```
        10              20              30              40
         |               |               |               |
ATG GAG GCC TAT CTT GTG GTC TTA ATT GCC ATT GCT GGC ATA GCT
Met Glu Ala Tyr Leu Val Val Leu Ile Ala Ile Ala Gly Ile Ala
         |               |               |
        -15             -10              -5

50              60              70              80              90
         |               |               |               |               |
CAT TCC AAT GAA CAC AAC CTG AGG TGC CCG CAG AAT GGA ACA GAA
His Ser Asn Glu His Asn Leu Arg Cys Pro Gln Asn Gly Thr Glu
         |               |                               |
        +1               5                              10

100             110             120             130
            |               |               |               |
ATG CCC GGT TTC AAC GAC TCG ATT AGG CTT CAA TTT TTA GCA ATG
Met Pro Gly Phe Asn Asp Ser Ile Arg Leu Gln Phe Leu Ala Met
         |               |                               |
        15              20                              25

140             150             160             170             180
            |               |               |               |               |
CAC AAT GGT TAC AGA TCA AAA CTT GCG CTA GGC CAC ATC AGC ATA
His Asn Gly Tyr Arg Ser Lys Leu Ala Leu Gly His Ile Ser Ile
         |               |                               |
        30              35                              40

190             200             210             220
            |               |               |               |
ACT GAA GAA TCC GAA AGT GAC GAT GAC GAT TTC GGT TTT TTA
Thr Glu Glu Ser Glu Ser Asp Asp Asp Asp Phe Gly Phe Leu
         |               |                               |
        45              50                              55
```

FIG. 8A

```
      230             240             250             260             270
       |               |               |               |               |
CCC GAT TTC GCT CCA AGG GCA TCG AAA ATG AGA TAT CTG GAA TAT
Pro Asp Phe Ala Pro Arg Ala Ser Lys Met Arg Tyr Leu Glu Tyr
         |                       |                   |
        60                      65                  70

280             290             300             310
               |               |               |               |
GAC TGT GAA GCT GAA AAA AGC GCC TAC ATG TCG GCT AGA AAT TGC
Asp Cys Glu Ala Glu Lys Ser Ala Tyr Met Ser Ala Arg Asn Cys
     |                       |                   |
    75                      80                  85

320             330             340             350             360
       |               |               |               |               |
TCG GAC AGT TCT TCT CCA CCA GAG GGC TAC GAT GAA AAC AAG TAT
Ser Asp Ser Ser Ser Pro Pro Glu Gly Tyr Asp Glu Asn Lys Tyr
 |                       |                       |
90                      95                     100

370             380             390             400
               |               |               |               |
ATT TTC GAA AAC TCA AAC AAT ATC AGT GAA GCT GCT CTG AAG GCC
Ile Phe Glu Asn Ser Asn Asn Ile Ser Glu Ala Ala Leu Lys Ala
 |                       |                       |
105                    110                     115

410             420             430             440             450
       |               |               |               |               |
ATG ATC TCG TGG GCA AAA GAG GCT TTC AAC CTA AAT AAA ACA AAA
Met Ile Ser Trp Ala Lys Glu Ala Phe Asn Leu Asn Lys Thr Lys
 |                       |                       |
120                    125                     130
```

FIG. 8B

```
      460               470               480               490
       |                 |                 |                 |
GAA GGA GAA GGA GTT CTG TAC CGG TCG AAC CAC GAC ATA TCA AAC
Glu Gly Glu Gly Val Leu Tyr Arg Ser Asn His Asp Ile Ser Asn
         |                 |                 |
        135               140               145

500               510               520               530               540
       |                 |                 |                 |                 |
TTC GCT AAT CTG GCT TGG GAC GCG CGT GAA AAG TTT GGT TGC GCA
Phe Ala Asn Leu Ala Trp Asp Ala Arg Glu Lys Phe Gly Cys Ala
         |                 |                 |
        150               155               160

550               560               570               580
            |                 |                 |                 |
GTT GTT AAC TGC CCT TTG GGA GAA ATC GAT GAT GAA ACC AAC CAT
Val Val Asn Cys Pro Leu Gly Glu Ile Asp Asp Glu Thr Asn His
         |                 |                 |
        165               170               175

590               600               610               620               630
       |                 |                 |                 |                 |
GAT GGA GAA ACC TAT GCA ACA ACC ATC CAT GTA GTC TGC CAC TAC
Asp Gly Glu Thr Tyr Ala Thr Thr Ile His Val Val Cys His Tyr
         |                 |                 |
        180               185               190

640               650               660               670
            |                 |                 |                 |
CCG AAA ATA AAC AAA ACT GAA GGA CAG CCG ATT TAC AAG GTA GGG
Pro Lys Ile Asn Lys Thr Glu Gly Gln Pro Ile Tyr Lys Val Gly
         |                 |                 |
        195               200               205
```

FIG. 8C

```
      680             690             700             710             720
       |               |               |               |               |
ACA CCA TGC GAC GAT TGC AGT GAA TAC ACA AAA AAA GCA GAC AAT
Thr Pro Cys Asp Asp Cys Ser Glu Tyr Thr Lys Lys Ala Asp Asn
             |                   |                   |
            210                 215                 220

730             740             750             760
               |               |               |               |
ACC ACG TCT GCG GAT CCG GTG TGT ATT CCG GAT GAC GGA GTC TGC
Thr Thr Ser Ala Asp Pro Val Cys Ile Pro Asp Asp Gly Val Cys
             |                   |                   |
            225                 230                 235

770             780             790             800             810
       |               |               |               |               |
TTT ATT GGC TCG AAA GCC GAT TAC GAT AGC AAG GAG TTT TAT CGA
Phe Ile Gly Ser Lys Ala Asp Tyr Asp Ser Lys Glu Phe Tyr Arg
             |                   |                   |
            240                 245                 250

820
               |
TTC CGA GAG TTA TGA
Phe Arg Glu Leu ---
             |
            255
```

FIG. 8D

```
Met Glu Ala Tyr --- --- --- --- --- --- --- --- --- --- --- 1FL
Met  .  Leu Leu Leu Arg Lys Phe Leu Leu Leu Trp Leu Ser Gly 3P
Met Lys Ser Tyr --- --- --- --- --- --- --- --- --- --- --- 4FL
Met Arg Leu Leu Arg Glu Ala Tyr --- --- --- --- --- --- --- 6FL

--- --- --- --- --- --- --- Leu Val Val Leu Ile Ala Ile Ala 1FL
Thr Phe Lys Arg Gly Arg Arg  .   .   .   .  Ala  .   .   .  3P
                             .   .   .   .  Leu Leu Ser Ser 2FL
                             .   .   .   .   .   .   .   .  3FL
--- --- --- --- --- --- ---  .  Met  .   .  Ala  .  Val  .  4FL
--- --- --- --- --- --- ---  .   .   .   .  Val  .   .   .  6FL

Gly Ile Ala His Ser Asn Glu His Asn Leu Arg Cys Pro Gln Asn 1FL
 .   .   .   .  Ala  .   .   .  Asp Pro Thr  .   .   .   .  3P
Ser Ala  .   .   .   .   .   .   .  Pro Ile  .  Ser  .   .  2FL
 .   .   .   .   .   .   .   .   .   .  Thr  .   .   .   .  3FL
 .   .   .   .  Ala  .   .   .  Asp  .  Ile  .   .  His  .  4FL
 .   .   .   .   .   .   .   .   .   .  Thr  .   .   .   .  6FL

Gly Thr Glu Met Pro --- Gly Phe Asn Asp Ser Ile Arg Leu Gln 1FL
 .  Glu Lys  .  Glu Lys  .   .  Asp  .  Ala  .   .   .  Lys 3P
 .   .  Gly  .  Phe ---  .   .   .   .   .  Met  .   .  Lys 2FL
 .   .   .   .   .  ---  .   .   .   .   .   .   .   .   .  3FL
Glu Gly  .   .  Glu Lys  .   .  Asp  .  Ala Met  .   .  Lys 4FL
 .   .   .   .   .  --- Asp  .  Ser  .   .   .   .   .   .  6FL

Phe Leu Ala Met His Asn Gly Tyr Arg Ser Lys Leu Ala Leu Gly 1FL
 .   .   .   .   .   .   .   .   .   .  Arg  .   .   .   .  3P
 .   .  Glu  .   .   .   .   .   .   .  Arg  .   .   .   .  2FL
 .   .   .   .   .   .   .   .   .   .   .   .   .   .   .  3FL
 .   .   .  Leu  .   .   .   .   .   .  Arg  .   .   .   .  4FL
 .   .   .   .   .   .   .   .   .   .  Asn  .   .   .   .  6FL
```

FIG. 9A

| | | | | | | | | | | | | | |
|---|---|---|---|---|---|---|---|---|---|---|---|---|---|
| His | Ile | Ser | Ile | Thr | Glu | Glu | Ser | Glu | Ser | --- | Asp | Asp | Asp | Asp | 1FL |
| . | Val | . | . | . | . | . | . | . | Asp | Tyr | . | Leu | --- | Tyr | 3P |
| . | . | . | . | . | . | . | . | . | . | . | --- | . | . | . | Tyr | 1P |
| . | . | . | . | . | . | . | Pro | . | . | Tyr | . | . | . | . | 2FL |
| . | . | . | . | . | Asp | . | . | . | . | . | --- | Glu | Ser | . | . | 3FL |
| . | Val | . | . | . | . | . | . | . | Asp | Tyr | . | Leu | --- | Tyr | 4FL |
| . | . | Gly | . | Ser | Lys | . | . | Ile | Gly | Asp | . | Tyr | . | . | 6FL |

| | | | | | | | | | | | | | |
|---|---|---|---|---|---|---|---|---|---|---|---|---|---|
| Asp | Phe | Gly | Phe | Leu | Pro | Asp | --- | Phe | Ala | Pro | Arg | Ala | Ser | Lys | 1FL |
| . | --- | --- | Leu | . | --- | --- | --- | Tyr | . | . | . | . | . | . | 3P |
| Glu | Tyr | . | . | . | . | . | --- | . | . | . | . | . | . | . | 1P |
| . | Tyr | . | Tyr | Ser | Glu | Val | Leu | Tyr | . | . | Ser | . | . | . | 2FL |
| Glu | Tyr | Asp | Tyr | Trp | Tyr | Ala | Pro | Thr | . | . | Thr | . | . | . | 3FL |
| . | --- | --- | Leu | Ser | --- | --- | --- | Tyr | . | . | Thr | . | . | . | 4FL |
| . | Tyr | Tyr | Tyr | Phe | Tyr | Ser | Ser | Tyr | . | . | Met | . | . | . | 6FL |

| | | | | | | | | | | | | | |
|---|---|---|---|---|---|---|---|---|---|---|---|---|---|
| Met | Arg | Tyr | Leu | Glu | Tyr | Asp | Cys | Glu | Ala | Glu | Lys | Ser | Ala | Tyr | 1FL |
| . | . | . | . | Lys | . | . | . | . | . | . | . | . | . | . | 3P |
| . | . | . | . | . | . | . | . | . | . | . | . | . | . | . | 1P |
| . | . | . | Met | . | . | . | . | . | . | . | . | . | . | . | 2FL |
| . | . | . | . | . | . | . | . | . | . | . | . | . | . | . | 3FL |
| . | . | . | . | Lys | . | . | . | . | . | . | . | . | . | . | 4FL |
| . | . | . | . | . | . | . | . | Asp | Ser | . | Arg | . | . | . | 6FL |

| | | | | | | | | | | | | | |
|---|---|---|---|---|---|---|---|---|---|---|---|---|---|
| Met | Ser | Ala | Arg | Asn | Cys | Ser | Asp | Ser | Ser | Ser | Pro | Pro | Glu | Gly | 1FL |
| Glu | . | . | Lys | Lys | . | Gln | Thr | Thr | Ala | . | Ser | Trp | . | Lys | 3P |
| Val | . | . | Ser | . | . | . | Asn | Ile | . | . | . | . | . | . | 1P |
| Lys | . | . | Ser | Ser | . | . | . | . | . | . | Ser | . | . | . | 2FL |
| . | . | . | . | . | . | . | . | . | . | . | . | . | . | . | 3FL |
| Glu | . | . | Lys | Lys | . | Gln | Thr | Thr | Ala | . | Ser | Ser | Thr | Lys | 4FL |
| . | . | . | Ser | . | . | . | . | . | . | . | . | . | . | . | 6FL |

FIG. 9B

| Tyr | Asp | Glu | Asn | Lys | Tyr | Ile | Phe | Glu | Asn | Ser | Asn | Asn | Ile | Ser | 1FL |
|---|---|---|---|---|---|---|---|---|---|---|---|---|---|---|---|
| . | . | . | . | Leu | Gln | Val | Ile | . | Asp | Pro | Lys | Asp | . | Asn | 3P |
| . | . | . | . | . | . | . | . | . | . | . | . | . | . | . | 1P |
| . | . | . | . | . | . | . | Leu | . | . | . | Ser | . | . | . | 2FL |
| --- | . | . | . | . | . | . | . | . | . | . | . | . | . | . | 3FL |
| . | . | . | . | Leu | Gln | Val | Ile | . | Asp | Pro | Arg | Asp | . | Asn | 4FL |
| . | . | . | . | . | . | . | Leu | . | . | . | Ser | . | . | Asn | 6FL |

| Glu | Ala | Ala | Leu | Lys | Ala | Met | Ile | Ser | Trp | Ala | Lys | Glu | Ala | Phe | 1FL |
|---|---|---|---|---|---|---|---|---|---|---|---|---|---|---|---|
| His | . | . | . | . | . | Ile | . | . | . | . | Thr | . | . | . | 3P |
| . | . | . | . | . | . | . | . | . | . | . | . | . | . | . | 1P |
| . | . | . | Arg | Leu | . | Ile | Leu | . | . | . | . | . | . | . | 2FL |
| . | . | . | . | . | . | . | . | . | . | . | . | . | . | . | 3FL |
| His | . | . | . | . | Thr | . | . | . | . | Thr | . | . | . | 4FL |
| . | . | . | Arg | Leu | . | Ile | . | . | . | Gly | . | . | . | . | 6FL |

| Asn | Leu | Asn | Lys | Thr | Lys | Glu | Gly | Glu | Gly | Val | Leu | Tyr | Arg | Ser | 1FL |
|---|---|---|---|---|---|---|---|---|---|---|---|---|---|---|---|
| . | . | . | . | . | --- | --- | . | . | . | . | Val | . | . | . | 3P |
| . | . | . | . | . | --- | --- | . | . | . | . | . | . | . | . | 1P |
| Asp | . | . | . | . | --- | --- | . | . | . | . | . | . | . | . | 2FL |
| . | . | . | . | . | Glu | . | . | . | . | . | . | . | . | . | 3FL |
| . | . | . | . | . | . | . | . | . | . | . | . | . | . | . | 4FL |
| . | . | . | Glu | . | --- | --- | . | . | . | . | . | . | . | . | 6FL |

| Asn | His | Asp | Ile | Ser | Asn | Phe | Ala | Asn | Leu | Ala | Trp | Asp | Ala | Arg | 1FL |
|---|---|---|---|---|---|---|---|---|---|---|---|---|---|---|---|
| Ile | Leu | . | . | . | . | . | . | . | . | . | . | . | Thr | . | 3P |
| . | Leu | Thr | . | . | . | . | . | . | . | . | . | . | Thr | . | 1P |
| . | Leu | Thr | . | . | . | . | . | . | . | . | . | . | Thr | . | 2FL |
| . | . | . | . | . | . | . | . | . | . | . | . | . | Thr | . | 3FL |
| . | Leu | Thr | . | . | . | . | . | . | . | . | . | . | Thr | . | 6FL |

FIG. 9C

| | | | | | | | | | | | | | |
|---|---|---|---|---|---|---|---|---|---|---|---|---|---|
| Glu | Lys | Phe | Gly | Cys | Ala | Val | Val | Asn | Cys | Pro | Leu | Gly | Glu | Ile | 1FL |
| . | . | Val | . | . | . | . | . | Lys | . | --- | --- | --- | --- | --- | 3P |
| . | . | . | . | . | . | . | . | . | . | . | . | . | Lys | Pro | 1P |
| . | . | . | . | . | . | . | Ala | Lys | . | . | . | --- | . | --- | 2FL |
| . | . | . | . | . | . | . | . | . | . | . | . | . | . | . | 3FL |
| . | . | . | . | . | . | . | . | Lys | . | . | . | | | | 6FL |

| | | | | | | | | | | | | |
|---|---|---|---|---|---|---|---|---|---|---|---|---|
| Asp | Asp | Glu | Thr | Asn | His | Asp | Gly | Glu | Thr | Tyr | Ala | Thr | Thr | Ile | 1FL |
| --- | --- | --- | --- | --- | --- | --- | --- | --- | Ser | --- | Pro | Arg | . | Thr | 3P |
| . | Ala | Ile | Ile | Thr | Asp | . | Glu | . | Asn | . | . | . | Ala | . | 1P |
| . | --- | --- | . | --- | --- | --- | --- | --- | Ser | --- | . | . | . | . | 2FL |
| . | Gly | Thr | . | Ile | . | . | . | . | . | . | . | . | . | . | 3FL |

| | | | | | | | | | | | | |
|---|---|---|---|---|---|---|---|---|---|---|---|---|
| His | Val | Val | Cys | His | Tyr | Pro | Lys | Ile | Asn | Lys | Thr | Glu | Gly | --- | 1FL |
| . | . | . | . | . | . | . | . | --- | --- | . | Ser | --- | Arg | Arg | 3P |
| . | . | . | . | . | . | . | . | . | . | . | . | . | . | --- | 1P |
| . | . | . | . | . | . | . | . | . | . | Glu | Gly | Glu | . | Lys | Glu | 2FL |
| . | . | . | . | . | . | . | . | Met | . | . | . | . | --- | 3FL |

| | | | | | | | | | | | | |
|---|---|---|---|---|---|---|---|---|---|---|---|---|
| --- | --- | Gln | Pro | Ile | Tyr | Lys | Val | Gly | Thr | Pro | Cys | Asp | Asp | Cys | 1FL |
| Lys | Glu | Asn | . | . | . | Thr | Thr | . | Asn | Arg | . | Gly | Gly | . | 3P |
| --- | --- | . | . | . | . | . | . | . | . | . | . | . | . | . | 1P |
| Gly | Lys | Gln | --- | . | . | . | . | . | . | . | . | Gly | . | . | 2FL |
| --- | --- | . | . | . | . | . | . | . | Lys | . | . | | | | 3FL |

| | | | | | | | | | | | | |
|---|---|---|---|---|---|---|---|---|---|---|---|---|
| Ser | Glu | Tyr | Thr | Lys | Lys | Ala | Asp | Asn | Thr | Thr | Ser | Ala | Asp | Pro | 1FL |
| . | Asp | . | | | | | | | | | | | | | 3P |
| . | . | . | . | . | . | . | . | . | . | . | . | . | . | . | 1P |
| . | . | . | . | . | . | . | . | . | . | . | . | Thr | . | . | 2FL |

| | | | | | | | | | | | | |
|---|---|---|---|---|---|---|---|---|---|---|---|---|
| Val | Cys | Ile | Pro | Asp | Asp | Gly | Val | Cys | Phe | Ile | Gly | Ser | Lys | Ala | 1FL |
| Gln | . | His | . | . | Ile | . | . | . | . | . | . | . | . | Gly | 1P |

| | | | | | | | | | | | | |
|---|---|---|---|---|---|---|---|---|---|---|---|---|
| Asp | Tyr | Asp | Ser | Lys | Glu | Phe | Tyr | Arg | Phe | Arg | Glu | Leu | * | | 1FL |
| . | . | . | . | . | . | . | . | . | . | . | . | . | * | | 1P |

FIG. 9D

```
EcoRI
|           10          20          30          40          50
|           *           *           *           *           *
GAATTCCGCA  AGGGATAAAT  ATCTAACACC  GTGCGTGTTG  ACTATTTTAC
                                            -35 box 60          70   >mRNA  80          90
            *           *           *           *
CTCTGGCGGT  GATAATGGTT  GCATGTACTA AGGAGGTTGT  ATG  GAA  CAA
            -10 box                SD_cro       M    E    Q>

λ-P_R -promoter
                                            Sall
                                            |
100         110         120         130         140
 *           *           *           *           *
CGC  ATA  ACC  CTG  AAA  GAT  AGC  TTG  GGA  TCC  GTC  GAC  CGA  GCA
 R    I    T    L    K    D    S    L    G    S    V    D    R    A>

BstEII
            150         160         170         180     |
             *           *           *           *       |
AAT  AAT  TCA  ACC  ACT  AAA  CAA  ATC  AAC  CGC  GTT  TCC  CGG  AGG
 N    N    S    T    T    K    Q    I    N    R    V    S    R    R>
                                                             SD (ligation point)        Bsu36I
            190  |         200  |         210         220
             *    |         *    |         *           *
TAACC       ATG  AAC  GAA  CAC  AAC  CTG  AGG  TGC  CCG  CAG  AAT  GGA
 * * *       M    N    E    H    N    L    R    C    P    Q    N    G>

230         240         250         260
             *           *           *           *
ACA  GAA  ATG  CCC  GGT  TTC  AAC  GAC  TCG  ATT  AGG  CTT  CAA  TTT
 T    E    M    P    G    F    N    D    S    I    R    L    Q    F>

270         280         290         300
             *           *           *           *
TTA  GCA  ATG  CAC  AAT  GGT  TAC  AGA  TCA  AAA  CTT  GCG  CTA  GGT
 L    A    M    H    N    G    Y    R    S    K    L    A    L    G>

310         320         330         340         350
 *           *           *           *           *
CAC  ATC  AGC  ATA  ACT  GAA  GAA  TCC  GAA  AGT  GAC  GAT  GAT  GAC
 H    I    S    I    T    E    E    S    E    S    D    D    D    D>

StyI
                                    |
            360         370         380         390
             *           *           | *           *
GAT  TTC  GGT  TTT  TTA  CCC  GAT  TTC  GCT  CCA  AGG  GCA  TCG  AAA
 D    F    G    F    L    P    D    F    A    P    R    A    S    K>
```

FIG. 15A

```
                    EcoRV
                      |
         400              410              420              430
          |*               *                *                *
ATG AGA  TAT  CTG GAA TAT GAC TGT GAA GCT GAA AAA AGC GCC
 M   R    Y    L   E   Y   D   C   E   A   E   K   S   A>

440              450              460              470
          *                *                *                *
TAC ATG TCG GCT AGA AAT TGC TCG GAC AGT TCT TCT CCA CCA
 Y   M   S   A   R   N   C   S   D   S   S   S   P   P>

480              490              500              510
          *                *                *                *
GAG GGC TAC GAT GAA AAC AAG TAT ATT TTC GAA AAC TCA AAC
 E   G   Y   D   E   N   K   Y   I   F   E   N   S   N>

520              530              540              550              560
   *                *                *                *                *
AAT ATC AGT GAA GCT GCT CTG AAG GCC ATG ATC TCG TGG GCA
 N   I   S   E   A   A   L   K   A   M   I   S   W   A>

570              580              590              600
               *                *                *                *
AAA GAG GCT TTC AAC CTA AAT AAA ACA AAA GAA GGA GAA GGA
 K   E   A   F   N   L   N   K   T   K   E   G   E   G>
         AgeI
          |
         610              620              630              640
          *                *                *                *
GTT CTG TAC CGG TCG AAC CAC GAC ATA TCA AAC TTC GCT AAT
 V   L   Y   R   S   N   H   D   I   S   N   F   A   N>

HpaI
                                                               |
         650              660              670              680 |
          *                *                *                *  |
CTG GCT TGG GAC GCG CGT GAA AAG TTT GGT TGC GCA GTT GTT
 L   A   W   D   A   R   E   K   F   G   C   A   V   V>

690              700              710              720
          *                *                *                *
AAC TGC CCT TTG GGA GAA ATC GAT GAT GAA ACC AAC CAT GAT
 N   C   P   L   G   E   I   D   D   E   T   N   H   D>

730              740              750              760              770
   *                *                *                *                *
GGA GAA ACC TAT GCA ACA ACC ATC CAT GTA GTC TGC CAC TAC
 G   E   T   Y   A   T   T   I   H   V   V   C   H   Y>
```

FIG. 15B

```
              780              790               800              810
               *                *                 *                *
CCG AAA ATA AAC AAA ACT GAA GGA CAG CCG ATT TAC AAG GTA
 P   K   I   N   K   T   E   G   Q   P   I   Y   K   V>

820              830               840              850
               *                *                 *                *
GGG ACA CCA TGC GAC GAT TGC AGT GAA TAC ACA AAA AAA GCA
 G   T   P   C   D   D   C   S   E   Y   T   K   K   A>

860              870               880              890
               *                *                 *                *
GAC AAT ACC ACG TCT GCG GAT CCG GTG TGT ATT CCG GAT GAC
 D   N   T   T   S   A   D   P   V   C   I   P   D   D>

Tth111I
  |         900              910               920              930
  |          *                *                 *                *
GGA GTC TGC TTT ATT GGC TCG AAA GCC GAT TAC GAT AGC AAG
 G   V   C   F   I   G   S   K   A   D   Y   D   S   K>

HindIII
                                              SpeI  (ligation point)
                                                |      |
 940              950              960          |  970 |         980
  *                *                *           |   *  |          *
GAG TTT TAT CGA TTC CGA GAG TTA TAA ACTAG TAAGCTTGCT
 E   F   Y   R   F   R   E   L   ***
```

```
            100          110         120         130         140         150         160
             *            *           *           *           *           *           *
NIF-1FL    TAC AGA TCA AAA CTT GCG CTA GGT CAC ATC AGC ATA ACT GAA GAA TCC GAA AGT GAC GAT GAT TTC GGT
            Y   R   S   K   L   A   L   G   H   I   S   I   T   E   E   S   E   S   D   D   D   F   G

PCR-NIF7   TAC AGA TCA AAA CTT GCG CTA GGT CAC ATC AGC ATA ACT GAA GAA TCC GAA AGT GAC GAT GAT TTC GGT
            Y   R   S   K   L   A   L   G   H   I   S   I   T   E   E   S   E   S   D   D   D   F   G

PCR-NIF20  TAC AGA TCG AAA CTT GCG CTA GGT CAC ATC AGC ATA ACT GAC GAA TCC GAA AGT GAC GAT GAA TAC GAT
            Y   R   S   K   L   A   L   G   H   I   S   I   T   D   E   S   E   S   D   D   E   Y   D

AcaNIF3    TAC AGA TCG AAA CTT GCG CTA GGT CAC ATC AGC ATA ACT GAC GAA TCC GAA AGT GAC TAT GAT TAC GGT
            Y   R   S   K   L   A   L   G   H   I   S   I   T   D   E   S   E   S   D   Y   D   Y   G

AcaNIF4    TAC AGA TCG AAA CTT GCG CTC GGT CAC GTC GGA ATA ACT GAC GAA TCC GAA AGT GAC TAT GAT TAC GGT
            Y   R   S   K   L   A   L   G   H   V   G   I   T   D   E   S   E   S   D   Y   D   Y   G

AcaNIF6    TAC AGA TCG TTG CTT GCG CTA GGT CAC ATC AGC ATA AGT AAA CAA CCG ATC GAT GAT TAC GAT TAC GGT
            Y   R   S   L   L   A   L   G   H   I   S   I   S   K   Q   P   I   D   D   Y   D   Y   G

AcaNIF7    TAC AGA TCA AAA CTT GCG CTA GGT CAC ATC AGC ATA ACT GAC GAA TCC GAA AGT GAC GAT GAT TTC GGT
            Y   R   S   K   L   A   L   G   H   I   S   I   T   D   E   S   E   S   D   D   D   F   G

AcaNIF19   TAC AGA TCG AAA CTT GCG CTA GGT CAC ATC AGC ATA ACT GAA GAA TCC GAA AGT GAC GAT GAA TAC GAT
            Y   R   S   K   L   A   L   G   H   I   S   I   T   E   E   S   E   S   D   D   E   Y   D

AcaNIF24   TAC AGA TCG AAA CTT GCG CTA GGT CAC ATC AGC ATA ACT GAC GAA TCC GAA AGT GAC GAT GAT TTC GGT
            Y   R   S   K   L   A   L   G   H   I   S   I   T   D   E   S   E   S   D   D   D   F   G

AcaNIF9    TAC AGA TCG AAA CTT GCG CTA GGT CAC ATC AGC ATA ACT GAA GAA TCC GAA --- --- GAT TAC GAT CTC --- TAC GAT
            Y   R   S   K   L   A   L   G   H   I   S   I   T   E   E   S   E           D   Y   D   L       Y   D

AcaNIF18   TAC AGA TCG AGA CTT GCG CTA GGT CAC GTC AGC ATA ACT GAA GAA TCC GAA --- --- GAT TAC GAT CTC --- TAC GAT
            Y   R   S   R   L   A   L   G   H   V   S   I   T   E   E   S   E           D   Y   D   L       Y   D
```

FIG. 16D

| | 240 | 250 | 260 | 270 | 280 | 290 | 300 |
|---|---|---|---|---|---|---|---|
| NIF-1FL | AAA AGC GCC TAC ATG TCG GCT - - - AGA AAT TGC TCG GAC AGT TCT TCT CCA CCA GAG GGC TAC GAT GAA AAC AAG TAT<br>K S A Y M S A R N C S D S S S P P E G Y D E N K Y | | | | | | |
| PCR-NIF7 | AAA AGC GCC TAC ATG TCG GCT - - - AGA AAT TGC TCG GAC AGT TCT TCT CCA CCA GAG GGC TAC GAT GAA AAC AAG TAT<br>K S A Y M S A R N C S D S S S P P E G Y D E N K Y | | | | | | |
| PCR-NIF20 | AAA AGC GCC TAC ATG TCG GCT - - - AGA AAT TGC TCG GAC AGT TCA TCT CCA CCA GAG GGC TAC GAT GAA AAC AAG TAT<br>K S A Y M S A R N C S D S S P P E G Y D E N K Y | | | | | | |
| AcaNIF3 | AGA AGC GCC TAC ACG TCG GCT - - - AGT GAT TGC TCG GAC AGT TCA TCT CCA CCA GAG GGC TAC GAT GAA AAC AAG TAT<br>R S A Y T S A S D C S D S S P P E G Y D E N K Y | | | | | | |
| AcaNIF4 | AAA AGC GCC TAC GTG TCG GCT - - - AGC AAT TGC TCG AAC ATT TCA TCT CCA CCA GAG GGC TAC GAT GAA AAC AAG TAT<br>K S A Y V S A S N C S N I S S P P E G Y D E N K Y | | | | | | |
| AcaNIF6 | AGA AGC GCC TAC ACG TCG GCT - - - AGT GAT TGC TCG GAC AGT TCA TCT CCA CCA GAG GGC TAC GAT GAA AAC AAG TAT<br>R S A Y T S A S D C S D S S P P E G Y D E N K Y | | | | | | |
| AcaNIF7 | AAA AGC GCC TAC ATG TCG GCT - - - AGA AAT TGC TCG GAC AGT TCT TCT CCA CCA GAG GGC TAC GAT GAA AAC AAG TAT<br>K S A Y M S A R N C S D S S S P P E G Y D E N K Y | | | | | | |
| AcaNIF19 | AAA AGC GCC TAC ATG TCG GCT - - - AGA AAT TGC TCG GAC AGT TCT TCT CCA CCA GAG GGC TAC GAT GAA AAC AAG TAT<br>K S A Y M S A R N C S D S S S P P E G Y D E N K Y | | | | | | |
| AcaNIF24 | AAA AGC GCC TAC ATG TCG GCT - - - AGA AAT TGC TCG GAC AGT TCT TCT CCA CCA GAG GGC TAC GAT GAA AAC AAG TAT<br>K S A Y M S A R N C S D S S S P P E G Y D E N K Y | | | | | | |
| AcaNIF9 | AAA AGC GCC TAC GAA TCG GCT - - - AAA AAA TGC CAG ACC ACT GCC TTT TCA TCG AAA TAC ACG AAA TAC GAC GAA AAC CTG CAA<br>K S A Y E S A K K C Q T T A F S S K Y T K Y D E N L Q | | | | | | |
| AcaNIF18 | AAA AGC GCC TAC GAA TCG GCT - - - AAA AAA TGC CAG ACC ACT GCC TTT TCA TGG GAG AAA TAT GAT GAA AAC CTG CAA<br>K S A Y E S A K K C Q T T A F S W E K Y D E N L Q | | | | | | |

```
            460         470         480         490         500         510         520         530
              *           *           *           *           *           *           *           *
NIF-1FL    TGG GAC GCG CGT GAA AAG TTT GGT TGC GCA GTT GTT AAC TGC CCT TTG GGA GAA ATC GAT GAT GAA ACC AAC CAT GAT
             W   D   A   R   E   K   F   G   C   A   V   V   N   C   P   L   G   E   I   D   D   E   T   N   H   D

PCR-NIF7   TGG GAC GCG CGT GAA AAG TTT GGT TGC GCA GTT GTT AAC TGC CCT TTG GGA GAA ATC GAT GAT GAA ACC ATC CAT GAT
             W   D   A   R   E   K   F   G   C   A   V   V   N   C   P   L   G   E   I   D   D   E   T   I   H   D

PCR-NIF20  TGG GAC ACG CGT GAA AAG TTT GGA TGT GCA GTT GTT AAC TGC CCT TTG GGA GAA ATC GAT GCA GAC ATC TAT GAT GAA
             W   D   T   R   E   K   F   G   C   A   V   V   N   C   P   L   G   E   I   D   A   D   I   Y   D   E

AcaNIF3    TGG GAC ACG CGT GAA AAG TTT GGA TGT GCA GTT GTT AAC TGC CCT TTG GGA GAA ATC GAT GCA GAC ATC TAT GAT GAA
             W   D   T   R   E   K   F   G   C   A   V   V   N   C   P   L   G   E   I   D   A   D   I   Y   D   E

AcaNIF4    TGG GAC ACG CGT GAA AAG TTT GGA TGT GCA GTT GTT AAC TGC CCT TTG GGA GAA ATC GAT ACA AGC AAC CGT GAT
             W   D   T   R   E   K   F   G   C   A   V   V   N   C   P   L   G   E   I   D   T   S   N   R   D

AcaNIF6    TGG GAC ACG CGT GAA AAG TTT GGT TGC GCA GTT GTT AAC TGC CCT TTG GGA GAA ATC GAT GCA GAC ATC TAT GAT GAA
             W   D   T   R   E   K   F   G   C   A   V   V   N   C   P   L   G   E   I   D   A   D   I   Y   D   E

AcaNIF7    TGG GAC GCG CGT GAA AAG TTT GGT TGC GCA GTT GTT AAC TGC CCT TTG GGA GAA ATC GAT GAT GAA ACC ATC CAT GAT
             W   D   A   R   E   K   F   G   C   A   V   V   N   C   P   L   G   E   I   D   D   E   T   I   H   D

AcaNIF19   TGG GAC GCG CGT GAA AAG TTT GGT TGC GCA GTT GTT AAC TGC CCT TTG GGA GAA ATC GAT GAT GAA ACC ATC CAT GAT
             W   D   A   R   E   K   F   G   C   A   V   V   N   C   P   L   G   E   I   D   D   E   T   I   H   D

AcaNIF24   TGG GAC ACC CGT GAA AAG GTT GGA TGC GCA GTT GTT AAC TGC CCT TTG GGA GAA ATC GAT GGA ACA ACC ATC GAT GAT
             W   D   T   R   E   K   V   G   C   A   V   V   N   C   P   L   G   E   I   D   G   T   T   I   D   D

AcaNIF9    TGG GAC ACC CGT GAA AAG GTT GGA TGC GCA GTT GTT AAG TGC CCT TCG GGA --- --- --- --- --- AAC ACC --- ---
             W   D   T   R   E   K   V   G   C   A   V   V   K   C   P   S   G                       N   T

AcaNIF18   TGG GAC ACT CGT GAA AAG GTT GGA TGC GCA GTT GTT AAG TGC TCT CCG AGA --- --- --- --- --- ACC ACC --- ---
             W   D   T   R   E   K   V   G   C   A   V   V   K   C   S   P   R                       T   T
```

```
           690*            700*            710*            720*            730*            740*            750*
NIF-1FL    GTG TGT ATT CCG GAT GAC GGA GTC TGC TTT ATT GGC TCG AAA GCC GAT TAC GAT AGC ---- ---- AAG GAG TTT TAT CGA
             V   C   I   P   D   D   G   V   C   F   I   G   S   K   A   D   Y   D   S                K   E   F   Y   R

PCR-NIF7   CAG TGT CAT CCG GAT ATC GGG GTC TGC TTT ATT GGC TCG AAA GCC GAT TAC GAT AGC ---- ---- AAG GAG TTT TAT CGA
             Q   C   H   P   D   I   G   V   C   F   I   G   S   K   A   D   Y   D   S                K   E   F   Y   R

PCR-NIF20  GTG TGT ATT CCG GAT GAC GGA GTC TGC TTT ATT GGC TCG AAA GCC GAT TAC GAT AGC ---- ---- AAG GAG TTT TAT CGA
             V   C   I   P   D   D   G   V   C   F   I   G   S   K   A   D   Y   D   S                K   E   F   Y   R

AcaNIF3    GTG TGT ATT CCG GAT GAC GGA GTC TGC TTT ATT GGC TCG AAA GCC GAT TAC GAT AGC ---- ---- AAG GAG TTT TAT CGT
             V   C   I   P   D   D   G   V   C   F   I   G   S   K   A   D   Y   D   S                K   E   F   Y   R

AcaNIF4    GTG TGT ATT GAC GAT GGA GTC TGC TTT ATT GGC TCG AAA GAC GAT TAC ATT AAG ---- ---- AAG GAG TTT TAT CGA
             V   C   I   D   D   G   V   C   F   I   G   S   K   D   D   Y   I   K                    K   E   F   Y   R

AcaNIF6    GTG TGT ATT CCG GAT GAC GGA GTC TGC TTT ATT GGC TCG AAA GAC GAT TAC ATT AGC ---- ---- AAG GAG TTT TAT CGA
             V   C   I   P   D   D   G   V   C   F   I   G   S   K   D   D   Y   I   S                K   E   F   Y   R

AcaNIF7    GTG TGT ATT CCG GAT GAC GGA GTC TGC TTT ATT GGC TCG AAA GCC GAT TAC GAT AGC ---- ---- AAG GAG TTT TAT CGA
             V   C   I   P   D   D   G   V   C   F   I   G   S   K   A   D   Y   D   S                K   E   F   Y   R

AcaNIF19   GTG TGT ATT CCG GAT GAC GGG GTC TGC TTT ATT GGC TCG AAA GCC GAT TAC GAT AGC ---- ---- AAG GAG TTT TAT CGA
             V   C   I   P   D   D   G   V   C   F   I   G   S   K   A   D   Y   D   S                K   E   F   Y   R

AcaNIF24   GTG TGT ATT CCA GAT GAC GGG GTC TGC TTT ATT GGC TCG AAA GCC GAT TAC GAT AGC ---- ---- AAG GAG TTT TAT CGA
             V   C   I   P   D   D   G   V   C   F   I   G   S   K   A   D   Y   D   S                K   E   F   Y   R

AcaNIF9    --- TGT CAT GCC GAT GAG GAA GTT TGC ATT ATC GCC TCT CGA GAC CTC GAC ATT TAC GGC CGC AAG AAA TAT TTT TAT CCG
                 C   H   A   D   E   E   V   C   I   I   A   S   R   D   L   D   I   Y   G   R   K   K   Y   F   Y   P

AcaNIF18   --- TGT CAC GCC GAT GAG GGA GTT TGC ATT ATC GCC TCT CGA GAC CTC GAC ATT TAC GGC CGC AAG AAA TAT TTT TAT CCG
                 C   H   A   D   E   G   V   C   I   I   A   S   R   D   L   D   I   Y   G   R   K   K   Y   F   Y   P
```

FIG. 16K

```
              760           770
               *             *
NIF-1FL    TTC CGA GAG TTA TGA ATAAGTCGAGACGTATAAAGAAG
            F   R   E   L   *

PCR-NIF7   TTC CGA GAG TTA TAA
            F   R   E   L   *

PCR-NIF20  TTC CGA GAG TTA TAA
            F   R   E   L   *

AcaNIF3    TTC CGA GAG TTA TGA ATAAGTCGACACGTATAAAGAAGTCAAACAAGCAAAAAAAAAAAAA
            F   R   E   L   *

AcaNIF4    TTC CGA GAG TTA TGA ATAAGTCGAGACGTATAAAGAAGTCAAGCAAGCAAAAAAAAAAAAAAAA
            F   R   E   L   *

AcaNIF6    TTC CGA GAG TTA TGA ATAAGTCGAGACGTATAAAGAAGTCAAGCAAGCAAAAAAAAAAAAAAAAAAAA
            F   R   E   L   *

AcaNIF7    TTC CGA GAG TTA TGA ATAAGTCGAGACGTATAAAGAAGTCAAGCAAGCAAAAAAAAAAAAAA
            F   R   E   L   *

AcaNIF19   TTC CGA GAG TTA TGA ATAAGTCGAGACGTATAAAGAAGTCAAGCAAGCAAAAAAAAAAAAAAAAAAAA
            F   R   E   L   *

AcaNIF24   TTT TGA GAG TTA TGA ATAAGTCGAGACGTATAAAGAAGTCAAGCAAGCAAAAAAAAAAAAAAAAAAAAAAAA
            F   *

AcaNIF9    TTT CGA GAG CTA TAA CTAACTCAGGTTGTAAAGAAGTTAAGCAAGCAAAAAAAAAAAAAA
            F   R   E   L   *

AcaNIF18   TTT CGA GAG TTA TAA CTAACTCAGGTTGTATAAACAAGTTAAGCAAGCAAGTAAATCTTTCGACCTACAAAAAAAAAAAAAAAAA
            F   R   E   L   *
```

FIG. 16L

```
              10                  20                  30                  40
               *                   *                   *                   *
    GAA TTC CGG TTG GCC ACC CTT GGC ATT GCT CTG GTC AAA GGA
                L   A   T   L   G   I   A   L   V   K   G 50                  60                  70                  80
           *                   *                   *                   *
    GAC GAA CCA ACG TGC AAG CAG AAT AAT GGA AGC ATG ACT AAC
     D   E   P   T   C   K   Q   N   N   G   S   M   T   N 90                 100                 110                 120
           *                   *                   *                   *
    GAG TTG AGG CGT AGA TTC TTG AGA CTG CAC AAT GGC TAC AGA
     E   L   R   R   R   F   L   R   L   H   N   G   Y   R 130                 140                 150                 160
           *                   *                   *                   *
    TCG ATT CTT GCG CTA GGT CAT GTC AAC ATA AGT GAA GAG TCA
     S   I   L   A   L   G   H   V   N   I   S   E   E   S 170                 180                 190                 200                 210
      *                   *                   *                   *                   *
    AAT GAA ACT TTC TTG TAC GCT CAT CGA GCT TCG AGA ATG AGA
     N   E   T   F   L   Y   A   H   R   A   S   R   M   R 220                 230                 240                 250
               *                   *                   *                   *
    ATT CTG GAC TAC GAC TGT GAC GCC GAA GGA AGT GCT TAC GAG
     I   L   D   Y   D   C   D   A   E   G   S   A   Y   E 260                 270                 280                 290
               *                   *                   *                   *
    TCA GCT ATC AAA CAA TGC TCG AGC AAT AAG TCT TCA TCT GCT
     S   A   I   K   Q   C   S   S   N   K   S   S   S   A 300                 310                 320                 330
               *                   *                   *                   *
    GAA TAC GAT GAA AAC GTG TAT GTT ATC GAC AAT ACA TAT GAA
     E   Y   D   E   N   V   Y   V   I   D   N   T   Y   E 340                 350                 360                 370
               *                   *                   *                   *
    GAT GAG GTT GAC CCT GCT TTA AAG GCC ATC AGC TCG TGG ACA
     D   E   V   D   P   A   L   K   A   I   S   S   W   T 380                 390                 400                 410                 420
      *                   *                   *                   *                   *
    AGC CAG GCT TTC AAC CTT ACT CAT GCA GAA GAA GGG ATT CCG
     S   Q   A   F   N   L   T   H   A   E   E   G   I   P
```

FIG. 19A

```
           430              440              450              460
            *                *                *                *
TAC CAG TGG AAC GAC AGC GTA TCG GAT TTT GCC AAT GTG GCT
 Y   Q   W   N   D   S   V   S   D   F   A   N   V   A 470              480              490              500
            *                *                *                *
TGG GAT GCT CGT GAG AAG CTT GGA TGT GCA GTT GTT ACG TGC
 W   D   A   R   E   K   L   G   C   A   V   V   T   C 510              520              530              540
        *                *                *                *
GAC CAG GGA AAC ACC ACC CAT GTA GTC TGC CAC TAT GGA CCG
 D   Q   G   N   T   T   H   V   V   C   H   Y   G   P 550              560              570              580
    *                *                *                *
AAA GCA GCA AAC AAA ACA GAA CCA ATT TAC AAG GTT GGC GTT
 K   A   A   N   K   T   E   P   I   Y   K   V   G   V 590              600              610              620              630
 *                *                *                *                *
CCA TGT TCA AAC TGC ACT GAA TAC ACA CGT GGC GAT GAA GAG
 P   C   S   N   C   T   E   Y   T   R   G   D   E   E 640              650              660              670
            *                *                *                *
AAA GTC TTC TGT CAC GCG GAT GAG GGA GTC TGC GTT ATT AAT
 K   V   F   C   H   A   D   E   G   V   C   V   I   N 680              690              700              710
            *                *                *                *
CTG CGA GAT CTT AAC AGT CAT CTT AAT ACG TCA CTC CGT TAT
 L   R   D   L   N   S   H   L   N   T   S   L   R   Y 720              730              740              750
        *                *                *                *
CCA CCT ATC TGA GAA TAA ATG AGC AAT GTT GAA AAA AAA AAA
 P   P   I   *

760
 *
AAA AAA AAA
```

FIG. 19B

SEQUENCE LISTING (1) GENERAL INFORMATION:

(iii) NUMBER OF SEQUENCES:        130

(2) INFORMATION FOR SEQ ID NO: 1:

(i) SEQUENCE CHARACTERISTICS:
      (A) LENGTH:         22 AMINO ACIDS
      (B) TYPE:           AMINO ACID
      (D) TOPOLOGY:       LINEAR (ii) MOLECULE TYPE:    PEPTIDE (ix) FEATURE:
      (D) OTHER INFORMATION:  Xaa in location 2 is Leu or Arg;
          Xaa in location 3 is Gln, Lys or Arg; Xaa in
          location 6 is Ala or Arg; Xaa in location 7
          is Leu or Met; Xaa in location 14 is Lys,
          Arg, Leu or Ile; Xaa in location 20 is Val or
          Ile; and X in location 21 is Ser, Gly or Asn.

(xi) SEQUENCE DESCRIPTION: SEQ ID NO: 1:

Arg Xaa Xaa Phe Leu Xaa Xaa His Asn Gly Tyr Arg Ser Xaa Leu
 1               5                  10                  15

Ala Leu Gly His Xaa Xaa Ile
            20

(2) INFORMATION FOR SEQ ID NO: 2:

(i) SEQUENCE CHARACTERISTICS:
      (A) LENGTH:         24 AMINO ACIDS
      (B) TYPE:           AMINO ACID
      (D) TOPOLOGY:       LINEAR (ii) MOLECULE TYPE:    PEPTIDE (ix) FEATURE:
      (D) OTHER INFORMATION:  Xaa in location 2 is His or Pro;
          Xaa in location 3 is Thr, Arg or Ser; Xaa in
          location 6 is Arg or Lys; Xaa in location 9
          is Ile or Tyr; Xaa in location 11 is Asp,
          Lys or Glu; Xaa in location 15 is Asp or
          Glu; Xaa in location 18 is Gly, Lys or Arg;
          and Xaa in location 22 is Glu, Met, Thr or
          Val.

(xi) SEQUENCE DESCRIPTION: SEQ ID NO: 2:

Ala Xaa Xaa Ala Ser Xaa Met Arg Xaa Leu Xaa Tyr Asp Cys Xaa
 1               5                  10                  15

Ala Glu Xaa Ser Ala Tyr Xaa Ser Ala
            20

(2) INFORMATION FOR SEQ ID NO: 3:

(i) SEQUENCE CHARACTERISTICS:
      (A) LENGTH:         21 AMINO ACIDS
      (B) TYPE:           AMINO ACID
      (D) TOPOLOGY:       LINEAR (ii) MOLECULE TYPE:    PEPTIDE (ix) FEATURE:
      (D) OTHER INFORMATION:  Xaa in location 2 is Asn or Asp;
          Xaa in location 6 is Val or Leu; Xaa in location
          10 is Ala or Thr; Xaa in location 14 is Leu,
          Val or Phe; and Xaa in location 20 is Thr,
          Lys or Asn.

(xi) SEQUENCE DESCRIPTION: SEQ ID NO: 3:

```
Ser Xaa Phe Ala Asn Xaa Ala Trp Asp Xaa Arg Glu Lys Xaa Gly
1               5                   10                  15

Cys Ala Val Val Xaa Cys
                20

(2) INFORMATION FOR SEQ ID NO: 4:

(i) SEQUENCE CHARACTERISTICS:
        (A) LENGTH:         9 AMINO ACIDS
        (B) TYPE:           AMINO ACID
        (D) TOPOLOGY:       LINEAR (ii) MOLECULE TYPE:     PEPTIDE (ix) FEATURE:
        (D) OTHER INFORMATION:  Xaa in location 6 is Tyr or Ile;
            and Xaa in location 7 is Gly or no residue.

(xi) SEQUENCE DESCRIPTION: SEQ ID NO: 4:

His Val Val Cys His Xaa Xaa Pro Lys
1               5

(2) INFORMATION FOR SEQ ID NO: 5:

(i) SEQUENCE CHARACTERISTICS:
        (A) LENGTH:         14 AMINO ACIDS
        (B) TYPE:           AMINO ACID
        (D) TOPOLOGY:       LINEAR (ii) MOLECULE TYPE:     PEPTIDE (ix) FEATURE:
        (D) OTHER INFORMATION:  Xaa in location 3 is Thr, Ser, Lys
            or Glu; Xaa in location 4 is Thr, Val or
            Ile; Xaa in location 6 is Val, Lys or Thr;
            Xaa in location 9 is Arg, Ser or Asp; Xaa in
            location 10 is Asn, Gly, Asp or Arg; Xaa in
            location 12 is Asn, Ser or Thr; and Xaa in
            location 13 is Gly, Glu or Asp.

(xi) SEQUENCE DESCRIPTION: SEQ ID NO: 5:

Ile Tyr Xaa Xaa Gly Xaa Pro Cys Xaa Xaa Cys Xaa Xaa Tyr
1               5                   10

(2) INFORMATION FOR SEQ ID NO: 6:

(i) SEQUENCE CHARACTERISTICS:
        (A) LENGTH:         10 AMINO ACIDS
        (B) TYPE:           AMINO ACID
        (D) TOPOLOGY:       LINEAR (ii) MOLECULE TYPE:     PEPTIDE (ix) FEATURE:
        (D) OTHER INFORMATION:  Xaa in location 2 is His, Ile or
            Asn; Xaa in location 3 is Ala, Pro or Asp;
            Xaa in location 5 is Glu, Val, Asp or Ile;
            Xaa in location 9 is Ile, Val or Phe.

(xi) SEQUENCE DESCRIPTION: SEQ ID NO: 6:

Cys Xaa Xaa Asp Xaa Gly Val Cys Xaa Ile
1               5                   10

(2) INFORMATION FOR SEQ ID NO: 7:

(i) SEQUENCE CHARACTERISTICS:
        (A) LENGTH:         28
        (B) TYPE:           NUCLEIC ACID
        (C) STRANDEDNESS:   SINGLE
        (D) TOPOLOGY:       LINEAR
```

(ii) MOLECULE TYPE:       NUCLEIC (ix) FEATURE:
             (D) OTHER INFORMATION: The letter "N" stands for G, A,
                 T or C; the letter "H" stands for A, T or C; the
                 letter "Y" stands for C or T.

(xi) SEQUENCE DESCRIPTION: SEQ ID NO: 7:

CTCGAATTCT NGCHATHYTN GGHTGGGC                                           28

(2) INFORMATION FOR SEQ ID NO: 8:

(i) SEQUENCE CHARACTERISTICS:
             (A) LENGTH:          29
             (B) TYPE:            NUCLEIC ACID
             (C) STRANDEDNESS:    SINGLE
             (D) TOPOLOGY:        LINEAR (ii) MOLECULE TYPE:       NUCLEIC (ix) FEATURE:
             (D) OTHER INFORMATION: The letter "Y" stands for C or T;
                 the letter "R" stands for G or A.

(xi) SEQUENCE DESCRIPTION: SEQ ID NO: 8:

CTCGAATTCT TYTCTGGRAA RCGRTCRAA                                          29

(2) INFORMATION FOR SEQ ID NO: 9:

(i) SEQUENCE CHARACTERISTICS:
             (A) LENGTH:          8 AMINO ACIDS
             (B) TYPE:            AMINO ACID
             (D) TOPOLOGY:        LINEAR (ii) MOLECULE TYPE:       PEPTIDE (xi) SEQUENCE DESCRIPTION: SEQ ID NO: 9:

Leu Ala Ile Leu Gly Trp Ala Arg
 1               5

(2) INFORMATION FOR SEQ ID NO: 10:

(i) SEQUENCE CHARACTERISTICS:
             (A) LENGTH:          8 AMINO ACIDS
             (B) TYPE:            AMINO ACID
             (D) TOPOLOGY:        LINEAR (ii) MOLECULE TYPE:       PEPTIDE (xi) SEQUENCE DESCRIPTION: SEQ ID NO: 10:

Leu Phe Asp Arg Phe Pro Glu Lys
 1               5

(2) INFORMATION FOR SEQ ID NO: 11:

(i) SEQUENCE CHARACTERISTICS:
             (A) LENGTH:          33
             (B) TYPE:            NUCLEIC ACID
             (C) STRANDEDNESS:    SINGLE
             (D) TOPOLOGY:        LINEAR (ii) MOLECULE TYPE:       NUCLEIC (xi) SEQUENCE DESCRIPTION: SEQ ID NO: 11:

ACCGAATTCA CCATGGAGGC CTATCTTGTG GTC                                     33

(2) INFORMATION FOR SEQ ID NO: 12:

```
    (i) SEQUENCE CHARACTERISTICS:
        (A) LENGTH:          28
        (B) TYPE:            NUCLEIC ACID
        (C) STRANDEDNESS:    SINGLE
        (D) TOPOLOGY:        LINEAR (ii) MOLECULE TYPE:       NUCLEIC (xi) SEQUENCE DESCRIPTION: SEQ ID NO: 12:

CTGGAATTCT CGCTTACGTT GCCTTGGC                                       28

(2) INFORMATION FOR SEQ ID NO: 13:

(i) SEQUENCE CHARACTERISTICS:
        (A) LENGTH:          24
        (B) TYPE:            NUCLEIC ACID
        (C) STRANDEDNESS:    SINGLE
        (D) TOPOLOGY:        LINEAR (ii) MOLECULE TYPE:       NUCLEIC (xi) SEQUENCE DESCRIPTION: SEQ ID NO: 13:

AACGAACACA ACCTGAGGTG CCCG                                           24

(2) INFORMATION FOR SEQ ID NO: 14:

(i) SEQUENCE CHARACTERISTICS:
        (A) LENGTH:          54
        (B) TYPE:            NUCLEIC ACID
        (C) STRANDEDNESS:    SINGLE
        (D) TOPOLOGY:        LINEAR (ii) MOLECULE TYPE:       NUCLEIC (xi) SEQUENCE DESCRIPTION: SEQ ID NO: 14:

CCTCCTCCTA GATCTAAGCT TACTAGTTTA TAACTCTCGG AATCGATAAA               50

ACTC                                                                 54

(2) INFORMATION FOR SEQ ID NO: 15:

(i) SEQUENCE CHARACTERISTICS:
        (A) LENGTH:          45 AMINO ACIDS
        (B) TYPE:            AMINO ACID
        (D) TOPOLOGY:        LINEAR (ii) MOLECULE TYPE:       PEPTIDE (ix) FEATURE:
        (D) OTHER INFORMATION: "Xaa" at locations 7, 10 and 18
            refers to any of the 20 naturally occurring amino
            acids, since no specific amino acid was
            identified during Edman degradation of the
            peptide.

(xi) SEQUENCE DESCRIPTION: SEQ ID NO: 15:

Asn Glu His Asn Leu Arg Xaa Pro Gln Xaa Gly Thr Glu Met Pro
1               5                  10                  15

Gly Phe Xaa Asp Ser Ile Arg Leu Gln Phe Leu Ala Met His Asn
                20                  25                  30

Gly Tyr Arg Ser Lys Leu Ala Leu Gly His Ile Ser Ile Thr Glu
                35                  40                  45

(2) INFORMATION FOR SEQ ID NO: 16:

(i) SEQUENCE CHARACTERISTICS:
        (A) LENGTH:          54
        (B) TYPE:            NUCLEIC ACID
        (C) STRANDEDNESS:    SINGLE
```

```
            (D) TOPOLOGY:        LINEAR (ii) MOLECULE TYPE:          NUCLEIC (xi) SEQUENCE DESCRIPTION: SEQ ID NO: 16:

CCTCCTCCTA GATCTAAGCT TACTAGTTTA TAACTCTCGG AATCGATAAA        50

ACTC                                                          54

(2) INFORMATION FOR SEQ ID NO: 17:

(i) SEQUENCE CHARACTERISTICS:
            (A) LENGTH:          24
            (B) TYPE:            NUCLEIC ACID
            (C) STRANDEDNESS:    SINGLE
            (D) TOPOLOGY:        LINEAR (ii) MOLECULE TYPE:          NUCLEIC (xi) SEQUENCE DESCRIPTION: SEQ ID NO: 17:

AACGAACACA ACCTGAGGTG CCCG                                    24

(2) INFORMATION FOR SEQ ID NO: 18:

(i) SEQUENCE CHARACTERISTICS:
            (A) LENGTH:          24
            (B) TYPE:            NUCLEIC ACID
            (C) STRANDEDNESS:    SINGLE
            (D) TOPOLOGY:        LINEAR (ii) MOLECULE TYPE:          NUCLEIC (xi) SEQUENCE DESCRIPTION: SEQ ID NO: 18:

ATGGAGGCCT ATCTTGTGGT CTTA                                    24

(2) INFORMATION FOR SEQ ID NO: 19:

(i) SEQUENCE CHARACTERISTICS:
            (A) LENGTH:          8 AMINO ACIDS
            (B) TYPE:            AMINO ACID
            (D) TOPOLOGY:        LINEAR (ii) MOLECULE TYPE:          PEPTIDE (xi) SEQUENCE DESCRIPTION: SEQ ID NO: 19:

Met Glu Ala Tyr Leu Val Val Leu
 1               5

(2) INFORMATION FOR SEQ ID NO: 20:

(i) SEQUENCE CHARACTERISTICS:
            (A) LENGTH:          27
            (B) TYPE:            NUCLEIC ACID
            (C) STRANDEDNESS:    SINGLE
            (D) TOPOLOGY:        LINEAR (ii) MOLECULE TYPE:          NUCLEIC (xi) SEQUENCE DESCRIPTION: SEQ ID NO: 20:

TCATAACTCT CGGAATCGAT AAAACTC                                 27

(2) INFORMATION FOR SEQ ID NO: 21:

(i) SEQUENCE CHARACTERISTICS:
            (A) LENGTH:          8 AMINO ACIDS
            (B) TYPE:            AMINO ACID
            (D) TOPOLOGY:        LINEAR (ii) MOLECULE TYPE:          PEPTIDE
```

(xi) SEQUENCE DESCRIPTION: SEQ ID NO: 21:

Glu Pro Tyr Arg Phe Arg Glu Leu
1               5

(2) INFORMATION FOR SEQ ID NO: 22:

(i) SEQUENCE CHARACTERISTICS:
        (A) LENGTH:        36
        (B) TYPE:          NUCLEIC ACID
        (C) STRANDEDNESS:  SINGLE
        (D) TOPOLOGY:      LINEAR (ii) MOLECULE TYPE:    NUCLEIC (xi) SEQUENCE DESCRIPTION: SEQ ID NO: 22:

CACAATGGTT ACAGATCGAG ACTTGCGCTA GGTCAC                                36

(2) INFORMATION FOR SEQ ID NO: 23:

(i) SEQUENCE CHARACTERISTICS:
        (A) LENGTH:        12 AMINO ACIDS
        (B) TYPE:          AMINO ACID
        (D) TOPOLOGY:      LINEAR (ii) MOLECULE TYPE:    PEPTIDE (xi) SEQUENCE DESCRIPTION: SEQ ID NO: 23:

His Asn Gly Tyr Arg Ser Lys Leu Ala Leu Gly His
1               5                   10

(2) INFORMATION FOR SEQ ID NO: 24:

(i) SEQUENCE CHARACTERISTICS:
        (A) LENGTH:        25
        (B) TYPE:          NUCLEIC ACID
        (C) STRANDEDNESS:  SINGLE
        (D) TOPOLOGY:      LINEAR (ii) MOLECULE TYPE:    NUCLEIC (xi) SEQUENCE DESCRIPTION: SEQ ID NO: 24:

TTTTTGGGTA GTGGCAGACT ACATG                                           25

(2) INFORMATION FOR SEQ ID NO: 25:

(i) SEQUENCE CHARACTERISTICS:
        (A) LENGTH:        9 AMINO ACIDS
        (B) TYPE:          AMINO ACID
        (D) TOPOLOGY:      LINEAR (ii) MOLECULE TYPE:    PEPTIDE (xi) SEQUENCE DESCRIPTION: SEQ ID NO: 25:

His Val Val Cys His Tyr Pro Lys Ile
1               5

(2) INFORMATION FOR SEQ ID NO: 26:

(i) SEQUENCE CHARACTERISTICS:
        (A) LENGTH:        25
        (B) TYPE:          NUCLEIC ACID
        (C) STRANDEDNESS:  SINGLE
        (D) TOPOLOGY:      LINEAR (ii) MOLECULE TYPE:    NUCLEIC (xi) SEQUENCE DESCRIPTION: SEQ ID NO: 26:

```
TCGCGGCCGC TTTTTTTTTT TTTTT                                          25
```

(2) INFORMATION FOR SEQ ID NO: 27:

(i) SEQUENCE CHARACTERISTICS:
        (A) LENGTH:        23
        (B) TYPE:          NUCLEIC ACID
        (C) STRANDEDNESS:  SINGLE
        (D) TOPOLOGY:      LINEAR (ii) MOLECULE TYPE:       NUCLEIC (xi) SEQUENCE DESCRIPTION: SEQ ID NO: 27:

```
AACGAACACA ACCTGACGTG CCC                                            23
```

(2) INFORMATION FOR SEQ ID NO: 28:

(i) SEQUENCE CHARACTERISTICS:
        (A) LENGTH:        25
        (B) TYPE:          NUCLEIC ACID
        (C) STRANDEDNESS:  SINGLE
        (D) TOPOLOGY:      LINEAR (ii) MOLECULE TYPE:       NUCLEIC (xi) SEQUENCE DESCRIPTION: SEQ ID NO: 28:

```
AACGAACACA AACCGATGTG CCAGC                                          25
```

(2) INFORMATION FOR SEQ ID NO: 29:

(i) SEQUENCE CHARACTERISTICS:
        (A) LENGTH:        24
        (B) TYPE:          NUCLEIC ACID
        (C) STRANDEDNESS:  SINGLE
        (D) TOPOLOGY:      LINEAR (ii) MOLECULE TYPE:       NUCLEIC (xi) SEQUENCE DESCRIPTION: SEQ ID NO: 29:

```
AACGAACACA AACCGATGTG CGAG                                           24
```

(2) INFORMATION FOR SEQ ID NO: 30:

(i) SEQUENCE CHARACTERISTICS:
        (A) LENGTH:        23
        (B) TYPE:          NUCLEIC ACID
        (C) STRANDEDNESS:  SINGLE
        (D) TOPOLOGY:      LINEAR (ii) MOLECULE TYPE:       NUCLEIC (xi) SEQUENCE DESCRIPTION: SEQ ID NO: 30:

```
AACGAACACG ACCCAACGTG TCC                                            23
```

(2) INFORMATION FOR SEQ ID NO: 31:

(i) SEQUENCE CHARACTERISTICS:
        (A) LENGTH:        54
        (B) TYPE:          NUCLEIC ACID
        (C) STRANDEDNESS:  SINGLE
        (D) TOPOLOGY:      LINEAR (ii) MOLECULE TYPE:       NUCLEIC (xi) SEQUENCE DESCRIPTION: SEQ ID NO: 31:

```
CCTCCTCCTA GATCTAAGCT TACTAGTTTA AAATCGATAA AACTCCTTGC               50
TATC                                                                 54
```

(2) INFORMATION FOR SEQ ID NO: 32:

(i) SEQUENCE CHARACTERISTICS:
        (A) LENGTH:       54
        (B) TYPE:         NUCLEIC ACID
        (C) STRANDEDNESS: SINGLE
        (D) TOPOLOGY:     LINEAR (ii) MOLECULE TYPE:     NUCLEIC (xi) SEQUENCE DESCRIPTION: SEQ ID NO: 32:

```
CCTCCTCCTA GATCTAAGCT TACTAGTTTA TAACTCTCGG AATCGATAAA          50

ACTC                                                            54
```

(2) INFORMATION FOR SEQ ID NO: 33:

(i) SEQUENCE CHARACTERISTICS:
        (A) LENGTH:       54
        (B) TYPE:         NUCLEIC ACID
        (C) STRANDEDNESS: SINGLE
        (D) TOPOLOGY:     LINEAR (ii) MOLECULE TYPE:     NUCLEIC (xi) SEQUENCE DESCRIPTION: SEQ ID NO: 33:

```
CCTCCTCCTA GATCTAAGCT TACTAGTTTA TAACTCTCGG AATCGATAAA          50

ACTC                                                            54
```

(2) INFORMATION FOR SEQ ID NO: 34:

(i) SEQUENCE CHARACTERISTICS:
        (A) LENGTH:       54
        (B) TYPE:         NUCLEIC ACID
        (C) STRANDEDNESS: SINGLE
        (D) TOPOLOGY:     LINEAR (ii) MOLECULE TYPE:     NUCLEIC (xi) SEQUENCE DESCRIPTION: SEQ ID NO: 34:

```
CCTCCTCCTA GATCTAAGCT TACTAGTTTA TAGCTCTCGA AACGGATAAA          50

AATA                                                            54
```

(2) INFORMATION FOR SEQ ID NO: 35:

(i) SEQUENCE CHARACTERISTICS:
        (A) LENGTH:       10 AMINO ACIDS
        (B) TYPE:         AMINO ACID
        (D) TOPOLOGY:     LINEAR (ii) MOLECULE TYPE:     PEPTIDE (ix) FEATURE:
        (D) OTHER INFORMATION:  "Xaa" at locations 4 and 7
            refers to any of the 20 naturally occurring amino
            acids, since no specific amino acid was identified
            during Edman degradation of the peptide.

(xi) SEQUENCE DESCRIPTION: SEQ ID NO: 35:

```
Asn Glu His Xaa Leu Thr Xaa Pro Gln Asn
1               5                   10
```

(2) INFORMATION FOR SEQ ID NO: 36:

(i) SEQUENCE CHARACTERISTICS:
        (A) LENGTH:       15 AMINO ACIDS
        (B) TYPE:         AMINO ACID
        (D) TOPOLOGY:     LINEAR (ii) MOLECULE TYPE:      PEPTIDE (ix) FEATURE:
             (D) OTHER INFORMATION:
                  "Xaa" at locations 7 and 10 refers to any of
                  the 20 naturally occurring amino acids,
                  since no specific amino acid was identified
                  during Edman degradation of the peptide.

(xi) SEQUENCE DESCRIPTION: SEQ ID NO: 36:

Asn Glu His Lys Pro Met Xaa Gln Gln Xaa Glu Thr Glu Met Pro
1               5                  10                  15

(2) INFORMATION FOR SEQ ID NO: 37:

(i) SEQUENCE CHARACTERISTICS:
            (A) LENGTH:          54
            (B) TYPE:            NUCLEIC ACID
            (C) STRANDEDNESS:    SINGLE
            (D) TOPOLOGY:        LINEAR (ii) MOLECULE TYPE:      NUCLEIC (xi) SEQUENCE DESCRIPTION: SEQ ID NO: 37:

GTCGCAACTG CGGCCCAGCC GGCCATGGCC GCTGACGAAC CAACGTGCAA         50

GCAG                                                          54

(2) INFORMATION FOR SEQ ID NO:    38:

(i) SEQUENCE CHARACTERISTICS:
            (A) LENGTH:          48
            (B) TYPE:            NUCLEIC ACID
            (C) STRANDEDNESS:    SINGLE
            (D) TOPOLOGY:        LINEAR (ii) MOLECULE TYPE:      NUCLEIC (xi) SEQUENCE DESCRIPTION: SEQ ID NO: 38:

GAGTTCTCGA CTTGCGGCCG CACCTCCGAT AGGTGGATAA CGGAGTGA           48

(2) INFORMATION FOR SEQ ID NO: 39:

(i) SEQUENCE CHARACTERISTICS:
            (A) LENGTH:          9 AMINO ACIDS
            (B) TYPE:            AMINO ACID
            (D) TOPOLOGY:        LINEAR (ii) MOLECULE TYPE:      PEPTIDE (xi) SEQUENCE DESCRIPTION: SEQ ID NO: 39:

Asn Glu His Glu Pro Thr Cys Lys Gln
1               5

(2) INFORMATION FOR SEQ ID NO: 40:

(i) SEQUENCE CHARACTERISTICS:
            (A) LENGTH:          9 AMINO ACIDS
            (B) TYPE:            AMINO ACID
            (D) TOPOLOGY:        LINEAR (ii) MOLECULE TYPE:      PEPTIDE (ix) FEATURE:
             (D) OTHER INFORMATION:

(xi) SEQUENCE DESCRIPTION: SEQ ID NO: 40:

Asn Glu His Asp Pro Thr Cys Pro Gln
1               5

(2) INFORMATION FOR SEQ ID NO: 41:

(i) SEQUENCE CHARACTERISTICS:
        (A) LENGTH:        9 AMINO ACIDS
        (B) TYPE:          AMINO ACID
        (D) TOPOLOGY:     LINEAR (ii) MOLECULE TYPE:     PEPTIDE (ix) FEATURE:
        (D) OTHER INFORMATION:

(xi) SEQUENCE DESCRIPTION: SEQ ID NO: 41:

Lys Gly Asp Glu Pro Thr Cys Lys Gln
 1             5

(2) INFORMATION FOR SEQ ID NO: 42:

(i) SEQUENCE CHARACTERISTICS:
        (A) LENGTH:        27
        (B) TYPE:          NUCLEIC ACID
        (C) STRANDEDNESS:  SINGLE
        (D) TOPOLOGY:     LINEAR (ii) MOLECULE TYPE:     NUCLEIC (xi) SEQUENCE DESCRIPTION: SEQ ID NO: 42:

AACGAACACG AACCAACGTG CAAGCAG                         27

(2) INFORMATION FOR SEQ ID NO: 43:

(i) SEQUENCE CHARACTERISTICS:
        (A) LENGTH:        52
        (B) TYPE:          NUCLEIC ACID
        (C) STRANDEDNESS:  SINGLE
        (D) TOPOLOGY:     LINEAR (ii) MOLECULE TYPE:     NUCLEIC (xi) SEQUENCE DESCRIPTION: SEQ ID NO: 43:

CCTCCTCCTT CTAGAAGCTT ACTAGTTTAG ATAGGTGGAT AACGGAGTGA         50

CG                                                                        52

(2) INFORMATION FOR SEQ ID NO: 44:

(i) SEQUENCE CHARACTERISTICS:
        (A) LENGTH:        54
        (B) TYPE:          NUCLEIC ACID
        (C) STRANDEDNESS:  SINGLE
        (D) TOPOLOGY:     LINEAR (ii) MOLECULE TYPE:     NUCLEIC (xi) SEQUENCE DESCRIPTION: SEQ ID NO: 44:

GTCGCAACTG CGGCCCAGCC GGCCATGGCC GCTAATGAAC ACAACCTGAG         50

GTGC                                                                       54

(2) INFORMATION FOR SEQ ID NO: 45:

(i) SEQUENCE CHARACTERISTICS:
        (A) LENGTH:        51
        (B) TYPE:          NUCLEIC ACID
        (C) STRANDEDNESS:  SINGLE
        (D) TOPOLOGY:     LINEAR (ii) MOLECULE TYPE:     NUCLEIC (xi) SEQUENCE DESCRIPTION: SEQ ID NO: 45:

GAGTTCTCGA CTTGCGGCCG CAGGTGGTAA CTCTCGGAAT CGATAAAACT C                51

(2) INFORMATION FOR SEQ ID NO: 46:

(i) SEQUENCE CHARACTERISTICS:
        (A) LENGTH:       21
        (B) TYPE:         NUCLEIC ACID
        (C) STRANDEDNESS: SINGLE
        (D) TOPOLOGY:     LINEAR (ii) MOLECULE TYPE:     NUCLEIC (ix) FEATURE:
        (D) OTHER INFORMATION:  The letter "S" stands for C or G.

(xi) SEQUENCE DESCRIPTION: SEQ ID NO: 46:

AATGAACACA ACCTGASGTG C                                                 21

(2) INFORMATION FOR SEQ ID NO: 47:

(i) SEQUENCE CHARACTERISTICS:
        (A) LENGTH:       21
        (B) TYPE:         NUCLEIC ACID
        (C) STRANDEDNESS: SINGLE
        (D) TOPOLOGY:     LINEAR (ii) MOLECULE TYPE:     NUCLEIC (xi) SEQUENCE DESCRIPTION: SEQ ID NO: 47:

AATGAACACG ACCCAACGTG T                                                 21

(2) INFORMATION FOR SEQ ID NO: 48:

(i) SEQUENCE CHARACTERISTICS:
        (A) LENGTH:       21
        (B) TYPE:         NUCLEIC ACID
        (C) STRANDEDNESS: SINGLE
        (D) TOPOLOGY:     LINEAR (ii) MOLECULE TYPE:     NUCLEIC (ix) FEATURE:
        (D) OTHER INFORMATION:  The letter "R" stands for A or G.

(xi) SEQUENCE DESCRIPTION: SEQ ID NO: 48:

AATGAACACA AACCGATRTG C                                                 21

(2) INFORMATION FOR SEQ ID NO: 49:

(i) SEQUENCE CHARACTERISTICS:
        (A) LENGTH:       21
        (B) TYPE:         NUCLEIC ACID
        (C) STRANDEDNESS: SINGLE
        (D) TOPOLOGY:     LINEAR (ii) MOLECULE TYPE:     NUCLEIC (xi) SEQUENCE DESCRIPTION: SEQ ID NO: 49:

TAACTCTCGG AATCGATAAA A                                                 21

(2) INFORMATION FOR SEQ ID NO: 50:

(i) SEQUENCE CHARACTERISTICS:
        (A) LENGTH:       21
        (B) TYPE:         NUCLEIC ACID
        (C) STRANDEDNESS: SINGLE
        (D) TOPOLOGY:     LINEAR

-continued

```
    (ii) MOLECULE TYPE:      NUCLEIC (ix) FEATURE:
         (D) OTHER INFORMATION:  The letter "S" stands for C or G.

(xi) SEQUENCE DESCRIPTION: SEQ ID NO: 50:
```

TAACTCTCGA AACSGATAAA A                                                  21

(2) INFORMATION FOR SEQ ID NO: 51:

```
    (i) SEQUENCE CHARACTERISTICS:
        (A) LENGTH:          35
        (B) TYPE:            NUCLEIC ACID
        (C) STRANDEDNESS:    SINGLE
        (D) TOPOLOGY:        LINEAR (ii) MOLECULE TYPE:      NUCLEIC (xi) SEQUENCE DESCRIPTION: SEQ ID NO: 51:
```

CCGGAATTCG TTAACGAACA CAACCTGAGG TGCCC                                   35

(2) INFORMATION FOR SEQ ID NO: 52:

```
    (i) SEQUENCE CHARACTERISTICS:
        (A) LENGTH:          33
        (B) TYPE:            NUCLEIC ACID
        (C) STRANDEDNESS:    SINGLE
        (D) TOPOLOGY:        LINEAR (ii) MOLECULE TYPE:      NUCLEIC (xi) SEQUENCE DESCRIPTION: SEQ ID NO: 52:
```

CCGGGCATTT CGGTACCTTG CTGCGGGCAC CTC                                     33

(2) INFORMATION FOR SEQ ID NO: 53:

```
    (i) SEQUENCE CHARACTERISTICS:
        (A) LENGTH:          36
        (B) TYPE:            NUCLEIC ACID
        (C) STRANDEDNESS:    SINGLE
        (D) TOPOLOGY:        LINEAR (ii) MOLECULE TYPE:      NUCLEIC (xi) SEQUENCE DESCRIPTION: SEQ ID NO: 53:
```

CCTAATCGAG TCTTGGAACC CGGGCATTTC TGTTCC                                  36

(2) INFORMATION FOR SEQ ID NO: 54:

```
    (i) SEQUENCE CHARACTERISTICS:
        (A) LENGTH:          43
        (B) TYPE:            NUCLEIC ACID
        (C) STRANDEDNESS:    SINGLE
        (D) TOPOLOGY:        LINEAR (ii) MOLECULE TYPE:      NUCLEIC (xi) SEQUENCE DESCRIPTION: SEQ ID NO: 54:
```

AACTGTCCGA GCATTGTCGT GCACTCATGT AGGCGCTTTT TTC                          43

(2) INFORMATION FOR SEQ ID NO: 55:

```
    (i) SEQUENCE CHARACTERISTICS:
        (A) LENGTH:          31
        (B) TYPE:            NUCLEIC ACID
        (C) STRANDEDNESS:    SINGLE
        (D) TOPOLOGY:        LINEAR (ii) MOLECULE TYPE:      NUCLEIC
```

(xi) SEQUENCE DESCRIPTION: SEQ ID NO: 55:

CAGAGCTTCA GAGATCTGGT TTGAGTTTTC G                                   31

(2) INFORMATION FOR SEQ ID NO: 56:

(i) SEQUENCE CHARACTERISTICS:
        (A) LENGTH:         34
        (B) TYPE:           NUCLEIC ACID
        (C) STRANDEDNESS:   SINGLE
        (D) TOPOLOGY:       LINEAR (ii) MOLECULE TYPE:     NUCLEIC (xi) SEQUENCE DESCRIPTION: SEQ ID NO: 56:

CTCCTTCTTT TGTTTTCTGC AGGTTGAAAG CCTC                                34

(2) INFORMATION FOR SEQ ID NO: 57:

(i) SEQUENCE CHARACTERISTICS:
        (A) LENGTH:         38
        (B) TYPE:           NUCLEIC ACID
        (C) STRANDEDNESS:   SINGLE
        (D) TOPOLOGY:       LINEAR (ii) MOLECULE TYPE:     NUCLEIC (xi) SEQUENCE DESCRIPTION: SEQ ID NO: 57:

CGGCTGTCCT TCAGTTTTCT GTATTTTCGG GTAGTGGC                            38

(2) INFORMATION FOR SEQ ID NO: 58:

(i) SEQUENCE CHARACTERISTICS:
        (A) LENGTH:         34
        (B) TYPE:           NUCLEIC ACID
        (C) STRANDEDNESS:   SINGLE
        (D) TOPOLOGY:       LINEAR (ii) MOLECULE TYPE:     NUCLEIC (xi) SEQUENCE DESCRIPTION: SEQ ID NO: 58:

GGATCCGCAG ACGTCGTTTG GTCTGCTTTT TTTG                                34

(2) INFORMATION FOR SEQ ID NO: 59:

(i) SEQUENCE CHARACTERISTICS:
        (A) LENGTH:         27
        (B) TYPE:           NUCLEIC ACID
        (C) STRANDEDNESS:   SINGLE
        (D) TOPOLOGY:       LINEAR (ii) MOLECULE TYPE:     NUCLEIC (xi) SEQUENCE DESCRIPTION: SEQ ID NO: 59:

CTCCCAAAGG GCAATTAACA ACTGCGC                                        27

(2) INFORMATION FOR SEQ ID NO: 60:

(i) SEQUENCE CHARACTERISTICS:
        (A) LENGTH:         27
        (B) TYPE:           NUCLEIC ACID
        (C) STRANDEDNESS:   SINGLE
        (D) TOPOLOGY:       LINEAR (ii) MOLECULE TYPE:     NUCLEIC (xi) SEQUENCE DESCRIPTION: SEQ ID NO: 60:

GTAAATCGGC TGTCCTTCAG TTTTCTG                                        27

(2) INFORMATION FOR SEQ ID NO: 61:

(i) SEQUENCE CHARACTERISTICS:
        (A) LENGTH:       17 AMINO ACIDS
        (B) TYPE:         AMINO ACID
        (D) TOPOLOGY:     LINEAR (ii) MOLECULE TYPE:     PEPTIDE (xi) SEQUENCE DESCRIPTION: SEQ ID NO: 61:

Ser Ala Phe Glu Leu Asp Ile Thr Asn Asn Gly Asn Gly Val
1               5                   10

Leu Met Arg
15

(2) INFORMATION FOR SEQ ID NO: 62:

(i) SEQUENCE CHARACTERISTICS:
        (A) LENGTH:       8 AMINO ACIDS
        (B) TYPE:         AMINO ACID
        (D) TOPOLOGY:     LINEAR (ii) MOLECULE TYPE:     PEPTIDE (xi) SEQUENCE DESCRIPTION: SEQ ID NO: 62:

Leu Ala Ile Leu Gly Trp Ala Arg
1               5

(2) INFORMATION FOR SEQ ID NO: 63:

(i) SEQUENCE CHARACTERISTICS:
        (A) LENGTH:       8 AMINO ACIDS
        (B) TYPE:         AMINO ACID
        (D) TOPOLOGY:     LINEAR (ii) MOLECULE TYPE:     PEPTIDE (xi) SEQUENCE DESCRIPTION: SEQ ID NO: 63:

Leu Phe Asp Arg Phe Pro Glu Lys
1               5

(2) INFORMATION FOR SEQ ID NO: 64:

(i) SEQUENCE CHARACTERISTICS:
        (A) LENGTH:       9 AMINO ACIDS
        (B) TYPE:         AMINO ACID
        (D) TOPOLOGY:     LINEAR (ii) MOLECULE TYPE:     PEPTIDE (xi) SEQUENCE DESCRIPTION: SEQ ID NO: 64:

Leu Glu Met Asp Cys Glu Ala Glu Lys
1               5

(2) INFORMATION FOR SEQ ID NO: 65:

(i) SEQUENCE CHARACTERISTICS:
        (A) LENGTH:       13 AMINO ACIDS
        (B) TYPE:         AMINO ACID
        (D) TOPOLOGY:     LINEAR (ii) MOLECULE TYPE:     PEPTIDE (xi) SEQUENCE DESCRIPTION: SEQ ID NO: 65:

Val Gly Thr Pro Cys Gly Asp Cys Ser Asn Tyr Thr Lys
1               5                   10

(2) INFORMATION FOR SEQ ID NO: 66:

(i) SEQUENCE CHARACTERISTICS:
        (A) LENGTH:         10 AMINO ACIDS
        (B) TYPE:           AMINO ACID
        (D) TOPOLOGY:       LINEAR (ii) MOLECULE TYPE:     PEPTIDE (xi) SEQUENCE DESCRIPTION: SEQ ID NO: 66:

Asp Glu Asn Ile Tyr Ile Phe Glu Asn Ser
1               5                   10

(2) INFORMATION FOR SEQ ID NO: 67:

(i) SEQUENCE CHARACTERISTICS:
        (A) LENGTH:         10 AMINO ACIDS
        (B) TYPE:           AMINO ACID
        (D) TOPOLOGY:       LINEAR (ii) MOLECULE TYPE:     PEPTIDE (ix) FEATURE:
        (D) OTHER INFORMATION:  Xaa in location 10 is Glu or His.

(xi) SEQUENCE DESCRIPTION: SEQ ID NO: 67:

Asp Glu Asn Ile Tyr Ile Phe Glu Asn Xaa
1               5                   10

(2) INFORMATION FOR SEQ ID NO: 68:

(i) SEQUENCE CHARACTERISTICS:
        (A) LENGTH:         11 AMINO ACIDS
        (B) TYPE:           AMINO ACID
        (D) TOPOLOGY:       LINEAR (ii) MOLECULE TYPE:     PEPTIDE (ix) FEATURE:
        (D) OTHER INFORMATION:  Xaa in location 3 is His or Gln;
            Xaa in location 10 is Arg or Gly;
            Xaa in location 11 is Ala or Tyr.

(xi) SEQUENCE DESCRIPTION: SEQ ID NO: 68:

Asp Ile Xaa Val Tyr Phe Ile Gly Gln Xaa Xaa
1               5                   10

(2) INFORMATION FOR SEQ ID NO: 69:

(i) SEQUENCE CHARACTERISTICS:
        (A) LENGTH:         14 AMINO ACIDS
        (B) TYPE:           AMINO ACID
        (D) TOPOLOGY:       LINEAR (ii) MOLECULE TYPE:     PEPTIDE (xi) SEQUENCE DESCRIPTION: SEQ ID NO: 69:

Asp Phe Ala Pro Arg Ala Ser Lys Met Arg Tyr Leu Glu Tyr
1               5                   10

(2) INFORMATION FOR SEQ ID NO: 70:

(i) SEQUENCE CHARACTERISTICS:
        (A) LENGTH:         19 AMINO ACIDS
        (B) TYPE:           AMINO ACID
        (D) TOPOLOGY:       LINEAR (ii) MOLECULE TYPE:     PEPTIDE (ix) FEATURE:

(D) OTHER INFORMATION:  Xaa in location 10 is Phe or Ala.

(xi) SEQUENCE DESCRIPTION: SEQ ID NO: 70:

Asp Tyr Ile Tyr Tyr Gln Leu Tyr Pro Xaa Pro Met Ala
1               5                   10

His Lys Met Arg Tyr Leu
    15

(2) INFORMATION FOR SEQ ID NO: 71:

(i) SEQUENCE CHARACTERISTICS:
        (A) LENGTH:        15 AMINO ACIDS
        (B) TYPE:          AMINO ACID
        (D) TOPOLOGY:      LINEAR (ii) MOLECULE TYPE:    PEPTIDE (ix) FEATURE:
        (D) OTHER INFORMATION:
            Xaa in locations 2, 9 and 14 refers to any
            of the 20 naturally occurring amino acids,
            since no specific amino acid was identified
            during Edman degradation of the peptide.

(xi) SEQUENCE DESCRIPTION: SEQ ID NO: 71:

Asp Xaa Met Gly Leu Gln Phe Leu Xaa Met His Asn Gly Xaa Arg
1               5                   10                  15

(2) INFORMATION FOR SEQ ID NO: 72:

(i) SEQUENCE CHARACTERISTICS:
        (A) LENGTH:        16 AMINO ACIDS
        (B) TYPE:          AMINO ACID
        (D) TOPOLOGY:      LINEAR (ii) MOLECULE TYPE:    PEPTIDE (ix) FEATURE:
        (D) OTHER INFORMATION:
            Xaa in location 10 is Met, Gln or Asn; and
            Xaa in locations 11 and 15 refers to any of
            the 20 naturally occurring amino acids,
            since no specific amino acid was identified
            during Edman degradation of the peptide.

(xi) SEQUENCE DESCRIPTION: SEQ ID NO: 72:

Asp Ala Met Arg Leu Gln Phe Leu Ala Xaa Xaa Asn Gly Tyr Xaa Gly
1               5                   10                  15

(2) INFORMATION FOR SEQ ID NO: 73:

(i) SEQUENCE CHARACTERISTICS:
        (A) LENGTH:        11 AMINO ACIDS
        (B) TYPE:          AMINO ACID
        (D) TOPOLOGY:      LINEAR (ii) MOLECULE TYPE:    PEPTIDE (xi) SEQUENCE DESCRIPTION: SEQ ID NO: 73:

Asp Ile Ser Asn Phe Ala Asn Leu Ala Trp Asp
1               5                   10

(2) INFORMATION FOR SEQ ID NO: 74:

(i) SEQUENCE CHARACTERISTICS:
        (A) LENGTH:        30 AMINO ACIDS
        (B) TYPE:          AMINO ACID
        (D) TOPOLOGY:      LINEAR (ii) MOLECULE TYPE:    PEPTIDE (xi) SEQUENCE DESCRIPTION: SEQ ID NO: 74:

Asp Glu Asn Lys Tyr Ile Phe Glu Asn Ser Asn Asn Ile Ser Glu
1               5                   10                  15

Ala Ala Leu Lys Ala Met Ile Ser Gly Ala Lys Gly Ala Phe Asn
                20                  25                  30

(2) INFORMATION FOR SEQ ID NO: 75:

(i) SEQUENCE CHARACTERISTICS:
        (A) LENGTH:       7 AMINO ACIDS
        (B) TYPE:         AMINO ACID
        (D) TOPOLOGY:     LINEAR (ii) MOLECULE TYPE:     PEPTIDE (xi) SEQUENCE DESCRIPTION: SEQ ID NO: 75:

Ala Met Ile Ser Trp Ala Lys
1               5

(2) INFORMATION FOR SEQ ID NO: 76:

(i) SEQUENCE CHARACTERISTICS:
        (A) LENGTH:       18 AMINO ACIDS
        (B) TYPE:         AMINO ACID
        (D) TOPOLOGY:     LINEAR (ii) MOLECULE TYPE:     PEPTIDE (ix) FEATURE:
        (D) OTHER INFORMATION:
            Xaa in location 1 refers to any of the 20
            naturally occurring amino acids, since no
            specific amino acid was identified during
            Edman degradation of the peptide.

(xi) SEQUENCE DESCRIPTION: SEQ ID NO: 76:

Xaa Ala Tyr Ala Val Val Asn Leu Pro Leu Gly Glu Ile Ala
1               5                   10

Pro Glu Ala Ile
15

(2) INFORMATION FOR SEQ ID NO: 77:

(i) SEQUENCE CHARACTERISTICS:
        (A) LENGTH:       8 AMINO ACIDS
        (B) TYPE:         AMINO ACID
        (D) TOPOLOGY:     LINEAR (ii) MOLECULE TYPE:     PEPTIDE (ix) FEATURE:
        (D) OTHER INFORMATION:
            Xaa in locations 1, 4 and 8 refers to any of
            the 20 naturally occurring amino acids, since
            no specific amino acid was identified during
            Edman degradation of the peptide.

(xi) SEQUENCE DESCRIPTION: SEQ ID NO: 77:

Xaa Phe Tyr Xaa Phe Arg Glu Xaa
1               5

(2) INFORMATION FOR SEQ ID NO: 78:

(i) SEQUENCE CHARACTERISTICS:
        (A) LENGTH:       31 AMINO ACIDS
        (B) TYPE:         AMINO ACID
        (D) TOPOLOGY:     LINEAR

```
        (ii) MOLECULE TYPE:        PEPTIDE (ix) FEATURE:
             (D) OTHER INFORMATION:
                 Xaa in locations 17, 18 and 20 refers to any
                 of the 20 naturally occurring amino acids,
                 since no specific amino acid was identified
                 during Edman degradation of the peptide.

(xi) SEQUENCE DESCRIPTION: SEQ ID NO: 78:

Gly Ala Phe Asn Leu Asn Leu Thr Glu Glu Gly Glu Gly
 1               5                  10

Val Leu Tyr Xaa Xaa Asn Xaa Asp Ile Ser Asn Phe Ala
 15                  20                  25

Asn Leu Ala Trp Asp
             30

(2) INFORMATION FOR SEQ ID NO: 79:

(i) SEQUENCE CHARACTERISTICS:
             (A) LENGTH:            20 AMINO ACIDS
             (B) TYPE:              AMINO ACID
             (D) TOPOLOGY:          LINEAR (ii) MOLECULE TYPE:        PEPTIDE (ix) FEATURE:
             (D) OTHER INFORMATION:
                 Xaa in locations 1, 2, 3, 9 and 10 refers to
                 any of the 20 naturally occurring amino
                 acids, since no specific amino acid was
                 identified during Edman degradation of the
                 peptide.

(xi) SEQUENCE DESCRIPTION: SEQ ID NO: 79:

Xaa Xaa Xaa Gly Val Leu Tyr Arg Xaa Xaa Leu Thr Ile Ser Asn
 1               5                  10                  15

Phe Ala Asn Leu Ala
             20

(2) INFORMATION FOR SEQ ID NO: 80:

(i) SEQUENCE CHARACTERISTICS:
             (A) LENGTH:                  825
             (B) TYPE:                    NUCLEIC ACID
             (C) STRANDEDNESS:            SINGLE
             (D) TOPOLOGY:                LINEAR (ii) MOLECULE TYPE:              NUCLEIC (ix) FEATURE:
             (A) NAME/KEY:   Coding Sequence
             (B) LOCATION:   1...822

(xi) SEQUENCE DESCRIPTION: SEQ ID NO: 80:

ATG GAG GCC TAT CTT GTG GTC TTA ATT GCC ATT GCT GGC ATA GCT CAT        48
Met Glu Ala Tyr Leu Val Val Leu Ile Ala Ile Ala Gly Ile Ala His
 1               5                  10                  15

TCC AAT GAA CAC AAC CTG AGG TGC CCG CAG AAT GGA ACA GAA ATG CCC        96
Ser Asn Glu His Asn Leu Arg Cys Pro Gln Asn Gly Thr Glu Met Pro
             20                  25                  30

GGT TTC AAC GAC TCG ATT AGG CTT CAA TTT TTA GCA ATG CAC AAT GGT       144
Gly Phe Asn Asp Ser Ile Arg Leu Gln Phe Leu Ala Met His Asn Gly
         35                  40                  45

TAC AGA TCA AAA CTT GCG CTA GGT CAC ATC AGC ATA ACT GAA GAA TCC       192
Tyr Arg Ser Lys Leu Ala Leu Gly His Ile Ser Ile Thr Glu Glu Ser
 50                  55                  60
```

```
GAA AGT GAC GAT GAT GAC GAT TTC GGT TTT TTA CCC GAT TTC GCT CCA      240
Glu Ser Asp Asp Asp Asp Asp Phe Gly Phe Leu Pro Asp Phe Ala Pro
65              70                  75                  80

AGG GCA TCG AAA ATG AGA TAT CTG GAA TAT GAC TGT GAA GCT GAA AAA      288
Arg Ala Ser Lys Met Arg Tyr Leu Glu Tyr Asp Cys Glu Ala Glu Lys
                85                  90                  95

AGC GCC TAC ATG TCG GCT AGA AAT TGC TCG GAC AGT TCT TCT CCA CCA      336
Ser Ala Tyr Met Ser Ala Arg Asn Cys Ser Asp Ser Ser Ser Pro Pro
            100                 105                 110

GAG GGC TAC GAT GAA AAC AAG TAT ATT TTC GAA AAC TCA AAC AAT ATC      384
Glu Gly Tyr Asp Glu Asn Lys Tyr Ile Phe Glu Asn Ser Asn Asn Ile
        115                 120                 125

AGT GAA GCT GCT CTG AAG GCC ATG ATC TCG TGG GCA AAA GAG GCT TTC      432
Ser Glu Ala Ala Leu Lys Ala Met Ile Ser Trp Ala Lys Glu Ala Phe
    130                 135                 140

AAC CTA AAT AAA ACA AAA GAA GGA GAA GGA GTT CTG TAC CGG TCG AAC      480
Asn Leu Asn Lys Thr Lys Glu Gly Glu Gly Val Leu Tyr Arg Ser Asn
145                 150                 155                 160

CAC GAC ATA TCA AAC TTC GCT AAT CTG GCT TGG GAC GCG CGT GAA AAG      528
His Asp Ile Ser Asn Phe Ala Asn Leu Ala Trp Asp Ala Arg Glu Lys
                165                 170                 175

TTT GGT TGC GCA GTT GTT AAC TGC CCT TTG GGA GAA ATC GAT GAT GAA      576
Phe Gly Cys Ala Val Val Asn Cys Pro Leu Gly Glu Ile Asp Asp Glu
            180                 185                 190

ACC AAC CAT GAT GGA GAA ACC TAT GCA ACA ACC ATC CAT GTA GTC TGC      624
Thr Asn His Asp Gly Glu Thr Tyr Ala Thr Thr Ile His Val Val Cys
        195                 200                 205

CAC TAC CCG AAA ATA AAC AAA ACT GAA GGA CAG CCG ATT TAC AAG GTA      672
His Tyr Pro Lys Ile Asn Lys Thr Glu Gly Gln Pro Ile Tyr Lys Val
    210                 215                 220

GGG ACA CCA TGC GAC GAT TGC AGT GAA TAC ACA AAA AAA GCA GAC AAT      720
Gly Thr Pro Cys Asp Asp Cys Ser Glu Tyr Thr Lys Lys Ala Asp Asn
225                 230                 235                 240

ACC ACG TCT GCG GAT CCG GTG TGT ATT CCG GAT GAC GGA GTC TGC TTT      768
Thr Thr Ser Ala Asp Pro Val Cys Ile Pro Asp Asp Gly Val Cys Phe
                245                 250                 255

ATT GGC TCG AAA GCC GAT TAC GAT AGC AAG GAG TTT TAT CGA TTC CGA      816
Ile Gly Ser Lys Ala Asp Tyr Asp Ser Lys Glu Phe Tyr Arg Phe Arg
            260                 265                 270

GAG TTA TGA                                                          825
Glu Leu
```

(2) INFORMATION FOR SEQ ID NO: 81:

(i) SEQUENCE CHARACTERISTICS:
        (A) LENGTH:      274 AMINO ACIDS
        (B) TYPE:        AMINO ACID
        (D) TOPOLOGY:    LINEAR (ii) MOLECULE TYPE:     PEPTIDE (xi) SEQUENCE DESCRIPTION: SEQ ID NO: 81:

```
Met Glu Ala Tyr Leu Val Val Leu Ile Ala Ile Ala Gly Ile Ala
1               5                   10                  15

His Ser Asn Glu His Asn Leu Arg Cys Pro Gln Asn Gly Thr Glu
                20                  25                  30

Met Pro Gly Phe Asn Asp Ser Ile Arg Leu Gln Phe Leu Ala Met
            35                  40                  45

His Asn Gly Tyr Arg Ser Lys Leu Ala Leu Gly His Ile Ser Ile
        50                  55                  60
```

-continued

```
Thr Glu Glu Ser Glu Ser Asp Asp Asp Asp Phe Gly Phe Leu
            65                  70                  75

Pro Asp Phe Ala Pro Arg Ala Ser Lys Met Arg Tyr Leu Glu Tyr
            80                  85                  90

Asp Cys Glu Ala Glu Lys Ser Ala Tyr Met Ser Ala Arg Asn Cys
            95                  100                 105

Ser Asp Ser Ser Ser Pro Pro Glu Gly Tyr Asp Glu Asn Lys Tyr
            110                 115                 120

Ile Phe Glu Asn Ser Asn Asn Ile Ser Glu Ala Ala Leu Lys Ala
            125                 130                 135

Met Ile Ser Trp Ala Lys Glu Ala Phe Asn Leu Asn Lys Thr Lys
            140                 145                 150

Glu Gly Glu Gly Val Leu Tyr Arg Ser Asn His Asp Ile Ser Asn
            155                 160                 165

Phe Ala Asn Leu Ala Trp Asp Ala Arg Glu Lys Phe Gly Cys Ala
            170                 175                 180

Val Val Asn Cys Pro Leu Gly Glu Ile Asp Asp Glu Thr Asn His
            185                 190                 195

Asp Gly Glu Thr Tyr Ala Thr Thr Ile His Val Val Cys His Tyr
            200                 205                 210

Pro Lys Ile Asn Lys Thr Glu Gly Gln Pro Ile Tyr Lys Val Gly
            215                 220                 225

Thr Pro Cys Asp Asp Cys Ser Glu Tyr Thr Lys Lys Ala Asp Asn
            230                 235                 240

Thr Thr Ser Ala Asp Pro Val Cys Ile Pro Asp Asp Gly Val Cys
            245                 250                 255

Phe Ile Gly Ser Lys Ala Asp Tyr Asp Ser Lys Glu Phe Tyr Arg
            260                 265                 270

Phe Arg Glu Leu (2) INFORMATION FOR SEQ ID NO: 82:

(i) SEQUENCE CHARACTERISTICS:
        (A) LENGTH:              232 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 82:

Met Glu Leu Leu Leu Arg Lys Phe Leu Leu Leu Trp Leu Ser Gly
 1               5                  10                  15

Thr Phe Lys Arg Gly Arg Arg Leu Val Val Leu Ala Ala Ile Ala
                20                  25                  30

Gly Ile Ala His Ala Asn Glu His Asp Pro Thr Cys Pro Gln Asn
                35                  40                  45

Gly Glu Lys Met Glu Lys Gly Phe Asp Ala Ile Arg Leu Lys
                50                  55                  60

Phe Leu Ala Met His Asn Gly Tyr Arg Ser Arg Leu Ala Leu Gly
                65                  70                  75

His Val Ser Ile Thr Glu Glu Ser Glu Asp Tyr Asp Leu Tyr Asp
                80                  85                  90

Leu Leu Tyr Ala Pro Arg Ala Ser Lys Met Arg Tyr Leu Lys Tyr
                95                  100                 105

Asp Cys Glu Ala Glu Lys Ser Ala Tyr Glu Ser Ala Lys Lys Cys
                110                 115                 120
```

-continued

```
Gln Thr Thr Ala Ser Ser Trp Glu Lys Tyr Asp Glu Asn Leu Gln
                125                 130                 135

Val Ile Glu Asp Pro Lys Asp Ile Asn His Ala Ala Leu Lys Ala
            140                 145                 150

Ile Ile Ser Trp Ala Thr Glu Ala Phe Asn Leu Asn Lys Thr Gly
            155                 160                 165

Glu Gly Val Val Tyr Arg Ser Ile Leu Asp Ile Ser Asn Phe Ala
            170                 175                 180

Asn Leu Ala Trp Asp Thr Arg Glu Lys Val Gly Cys Ala Val Val
            185                 190                 195

Lys Cys Ser Pro Arg Thr Thr His Val Val Cys His Tyr Pro Lys
            200                 205                 210

Lys Ser Arg Arg Lys Glu Asn Pro Ile Tyr Thr Thr Gly Asn Arg
            215                 220                 225

Cys Gly Gly Cys Ser Asp Tyr
            230
```

(2) INFORMATION FOR SEQ ID NO: 83:

(i) SEQUENCE CHARACTERISTICS:
        (A) LENGTH:          208 AMINO ACIDS
        (B) TYPE:            AMINO ACID
        (D) TOPOLOGY:        LINEAR (ii) MOLECULE TYPE:         PEPTIDE (xi) SEQUENCE DESCRIPTION: SEQ ID NO: 83:

```
Glu Ser Asp Asp Tyr Glu Tyr Gly Phe Leu Pro Asp Phe Ala Pro
1               5                   10                  15

Arg Ala Ser Lys Met Arg Tyr Leu Glu Tyr Asp Cys Glu Ala Glu Lys
                20                  25                  30

Ser Ala Tyr Val Ser Ala Ser Asn Cys Ser Asn Ile Ser Ser Pro Pro
            35                  40                  45

Glu Gly Tyr Asp Glu Asn Lys Tyr Ile Phe Glu Asn Ser Asn Asn Ile
50                  55                  60

Ser Glu Ala Ala Leu Lys Ala Met Ile Ser Trp Ala Lys Glu Ala Phe
65                  70                  75                  80

Asn Leu Asn Lys Thr Gly Glu Gly Val Leu Tyr Arg Ser Asn Leu Thr
                85                  90                  95

Ile Ser Asn Phe Ala Asn Leu Ala Trp Asp Thr Arg Glu Lys Phe Gly
                100                 105                 110

Cys Ala Val Val Asn Cys Pro Leu Gly Lys Pro Asp Ala Ile Ile Thr
            115                 120                 125

Asp Asp Glu Glu Asn Tyr Ala Thr Ala Ile His Val Val Cys His Tyr
            130                 135                 140

Pro Lys Ile Asn Lys Thr Glu Gly Gln Pro Ile Tyr Lys Val Gly Thr
145                 150                 155                 160

Pro Cys Asp Asp Cys Ser Glu Tyr Thr Lys Lys Ala Asp Asn Thr Thr
            165                 170                 175

Ser Ala Asp Pro Gln Cys His Pro Asp Ile Gly Val Cys Phe Ile Gly
            180                 185                 190

Ser Lys Gly Asp Tyr Asp Ser Lys Glu Phe Tyr Arg Phe Arg Glu Leu
            195                 200                 205
```

(2) INFORMATION FOR SEQ ID NO: 84:

(i) SEQUENCE CHARACTERISTICS:
    (A) LENGTH:        231 AMINO ACIDS
    (B) TYPE:          AMINO ACID
    (D) TOPOLOGY:      LINEAR (ii) MOLECULE TYPE:    PEPTIDE (xi) SEQUENCE DESCRIPTION: SEQ ID NO: 84:

```
Leu Leu Leu Ser Ser Ala Ala His Ser Asn Glu His Asn Pro Ile
 1               5                  10                  15

Cys Ser Gln Asn Gly Thr Gly Met Phe Gly Phe Asn Asp Ser Met Arg
            20                  25                  30

Leu Lys Phe Leu Glu Met His Asn Gly Tyr Arg Ser Arg Leu Ala Leu
        35                  40                  45

Gly His Ile Ser Ile Thr Glu Glu Pro Glu Ser Tyr Asp Asp Asp
 50                  55                  60

Asp Tyr Gly Tyr Ser Glu Val Leu Tyr Ala Pro Ser Ala Ser Lys Met
 65              70                  75                  80

Arg Tyr Met Glu Tyr Asp Cys Glu Ala Glu Lys Ser Ala Tyr Lys Ser
                85                  90                  95

Ala Ser Ser Cys Ser Asp Ser Ser Ser Pro Glu Gly Tyr Asp Glu
            100                 105                 110

Asn Lys Tyr Ile Leu Glu Asn Ser Ser Asn Ile Ser Glu Ala Ala Arg
        115                 120                 125

Leu Ala Ile Leu Ser Trp Ala Lys Glu Ala Phe Asp Leu Asn Lys Thr
130                 135                 140

Gly Glu Gly Val Leu Tyr Arg Ser Asn Leu Thr Ile Ser Asn Phe Ala
145                 150                 155                 160

Asn Leu Ala Trp Asp Thr Arg Glu Lys Phe Gly Cys Ala Val Ala Lys
                165                 170                 175

Cys Pro Leu Lys Asp Thr Ser Ala Thr Thr Ile His Val Val Cys His
            180                 185                 190

Tyr Pro Lys Ile Glu Gly Glu Glu Lys Glu Gly Lys Gln Ile Tyr Lys
        195                 200                 205

Val Gly Thr Pro Cys Gly Asp Cys Ser Glu Tyr Thr Lys Lys Ala Asp
    210                 215                 220

Asn Thr Thr Ser Thr Asp Pro
225                 230
```

(2) INFORMATION FOR SEQ ID NO: 85:

(i) SEQUENCE CHARACTERISTICS:
        (A) LENGTH:        224 AMINO ACIDS
        (B) TYPE:          AMINO ACID
        (D) TOPOLOGY:      LINEAR (ii) MOLECULE TYPE:    PEPTIDE (xi) SEQUENCE DESCRIPTION: SEQ ID NO: 85:

```
Leu Val Val Leu Ile Ala Ile Ala Gly Ile Ala His Ser Asn Glu His
 1               5                  10                  15

Asn Leu Thr Cys Pro Gln Asn Gly Thr Glu Met Pro Gly Phe Asn Asp
            20                  25                  30

Ser Ile Arg Leu Gln Phe Leu Ala Met His Asn Gly Tyr Arg Ser Lys
        35                  40                  45

Leu Ala Leu Gly His Ile Ser Ile Thr Asp Glu Ser Glu Ser Glu Ser
 50                  55                  60

Asp Asp Glu Tyr Asp Tyr Trp Tyr Ala Pro Thr Ala Pro Thr Ala Ser
```

```
                65                  70                  75                  80
Lys Met Arg Tyr Leu Glu Tyr Asp Cys Glu Ala Glu Lys Ser Ala Tyr
                    85                  90                  95
Met Ser Ala Arg Asn Cys Ser Asp Ser Ser Pro Pro Glu Gly Asp
                100                 105                 110
Glu Asn Lys Tyr Ile Phe Glu Asn Ser Asn Asn Ile Ser Glu Ala Ala
                115                 120                 125
Leu Lys Ala Met Ile Ser Trp Ala Lys Glu Ala Phe Asn Leu Asn Lys
                130                 135                 140
Thr Glu Glu Gly Glu Gly Val Leu Tyr Arg Ser Asn His Asp Ile Ser
145                 150                 155                 160
Asn Phe Ala Asn Leu Ala Trp Asp Thr Arg Glu Lys Phe Gly Cys Ala
                165                 170                 175
Val Val Asn Cys Pro Leu Gly Glu Ile Asp Gly Thr Thr Ile His Asp
                180                 185                 190
Gly Glu Thr Tyr Ala Thr Thr Ile His Val Val Cys His Tyr Pro Lys
                195                 200                 205
Met Asn Lys Thr Glu Gly Gln Pro Ile Tyr Lys Val Gly Lys Pro Cys
                210                 215                 220

(2) INFORMATION FOR SEQ ID NO: 86:

(i) SEQUENCE CHARACTERISTICS:
        (A) LENGTH:              146 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 86:

Met Lys Ser Tyr Leu Met Val Leu Ala Ala Val Ala Gly Ile Ala His
1                   5                   10                  15
Ala Asn Glu His Asp Leu Ile Cys Pro His Asn Glu Gly Glu Met Glu
                20                  25                  30
Lys Gly Phe Asp Asp Ala Met Arg Leu Lys Phe Leu Ala Leu His Asn
                35                  40                  45
Gly Tyr Arg Ser Arg Leu Ala Leu Gly His Val Ser Ile Thr Glu Glu
                50                  55                  60
Ser Glu Asp Tyr Asp Leu Tyr Asp Leu Ser Tyr Ala Pro Thr Ala Ser
65                  70                  75                  80
Lys Met Arg Tyr Leu Lys Tyr Asp Cys Glu Ala Glu Lys Ser Ala Tyr
                    85                  90                  95
Glu Ser Ala Lys Lys Cys Gln Thr Thr Ala Ser Ser Ser Thr Lys Tyr
                100                 105                 110
Asp Glu Asn Leu Gln Val Ile Glu Asp Pro Arg Asp Ile Asn His Ala
                115                 120                 125
Ala Leu Lys Ala Thr Ile Ser Trp Ala Thr Glu Ala Phe Asn Leu Asn
                130                 135                 140
Lys Thr
145

(2) INFORMATION FOR SEQ ID NO: 87:

(i) SEQUENCE CHARACTERISTICS:
        (A) LENGTH:              189 AMINO ACIDS
        (B) TYPE:                AMINO ACID
        (D) TOPOLOGY:            LINEAR
```

(ii) MOLECULE TYPE:          PEPTIDE (xi) SEQUENCE DESCRIPTION: SEQ ID NO: 87:

```
Met Arg Leu Leu Arg Glu Ala Tyr Leu Val Val Leu Val Ala Ile Ala
 1               5                  10                  15

Gly Ile Ala His Ser Asn Glu His Asn Leu Thr Cys Pro Gln Asn Gly
                20                  25                  30

Thr Glu Met Pro Asp Phe Ser Asp Ser Ile Arg Leu Gln Phe Leu Ala
            35                  40                  45

Met His Asn Gly Tyr Arg Ser Asn Leu Ala Leu Gly His Ile Gly Ile
        50                  55                  60

Ser Lys Glu Ser Ile Gly Asp Asp Tyr Asp Asp Asp Tyr Tyr Tyr Phe
65                  70                  75                  80

Tyr Ser Ser Tyr Ala Pro Met Ala Ser Lys Met Arg Tyr Leu Glu Tyr
                85                  90                  95

Asp Cys Asp Ser Glu Arg Ser Ala Tyr Met Ser Ala Ser Asn Cys Ser
            100                 105                 110

Asp Ser Ser Pro Pro Glu Gly Tyr Asp Glu Asn Lys Tyr Ile Leu
        115                 120                 125

Glu Asn Ser Ser Asn Ile Asn Glu Ala Ala Arg Leu Ala Ile Ile Ser
    130                 135                 140

Trp Gly Lys Glu Ala Phe Asn Leu Asn Glu Thr Gly Glu Gly Val Leu
145                 150                 155                 160

Tyr Arg Ser Asn Leu Thr Ile Ser Asn Phe Ala Asn Leu Ala Trp Asp
                165                 170                 175

Thr Arg Glu Lys Phe Gly Cys Ala Val Val Lys Cys Pro
            180                 185
```

(2) INFORMATION FOR SEQ ID NO: 88:

(i) SEQUENCE CHARACTERISTICS:
        (A) LENGTH:           980
        (B) TYPE:             NUCLEIC ACID
        (C) STRANDEDNESS:     SINGLE
        (D) TOPOLOGY:         LINEAR (ii) MOLECULE TYPE:       NUCLEIC (ix) FEATURE:
        (A) NAME/KEY:  Coding Sequence
        (B) LOCATION:  91...962

(xi) SEQUENCE DESCRIPTION: SEQ ID NO: 88:

```
GAATTCCGCA AGGGATAAAT ATCTAACACC GTGCGTGTTG ACTATTTTAC CTCTGGCGGT      60

GATAATGGTT GCATGTACTA AGGAGGTTGT  ATG GAA CAA CGC ATA ACC CTG AAA     114
                                 Met Glu Gln Arg Ile Thr Leu Lys
                                  1               5

GAT AGC TTG GGA TCC GTC GAC CGA GCA AAT AAT TCA ACC ACT AAA CAA       162
Asp Ser Leu Gly Ser Val Asp Arg Ala Asn Asn Ser Thr Thr Lys Gln
        10                  15                  20

ATC AAC CGC GTT TCC CGG AGG TAACC ATG AAC GAA CAC AAC CTG AGG         209
Ile Asn Arg Val Ser Arg Arg  ***  Met Asn Glu His Asn Leu Arg
 25                  30                          35

TGC CCG CAG AAT GGA ACA GAA ATG CCC GGT TTC AAC GAC TCG ATT AGG       257
Cys Pro Gln Asn Gly Thr Glu Met Pro Gly Phe Asn Asp Ser Ile Arg
        40                  45                  50

CTT CAA TTT TTA GCA ATG CAC AAT GGT TAC AGA TCA AAA CTT GCG CTA       305
Leu Gln Phe Leu Ala Met His Asn Gly Tyr Arg Ser Lys Leu Ala Leu
55                  60                  65                  70
```

-continued

```
GGT CAC ATC AGC ATA ACT GAA GAA TCC GAA AGT GAC GAT GAT GAC GAT        353
Gly His Ile Ser Ile Thr Glu Glu Ser Glu Ser Asp Asp Asp Asp Asp
             75                  80                  85

TTC GGT TTT TTA CCC GAT TTC GCT CCA AGG GCA TCG AAA ATG AGA TAT        401
Phe Gly Phe Leu Pro Asp Phe Ala Pro Arg Ala Ser Lys Met Arg Tyr
             90                  95                 100

CTG GAA TAT GAC TGT GAA GCT GAA AAA AGC GCC TAC ATG TCG GCT AGA        449
Leu Glu Tyr Asp Cys Glu Ala Glu Lys Ser Ala Tyr Met Ser Ala Arg
        105                 110                 115

AAT TGC TCG GAC AGT TCT TCT CCA CCA GAG GGC TAC GAT GAA AAC AAG        497
Asn Cys Ser Asp Ser Ser Ser Pro Pro Glu Gly Tyr Asp Glu Asn Lys
        120                 125                 130

TAT ATT TTC GAA AAC TCA AAC AAT ATC AGT GAA GCT GCT CTG AAG GCC        545
Tyr Ile Phe Glu Asn Ser Asn Asn Ile Ser Glu Ala Ala Leu Lys Ala
135                 140                 145                 150

ATG ATC TCG TGG GCA AAA GAG GCT TTC AAC CTA AAT AAA ACA AAA GAA        593
Met Ile Ser Trp Ala Lys Glu Ala Phe Asn Leu Asn Lys Thr Lys Glu
                155                 160                 165

GGA GAA GGA GTT CTG TAC CGG TCG AAC CAC GAC ATA TCA AAC TTC GCT        641
Gly Glu Gly Val Leu Tyr Arg Ser Asn His Asp Ile Ser Asn Phe Ala
            170                 175                 180

AAT CTG GCT TGG GAC GCG CGT GAA AAG TTT GGT TGC GCA GTT GTT AAC        689
Asn Leu Ala Trp Asp Ala Arg Glu Lys Phe Gly Cys Ala Val Val Asn
        185                 190                 195

TGC CCT TTG GGA GAA ATC GAT GAT GAA ACC AAC CAT GAT GGA GAA ACC        737
Cys Pro Leu Gly Glu Ile Asp Asp Glu Thr Asn His Asp Gly Glu Thr
        200                 205                 210

TAT GCA ACA ACC ATC CAT GTA GTC TGC CAC TAC CCG AAA ATA AAC AAA        785
Tyr Ala Thr Thr Ile His Val Val Cys His Tyr Pro Lys Ile Asn Lys
215                 220                 225                 230

ACT GAA GGA CAG CCG ATT TAC AAG GTA GGG ACA CCA TGC GAC GAT TGC        833
Thr Glu Gly Gln Pro Ile Tyr Lys Val Gly Thr Pro Cys Asp Asp Cys
                235                 240                 245

AGT GAA TAC ACA AAA AAA GCA GAC AAT ACC ACG TCT GCG GAT CCG GTG        881
Ser Glu Tyr Thr Lys Lys Ala Asp Asn Thr Thr Ser Ala Asp Pro Val
            250                 255                 260

TGT ATT CCG GAT GAC GGA GTC TGC TTT ATT GGC TCG AAA GCC GAT TAC        929
Cys Ile Pro Asp Asp Gly Val Cys Phe Ile Gly Ser Lys Ala Asp Tyr
        265                 270                 275

GAT AGC AAG GAG TTT TAT CGA TTC CGA GAG TTA TAAACTAGTA AGCTTGCT       980
Asp Ser Lys Glu Phe Tyr Arg Phe Arg Glu Leu
        280                 285
```

(2) INFORMATION FOR SEQ ID NO: 89:

(i) SEQUENCE CHARACTERISTICS:
        (A) LENGTH:           848
        (B) TYPE:              NUCLEIC ACID
        (C) STRANDEDNESS:    SINGLE
        (D) TOPOLOGY:        LINEAR (ii) MOLECULE TYPE:          NUCLEIC (ix) FEATURE:
        (A) NAME/KEY:   Coding Sequence
        (B) LOCATION:    1...822

(xi) SEQUENCE DESCRIPTION: SEQ ID NO: 89:

```
ATG GAG GCC TAT CTT GTG GTC TTA ATT GCC ATT GCT GGC ATA GCT CAT         48
Met Glu Ala Tyr Leu Val Val Leu Ile Ala Ile Ala Gly Ile Ala His
1               5                  10                  15

TCC AAT GAA CAC AAC CTG AGG TGC CCG CAG AAT GGA ACA GAA ATG CCC         96
Ser Asn Glu His Asn Leu Arg Cys Pro Gln Asn Gly Thr Glu Met Pro
```

```
                    20              25              30
GGT TTC AAC GAC TCG ATT AGG CTT CAA TTT TTA GCA ATG CAC AAT GGT     144
Gly Phe Asn Asp Ser Ile Arg Leu Gln Phe Leu Ala Met His Asn Gly
             35                  40                  45

TAC AGA TCA AAA CTT GCG CTA GGT CAC ATC AGC ATA ACT GAA GAA TCC     192
Tyr Arg Ser Lys Leu Ala Leu Gly His Ile Ser Ile Thr Glu Glu Ser
     50                  55                  60

GAA AGT GAC GAT GAT GAC GAT TTC GGT TTT TTA CCC GAT TTC GCT CCA     240
Glu Ser Asp Asp Asp Asp Asp Phe Gly Phe Leu Pro Asp Phe Ala Pro
 65                  70                  75                  80

AGG GCA TCG AAA ATG AGA TAT CTG GAA TAT GAC TGT GAA GCT GAA AAA     288
Arg Ala Ser Lys Met Arg Tyr Leu Glu Tyr Asp Cys Glu Ala Glu Lys
                 85                  90                  95

AGC GCC TAC ATG TCG GCT AGA AAT TGC TCG GAC AGT TCT TCT CCA CCA     336
Ser Ala Tyr Met Ser Ala Arg Asn Cys Ser Asp Ser Ser Ser Pro Pro
             100                 105                 110

GAG GGC TAC GAT GAA AAC AAG TAT ATT TTC GAA AAC TCA AAC AAT ATC     384
Glu Gly Tyr Asp Glu Asn Lys Tyr Ile Phe Glu Asn Ser Asn Asn Ile
         115                 120                 125

AGT GAA GCT GCT CTG AAG GCC ATG ATC TCG TGG GCA AAA GAG GCT TTC     432
Ser Glu Ala Ala Leu Lys Ala Met Ile Ser Trp Ala Lys Glu Ala Phe
     130                 135                 140

AAC CTA AAT AAA ACA AAA GAA GGA GAA GGA GTT CTG TAC CGG TCG AAC     480
Asn Leu Asn Lys Thr Lys Glu Gly Glu Gly Val Leu Tyr Arg Ser Asn
145                 150                 155                 160

CAC GAC ATA TCA AAC TTC GCT AAT CTG GCT TGG GAC GCG CGT GAA AAG     528
His Asp Ile Ser Asn Phe Ala Asn Leu Ala Trp Asp Ala Arg Glu Lys
                 165                 170                 175

TTT GGT TGC GCA GTT GTT AAC TGC CCT TTG GGA GAA ATC GAT GAT GAA     576
Phe Gly Cys Ala Val Val Asn Cys Pro Leu Gly Glu Ile Asp Asp Glu
             180                 185                 190

ACC AAC CAT GAT GGA GAA ACC TAT GCA ACA ACC ATC CAT GTA GTC TGC     624
Thr Asn His Asp Gly Glu Thr Tyr Ala Thr Thr Ile His Val Val Cys
         195                 200                 205

CAC TAC CCG AAA ATA AAC AAA ACT GAA GGA CAG CCG ATT TAC AAG GTA     672
His Tyr Pro Lys Ile Asn Lys Thr Glu Gly Gln Pro Ile Tyr Lys Val
     210                 215                 220

GGG ACA CCA TGC GAC GAT TGC AGT GAA TAC ACA AAA AAA GCA GAC AAT     720
Gly Thr Pro Cys Asp Asp Cys Ser Glu Tyr Thr Lys Lys Ala Asp Asn
225                 230                 235                 240

ACC ACG TCT GCG GAT CCG GTG TGT ATT CCG GAT GAC GGA GTC TGC TTT     768
Thr Thr Ser Ala Asp Pro Val Cys Ile Pro Asp Asp Gly Val Cys Phe
                 245                 250                 255

ATT GGC TCG AAA GCC GAT TAC GAT AGC AAG GAG TTT TAT CGA TTC CGA     816
Ile Gly Ser Lys Ala Asp Tyr Asp Ser Lys Glu Phe Tyr Arg Phe Arg
             260                 265                 270

GAG TTA TGAATAAGTC GAGACGTATA AAGAAG                                848
Glu Leu (2) INFORMATION FOR SEQ ID NO: 90:

(i) SEQUENCE CHARACTERISTICS:
        (A) LENGTH:              825
        (B) TYPE:                NUCLEIC ACID
        (C) STRANDEDNESS:        SINGLE
        (D) TOPOLOGY:            LINEAR (ii) MOLECULE TYPE:           NUCLEIC (ix) FEATURE:
        (A) NAME/KEY:  Coding Sequence
        (B) LOCATION:  1...822
```

(xi) SEQUENCE DESCRIPTION: SEQ ID NO: 90:

```
ATG GAG GCC TAT CTT GTG GTC TTA ATT GCC ATT GCT GGC ATA GCC CAC          48
Met Glu Ala Tyr Leu Val Val Leu Ile Ala Ile Ala Gly Ile Ala His
 1               5                  10                  15

TCC AAT GAA CAC AAA CCG ATG TGC CAG CAG AAT GGA ACA GAA ATG CCC          96
Ser Asn Glu His Lys Pro Met Cys Gln Gln Asn Gly Thr Glu Met Pro
            20                  25                  30

GAT TTC AAC GAC TCG ATT AGG CTT CAA TTT TTA GCA ATG CAC AAT GGT         144
Asp Phe Asn Asp Ser Ile Arg Leu Gln Phe Leu Ala Met His Asn Gly
        35                  40                  45

TAC AGA TCA AAA CTT GCG CTA GGT CAC ATC AGC ATA ACT GAA GAA TCC         192
Tyr Arg Ser Lys Leu Ala Leu Gly His Ile Ser Ile Thr Glu Glu Ser
    50                  55                  60

GAA AGT GAC GAT GAT GAC GAT TTC GGT TTT TTA CCC GAT TTC GCT CCA         240
Glu Ser Asp Asp Asp Asp Asp Phe Gly Phe Leu Pro Asp Phe Ala Pro
 65                  70                  75                  80

AGG GCA TCG AAA ATG AGA TAT CTG GAA TAT GAC TGT GAA GCT GAA AAA         288
Arg Ala Ser Lys Met Arg Tyr Leu Glu Tyr Asp Cys Glu Ala Glu Lys
                85                  90                  95

AGC GCC TAC ATG TCG GCT AGA AAT TGC TCG GAC AGT TCT TCT CCA CCA         336
Ser Ala Tyr Met Ser Ala Arg Asn Cys Ser Asp Ser Ser Ser Pro Pro
            100                 105                 110

GAG GGC TAC GAT GAA AAC AAG TAT ATT TTC GAA AAC TCA AAC AAT ATC         384
Glu Gly Tyr Asp Glu Asn Lys Tyr Ile Phe Glu Asn Ser Asn Asn Ile
        115                 120                 125

AGT GAA GCT GCT CTG AAG GCC ATG ATC TCG TGG GCA AAA GAG GCT TTC         432
Ser Glu Ala Ala Leu Lys Ala Met Ile Ser Trp Ala Lys Glu Ala Phe
    130                 135                 140

AAC CTA AAT AAA ACA GAA GAA GGA GAA GAA GTT TTG TAC CGG TCG AAC         480
Asn Leu Asn Lys Thr Glu Glu Gly Glu Glu Val Leu Tyr Arg Ser Asn
145                 150                 155                 160

CAC GAC ATA TCA AAC TTC GCT AAT CTG GCT TGG GAC GCG CGT GAA AAG         528
His Asp Ile Ser Asn Phe Ala Asn Leu Ala Trp Asp Ala Arg Glu Lys
                165                 170                 175

TTT GGT TGC GCA GTT GTT AAC TGC CCT TTG GGA GAA ATC GAT GAT GAA         576
Phe Gly Cys Ala Val Val Asn Cys Pro Leu Gly Glu Ile Asp Asp Glu
            180                 185                 190

ACC ATC CAT GAT GGA GAA ACC TAT GCA ACA ACC ATC CAT GTA GTC TGC         624
Thr Ile His Asp Gly Glu Thr Tyr Ala Thr Thr Ile His Val Val Cys
        195                 200                 205

CAC TAC CCG AAA ATA AAC AAA ACT GAA GGA GAG CCG ATT TAC AAG GTA         672
His Tyr Pro Lys Ile Asn Lys Thr Glu Gly Glu Pro Ile Tyr Lys Val
    210                 215                 220

GGG ACA CCA TGC GAC GAT TGC AGT GAA TAC ACA AAA AAA GCA GAC AAT         720
Gly Thr Pro Cys Asp Asp Cys Ser Glu Tyr Thr Lys Lys Ala Asp Asn
225                 230                 235                 240

ACC ACG TCT GCG GAT CCG CAG TGT CAT CCG GAT ATC GGG GTC TGC TTT         768
Thr Thr Ser Ala Asp Pro Gln Cys His Pro Asp Ile Gly Val Cys Phe
                245                 250                 255

ATT GGC TCG AAA GCC GAT TAC GAT AGC AAG GAG TTT TAT CGA TTC CGA         816
Ile Gly Ser Lys Ala Asp Tyr Asp Ser Lys Glu Phe Tyr Arg Phe Arg
            260                 265                 270

GAG TTA TAA                                                             825
Glu Leu
```

(2) INFORMATION FOR SEQ ID NO: 91:

(i) SEQUENCE CHARACTERISTICS:
        (A) LENGTH:                 792

```
          (B) TYPE:                 NUCLEIC ACID
          (C) STRANDEDNESS:         SINGLE
          (D) TOPOLOGY:             LINEAR (ii) MOLECULE TYPE:             NUCLEIC (ix) FEATURE:
          (D) OTHER INFORMATION:  The letter "N" at location 678 is an
              undetermined nucleotide; "Xaa" at location 226 is an
              undetermined amino acid.
          (A) NAME/KEY:  Coding Sequence
          (B) LOCATION:  1...789

(xi) SEQUENCE DESCRIPTION: SEQ ID NO: 91:
```

```
GCT GGC ATA GCT CAC TCG AAT GAA CAC AAC CTG ACG TGC CCG CAG AAT        48
Ala Gly Ile Ala His Ser Asn Glu His Asn Leu Thr Cys Pro Gln Asn
 1               5                  10                  15

GGA ACA GAA ATG CCC GGT TTC AAC GAC TCG ATT AGA CTT CAG TTT TTA        96
Gly Thr Glu Met Pro Gly Phe Asn Asp Ser Ile Arg Leu Gln Phe Leu
             20                  25                  30

GCA ATG CAC AAT GGT TAC AGA TCG AAA CTT GCG CTA GGT CAC ATC AGC       144
Ala Met His Asn Gly Tyr Arg Ser Lys Leu Ala Leu Gly His Ile Ser
         35                  40                  45

ATA ACT GAC GAA TCC GAA TCC GAA AGT GAC GAT GAA TAC GAT TAT TGG       192
Ile Thr Asp Glu Ser Glu Ser Glu Ser Asp Asp Glu Tyr Asp Tyr Trp
     50                  55                  60

TAC GCT CCA ACG GCA TAC GCT CCA ACG GCA TCG AAA ATG AGA TAT CTA       240
Tyr Ala Pro Thr Ala Tyr Ala Pro Thr Ala Ser Lys Met Arg Tyr Leu
 65                  70                  75                  80

GAA TAT GAC TGT GAA GCT GAA AAA AGC GCC TAC ATG TCG GCT AGA AAT       288
Glu Tyr Asp Cys Glu Ala Glu Lys Ser Ala Tyr Met Ser Ala Arg Asn
                 85                  90                  95

TGC TCG GAC AGT TCT TCT CCA CCA GAG GGC TAC GAT GAA AAC AAG TAT       336
Cys Ser Asp Ser Ser Ser Pro Pro Glu Gly Tyr Asp Glu Asn Lys Tyr
            100                 105                 110

ATT TTC GAA AAC TCA AAC AAT ATC AGT GAA GCT GCT CGA CTG GCC ATT       384
Ile Phe Glu Asn Ser Asn Asn Ile Ser Glu Ala Ala Arg Leu Ala Ile
        115                 120                 125

CTC TCG TGG GCA AAA GAG GCT TTC GAT CTA AAT AAA ACA GGA GAA GGA       432
Leu Ser Trp Ala Lys Glu Ala Phe Asp Leu Asn Lys Thr Gly Glu Gly
    130                 135                 140

GTT CTG TAC CGG TCG AAC CTC ACC ATA TCG AAC TTC GCT AAT CTG GCT       480
Val Leu Tyr Arg Ser Asn Leu Thr Ile Ser Asn Phe Ala Asn Leu Ala
145                 150                 155                 160

TGG GAC ACG CGT GAA AAG TTT GGA TGT GCA GTT GTT AAC TGC CCT TTG       528
Trp Asp Thr Arg Glu Lys Phe Gly Cys Ala Val Val Asn Cys Pro Leu
                165                 170                 175

GGA GAA ATC GAT GCA GAC ATC TAT GAT GAA GAA ACC TAT GCA ACA ACC       576
Gly Glu Ile Asp Ala Asp Ile Tyr Asp Glu Glu Thr Tyr Ala Thr Thr
            180                 185                 190

ATC CAT GTA GTC TGC CAC ATC CCG AAA ATA AAC AAA ACT GAA GGA GAG       624
Ile His Val Val Cys His Ile Pro Lys Ile Asn Lys Thr Glu Gly Glu
        195                 200                 205

CCG ATT TAC AAG GTA GGG ACA CCA TGC GAC GAT TGC AGT GAA TAC ACA       672
Pro Ile Tyr Lys Val Gly Thr Pro Cys Asp Asp Cys Ser Glu Tyr Thr
    210                 215                 220

AAA AAN GCA GAC AAT ACC ACG TCT GCG GAT CCG GTG TGT ATT CCG GAT       720
Lys Xaa Ala Asp Asn Thr Thr Ser Ala Asp Pro Val Cys Ile Pro Asp
225                 230                 235                 240

GAC GGA GTC TGC TTT ATT GGC TCG AAA GCC GAT TAC GAT AGC AAG GAG       768
Asp Gly Val Cys Phe Ile Gly Ser Lys Ala Asp Tyr Asp Ser Lys Glu
                245                 250                 255
```

-continued

```
TTT TAT CGA TTC CGA GAG TTA TAA                                              792
Phe Tyr Arg Phe Arg Glu Leu
            260

(2) INFORMATION FOR SEQ ID NO: 92:

(i) SEQUENCE CHARACTERISTICS:
        (A) LENGTH:              864
        (B) TYPE:                NUCLEIC ACID
        (C) STRANDEDNESS:        SINGLE
        (D) TOPOLOGY:            LINEAR (ii) MOLECULE TYPE:          NUCLEIC (ix) FEATURE:
        (A) NAME/KEY: Coding Sequence
        (B) LOCATION: 2...811

(xi) SEQUENCE DESCRIPTION: SEQ ID NO: 92:

G GAG GCC TAT CTT GTG GTC TTA GTT GCC ATT GCT GGC ATA GCC CAC TCC             49
  Glu Ala Tyr Leu Val Val Leu Val Ala Ile Ala Gly Ile Ala His Ser
  1               5                  10                  15

AAT GAA CAC AAA CCG ATG TGC CAG CAG AAT GAA ACA GAA ATG CCC GGT               97
Asn Glu His Lys Pro Met Cys Gln Gln Asn Glu Thr Glu Met Pro Gly
                20                  25                  30

TTC AAC GAC TTG ATG AGG CTT CAA TTT TTA GCA ATG CAC AAC GGT TAC              145
Phe Asn Asp Leu Met Arg Leu Gln Phe Leu Ala Met His Asn Gly Tyr
        35                  40                  45

AGA TCG AAA CTT GCG CTA GGT CAC ATC AGC ATA ACT GAC GAA TCC GAA              193
Arg Ser Lys Leu Ala Leu Gly His Ile Ser Ile Thr Asp Glu Ser Glu
    50                  55                  60

AGT GAC TAT GAT TAC GAT TAC GGT TTT TTA CCC GAT TTC GCT CCA AGT              241
Ser Asp Tyr Asp Tyr Asp Tyr Gly Phe Leu Pro Asp Phe Ala Pro Ser
65              70                  75                  80

GCA TCG AAA ATG AGA TAT CTG GAA TAT GAC TGT GAA GCT GAA AGA AGC              289
Ala Ser Lys Met Arg Tyr Leu Glu Tyr Asp Cys Glu Ala Glu Arg Ser
                85                  90                  95

GCC TAC ACG TCG GCT AGT GAT TGC TCG GAC AGT TCA TCT CCA CCA GAG              337
Ala Tyr Thr Ser Ala Ser Asp Cys Ser Asp Ser Ser Ser Pro Pro Glu
            100                 105                 110

GGC TAC GAT GAA AAC AAG TAT ATT TTC GAA AAT TCA AAC AAT ATC AGT              385
Gly Tyr Asp Glu Asn Lys Tyr Ile Phe Glu Asn Ser Asn Asn Ile Ser
        115                 120                 125

GAA GCT GCT CTG AAG GCC ATG ATC TCG TGG GCA AAA GAG GCC TTT AAC              433
Glu Ala Ala Leu Lys Ala Met Ile Ser Trp Ala Lys Glu Ala Phe Asn
    130                 135                 140

CTA AAT AAA ACA GAA AAA GGA GTT CTG TAC CAG CCC AAC CAC GAC ATA              481
Leu Asn Lys Thr Glu Lys Gly Val Leu Tyr Gln Pro Asn His Asp Ile
145                 150                 155                 160

TCC AAC TTC GCT AAT CTG GCT TGG GAC ACG CGT GAA AAG TTT GGA TGT              529
Ser Asn Phe Ala Asn Leu Ala Trp Asp Thr Arg Glu Lys Phe Gly Cys
                165                 170                 175

GCA GTT GTT AAC TGC CCT TTG GGA GAA ATC GAT GCA GAC ATC TAT GAT              577
Ala Val Val Asn Cys Pro Leu Gly Glu Ile Asp Ala Asp Ile Tyr Asp
            180                 185                 190

GAA GAA ACC TAT GCA ACA ACC ATC CAT GTA GTC TGC CAC TAC CCG AAA              625
Glu Glu Thr Tyr Ala Thr Thr Ile His Val Val Cys His Tyr Pro Lys
        195                 200                 205

ATA AAC AAA ACT GAA GGA GAG CCG ATT TAC AAG GTA GGG ACA CCA TGC              673
Ile Asn Lys Thr Glu Gly Glu Pro Ile Tyr Lys Val Gly Thr Pro Cys
    210                 215                 220

GAC GAT TGC AGT GAA TAC ACA AAA AAA GCA GAC AAT ACC ACG TCT GCG              721
Asp Asp Cys Ser Glu Tyr Thr Lys Lys Ala Asp Asn Thr Thr Ser Ala
```

-continued

```
        225                 230                 235                 240
GAT CCG GTG TGT ATT CCG GAT GAC GGA GTC TGC TTT ATT GGC TCG AAA        769
Asp Pro Val Cys Ile Pro Asp Asp Gly Val Cys Phe Ile Gly Ser Lys
                245                 250                 255

GAC GAT TAC ATT AAG AAG AAG TTT TAT CGT TTC CGA GAG TTA TGAATAAGTC     821
Asp Asp Tyr Ile Lys Lys Lys Phe Tyr Arg Phe Arg Glu Leu
                260                 265                 270

GACACGTATA AAGAAGTCAA ACAAGCAAAA AAAAAAAAA AAA                         864

(2) INFORMATION FOR SEQ ID NO: 93:

(i) SEQUENCE CHARACTERISTICS:
        (A) LENGTH:              877
        (B) TYPE:                NUCLEIC ACID
        (C) STRANDEDNESS:        SINGLE
        (D) TOPOLOGY:            LINEAR (ii) MOLECULE TYPE:          NUCLEIC (ix) FEATURE:
        (A) NAME/KEY:  Coding Sequence
        (B) LOCATION:  1...822

(xi) SEQUENCE DESCRIPTION: SEQ ID NO: 93:

TAT CTT GTG GTC TTA ATT GCC ATT GTT GGC ATA GCT CAC TCC AAT GAA         48
Tyr Leu Val Val Leu Ile Ala Ile Val Gly Ile Ala His Ser Asn Glu
1               5                   10                  15

CAC AAA CCG ATG TGC GAG CGG AAT GAA ACA GAA ATG CCT GGT TTC AAC         96
His Lys Pro Met Cys Glu Arg Asn Glu Thr Glu Met Pro Gly Phe Asn
                20                  25                  30

GAC TCG ATG AGG CTT CAA TTT TTA GCA ATG CAC AAT GGT TAC AGA TCG        144
Asp Ser Met Arg Leu Gln Phe Leu Ala Met His Asn Gly Tyr Arg Ser
            35                  40                  45

TTG CTT GCG CTC GGT CAC GTC GGA ATA AGT AAA CAA CCG ATC GAT GAT        192
Leu Leu Ala Leu Gly His Val Gly Ile Ser Lys Gln Pro Ile Asp Asp
50                  55                  60

GAT TAC TAC GAT GAT GAT TAC TAC TAT TTC TAT TCA TCA TAT GCT CCA        240
Asp Tyr Tyr Asp Asp Asp Tyr Tyr Tyr Phe Tyr Ser Ser Tyr Ala Pro
65                  70                  75                  80

AGG GCA TCG AAA ATG AGA TAT CTG GAA TAT GAC TGT GAA GCT GAA AAA        288
Arg Ala Ser Lys Met Arg Tyr Leu Glu Tyr Asp Cys Glu Ala Glu Lys
                85                  90                  95

AGC GCC TAC GTG TCG GCT AGC AAT TGC TCG AAC ATT TCA TCT CCA CCA        336
Ser Ala Tyr Val Ser Ala Ser Asn Cys Ser Asn Ile Ser Ser Pro Pro
                100                 105                 110

GAG GGC TAC GAT GAA AAC AAG TAT ATT TTC GAA AAC TCA AAC AAT ATC        384
Glu Gly Tyr Asp Glu Asn Lys Tyr Ile Phe Glu Asn Ser Asn Asn Ile
            115                 120                 125

AGT GAA GCT GCT CTG AAG GCC ATG ATC TCG TGG GCA AAA GAG GCT TTC        432
Ser Glu Ala Ala Leu Lys Ala Met Ile Ser Trp Ala Lys Glu Ala Phe
        130                 135                 140

AAC CTA AAT AAA ACA GAA GAA GGA GAA GGA GTT CTG TAC CGG TCG AAC        480
Asn Leu Asn Lys Thr Glu Glu Gly Glu Gly Val Leu Tyr Arg Ser Asn
145                 150                 155                 160

CAC GAC ATA TCA AAC TTC GCT AAT CTG GCT TGG GAC ACG CGT GAA AAG        528
His Asp Ile Ser Asn Phe Ala Asn Leu Ala Trp Asp Thr Arg Glu Lys
                165                 170                 175

TTT GGT TGC GCA GTT GTT AAC TGC CCT TTG GGA GAA ATC GAT ACA ACA        576
Phe Gly Cys Ala Val Val Asn Cys Pro Leu Gly Glu Ile Asp Thr Thr
                180                 185                 190

AGC AAC CGT GAT GGA GAA ACC TAT GCA ACA GCC ATC CAT GTA GTC TGC        624
Ser Asn Arg Asp Gly Glu Thr Tyr Ala Thr Ala Ile His Val Val Cys
```

```
                    195                 200                     205
CAC TAC CCA AAA ATA CTC GAA AAG GAA GAA AAA CAG ATT TAC GAG GTG        672
His Tyr Pro Lys Ile Leu Glu Lys Glu Glu Lys Gln Ile Tyr Glu Val
        210                 215                 220

GGG AAA CCA TGC GAT CGT TGC AGT GAA TAC TCA AAA AAC GCA AAC AAT        720
Gly Lys Pro Cys Asp Arg Cys Ser Glu Tyr Ser Lys Asn Ala Asn Asn
225                 230                 235                 240

ATC ACG TCT CCG AAT TGG GTG TGT AAT GAC GAT GAT GGA GTC TGC TTT        768
Ile Thr Ser Pro Asn Trp Val Cys Asn Asp Asp Asp Gly Val Cys Phe
                245                 250                 255

ATT GGC TCG AAA GAC GAT TAC ATT AGC AAG GAG TTT TAT CGA TTC CGA        816
Ile Gly Ser Lys Asp Asp Tyr Ile Ser Lys Glu Phe Tyr Arg Phe Arg
            260                 265                 270

GAG TTA TGAATAAGTC GAGACGTATA AAGAAGTCAA GCAAGCAAAA AAAAAAAAAA         872
Glu Leu

AAAAA                                                                  877

(2) INFORMATION FOR SEQ ID NO: 94:

(i) SEQUENCE CHARACTERISTICS:
         (A) LENGTH:           864
         (B) TYPE:             NUCLEIC ACID
         (C) STRANDEDNESS:     SINGLE
         (D) TOPOLOGY:         LINEAR (ii) MOLECULE TYPE:        NUCLEIC (ix) FEATURE:
         (A) NAME/KEY:  Coding Sequence
         (B) LOCATION:  3...803

(xi) SEQUENCE DESCRIPTION: SEQ ID NO: 94:

AT CTT GTG GTC TTA GTT GCC ATT GCT GGC ATA GCC CAC TCC AAT GAA         47
   Leu Val Val Leu Val Ala Ile Ala Gly Ile Ala His Ser Asn Glu
   1               5                   10                  15

CAC AAA CCG ATG TGC CAG CAG AAT GAA ACA GAA ATG CCC GGT TTC AAC        95
His Lys Pro Met Cys Gln Gln Asn Glu Thr Glu Met Pro Gly Phe Asn
                20                  25                  30

GAC TTG ATG AGG CTT CAA TTT TTA GCA ATG CAC AAC GGT TAC AGA TCG        143
Asp Leu Met Arg Leu Gln Phe Leu Ala Met His Asn Gly Tyr Arg Ser
            35                  40                  45

AAA CTT GCG CTA GGT CAC ATC AGC ATA ACT GAC GAA TCC GAA AGT GAC        191
Lys Leu Ala Leu Gly His Ile Ser Ile Thr Asp Glu Ser Glu Ser Asp
        50                  55                  60

TAT GAT TAC GAT TAC GGT TTT TTA CCC GAT TTC GCT CCA AGT GCA TCG        239
Tyr Asp Tyr Asp Tyr Gly Phe Leu Pro Asp Phe Ala Pro Ser Ala Ser
65                  70                  75

AAA ATG AGA TAT CTG GAA TAT GAC TGT GAA GCT GAA AGA AGC GCC TAC        287
Lys Met Arg Tyr Leu Glu Tyr Asp Cys Glu Ala Glu Arg Ser Ala Tyr
80                  85                  90                  95

ACG TCG GCT AGT GAT TGC TCG GAC AGT TCA TCT CCA CCA GAG GGC TAC        335
Thr Ser Ala Ser Asp Cys Ser Asp Ser Ser Ser Pro Pro Glu Gly Tyr
                100                 105                 110

GAT GAA AAC AAG TAT ATT TTC GAA AAT TCA AAC AAT ATC AGT GAA GCT        383
Asp Glu Asn Lys Tyr Ile Phe Glu Asn Ser Asn Asn Ile Ser Glu Ala
            115                 120                 125

GCT CTG AAG GCC ATG ATC TCG TGG GCA AAA GAG GCC TTT AAC CTA AAT        431
Ala Leu Lys Ala Met Ile Ser Trp Ala Lys Glu Ala Phe Asn Leu Asn
        130                 135                 140

AAA ACA GAA AAA GGA GTT CTG TAC CAG CCC AAC CAC GAC ATA TCC AAC        479
Lys Thr Glu Lys Gly Val Leu Tyr Gln Pro Asn His Asp Ile Ser Asn
145                 150                 155
```

```
TTC GCT AAT CTG GCT TGG GAC ACG CGT GAA AAG TTT GGA TGT GCA GTT        527
Phe Ala Asn Leu Ala Trp Asp Thr Arg Glu Lys Phe Gly Cys Ala Val
160                 165                 170                 175

GTT AAC TGC CCT TTG GGA GAA ATC GAT GCA GAC ATC TAT GAT GAA GAA        575
Val Asn Cys Pro Leu Gly Glu Ile Asp Ala Asp Ile Tyr Asp Glu Glu
                180                 185                 190

ACC TAT GCA ACA ACC ATC CAT GTA GTC TGC CAC TAC CCG AAA ATA AAC        623
Thr Tyr Ala Thr Thr Ile His Val Val Cys His Tyr Pro Lys Ile Asn
            195                 200                 205

AAA ACT GAA GGA GAG CCG ATT TAC AAG GTA GGG ACA CCA TGC GAC GAT        671
Lys Thr Glu Gly Glu Pro Ile Tyr Lys Val Gly Thr Pro Cys Asp Asp
        210                 215                 220

TGC AGT GAA TAC ACA AAA AAA GCA GAC AAT ACC ACG TCT GCG GAT CCG        719
Cys Ser Glu Tyr Thr Lys Lys Ala Asp Asn Thr Thr Ser Ala Asp Pro
225                 230                 235

GTG TGT ATT CCG GAT GAC GGA GTC TGC TTT ATT GGC TCG AAA GCC GAT        767
Val Cys Ile Pro Asp Asp Gly Val Cys Phe Ile Gly Ser Lys Ala Asp
240                 245                 250                 255

TAC GAT AGC AAG GAG TTT TAT CGA TTC CGA GAG TTA TGAATAAGTC             813
Tyr Asp Ser Lys Glu Phe Tyr Arg Phe Arg Glu Leu
                260                 265

GAGACGTATA AAGAAGTCAA GCAAGCAAAA AAAAAAAAAA AAAAAAAAAA A               864

(2) INFORMATION FOR SEQ ID NO: 95:

(i) SEQUENCE CHARACTERISTICS:
        (A) LENGTH:              868
        (B) TYPE:                NUCLEIC ACID
        (C) STRANDEDNESS:        SINGLE
        (D) TOPOLOGY:            LINEAR (ii) MOLECULE TYPE:          NUCLEIC (ix) FEATURE:
        (A) NAME/KEY:  Coding Sequence
        (B) LOCATION:  2...817

(xi) SEQUENCE DESCRIPTION: SEQ ID NO: 95:

G GCC TAT CTT GTG GTC TTA ATT GCC ATT GCT GGC ATA GCT CAC TCC AAT      49
  Ala Tyr Leu Val Val Leu Ile Ala Ile Ala Gly Ile Ala His Ser Asn
  1               5                   10                  15

GAA CAC AAC CTG AGG TGC CCG CAG AAT GGA ACA GAA ATG CCC GAT TTC        97
Glu His Asn Leu Arg Cys Pro Gln Asn Gly Thr Glu Met Pro Asp Phe
            20                  25                  30

AAC GAC TCG ATT AGG CTT CAA TTT TTA GCA ATG CAC AAT GGT TAC AGA        145
Asn Asp Ser Ile Arg Leu Gln Phe Leu Ala Met His Asn Gly Tyr Arg
        35                  40                  45

TCA AAA CTT GCG CTA GGT CAC ATC AGC ATA ACT GAA GAA TCC GAA AGT        193
Ser Lys Leu Ala Leu Gly His Ile Ser Ile Thr Glu Glu Ser Glu Ser
50                  55                  60

GAC GAT GAT GAC GAT TTC GGT TTT TTA CCC GAT TTC GCT CCA AGG GCA        241
Asp Asp Asp Asp Asp Phe Gly Phe Leu Pro Asp Phe Ala Pro Arg Ala
65                  70                  75                  80

TCG AAA ATG AGA TAT CTG GAA TAT GAC TGT GAA GCT GAA AAA AGC GCC        289
Ser Lys Met Arg Tyr Leu Glu Tyr Asp Cys Glu Ala Glu Lys Ser Ala
                85                  90                  95

TAC ATG TCG GCT AGA AAT TGC TCG GAC AGT TCT TCT CCA CCA GAG GGC        337
Tyr Met Ser Ala Arg Asn Cys Ser Asp Ser Ser Ser Pro Pro Glu Gly
            100                 105                 110

TAC GAT GAA AAC AAG TAT ATT TTC GAA AAC TCA AAC AAT ATC AGT GAA        385
Tyr Asp Glu Asn Lys Tyr Ile Phe Glu Asn Ser Asn Asn Ile Ser Glu
        115                 120                 125
```

```
GCT GCT CTG AAG GCC ATG ATC TCG TGG GCA AAA GAG GCT TTC AAC CTA      433
Ala Ala Leu Lys Ala Met Ile Ser Trp Ala Lys Glu Ala Phe Asn Leu
    130                 135                 140

AAT AAA ACA GAA GAA GGA GAA GGA GTT CTG TAC CGG TCG AAC CAC GAC      481
Asn Lys Thr Glu Glu Gly Glu Gly Val Leu Tyr Arg Ser Asn His Asp
145                 150                 155                 160

ATA TCA AAC TTC GCT AAT CTG GCT TGG GAC GCG CGT GAA AAG TTT GGT      529
Ile Ser Asn Phe Ala Asn Leu Ala Trp Asp Ala Arg Glu Lys Phe Gly
                165                 170                 175

TGC GCA GTT GTT AAC TGC CCT TTG GGA GAA ATC GAT GAT GAA ACC ATC      577
Cys Ala Val Val Asn Cys Pro Leu Gly Glu Ile Asp Asp Glu Thr Ile
            180                 185                 190

CAT GAT GGA GAA ACC TAT GCA ACA ACC ATC CAT GTA GTC TGC CAC TAC      625
His Asp Gly Glu Thr Tyr Ala Thr Thr Ile His Val Val Cys His Tyr
                195                 200                 205

CCG AAA ATA AAC AAA ACT GAA GGA CAG CCG ATT TAC AAG GTA GGG ACA      673
Pro Lys Ile Asn Lys Thr Glu Gly Gln Pro Ile Tyr Lys Val Gly Thr
        210                 215                 220

CCA TGC GAC GAT TGC AGT GAA TAC ACA AAA AAA GCA GAC AAT ACC ACG      721
Pro Cys Asp Asp Cys Ser Glu Tyr Thr Lys Lys Ala Asp Asn Thr Thr
225                 230                 235                 240

TCT GCG GAT CCG GTG TGT ATT CCG GAT GAC GGA GTC TGC TTT ATT GGC      769
Ser Ala Asp Pro Val Cys Ile Pro Asp Asp Gly Val Cys Phe Ile Gly
                245                 250                 255

TCG AAA GCC GAT TAC GAT AGC AAG GAG TTT TAT CGA TTC CGA GAG TTA      817
Ser Lys Ala Asp Tyr Asp Ser Lys Glu Phe Tyr Arg Phe Arg Glu Leu
            260                 265                 270

TGAATAAGTC GAGACGTATA AAGAAGTCAA GCAAGCAAAA AAAAAAAAA A              868

(2) INFORMATION FOR SEQ ID NO: 96:

(i) SEQUENCE CHARACTERISTICS:
        (A) LENGTH:          884
        (B) TYPE:            NUCLEIC ACID
        (C) STRANDEDNESS:    SINGLE
        (D) TOPOLOGY:        LINEAR (ii) MOLECULE TYPE:      NUCLEIC (ix) FEATURE:
        (A) NAME/KEY:  Coding Sequence
        (B) LOCATION:  1...822

(xi) SEQUENCE DESCRIPTION: SEQ ID NO: 96:

ATG GAG GCC TAT CTT GTG GTC TTA ATT GCC ATT GCT GGC ATA GCT CAC       48
Met Glu Ala Tyr Leu Val Val Leu Ile Ala Ile Ala Gly Ile Ala His
1               5                   10                  15

TCC AAT GAA CAC AAC CTG AGG TGC CCG CAG AAT GGA ACA GAA ATG CCC       96
Ser Asn Glu His Asn Leu Arg Cys Pro Gln Asn Gly Thr Glu Met Pro
            20                  25                  30

GAT TTC AAC GAC TCG ATT AGG CTT CAA TTT TTA GCA ATG CAC AAT GGT      144
Asp Phe Asn Asp Ser Ile Arg Leu Gln Phe Leu Ala Met His Asn Gly
        35                  40                  45

TAC AGA TCA AAA CTT GCG CTA GGT CAC ATC AGC ATA ACT GAA GAA TCC      192
Tyr Arg Ser Lys Leu Ala Leu Gly His Ile Ser Ile Thr Glu Glu Ser
    50                  55                  60

GAA AGT GAC GAT GAT GAC GAT TTC GGT TTT TTA CCC GAT TTC GCT CCA      240
Glu Ser Asp Asp Asp Asp Asp Phe Gly Phe Leu Pro Asp Phe Ala Pro
65                  70                  75                  80

AGG GCA TCG AAA ATG AGA TAT CTG GAA TAT GAC TGT GAA GCT GAA AAA      288
Arg Ala Ser Lys Met Arg Tyr Leu Glu Tyr Asp Cys Glu Ala Glu Lys
                85                  90                  95
```

```
AGC GCC TAC ATG TCG GCT AGA AAT TGC TCG GAC AGT TCT TCT CCA CCA          336
Ser Ala Tyr Met Ser Ala Arg Asn Cys Ser Asp Ser Ser Ser Pro Pro
            100                 105                 110

GAG GGC TAC GAT GAA AAC AAG TAT ATT TTC GAA AAC TCA AAC AAT ATC          384
Glu Gly Tyr Asp Glu Asn Lys Tyr Ile Phe Glu Asn Ser Asn Asn Ile
            115                 120                 125

AGT GAA GCT GCT CTG AAG GCC ATG ATC TCG TGG GCA AAA GAG GCT TTC          432
Ser Glu Ala Ala Leu Lys Ala Met Ile Ser Trp Ala Lys Glu Ala Phe
130                 135                 140

AAC CTA AAT AAA ACA GAA GAA GGA GAA GGA GTT CTG TAC CGG TCG AAC          480
Asn Leu Asn Lys Thr Glu Glu Gly Glu Gly Val Leu Tyr Arg Ser Asn
145                 150                 155                 160

CAC GAC ATA TCA AAC TTC GCT AAT CTG GCT TGG GAC GCG CGT GAA AAG          528
His Asp Ile Ser Asn Phe Ala Asn Leu Ala Trp Asp Ala Arg Glu Lys
                165                 170                 175

TTT GGT TGC GCA GTT GTT AAC TGC CCT TTG GGA GAA ATC GAT GAT GAA          576
Phe Gly Cys Ala Val Val Asn Cys Pro Leu Gly Glu Ile Asp Asp Glu
                180                 185                 190

ACC ATC CAT GAT GGA GAA ACC TAT GCA ACA ACC ATC CAT GTA GTC TGC          624
Thr Ile His Asp Gly Glu Thr Tyr Ala Thr Thr Ile His Val Val Cys
                195                 200                 205

CAC TAC CCG AAA ATA AAC AAA ACT GAA GGA CAG CCG ATT TAC AAG GTA          672
His Tyr Pro Lys Ile Asn Lys Thr Glu Gly Gln Pro Ile Tyr Lys Val
210                 215                 220

GGG ACA CCA TGC GAC GAT TGC AGT GGA TAC ACA AAA AAA GCA GAC AAT          720
Gly Thr Pro Cys Asp Asp Cys Ser Gly Tyr Thr Lys Lys Ala Asp Asn
225                 230                 235                 240

ACC ACG TCT GCG GAT CCG GTG TGT ATT CCG GAT GAC GGA GTC TGC TTT          768
Thr Thr Ser Ala Asp Pro Val Cys Ile Pro Asp Asp Gly Val Cys Phe
                245                 250                 255

ATT GGC TCG AAA GCC GAT TAC GAT AGC AAG GAG TTT TAT CGA TTC CGA          816
Ile Gly Ser Lys Ala Asp Tyr Asp Ser Lys Glu Phe Tyr Arg Phe Arg
                260                 265                 270

GAG TTA TGAATAAGTC GAGACGTATA AAGAAGTCAA GCAAGCAAAA AAAAAAAAA           872
Glu Leu

AAAAAAAAAA AA                                                            884

(2) INFORMATION FOR SEQ ID NO: 97:

(i) SEQUENCE CHARACTERISTICS:
        (A) LENGTH:             888
        (B) TYPE:               NUCLEIC ACID
        (C) STRANDEDNESS:       SINGLE
        (D) TOPOLOGY:           LINEAR (ii) MOLECULE TYPE:         NUCLEIC (ix) FEATURE:
        (A) NAME/KEY:  Coding Sequence
        (B) LOCATION: 1...810

(xi) SEQUENCE DESCRIPTION: SEQ ID NO: 97:

ATG GAG GCC TAT CTT GTG GTC TTA ATT GCC ATT GCT GGC ATA GCT CAC           48
Met Glu Ala Tyr Leu Val Val Leu Ile Ala Ile Ala Gly Ile Ala His
1                   5                   10                  15

TCC AAT GAA CAC AAC CTG ACG TGC CCG CAG AAT GGA ACA GAA ATG CCC           96
Ser Asn Glu His Asn Leu Thr Cys Pro Gln Asn Gly Thr Glu Met Pro
                20                  25                  30

GGT TTC AAC GAC TCG ATT AGA CTT CAG TTT TTA GCA ATG CAC AAT GGT          144
Gly Phe Asn Asp Ser Ile Arg Leu Gln Phe Leu Ala Met His Asn Gly
            35                  40                  45
```

```
TAC AGA TCG AAA CTT GCG CTA GGT CAC ATC AGC ATA ACT GAC GAA TCC        192
Tyr Arg Ser Lys Leu Ala Leu Gly His Ile Ser Ile Thr Asp Glu Ser
     50                  55                  60

GAA TCC GAA AGT GAC GAT GAA TAC GAT TAT TGG TAC GCT CCA ACG GCA        240
Glu Ser Glu Ser Asp Asp Glu Tyr Asp Tyr Trp Tyr Ala Pro Thr Ala
 65                  70                  75                  80

TAC GCT CCA ACG GCA TCG AAA ATG AGA TAT CTA GAA TAT GAC TGT GAA        288
Tyr Ala Pro Thr Ala Ser Lys Met Arg Tyr Leu Glu Tyr Asp Cys Glu
                 85                  90                  95

GCT GAA AAA AGC GCC TAC ATG TCG GCT AGA AAT TGC TCG GAC AGT TCT        336
Ala Glu Lys Ser Ala Tyr Met Ser Ala Arg Asn Cys Ser Asp Ser Ser
                100                 105                 110

TCT CCA CCA GAG GGC TAC GAT GAA AAC AAG TAT ATT TTC GAA AAC TCA        384
Ser Pro Pro Glu Gly Tyr Asp Glu Asn Lys Tyr Ile Phe Glu Asn Ser
            115                 120                 125

AAC AAT ATC AGT GAA GCT GCT CTG AAG GCC ATG ATC TCG TGG GCA AAA        432
Asn Asn Ile Ser Glu Ala Ala Leu Lys Ala Met Ile Ser Trp Ala Lys
130                 135                 140

GAG GCT TTC AAC CTA AAT AAA ACA GAA GAA GGA GAA GGA GTT CTG TAC        480
Glu Ala Phe Asn Leu Asn Lys Thr Glu Glu Gly Glu Gly Val Leu Tyr
145                 150                 155                 160

CGG TCG AAC CAC GAC ATA TCA AAC TTC GCT AAT CTG GCT TGG GAC ACG        528
Arg Ser Asn His Asp Ile Ser Asn Phe Ala Asn Leu Ala Trp Asp Thr
                165                 170                 175

CGT GAA AAG TTT GGT TGC GCA GTT GTT AAC TGC CCT TTG GGA GAA ATC        576
Arg Glu Lys Phe Gly Cys Ala Val Val Asn Cys Pro Leu Gly Glu Ile
                180                 185                 190

GAT GGA ACA ACC ATC GAT GAT GGA GAA ACC TAT GCA ACA ACC ATC CAT        624
Asp Gly Thr Thr Ile Asp Asp Gly Glu Thr Tyr Ala Thr Thr Ile His
            195                 200                 205

GTA GTC TGC CAC TAC CCG AAA ATG AAC AAA ACT GAA GGA GAA CCG ATT        672
Val Val Cys His Tyr Pro Lys Met Asn Lys Thr Glu Gly Glu Pro Ile
210                 215                 220

TAC AAG GTA GGG AAA CCA TGC CGA GAT TGC AGT GAA TAC CCA GAA AAA        720
Tyr Lys Val Gly Lys Pro Cys Arg Asp Cys Ser Glu Tyr Pro Glu Lys
225                 230                 235                 240

GTA GCC AAT ACC ACA CAA TGT CAT CCA GAT GTC GGG GTC TGC TTT ATT        768
Val Ala Asn Thr Thr Gln Cys His Pro Asp Val Gly Val Cys Phe Ile
                245                 250                 255

GGC TCG AAA GCC GAT TAC GAT AGC AAG GAG TTT TAT CGA TTT TGAGAGTTAT    820
Gly Ser Lys Ala Asp Tyr Asp Ser Lys Glu Phe Tyr Arg Phe
                260                 265                 270

GAATAAGTCG AGACGTATAA AGAAGTCAAG CAAGCAAAAA AAAAAAAAAA AAAAAAAAA      880

AAAAAAAA                                                               888

(2) INFORMATION FOR SEQ ID NO: 98:

(i) SEQUENCE CHARACTERISTICS:
        (A) LENGTH:            799
        (B) TYPE:              NUCLEIC ACID
        (C) STRANDEDNESS:      SINGLE
        (D) TOPOLOGY:          LINEAR (ii) MOLECULE TYPE:        NUCLEIC (ix) FEATURE:
        (A) NAME/KEY:   Coding Sequence
        (B) LOCATION:   2...736

(xi) SEQUENCE DESCRIPTION: SEQ ID NO: 98:

G AAG TCA TAT CTT GTG GTC TTA GCT GCC ATC GCT GGC ATA GCT CAC GCC      49
  Lys Ser Tyr Leu Val Val Leu Ala Ala Ile Ala Gly Ile Ala His Ala
```

-continued

```
         1               5                  10                 15
AAT GAA CAC GAC CCA ACG TGT CCG CAG AAT GAA GTA GAA ATG GAG AAA            97
Asn Glu His Asp Pro Thr Cys Pro Gln Asn Glu Val Glu Met Glu Lys
             20                  25                  30

GGT TTC GAC GAC GCA ATG AGG CTC AAA TTT TTG GCA CTG CAC AAT GGT           145
Gly Phe Asp Asp Ala Met Arg Leu Lys Phe Leu Ala Leu His Asn Gly
         35                  40                  45

TAC AGA TCG AAA CTT GCG CTA GGT CAC GTC AGC ATA ACT GAA GAA TCC           193
Tyr Arg Ser Lys Leu Ala Leu Gly His Val Ser Ile Thr Glu Glu Ser
     50                  55                  60

GAA GAT TAC GAT CTC TAC GAT TTA TTG TAC GCA CCA ACG GCA TCG AAA           241
Glu Asp Tyr Asp Leu Tyr Asp Leu Leu Tyr Ala Pro Thr Ala Ser Lys
65                  70                  75                  80

ATG AGA TAT CTG GAA TAT GAT TGT GAA GCC GAA AAA AGC GCC TAC GAA           289
Met Arg Tyr Leu Glu Tyr Asp Cys Glu Ala Glu Lys Ser Ala Tyr Glu
                 85                  90                  95

TCG GCT AAA AAA TGC CAG ACC ACT GCC TTT TCA TCG ACG AAA TAC GAC           337
Ser Ala Lys Lys Cys Gln Thr Thr Ala Phe Ser Ser Thr Lys Tyr Asp
             100                 105                 110

GAA AAC CTG CAA GTT ATC GAG GAC CCA AGG GAT ATC AAT CAT GCT GCT           385
Glu Asn Leu Gln Val Ile Glu Asp Pro Arg Asp Ile Asn His Ala Ala
         115                 120                 125

CTG AAG GCC ATT ATC TCG TGG GCA ACA GAG GCT TTC AAC CTA AAT AAA           433
Leu Lys Ala Ile Ile Ser Trp Ala Thr Glu Ala Phe Asn Leu Asn Lys
     130                 135                 140

ACA GGA GAA GGA GTT GTG TAC CGG TCG ATC CTC AAC ATA TCA AAC TTC           481
Thr Gly Glu Gly Val Val Tyr Arg Ser Ile Leu Asn Ile Ser Asn Phe
145                 150                 155                 160

GCT AAT CTG GCT TGG GAC ACC CGT GAA AAG GTT GGA TGC GCA GTT GTT           529
Ala Asn Leu Ala Trp Asp Thr Arg Glu Lys Val Gly Cys Ala Val Val
                 165                 170                 175

AAG TGC CCT TCG GGA AAC ACC CAC GTA GTC TGC CAC TAC CCA AAA ATA           577
Lys Cys Pro Ser Gly Asn Thr His Val Val Cys His Tyr Pro Lys Ile
             180                 185                 190

GTC AAG AAG GAA GGA AAA CCA ATT TAC TCC ATT GGC AAA CCG TGC CGC           625
Val Lys Lys Glu Gly Lys Pro Ile Tyr Ser Ile Gly Lys Pro Cys Arg
         195                 200                 205

GGT TGC AAT GAT TAC GCA AGC AAA TTC TTC TGT CAC GCC GAT GAG GGA           673
Gly Cys Asn Asp Tyr Ala Ser Lys Phe Phe Cys His Ala Asp Glu Gly
     210                 215                 220

GTT TGC ATT ATC GCC TCT CGA GAC CTC GAC ATT TAC GGC CGC AAG AAA           721
Val Cys Ile Ile Ala Ser Arg Asp Leu Asp Ile Tyr Gly Arg Lys Lys
225                 230                 235                 240

TAT TTT TAT CCG TTT CGA GAG CTA TAACTAACTC AGGTTGTATA AAGAAGTTAA          775
Tyr Phe Tyr Pro Phe Arg Glu Leu
                 245

GCAAGCAAAA AAAAAAAAAA AAAA                                                799

(2) INFORMATION FOR SEQ ID NO: 99:

(i) SEQUENCE CHARACTERISTICS:
        (A) LENGTH:              797
        (B) TYPE:                NUCLEIC ACID
        (C) STRANDEDNESS:        SINGLE
        (D) TOPOLOGY:            LINEAR (ii) MOLECULE TYPE:          NUCLEIC (ix) FEATURE:
        (A) NAME/KEY:   Coding Sequence
        (B) LOCATION:   3...725
```

(xi) SEQUENCE DESCRIPTION: SEQ ID NO: 99:

```
TA GCT ACC ATC GCT GGC ATA GCT CAC GCC AAT GAA CAC GAC CCA ACG         47
   Ala Thr Ile Ala Gly Ile Ala His Ala Asn Glu His Asp Pro Thr
   1               5                   10                  15

TGT CCG CAG AAT GGA GAA AAA ATG GAG AAA GGT TTC GAC GAC GCA ATG        95
Cys Pro Gln Asn Gly Glu Lys Met Glu Lys Gly Phe Asp Asp Ala Met
                    20                  25                  30

AGG CTC AAA TTT TTG GCA CTG CAC AAT GGT TAC AGA TCG AGA CTT GCG       143
Arg Leu Lys Phe Leu Ala Leu His Asn Gly Tyr Arg Ser Arg Leu Ala
                35                  40                  45

CTA GGT CAC GTC AGC ATA ACT GAA GAA TCC GAA GAT TAC GAT CTC TAC       191
Leu Gly His Val Ser Ile Thr Glu Glu Ser Glu Asp Tyr Asp Leu Tyr
            50                  55                  60

GAT TTA TTG TAC GCG CCA ACG GCA TCA AAA ATG AGA TAT CTG AAA TAC       239
Asp Leu Leu Tyr Ala Pro Thr Ala Ser Lys Met Arg Tyr Leu Lys Tyr
65                  70                  75

GAC TGT GAA GCC GAA AAA AGC GCC TAC GAA TCG GCT AAA AAA TGC CAG       287
Asp Cys Glu Ala Glu Lys Ser Ala Tyr Glu Ser Ala Lys Lys Cys Gln
80                  85                  90                  95

ACC ACT GCC TTT TCA TGG GAG AAA TAT GAT GAA AAC CTG CAA GTT ATC       335
Thr Thr Ala Phe Ser Trp Glu Lys Tyr Asp Glu Asn Leu Gln Val Ile
                100                 105                 110

GAG GAC CCA AGG GAT ATC AAT CAT GCT GCT CTG AAG GCC ATT ATC TCG       383
Glu Asp Pro Arg Asp Ile Asn His Ala Ala Leu Lys Ala Ile Ile Ser
                115                 120                 125

TGG GCA ACA GAG GCT TTC AAC CTA AAT AAA ACA GGA GAA GGA GTT GTG       431
Trp Ala Thr Glu Ala Phe Asn Leu Asn Lys Thr Gly Glu Gly Val Val
            130                 135                 140

TAC CGG TCG ATC CTC AAC ATA TCA AAC TTC GCT AAT CTG GCT TGG GAC       479
Tyr Arg Ser Ile Leu Asn Ile Ser Asn Phe Ala Asn Leu Ala Trp Asp
145                 150                 155

ACT CGT GAA AAG GTT GGA TGC GCA GTT GTT AAG TGC TCT CCG AGA ACC       527
Thr Arg Glu Lys Val Gly Cys Ala Val Val Lys Cys Ser Pro Arg Thr
160                 165                 170                 175

ACC CAT GTA GTC TGT CAC TAC CCA AAA ATA GTG GAA AAG GAA GGA AAA       575
Thr His Val Val Cys His Tyr Pro Lys Ile Val Glu Lys Glu Gly Lys
                180                 185                 190

CCA ATT TAC ACC ACT GGC GTG CCG TGC CGC GGT TGC AGT GGT TAC GCA       623
Pro Ile Tyr Thr Thr Gly Val Pro Cys Arg Gly Cys Ser Gly Tyr Ala
                195                 200                 205

AAC AAA TTC TTC TGT CAC GCC GAT GAG GGA GTT TGC ATT ATC GCC TCT       671
Asn Lys Phe Phe Cys His Ala Asp Glu Gly Val Cys Ile Ile Ala Ser
                210                 215                 220

CGA GAC CTC GAC ATT TAC GGC CGC AAG AAA TAT TTT TAT CCG TTT CGA       719
Arg Asp Leu Asp Ile Tyr Gly Arg Lys Lys Tyr Phe Tyr Pro Phe Arg
225                 230                 235

GAG TTA TAACTAACTC AGGTTGTATA AACAAGTTAA GCAAGCAAGT AAATCTTTCG        775
Glu Leu
240

ACCTACAAAA AAAAAAAAAA AA                                              797

(2) INFORMATION FOR SEQ ID NO: 100:

(i) SEQUENCE CHARACTERISTICS:
          (A) LENGTH:            765
          (B) TYPE:              NUCLEIC ACID
          (C) STRANDEDNESS:      SINGLE
          (D) TOPOLOGY:          LINEAR (ii) MOLECULE TYPE:          NUCLEIC
```

```
      (ix) FEATURE:
            (A) NAME/KEY:  Coding Sequence
            (B) LOCATION:  10...723

(xi) SEQUENCE DESCRIPTION: SEQ ID NO: 100:

GAATTCCGG TTG GCC ACC CTT GGC ATT GCT CTG GTC AAA GGA GAC GAA CCA          51
          Leu Ala Thr Leu Gly Ile Ala Leu Val Lys Gly Asp Glu Pro
            1               5                  10

ACG TGC AAG CAG AAT AAT GGA AGC ATG ACT AAC GAG TTG AGG CGT AGA           99
Thr Cys Lys Gln Asn Asn Gly Ser Met Thr Asn Glu Leu Arg Arg Arg
 15                  20                  25                  30

TTG AGA CTG CAC AAT GGC TAC AGA TCG ATT CTT GCG CTA GGT CAT              147
Leu Arg Leu His Asn Gly Tyr Arg Ser Ile Leu Ala Leu Gly His
                35                  40                  45

GTC AAC ATA AGT GAA GAG TCA AAT GAA ACT TTC TTG TAC GCT CAT CGA          195
Val Asn Ile Ser Glu Glu Ser Asn Glu Thr Phe Leu Tyr Ala His Arg
                50                  55                  60

GCT TCG AGA ATG AGA ATT CTG GAC TAC GAC TGT GAC GCC GAA GGA AGT          243
Ala Ser Arg Met Arg Ile Leu Asp Tyr Asp Cys Asp Ala Glu Gly Ser
             65                  70                  75

GCT TAC GAG TCA GCT ATC AAA CAA TGC TCG AGC AAT AAG TCT TCA TCT          291
Ala Tyr Glu Ser Ala Ile Lys Gln Cys Ser Ser Asn Lys Ser Ser Ser
 80                  85                  90

GCT GAA TAC GAT GAA AAC GTG TAT GTT ATC GAC AAT ACA TAT GAA GAT          339
Ala Glu Tyr Asp Glu Asn Val Tyr Val Ile Asp Asn Thr Tyr Glu Asp
 95                 100                 105                 110

GAG GTT GAC CCT GCT TTA AAG GCC ATC AGC TCG TGG ACA AGC CAG GCT          387
Glu Val Asp Pro Ala Leu Lys Ala Ile Ser Ser Trp Thr Ser Gln Ala
                115                 120                 125

TTC AAC CTT ACT CAT GCA GAA GAA GGG ATT CCG TAC CAG TGG AAC GAC          435
Phe Asn Leu Thr His Ala Glu Glu Gly Ile Pro Tyr Gln Trp Asn Asp
            130                 135                 140

AGC GTA TCG GAT TTT GCC AAT GTG GCT TGG GAT GCT CGT GAG AAG CTT          483
Ser Val Ser Asp Phe Ala Asn Val Ala Trp Asp Ala Arg Glu Lys Leu
            145                 150                 155

GGA TGT GCA GTT GTT ACG TGC GAC CAG GGA AAC ACC ACC CAT GTA GTC          531
Gly Cys Ala Val Val Thr Cys Asp Gln Gly Asn Thr Thr His Val Val
 160                 165                 170

TGC CAC TAT GGA CCG AAA GCA GCA AAC AAA ACA GAA CCA ATT TAC AAG          579
Cys His Tyr Gly Pro Lys Ala Ala Asn Lys Thr Glu Pro Ile Tyr Lys
 175                 180                 185                 190

GTT GGC GTT CCA TGT TCA AAC TGC ACT GAA TAC ACA CGT GGC GAT GAA          627
Val Gly Val Pro Cys Ser Asn Cys Thr Glu Tyr Thr Arg Gly Asp Glu
                195                 200                 205

GAG AAA GTC TTC TGT CAC GCG GAT GAG GGA GTC TGC GTT ATT AAT CTG          675
Glu Lys Val Phe Cys His Ala Asp Glu Gly Val Cys Val Ile Asn Leu
                210                 215                 220

CGA GAT CTT AAC AGT CAT CTT AAT ACG TCA CTC CGT TAT CCA CCT ATC          723
Arg Asp Leu Asn Ser His Leu Asn Thr Ser Leu Arg Tyr Pro Pro Ile
        225                 230                 235

TGAGAATAAA TGAGCAATGT TGAAAAAAAA AAAAAAAAA AA                            765

(2) INFORMATION FOR SEQ ID NO: 101:

(i) SEQUENCE CHARACTERISTICS:
            (A) LENGTH:          4 AMINO ACIDS
            (B) TYPE:            AMINO ACID
            (D) TOPOLOGY:        LINEAR (ii) MOLECULE TYPE:        PEPTIDE (xi) SEQUENCE DESCRIPTION: SEQ ID NO: 101:
```

```
Met Asn Glu His
  1
```

(2) INFORMATION FOR SEQ ID NO: 102:

(i) SEQUENCE CHARACTERISTICS:
        (A) LENGTH:                   5 AMINO ACIDS
        (B) TYPE:                     AMINO ACID
        (D) TOPOLOGY:               LINEAR (ii) MOLECULE TYPE:          PEPTIDE (xi) SEQUENCE DESCRIPTION: SEQ ID NO: 102:

```
Asn Glu His Asp Pro
  1               5
```

(2) INFORMATION FOR SEQ ID NO: 103:

(i) SEQUENCE CHARACTERISTICS:
        (A) LENGTH:                   289 AMINO ACIDS
        (B) TYPE:                     AMINO ACID
        (C) STRANDEDNESS:           SINGLE
        (D) TOPOLOGY:               LINEAR (ii) MOLECULE TYPE:          PEPTIDE (xi) SEQUENCE DESCRIPTION: SEQ ID NO: 103:

```
Met Gln Arg Ile Thr Leu Lys Asp Ser Leu Gly Ser Val Asp Arg
  1               5                  10                  15

Ala Asn Asn Ser Thr Thr Lys Gln Ile Asn Arg Val Ser Arg Arg Met
                 20                  25                  30

Asn Glu His Asn Leu Arg Cys Pro Gln Asn Gly Thr Glu Met Pro Gly
                 35                  40                  45

Phe Asn Asp Ser Ile Arg Leu Gln Phe Leu Ala Met His Asn Gly Tyr
     50                  55                  60

Arg Ser Lys Leu Ala Leu Gly His Ile Ser Ile Thr Glu Glu Ser Glu
 65                  70                  75                  80

Ser Asp Asp Asp Asp Phe Gly Phe Leu Pro Asp Phe Ala Pro Arg
                     85                  90                  95

Ala Ser Lys Met Arg Tyr Leu Glu Tyr Asp Cys Glu Ala Glu Lys Ser
                100                 105                 110

Ala Tyr Met Ser Ala Arg Asn Cys Ser Asp Ser Ser Pro Pro Glu
             115                 120                 125

Gly Tyr Asp Glu Asn Lys Tyr Ile Phe Glu Asn Ser Asn Asn Ile Ser
             130                 135                 140

Glu Ala Ala Leu Lys Ala Met Ile Ser Trp Ala Lys Glu Ala Phe Asn
145                 150                 155                 160

Leu Asn Lys Thr Lys Glu Gly Glu Gly Val Leu Tyr Arg Ser Asn His
                 165                 170                 175

Asp Ile Ser Asn Phe Ala Asn Leu Ala Trp Asp Ala Arg Glu Lys Phe
             180                 185                 190

Gly Cys Ala Val Val Asn Cys Pro Leu Gly Glu Ile Asp Asp Glu Thr
             195                 200                 205

Asn His Asp Gly Glu Thr Tyr Ala Thr Thr Ile His Val Val Cys His
             210                 215                 220

Tyr Pro Lys Ile Asn Lys Thr Glu Gly Gln Pro Ile Tyr Lys Val Gly
225                 230                 235                 240

Thr Pro Cys Asp Asp Cys Ser Glu Tyr Thr Lys Lys Ala Asp Asn Thr
                 245                 250                 255
```

```
Thr Ser Ala Asp Pro Val Cys Ile Pro Asp Asp Gly Val Cys Phe Ile
        260                 265                 270

Gly Ser Lys Ala Asp Tyr Asp Ser Lys Glu Phe Tyr Arg Phe Arg Glu
        275                 280                 285

Leu (2) INFORMATION FOR SEQ ID NO: 104:

(i) SEQUENCE CHARACTERISTICS:
        (A) LENGTH:            274 AMINO ACIDS
        (B) TYPE:              AMINO ACID
        (D) TOPOLOGY:          LINEAR (ii) MOLECULE TYPE:        PEPTIDE (xi) SEQUENCE DESCRIPTION: SEQ ID NO: 104:

Met Glu Ala Tyr Leu Val Val Leu Ile Ala Ile Ala Gly Ile Ala His
  1              5                  10                 15

Ser Asn Glu His Asn Leu Arg Cys Pro Gln Asn Gly Thr Glu Met Pro
             20                 25                 30

Gly Phe Asn Asp Ser Ile Arg Leu Gln Phe Leu Ala Met His Asn Gly
         35                 40                 45

Tyr Arg Ser Lys Leu Ala Leu Gly His Ile Ser Ile Thr Glu Glu Ser
 50                 55                 60

Glu Ser Asp Asp Asp Asp Phe Gly Phe Leu Pro Asp Phe Ala Pro
 65                 70                 75                 80

Arg Ala Ser Lys Met Arg Tyr Leu Glu Tyr Asp Cys Glu Ala Glu Lys
                85                 90                 95

Ser Ala Tyr Met Ser Ala Arg Asn Cys Ser Asp Ser Ser Ser Pro Pro
            100                 105                110

Glu Gly Tyr Asp Glu Asn Lys Tyr Ile Phe Glu Asn Ser Asn Asn Ile
            115                 120                125

Ser Glu Ala Ala Leu Lys Ala Met Ile Ser Trp Ala Lys Glu Ala Phe
130                 135                 140

Asn Leu Asn Lys Thr Lys Glu Gly Glu Gly Val Leu Tyr Arg Ser Asn
145                 150                 155                160

His Asp Ile Ser Asn Phe Ala Asn Leu Ala Trp Asp Ala Arg Glu Lys
                165                 170                 175

Phe Gly Cys Ala Val Val Asn Cys Pro Leu Gly Glu Ile Asp Asp Glu
            180                 185                 190

Thr Asn His Asp Gly Glu Thr Tyr Ala Thr Thr Ile His Val Val Cys
            195                 200                 205

His Tyr Pro Lys Ile Asn Lys Thr Glu Gly Gln Pro Ile Tyr Lys Val
        210                 215                 220

Gly Thr Pro Cys Asp Asp Cys Ser Glu Tyr Thr Lys Lys Ala Asp Asn
225                 230                 235                 240

Thr Thr Ser Ala Asp Pro Val Cys Ile Pro Asp Asp Gly Val Cys Phe
                245                 250                 255

Ile Gly Ser Lys Ala Asp Tyr Asp Ser Lys Glu Phe Tyr Arg Phe Arg
            260                 265                 270

Glu Leu (2) INFORMATION FOR SEQ ID NO: 105:

(i) SEQUENCE CHARACTERISTICS:
        (A) LENGTH:            274 AMINO ACIDS
```

```
        (B) TYPE:            AMINO ACID
        (D) TOPOLOGY:        LINEAR (ii) MOLECULE TYPE:      PEPTIDE (xi) SEQUENCE DESCRIPTION: SEQ ID NO: 105:

Met Glu Ala Tyr Leu Val Val Leu Ile Ala Ile Ala Gly Ile Ala His
1               5                   10                  15

Ser Asn Glu His Lys Pro Met Cys Gln Gln Asn Gly Thr Glu Met Pro
            20                  25                  30

Asp Phe Asn Asp Ser Ile Arg Leu Gln Phe Leu Ala Met His Asn Gly
        35                  40                  45

Tyr Arg Ser Lys Leu Ala Leu Gly His Ile Ser Ile Thr Glu Glu Ser
50                  55                  60

Glu Ser Asp Asp Asp Asp Phe Gly Phe Leu Pro Asp Phe Ala Pro
65                  70                  75                  80

Arg Ala Ser Lys Met Arg Tyr Leu Gly Tyr Asp Cys Glu Ala Glu Lys
                85                  90                  95

Ser Ala Tyr Met Ser Ala Arg Asn Cys Ser Asp Ser Ser Pro Pro
            100                 105                 110

Glu Gly Tyr Asp Glu Asn Lys Tyr Ile Phe Glu Asn Ser Asn Asn Ile
        115                 120                 125

Ser Glu Ala Ala Leu Lys Ala Met Ile Ser Trp Ala Lys Glu Ala Phe
130                 135                 140

Asn Leu Asn Lys Thr Glu Glu Gly Glu Glu Val Leu Tyr Arg Ser Asn
145                 150                 155                 160

His Asp Ile Ser Asn Phe Ala Asn Leu Ala Trp Asp Ala Arg Glu Lys
                165                 170                 175

Phe Gly Cys Ala Val Val Asn Cys Pro Leu Gly Glu Ile Asp Asp Glu
            180                 185                 190

Thr Ile His Asp Gly Glu Thr Tyr Ala Thr Thr Ile His Val Val Cys
        195                 200                 205

His Tyr Pro Lys Ile Asn Lys Thr Glu Gly Glu Pro Ile Tyr Lys Val
210                 215                 220

Gly Thr Pro Cys Asp Asp Cys Ser Glu Tyr Thr Lys Lys Ala Asp Asn
225                 230                 235                 240

Thr Thr Ser Ala Asp Pro Gln Cys His Pro Asp Ile Gly Val Cys Phe
                245                 250                 255

Ile Gly Ser Lys Ala Asp Tyr Asp Ser Lys Glu Phe Tyr Arg Phe Arg
            260                 265                 270

Glu Leu (2) INFORMATION FOR SEQ ID NO: 106:

(i) SEQUENCE CHARACTERISTICS:
        (A) LENGTH:          263 AMINO ACIDS
        (B) TYPE:            AMINO ACID
        (D) TOPOLOGY:        LINEAR (ii) MOLECULE TYPE:      PEPTIDE (ix) FEATURE:
        (D) OTHER INFORMATION:  Xaa in location 226 is an
            undetermined amino acid.

(xi) SEQUENCE DESCRIPTION: SEQ ID NO: 106:

Ala Gly Ile Ala His Ser Asn Glu His Asn Leu Thr Cys Pro Gln Asn
1               5                   10                  15
```

```
Gly Thr Glu Met Pro Gly Phe Asn Asp Ser Ile Arg Leu Gln Phe Leu
             20                  25                  30

Ala Met His Asn Gly Tyr Arg Ser Lys Leu Ala Leu Gly His Ile Ser
         35                  40                  45

Ile Thr Asp Glu Ser Glu Ser Glu Ser Asp Asp Glu Tyr Asp Tyr Trp
     50                  55                  60

Tyr Ala Pro Thr Ala Tyr Ala Pro Thr Ala Ser Lys Met Arg Tyr Leu
 65                  70                  75                  80

Glu Tyr Asp Cys Glu Ala Glu Lys Ser Ala Tyr Met Ser Ala Arg Asn
                 85                  90                  95

Cys Ser Asp Ser Ser Pro Pro Glu Gly Tyr Asp Glu Asn Lys Tyr
                100                 105                 110

Ile Phe Glu Asn Ser Asn Asn Ile Ser Glu Ala Ala Arg Leu Ala Ile
             115                 120                 125

Leu Ser Trp Ala Lys Glu Ala Phe Asp Leu Asn Lys Thr Gly Glu Gly
         130                 135                 140

Val Leu Tyr Arg Ser Asn Leu Thr Ile Ser Asn Phe Ala Asn Leu Ala
145                 150                 155                 160

Trp Asp Thr Arg Glu Lys Phe Gly Cys Ala Val Val Asn Cys Pro Leu
                165                 170                 175

Gly Glu Ile Asp Ala Asp Ile Tyr Asp Glu Glu Thr Tyr Ala Thr Thr
            180                 185                 190

Ile His Val Val Cys His Ile Pro Lys Ile Asn Lys Thr Glu Gly Glu
        195                 200                 205

Pro Ile Tyr Lys Val Gly Thr Pro Cys Asp Asp Cys Ser Glu Tyr Thr
    210                 215                 220

Lys Xaa Ala Asp Asn Thr Thr Ser Ala Asp Pro Val Cys Ile Pro Asp
225                 230                 235                 240

Asp Gly Val Cys Phe Ile Gly Ser Lys Ala Asp Tyr Asp Ser Lys Glu
                245                 250                 255

Phe Tyr Arg Phe Arg Glu Leu
            260

(2) INFORMATION FOR SEQ ID NO: 107:

(i) SEQUENCE CHARACTERISTICS:
        (A) LENGTH:        270 AMINO ACIDS
        (B) TYPE:          AMINO ACID
        (D) TOPOLOGY:      LINEAR (ii) MOLECULE TYPE:        PEPTIDE (xi) SEQUENCE DESCRIPTION: SEQ ID NO: 107:

Glu Ala Tyr Leu Val Val Leu Val Ala Ile Ala Gly Ile Ala His Ser
 1               5                  10                  15

Asn Glu His Lys Pro Met Cys Gln Gln Asn Glu Thr Glu Met Pro Gly
             20                  25                  30

Phe Asn Asp Leu Met Arg Leu Gln Phe Leu Ala Met His Asn Gly Tyr
         35                  40                  45

Arg Ser Lys Leu Ala Leu Gly His Ile Ser Ile Thr Asp Glu Ser Glu
     50                  55                  60

Ser Asp Tyr Asp Tyr Asp Tyr Gly Phe Leu Pro Asp Phe Ala Pro Ser
 65                  70                  75                  80

Ala Ser Lys Met Arg Tyr Leu Glu Tyr Asp Cys Glu Ala Glu Arg Ser
                 85                  90                  95

Ala Tyr Thr Ser Ala Ser Asp Cys Ser Asp Ser Ser Ser Pro Pro Glu
```

-continued

```
                    100                 105                 110
Gly Tyr Asp Glu Asn Lys Tyr Ile Phe Glu Asn Ser Asn Asn Ile Ser
        115                 120                 125

Glu Ala Ala Leu Lys Ala Met Ile Ser Trp Ala Lys Glu Ala Phe Asn
130                 135                 140

Leu Asn Lys Thr Glu Lys Gly Val Leu Tyr Gln Pro Asn His Asp Ile
145                 150                 155                 160

Ser Asn Phe Ala Asn Leu Ala Trp Asp Thr Arg Glu Lys Phe Gly Cys
                165                 170                 175

Ala Val Val Asn Cys Pro Leu Gly Ile Asp Ala Asp Ile Tyr Asp
                180                 185                 190

Glu Glu Thr Tyr Ala Thr Thr Ile His Val Val Cys His Tyr Pro Lys
                195                 200                 205

Ile Asn Lys Thr Glu Gly Glu Pro Ile Tyr Lys Val Gly Thr Pro Cys
210                 215                 220

Asp Asp Cys Ser Glu Tyr Thr Lys Lys Ala Asp Asn Thr Thr Ser Ala
225                 230                 235                 240

Asp Pro Val Cys Ile Pro Asp Asp Gly Val Cys Phe Ile Gly Ser Lys
                245                 250                 255

Asp Asp Tyr Ile Lys Lys Lys Phe Tyr Arg Phe Arg Glu Leu
                260                 265                 270
```

(2) INFORMATION FOR SEQ ID NO: 108:

(i) SEQUENCE CHARACTERISTICS:
        (A) LENGTH:        274 AMINO ACIDS
        (B) TYPE:          AMINO ACID
        (D) TOPOLOGY:     LINEAR (ii) MOLECULE TYPE:     PEPTIDE (xi) SEQUENCE DESCRIPTION: SEQ ID NO: 108:

```
Tyr Leu Val Val Leu Ile Ala Ile Val Gly Ile Ala His Ser Asn Glu
1               5                   10                  15

His Lys Pro Met Cys Glu Arg Asn Glu Thr Glu Met Pro Gly Phe Asn
                20                  25                  30

Asp Ser Met Arg Leu Gln Phe Leu Ala Met His Asn Gly Tyr Arg Ser
            35                  40                  45

Leu Leu Ala Leu Gly His Val Gly Ile Ser Lys Gln Pro Ile Asp Asp
50                  55                  60

Asp Tyr Tyr Asp Asp Tyr Tyr Phe Tyr Ser Ser Tyr Ala Pro
65              70                  75                  80

Arg Ala Ser Lys Met Arg Tyr Leu Glu Tyr Asp Cys Glu Ala Glu Lys
                85                  90                  95

Ser Ala Tyr Val Ser Ala Ser Asn Cys Ser Asn Ile Ser Ser Pro Pro
                100                 105                 110

Glu Gly Tyr Asp Glu Asn Lys Tyr Ile Phe Glu Asn Ser Asn Asn Ile
            115                 120                 125

Ser Glu Ala Ala Leu Lys Ala Met Ile Ser Trp Ala Lys Glu Ala Phe
130                 135                 140

Asn Leu Asn Lys Thr Glu Glu Gly Glu Gly Val Leu Tyr Arg Ser Asn
145                 150                 155                 160

His Asp Ile Ser Asn Phe Ala Asn Leu Ala Trp Asp Thr Arg Glu Lys
                165                 170                 175

Phe Gly Cys Ala Val Val Asn Cys Pro Leu Gly Glu Ile Asp Thr Thr
                180                 185                 190
```

```
Ser Asn Arg Asp Gly Glu Thr Tyr Ala Thr Ala Ile His Val Val Cys
        195                 200                 205

His Tyr Pro Lys Ile Leu Glu Lys Glu Lys Gln Ile Tyr Glu Val
    210                 215                 220

Gly Lys Pro Cys Asp Arg Cys Ser Glu Tyr Ser Lys Asn Ala Asn Asn
225                 230                 235                 240

Ile Thr Ser Pro Asn Trp Val Cys Asn Asp Asp Gly Val Cys Phe
                245                 250                 255

Ile Gly Ser Lys Asp Asp Tyr Ile Ser Lys Glu Phe Tyr Arg Phe Arg
                260                 265                 270

Glu Leu (2) INFORMATION FOR SEQ ID NO: 109:

(i) SEQUENCE CHARACTERISTICS:
        (A) LENGTH:        267 AMINO ACIDS
        (B) TYPE:          AMINO ACID
        (D) TOPOLOGY:      LINEAR (ii) MOLECULE TYPE:     PEPTIDE (xi) SEQUENCE DESCRIPTION: SEQ ID NO: 109:

Leu Val Leu Val Ala Ile Ala Gly Ile Ala His Ser Asn Glu His
1               5                   10                  15

Lys Pro Met Cys Gln Gln Asn Glu Thr Glu Met Pro Gly Phe Asn Asp
                20                  25                  30

Leu Met Arg Leu Gln Phe Leu Ala Met His Asn Gly Tyr Arg Ser Lys
                35                  40                  45

Leu Ala Leu Gly His Ile Ser Ile Thr Asp Glu Ser Glu Ser Asp Tyr
    50                  55                  60

Asp Tyr Asp Tyr Gly Phe Leu Pro Asp Phe Ala Pro Ser Ala Ser Lys
65                  70                  75                  80

Met Arg Tyr Leu Glu Tyr Asp Cys Glu Ala Glu Arg Ser Ala Tyr Thr
                85                  90                  95

Ser Ala Ser Asp Cys Ser Asp Ser Ser Pro Pro Glu Gly Tyr Asp
                100                 105                 110

Glu Asn Lys Tyr Ile Phe Glu Asn Ser Asn Asn Ile Ser Glu Ala Ala
                115                 120                 125

Leu Lys Ala Met Ile Ser Trp Ala Lys Glu Ala Phe Asn Leu Asn Lys
130                 135                 140

Thr Glu Lys Gly Val Leu Tyr Gln Pro Asn His Asp Ile Ser Asn Phe
145                 150                 155                 160

Ala Asn Leu Ala Trp Asp Thr Arg Glu Lys Phe Gly Cys Ala Val Val
                165                 170                 175

Asn Cys Pro Leu Gly Glu Ile Asp Ala Asp Ile Tyr Asp Glu Glu Thr
                180                 185                 190

Tyr Ala Thr Thr Ile His Val Val Cys His Tyr Pro Lys Ile Asn Lys
                195                 200                 205

Thr Glu Gly Glu Pro Ile Tyr Lys Val Gly Thr Pro Cys Asp Asp Cys
                210                 215                 220

Ser Glu Tyr Thr Lys Lys Ala Asp Asn Thr Thr Ser Ala Asp Pro Val
225                 230                 235                 240

Cys Ile Pro Asp Asp Gly Val Cys Phe Ile Gly Ser Lys Ala Asp Tyr
                245                 250                 255

Asp Ser Lys Glu Phe Tyr Arg Phe Arg Glu Leu
```

```
                              260                 265

(2) INFORMATION FOR SEQ ID NO: 110:

(i) SEQUENCE CHARACTERISTICS:
         (A) LENGTH:          272 AMINO ACIDS
         (B) TYPE:            AMINO ACID
         (D) TOPOLOGY:        LINEAR (ii) MOLECULE TYPE:       PEPTIDE (xi) SEQUENCE DESCRIPTION: SEQ ID NO: 110:

Ala Tyr Leu Val Val Leu Ile Ala Ile Ala Gly Ile Ala His Ser Asn
 1               5                  10                  15

Glu His Asn Leu Arg Cys Pro Gln Asn Gly Thr Glu Met Pro Asp Phe
             20                  25                  30

Asn Asp Ser Ile Arg Leu Gln Phe Leu Ala Met His Asn Gly Tyr Arg
         35                  40                  45

Ser Lys Leu Ala Leu Gly His Ile Ser Ile Thr Glu Glu Ser Glu Ser
 50                  55                  60

Asp Asp Asp Asp Phe Gly Phe Leu Pro Asp Phe Ala Pro Arg Ala
65                  70                  75                  80

Ser Lys Met Arg Tyr Leu Glu Tyr Asp Cys Glu Ala Glu Lys Ser Ala
             85                  90                  95

Tyr Met Ser Ala Arg Asn Cys Ser Asp Ser Ser Pro Pro Glu Gly
            100                 105                 110

Tyr Asp Glu Asn Lys Tyr Ile Phe Glu Asn Ser Asn Ile Ser Glu
            115                 120                 125

Ala Ala Leu Lys Ala Met Ile Ser Trp Ala Lys Glu Ala Phe Asn Leu
130                 135                 140

Asn Lys Thr Glu Glu Gly Gly Val Leu Tyr Arg Ser Asn His Asp
145                 150                 155                 160

Ile Ser Asn Phe Ala Asn Leu Ala Trp Asp Ala Arg Glu Lys Phe Gly
            165                 170                 175

Cys Ala Val Val Asn Cys Pro Leu Gly Glu Ile Asp Asp Glu Thr Ile
            180                 185                 190

His Asp Gly Glu Thr Tyr Ala Thr Thr Ile His Val Val Cys His Tyr
        195                 200                 205

Pro Lys Ile Asn Lys Thr Glu Gly Gln Pro Ile Tyr Lys Val Gly Thr
210                 215                 220

Pro Cys Asp Asp Cys Ser Glu Tyr Thr Lys Lys Ala Asp Asn Thr Thr
225                 230                 235                 240

Ser Ala Asp Pro Val Cys Ile Pro Asp Asp Gly Val Cys Phe Ile Gly
            245                 250                 255

Ser Lys Ala Asp Tyr Asp Ser Lys Glu Phe Tyr Arg Phe Arg Glu Leu
            260                 265                 270

(2) INFORMATION FOR SEQ ID NO: 111:

(i) SEQUENCE CHARACTERISTICS:
         (A) LENGTH:          274 AMINO ACIDS
         (B) TYPE:            AMINO ACID
         (D) TOPOLOGY:        LINEAR (ii) MOLECULE TYPE:       PEPTIDE (xi) SEQUENCE DESCRIPTION: SEQ ID NO: 111:

Met Glu Ala Tyr Leu Val Val Leu Ile Ala Ile Ala Gly Ile Ala His
 1               5                  10                  15
```

```
Ser Asn Glu His Asn Leu Arg Cys Pro Gln Asn Gly Thr Glu Met Pro
            20                  25                  30

Asp Phe Asn Asp Ser Ile Arg Leu Gln Phe Leu Ala Met His Asn Gly
             35                  40                  45

Tyr Arg Ser Lys Leu Ala Leu Gly His Ile Ser Ile Thr Glu Glu Ser
         50                  55                  60

Glu Ser Asp Asp Asp Asp Phe Gly Phe Leu Pro Asp Phe Ala Pro
 65                  70                  75                  80

Arg Ala Ser Lys Met Arg Tyr Leu Glu Tyr Asp Cys Glu Ala Glu Lys
                 85                  90                  95

Ser Ala Tyr Met Ser Ala Arg Asn Cys Ser Asp Ser Ser Pro Pro
                100                 105                 110

Glu Gly Tyr Asp Glu Asn Lys Tyr Ile Phe Glu Asn Ser Asn Asn Ile
            115                 120                 125

Ser Glu Ala Ala Leu Lys Ala Met Ile Ser Trp Ala Lys Glu Ala Phe
130                 135                 140

Asn Leu Asn Lys Thr Glu Glu Gly Gly Val Leu Tyr Arg Ser Asn
145                 150                 155                 160

His Asp Ile Ser Asn Phe Ala Asn Leu Ala Trp Asp Ala Arg Glu Lys
                165                 170                 175

Phe Gly Cys Ala Val Val Asn Cys Pro Leu Gly Glu Ile Asp Asp Glu
                180                 185                 190

Thr Ile His Asp Gly Glu Thr Tyr Ala Thr Thr Ile His Val Val Cys
            195                 200                 205

His Tyr Pro Lys Ile Asn Lys Thr Glu Gly Gln Pro Ile Tyr Lys Val
        210                 215                 220

Gly Thr Pro Cys Asp Asp Cys Ser Gly Tyr Thr Lys Lys Ala Asp Asn
225                 230                 235                 240

Thr Thr Ser Ala Asp Pro Val Cys Ile Pro Asp Asp Gly Val Cys Phe
                245                 250                 255

Ile Gly Ser Lys Ala Asp Tyr Asp Ser Lys Glu Phe Tyr Arg Phe Arg
            260                 265                 270

Glu Leu (2) INFORMATION FOR SEQ ID NO: 112:

(i) SEQUENCE CHARACTERISTICS:
        (A) LENGTH:      270 AMINO ACIDS
        (B) TYPE:        AMINO ACID
        (D) TOPOLOGY:    LINEAR (ii) MOLECULE TYPE:     PEPTIDE (xi) SEQUENCE DESCRIPTION: SEQ ID NO: 112:

Met Glu Ala Tyr Leu Val Val Leu Ile Ala Ile Ala Gly Ile Ala His
 1               5                  10                  15

Ser Asn Glu His Asn Leu Thr Cys Pro Gln Asn Gly Thr Glu Met Pro
            20                  25                  30

Gly Phe Asn Asp Ser Ile Arg Leu Gln Phe Leu Ala Met His Asn Gly
             35                  40                  45

Tyr Arg Ser Lys Leu Ala Leu Gly His Ile Ser Ile Thr Asp Glu Ser
         50                  55                  60

Glu Ser Glu Ser Asp Asp Glu Tyr Asp Tyr Trp Tyr Ala Pro Thr Ala
 65                  70                  75                  80

Tyr Ala Pro Thr Ala Ser Lys Met Arg Tyr Leu Glu Tyr Asp Cys Glu
```

-continued

```
                85                  90                  95
Ala Glu Lys Ser Ala Tyr Met Ser Ala Arg Asn Cys Ser Asp Ser Ser
            100                 105                 110

Ser Pro Pro Glu Gly Tyr Asp Glu Asn Lys Tyr Ile Phe Glu Asn Ser
            115                 120                 125

Asn Asn Ile Ser Glu Ala Ala Leu Lys Ala Met Ile Ser Trp Ala Lys
            130                 135                 140

Glu Ala Phe Asn Leu Asn Lys Thr Glu Glu Gly Glu Gly Val Leu Tyr
145                 150                 155                 160

Arg Ser Asn His Asp Ile Ser Asn Phe Ala Asn Leu Ala Trp Asp Thr
                165                 170                 175

Arg Glu Lys Phe Gly Cys Ala Val Val Asn Cys Pro Leu Gly Glu Ile
            180                 185                 190

Asp Gly Thr Thr Ile Asp Asp Gly Glu Thr Tyr Ala Thr Thr Ile His
            195                 200                 205

Val Val Cys His Tyr Pro Lys Met Asn Lys Thr Glu Gly Glu Pro Ile
            210                 215                 220

Tyr Lys Val Gly Lys Pro Cys Arg Asp Cys Ser Glu Tyr Pro Glu Lys
225                 230                 235                 240

Val Ala Asn Thr Thr Gln Cys His Pro Asp Val Gly Val Cys Phe Ile
                245                 250                 255

Gly Ser Lys Ala Asp Tyr Asp Ser Lys Glu Phe Tyr Arg Phe
            260                 265                 270

(2) INFORMATION FOR SEQ ID NO:     113:

(i) SEQUENCE CHARACTERISTICS:
         (A) LENGTH:         248 AMINO ACIDS
         (B) TYPE:           AMINO ACID
         (D) TOPOLOGY:       LINEAR (ii) MOLECULE TYPE:      PEPTIDE (xi) SEQUENCE DESCRIPTION: SEQ ID NO: 113:

Lys Ser Tyr Leu Val Val Leu Ala Ala Ile Ala Gly Ile Ala His Ala
1               5                   10                  15

Asn Glu His Asp Pro Thr Cys Pro Gln Asn Glu Val Glu Met Glu Lys
                20                  25                  30

Gly Phe Asp Asp Ala Met Arg Leu Lys Phe Leu Ala Leu His Asn Gly
            35                  40                  45

Tyr Arg Ser Lys Leu Ala Leu Gly His Val Ser Ile Thr Glu Glu Ser
50                  55                  60

Glu Asp Tyr Asp Leu Tyr Asp Leu Leu Tyr Ala Pro Thr Ala Ser Lys
65                  70                  75                  80

Met Arg Tyr Leu Glu Tyr Asp Cys Glu Ala Glu Lys Ser Ala Tyr Glu
                85                  90                  95

Ser Ala Lys Lys Cys Gln Thr Thr Ala Phe Ser Ser Thr Lys Tyr Asp
            100                 105                 110

Glu Asn Leu Gln Val Ile Glu Asp Pro Arg Asp Ile Asn His Ala Ala
            115                 120                 125

Leu Lys Ala Ile Ile Ser Trp Ala Thr Glu Ala Phe Asn Leu Asn Lys
            130                 135                 140

Thr Gly Glu Gly Val Val Tyr Arg Ser Ile Leu Asn Ile Ser Asn Phe
145                 150                 155                 160

Ala Asn Leu Ala Trp Asp Thr Arg Glu Lys Val Gly Cys Ala Val Val
                165                 170                 175
```

-continued

```
Lys Cys Pro Ser Gly Asn Thr His Val Cys His Tyr Pro Lys Ile
            180                 185                 190

Val Lys Lys Glu Gly Lys Pro Ile Tyr Ser Ile Gly Lys Pro Cys Arg
195                 200                 205

Gly Cys Asn Asp Tyr Ala Ser Lys Phe Phe Cys His Ala Asp Glu Gly
            210                 215                 220

Val Cys Ile Ile Ala Ser Arg Asp Leu Asp Ile Tyr Gly Arg Lys Lys
225                 230                 235                 240

Tyr Phe Tyr Pro Phe Arg Glu Leu
                245
```

(2) INFORMATION FOR SEQ ID NO: 114:

(i) SEQUENCE CHARACTERISTICS:
        (A) LENGTH:        241 AMINO ACIDS
        (B) TYPE:          AMINO ACID
        (D) TOPOLOGY:     LINEAR (ii) MOLECULE TYPE:     PEPTIDE (xi) SEQUENCE DESCRIPTION: SEQ ID NO: 114:

```
Ala Thr Ile Ala Gly Ile Ala His Ala Asn Glu His Asp Pro Thr Cys
1               5                   10                  15

Pro Gln Asn Gly Glu Lys Met Glu Lys Gly Phe Asp Asp Ala Met Arg
            20                  25                  30

Leu Lys Phe Leu Ala Leu His Asn Gly Tyr Arg Ser Arg Leu Ala Leu
            35                  40                  45

Gly His Val Ser Ile Thr Glu Glu Ser Glu Asp Tyr Asp Leu Tyr Asp
        50                  55                  60

Leu Leu Tyr Ala Pro Thr Ala Ser Lys Met Arg Tyr Leu Lys Tyr Asp
65                  70                  75                  80

Cys Glu Ala Glu Lys Ser Ala Tyr Glu Ser Ala Lys Lys Cys Gln Thr
                85                  90                  95

Thr Ala Phe Ser Trp Glu Lys Tyr Asp Glu Asn Leu Gln Val Ile Glu
            100                 105                 110

Asp Pro Arg Asp Ile Asn His Ala Ala Leu Lys Ala Ile Ile Ser Trp
            115                 120                 125

Ala Thr Glu Ala Phe Asn Leu Asn Lys Thr Gly Glu Gly Val Val Tyr
        130                 135                 140

Arg Ser Ile Leu Asn Ile Ser Asn Phe Ala Asn Leu Ala Trp Asp Thr
145                 150                 155                 160

Arg Glu Lys Val Gly Cys Ala Val Lys Cys Ser Pro Arg Thr Thr
                165                 170                 175

His Val Val Cys His Tyr Pro Lys Ile Val Glu Lys Glu Gly Lys Pro
            180                 185                 190

Ile Tyr Thr Thr Gly Val Pro Cys Arg Gly Cys Ser Gly Tyr Ala Asn
        195                 200                 205

Lys Phe Phe Cys His Ala Asp Glu Gly Val Cys Ile Ile Ala Ser Arg
        210                 215                 220

Asp Leu Asp Ile Tyr Gly Arg Lys Lys Tyr Phe Tyr Pro Phe Arg Glu
225                 230                 235                 240

Leu
```

(2) INFORMATION FOR SEQ ID NO: 115:

(i) SEQUENCE CHARACTERISTICS:

```
        (A) LENGTH:            238 AMINO ACIDS
        (B) TYPE:              AMINO ACID
        (D) TOPOLOGY:          LINEAR (ii) MOLECULE TYPE:        PEPTIDE (xi) SEQUENCE DESCRIPTION: SEQ ID NO: 115:

Leu Ala Thr Leu Gly Ile Ala Leu Val Lys Gly Asp Glu Pro Thr Cys
 1               5                  10                  15

Lys Gln Asn Asn Gly Ser Met Thr Asn Glu Leu Arg Arg Phe Leu
             20                  25                  30

Arg Leu His Asn Gly Tyr Arg Ser Ile Leu Ala Leu Gly His Val Asn
             35                  40                  45

Ile Ser Glu Glu Ser Asn Glu Thr Phe Leu Tyr Ala His Arg Ala Ser
 50                  55                  60

Arg Met Arg Ile Leu Asp Tyr Asp Cys Asp Ala Glu Gly Ser Ala Tyr
 65                  70                  75                  80

Glu Ser Ala Ile Lys Gln Cys Ser Ser Asn Lys Ser Ser Ser Ala Glu
                 85                  90                  95

Tyr Asp Glu Asn Val Tyr Val Ile Asp Asn Thr Tyr Glu Asp Glu Val
                100                 105                 110

Asp Pro Ala Leu Lys Ala Ile Ser Ser Trp Thr Ser Gln Ala Phe Asn
                115                 120                 125

Leu Thr His Ala Glu Glu Gly Ile Pro Tyr Gln Trp Asn Asp Ser Val
            130                 135                 140

Ser Asp Phe Ala Asn Val Ala Trp Asp Ala Arg Glu Lys Leu Gly Cys
145                 150                 155                 160

Ala Val Val Thr Cys Asp Gln Gly Asn Thr Thr His Val Val Cys His
                165                 170                 175

Tyr Gly Pro Lys Ala Ala Asn Lys Thr Glu Pro Ile Tyr Lys Val Gly
                180                 185                 190

Val Pro Cys Ser Asn Cys Thr Glu Tyr Thr Arg Gly Asp Glu Glu Lys
                195                 200                 205

Val Phe Cys His Ala Asp Glu Gly Val Cys Val Ile Asn Leu Arg Asp
            210                 215                 220

Leu Asn Ser His Leu Asn Thr Ser Leu Arg Tyr Pro Pro Ile
225                 230                 235

(2) INFORMATION FOR SEQ ID NO: 116:

(i) SEQUENCE CHARACTERISTICS:
        (A) LENGTH:            774 BASE PAIRS
        (B) TYPE:              NUCLEIC ACID
        (C) STRANDEDNESS:      SINGLE
        (D) TOPOLOGY:          LINEAR (ii) MOLECULE TYPE:                NUCLEIC (xi) SEQUENCE DESCRIPTION: SEQ ID NO: 116:

AACGAACACA ACCTGAGGTG CCCGCAGAAT GGAACAGAAA TGCCCGGTTT CAACGACTCG      60

ATTAGGCTTC AATTTTTAGC AATGCACAAT GGTTACAGAT CAAAACTTGC GCTAGGTCAC    120

ATCAGCATAA CTGAAGAATC CGAAAGTGAC GATGATGACG ATTTCGGTTT TTTACCCGAT    180

TTCGCTCCAA GGGCATCGAA AATGAGATAT CTGGAATATG ACTGTGAAGC TGAAAAAAGC    240

GCCTACATGT CGGCTAGAAA TTGCTCGGAC AGTTCTTCTC CACCAGAGGG CTACGATGAA    300

AACAAGTATA TTTTCGAAAA CTCAAACAAT ATCAGTGAAG CTGCTCTGAA GGCCATGATC    360

TCGTGGGCAA AGAGGCTTT CAACCTAAAT AAAACAAAAG AAGGAGAAGG AGTTCTGTAC    420
```

```
CGGTCGAACC ACGACATATC AAACTTCGCT AATCTGGCTT GGGACGCGCG TGAAAAGTTT      480

GGTTGCGCAG TTGTTAACTG CCCTTTGGGA GAAATCGATG ATGAAACCAA CCATGATGGA      540

GAAACCTATG CAACAACCAT CCATGTAGTC TGCCACTACC CGAAAATAAA CAAAACTGAA      600

GGACAGCCGA TTTACAAGGT AGGGACACCA TGCGACGATT GCAGTGAATA CACAAAAAAA      660

GCAGACAATA CCACGTCTGC GGATCCGGTG TGTATTCCGG ATGACGGAGT CTGCTTTATT      720

GGCTCGAAAG CCGATTACGA TAGCAAGGAG TTTTATCGAT TCCGAGAGTT ATAA           774
```

(2) INFORMATION FOR SEQ ID NO: 117:

(i) SEQUENCE CHARACTERISTICS:
        (A) LENGTH:                257 AMINO ACIDS
        (B) TYPE:                  AMINO ACID
        (D) TOPOLOGY:            LINEAR (ii) MOLECULE TYPE:         PEPTIDE (xi) SEQUENCE DESCRIPTION: SEQ ID NO: 117:

```
Asn Glu His Asn Leu Arg Cys Pro Gln Asn Gly Thr Glu Met Pro Gly
1               5                   10                  15

Phe Asn Asp Ser Ile Arg Leu Gln Phe Leu Ala Met His Asn Gly Tyr
            20                  25                  30

Arg Ser Lys Leu Ala Leu Gly His Ile Ser Ile Thr Glu Glu Ser Glu
        35                  40                  45

Ser Asp Asp Asp Asp Phe Gly Phe Leu Pro Asp Phe Ala Pro Arg
50                  55                  60

Ala Ser Lys Met Arg Tyr Leu Glu Tyr Asp Cys Glu Ala Glu Lys Ser
65                  70                  75                  80

Ala Tyr Met Ser Ala Arg Asn Cys Ser Asp Ser Ser Pro Pro Glu
            85                  90                  95

Gly Tyr Asp Glu Asn Lys Tyr Ile Phe Glu Asn Ser Asn Asn Ile Ser
            100                 105                 110

Glu Ala Ala Leu Lys Ala Met Ile Ser Trp Ala Lys Glu Ala Phe Asn
        115                 120                 125

Leu Asn Lys Thr Lys Glu Gly Glu Gly Val Leu Tyr Arg Ser Asn His
    130                 135                 140

Asp Ile Ser Asn Phe Ala Asn Leu Ala Trp Asp Ala Arg Glu Lys Phe
145                 150                 155                 160

Gly Cys Ala Val Val Asn Cys Pro Leu Gly Glu Ile Asp Asp Glu Thr
                165                 170                 175

Asn His Asp Gly Glu Thr Tyr Ala Thr Thr Ile His Val Val Cys His
            180                 185                 190

Tyr Pro Lys Ile Asn Lys Thr Glu Gly Gln Pro Ile Tyr Lys Val Gly
        195                 200                 205

Thr Pro Cys Asp Asp Cys Ser Glu Tyr Thr Lys Lys Ala Asp Asn Thr
    210                 215                 220

Thr Ser Ala Asp Pro Val Cys Ile Pro Asp Asp Gly Val Cys Phe Ile
225                 230                 235                 240

Gly Ser Lys Ala Asp Tyr Asp Ser Lys Glu Phe Tyr Arg Phe Arg Glu
                245                 250                 255

Leu
```

(2) INFORMATION FOR SEQ ID NO: 118:

(i) SEQUENCE CHARACTERISTICS:

```
          (A) LENGTH:               250 AMINO ACIDS
          (B) TYPE:                 AMINO ACID
          (D) TOPOLOGY:             LINEAR (ii) MOLECULE TYPE:            PEPTIDE (xi) SEQUENCE DESCRIPTION: SEQ ID NO: 118:

Asn Leu Thr Cys Pro Gln Asn Gly Thr Glu Met Pro Gly Phe Asn Asp
 1               5                  10                  15

Ser Ile Arg Leu Gln Phe Leu Ala Met His Asn Gly Tyr Arg Ser Lys
            20                  25                  30

Leu Ala Leu Gly His Ile Ser Ile Thr Asp Glu Ser Glu Ser Glu Ser
        35                  40                  45

Asp Asp Glu Tyr Asp Tyr Trp Tyr Ala Pro Thr Ala Tyr Ala Pro Thr
50                  55                  60

Ala Ser Lys Met Arg Tyr Leu Glu Tyr Asp Cys Glu Ala Glu Lys Ser
65                  70                  75                  80

Ala Tyr Met Ser Ala Arg Asn Cys Ser Asp Ser Ser Pro Pro Glu
                85                  90                  95

Gly Tyr Asp Glu Asn Lys Tyr Ile Phe Glu Asn Ser Asn Asn Ile Ser
                100                 105                 110

Glu Ala Ala Leu Lys Ala Met Ile Ser Trp Ala Lys Glu Ala Phe Asn
            115                 120                 125

Leu Asn Lys Thr Glu Glu Gly Glu Gly Val Leu Tyr Arg Ser Asn His
130                 135                 140

Asp Ile Ser Asn Phe Ala Asn Leu Ala Trp Asp Thr Arg Glu Lys Phe
145                 150                 155                 160

Gly Cys Ala Val Val Asn Cys Pro Leu Gly Glu Ile Asp Gly Thr Thr
                165                 170                 175

Ile Asp Asp Gly Glu Thr Tyr Ala Thr Thr Ile His Val Val Cys His
            180                 185                 190

Tyr Pro Lys Met Asn Lys Thr Glu Gly Glu Pro Ile Tyr Lys Val Gly
        195                 200                 205

Lys Pro Cys Arg Asp Cys Ser Glu Tyr Pro Glu Lys Val Ala Asn Thr
210                 215                 220

Thr Gln Cys His Pro Asp Val Gly Val Cys Phe Ile Gly Ser Lys Ala
225                 230                 235                 240

Asp Tyr Asp Ser Lys Glu Phe Tyr Arg Phe
                245                 250

(2) INFORMATION FOR SEQ ID NO:  119:

(i) SEQUENCE CHARACTERISTICS:
          (A) LENGTH:               254 AMINO ACIDS
          (B) TYPE:                 AMINO ACID
          (D) TOPOLOGY:             LINEAR (ii) MOLECULE TYPE:            PEPTIDE (xi) SEQUENCE DESCRIPTION: SEQ ID NO: 119:

Asn Glu His Lys Pro Met Cys Gln Gln Asn Glu Thr Glu Met Pro Gly
 1               5                  10                  15

Phe Asn Asp Leu Met Arg Leu Gln Phe Leu Ala Met His Asn Gly Tyr
            20                  25                  30

Arg Ser Lys Leu Ala Leu Gly His Ile Ser Ile Thr Asp Glu Ser Glu
        35                  40                  45

Ser Asp Tyr Asp Tyr Asp Tyr Gly Phe Leu Pro Asp Phe Ala Pro Ser
50                  55                  60
```

-continued

```
Ala Ser Lys Met Arg Tyr Leu Glu Tyr Asp Cys Glu Ala Arg Ser
 65                  70                  75                  80

Ala Tyr Thr Ser Ala Ser Asp Cys Ser Asp Ser Ser Pro Pro Glu
                 85                  90                  95

Gly Tyr Asp Glu Asn Lys Tyr Ile Phe Glu Asn Ser Asn Asn Ile Ser
                100                 105                 110

Glu Ala Ala Leu Lys Ala Met Ile Ser Trp Ala Lys Glu Ala Phe Asn
            115                 120                 125

Leu Asn Lys Thr Glu Lys Gly Val Leu Tyr Gln Pro Asn His Asp Ile
130                 135                 140

Ser Asn Phe Ala Asn Leu Ala Trp Asp Thr Arg Glu Lys Phe Gly Cys
145                 150                 155                 160

Ala Val Val Asn Cys Pro Leu Gly Glu Ile Asp Ala Asp Ile Tyr Asp
                165                 170                 175

Glu Glu Thr Tyr Ala Thr Thr Ile His Val Val Cys His Tyr Pro Lys
                180                 185                 190

Ile Asn Lys Thr Glu Gly Glu Pro Ile Tyr Lys Val Gly Thr Pro Cys
                195                 200                 205

Asp Asp Cys Ser Glu Tyr Thr Lys Lys Ala Asp Asn Thr Thr Ser Ala
210                 215                 220

Asp Pro Val Cys Ile Pro Asp Asp Gly Val Cys Phe Ile Gly Ser Lys
225                 230                 235                 240

Ala Asp Tyr Asp Ser Lys Glu Phe Tyr Arg Phe Arg Glu Leu
                245                 250

(2) INFORMATION FOR SEQ ID NO: 120:

(i) SEQUENCE CHARACTERISTICS:
        (A) LENGTH:            260 AMINO ACIDS
        (B) TYPE:              AMINO ACID
        (D) TOPOLOGY:          LINEAR (ii) MOLECULE TYPE:        PEPTIDE (xi) SEQUENCE DESCRIPTION: SEQ ID NO: 120:

Asn Glu His Lys Pro Met Cys Glu Arg Asn Glu Thr Glu Met Pro Gly
 1               5                  10                  15

Phe Asn Asp Ser Met Arg Leu Gln Phe Leu Ala Met His Asn Gly Tyr
                 20                  25                  30

Arg Ser Leu Leu Ala Leu Gly His Val Gly Ile Ser Lys Gln Pro Ile
             35                  40                  45

Asp Asp Asp Tyr Tyr Asp Asp Tyr Tyr Phe Tyr Ser Ser Tyr
 50                  55                  60

Ala Pro Arg Ala Ser Lys Met Arg Tyr Leu Glu Tyr Asp Cys Glu Ala
 65                  70                  75                  80

Glu Lys Ser Ala Tyr Val Ser Ala Ser Asn Cys Ser Asn Ile Ser Ser
                 85                  90                  95

Pro Pro Glu Gly Tyr Asp Glu Asn Lys Tyr Ile Phe Glu Asn Ser Asn
                100                 105                 110

Asn Ile Ser Glu Ala Ala Leu Lys Ala Met Ile Ser Trp Ala Lys Glu
            115                 120                 125

Ala Phe Asn Leu Asn Lys Thr Glu Glu Gly Glu Val Leu Tyr Arg
            130                 135                 140

Ser Asn His Asp Ile Ser Asn Phe Ala Asn Leu Ala Trp Asp Thr Arg
145                 150                 155                 160
```

```
Glu Lys Phe Gly Cys Ala Val Val Asn Cys Pro Leu Gly Glu Ile Asp
                165                 170                 175

Thr Thr Ser Asn Arg Asp Gly Glu Thr Tyr Ala Thr Ala Ile His Val
            180                 185                 190

Val Cys His Tyr Pro Lys Ile Leu Glu Lys Glu Lys Gln Ile Tyr
        195                 200                 205

Glu Val Gly Lys Pro Cys Asp Arg Cys Ser Glu Tyr Ser Lys Asn Ala
    210                 215                 220

Asn Asn Ile Thr Ser Pro Asn Trp Val Cys Asn Asp Asp Gly Val
225             230                 235                 240

Cys Phe Ile Gly Ser Lys Asp Asp Tyr Ile Ser Lys Glu Phe Tyr Arg
                245                 250                 255

Phe Arg Glu Leu
        260

(2) INFORMATION FOR SEQ ID NO: 121:

(i) SEQUENCE CHARACTERISTICS:
        (A) LENGTH:              232 AMINO ACIDS
        (B) TYPE:                AMINO ACID
        (D) TOPOLOGY:            LINEAR (ii) MOLECULE TYPE:          PEPTIDE (xi) SEQUENCE DESCRIPTION: SEQ ID NO: 121:

Asn Glu His Asp Pro Thr Cys Pro Gln Asn Glu Val Glu Met Glu Lys
1               5                   10                  15

Gly Phe Asp Asp Ala Met Arg Leu Lys Phe Leu Ala Leu His Asn Gly
            20                  25                  30

Tyr Arg Ser Lys Leu Ala Leu Gly His Val Ser Ile Thr Glu Glu Ser
        35                  40                  45

Glu Asp Tyr Asp Leu Tyr Asp Leu Leu Tyr Ala Pro Thr Ala Ser Lys
    50                  55                  60

Met Arg Tyr Leu Glu Tyr Asp Cys Glu Ala Glu Lys Ser Ala Tyr Glu
65              70                  75                  80

Ser Ala Lys Lys Cys Gln Thr Thr Ala Phe Ser Thr Lys Tyr Asp
                85                  90                  95

Glu Asn Leu Gln Val Ile Glu Asp Pro Arg Asp Ile Asn His Ala Ala
            100                 105                 110

Leu Lys Ala Ile Ile Ser Trp Ala Thr Glu Ala Phe Asn Leu Asn Lys
        115                 120                 125

Thr Gly Glu Gly Val Val Tyr Arg Ser Ile Leu Asn Ile Ser Asn Phe
    130                 135                 140

Ala Asn Leu Ala Trp Asp Thr Arg Glu Lys Val Gly Cys Ala Val Val
145             150                 155                 160

Lys Cys Pro Ser Gly Asn Thr His Val Val Cys His Tyr Pro Lys Ile
                165                 170                 175

Val Lys Lys Glu Gly Lys Pro Ile Tyr Ser Ile Gly Lys Pro Cys Arg
            180                 185                 190

Gly Cys Asn Asp Tyr Ala Ser Lys Phe Phe Cys His Ala Asp Glu Gly
        195                 200                 205

Val Cys Ile Ile Ala Ser Arg Asp Leu Asp Ile Tyr Gly Arg Lys Lys
    210                 215                 220

Tyr Phe Tyr Pro Phe Arg Glu Leu
225             230
```

(2) INFORMATION FOR SEQ ID NO: 122:

(i) SEQUENCE CHARACTERISTICS:
        (A) LENGTH:              681 BASE PAIRS
        (B) TYPE:                NUCLEIC ACID
        (C) STRANDEDNESS:       SINGLE
        (D) TOPOLOGY:           LINEAR (ii) MOLECULE TYPE:         NUCLEIC (xi) SEQUENCE DESCRIPTION: SEQ ID NO: 122:

```
GACGAACCAA CGTGCAAGCA GAATAATGGA AGCATGACTA ACGAGTTGAG GCGTAGATTC      60
TTGAGACTGC ACAATGGCTA CAGATCGATT CTTGCGCTAG GTCATGTCAA CATAAGTGAA     120
GAGTCAAATG AAACTTTCTT GTACGCTCAT CGAGCTTCGA GAATGAGAAT TCTGGACTAC     180
GACTGTGACG CCGAAGGAAG TGCTTACGAG TCAGCTATCA AACAATGCTC GAGCAATAAG     240
TCTTCATCTG CTGAATACGA TGAAAACGTG TATGTTATCG ACAATACATA TGAAGATGAG     300
GTTGACCCTG CTTTAAAGGC CATCAGCTCG TGGACAAGCC AGGCTTTCAA CCTTACTCAT     360
GCAGAAGAAG GGATTCCGTA CCAGTGGAAC GACAGCGTAT CGGATTTTGC CAATGTGGCT     420
TGGGATGCTC GTGAGAAGCT TGGATGTGCA GTTGTTACGT GCGACCAGGG AAACACCACC     480
CATGTAGTCT GCCACTATGG ACCGAAAGCA GCAAACAAAA CAGAACCAAT TTACAAGGTT     540
GGCGTTCCAT GTTCAAACTG CACTGAATAC ACACGTGGCG ATGAAGAGAA AGTCTTCTGT     600
CACGCGGATG AGGGAGTCTG CGTTATTAAT CTGCGAGATC TTAACAGTCA TCTTAATACG     660
TCACTCCGTT ATCCACCTAT C                                                681
```

(2) INFORMATION FOR SEQ ID NO: 123:

(i) SEQUENCE CHARACTERISTICS:
        (A) LENGTH:              227 AMINO ACIDS
        (B) TYPE:                AMINO ACID
        (D) TOPOLOGY:           LINEAR (ii) MOLECULE TYPE:         PEPTIDE (xi) SEQUENCE DESCRIPTION: SEQ ID NO: 123:

```
Asp Glu Pro Thr Cys Lys Gln Asn Asn Gly Ser Met Thr Asn Glu Leu
 1               5                  10                  15

Arg Arg Arg Phe Leu Arg Leu His Asn Gly Tyr Arg Ser Ile Leu Ala
            20                  25                  30

Leu Gly His Val Asn Ile Ser Glu Glu Ser Asn Glu Thr Phe Leu Tyr
        35                  40                  45

Ala His Arg Ala Ser Arg Met Arg Ile Leu Asp Tyr Asp Cys Asp Ala
     50                  55                  60

Glu Gly Ser Ala Tyr Glu Ser Ala Ile Lys Gln Cys Ser Ser Asn Lys
65                  70                  75                  80

Ser Ser Ser Ala Glu Tyr Asp Glu Asn Val Tyr Val Ile Asp Asn Thr
                85                  90                  95

Tyr Glu Asp Glu Val Asp Pro Ala Leu Lys Ala Ile Ser Ser Trp Thr
            100                 105                 110

Ser Gln Ala Phe Asn Leu Thr His Ala Glu Gly Ile Pro Tyr Gln
        115                 120                 125

Trp Asn Asp Ser Val Ser Asp Phe Ala Asn Val Ala Trp Asp Ala Arg
    130                 135                 140

Glu Lys Leu Gly Cys Ala Val Val Thr Cys Asp Gln Gly Asn Thr Thr
145                 150                 155                 160

His Val Val Cys His Tyr Gly Pro Lys Ala Ala Asn Lys Thr Glu Pro
```

```
                   165                 170                 175
Ile Tyr Lys Val Gly Val Pro Cys Ser Asn Cys Thr Glu Tyr Thr Arg
            180                 185                 190

Gly Asp Glu Glu Lys Val Phe Cys His Ala Asp Glu Gly Val Cys Val
        195                 200                 205

Ile Asn Leu Arg Asp Leu Asn Ser His Leu Asn Thr Ser Leu Arg Tyr
    210                 215                 220

Pro Pro Ile
225
```

(2) INFORMATION FOR SEQ ID NO: 124:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (xi) SEQUENCE DESCRIPTION: SEQ ID NO: 124:

```
AACGAACACG AACCAACGTG CAAGCAGAAT AATGGAAGCA TGACTAACGA GTTGAGGCGT      60
AGATTCTTGA GACTGCACAA TGGCTACAGA TCGATTCTTG CGCTAGGTCA TGTCAACATA     120
AGTGAAGAGT CAAATGAAAC TTTCTTGTAC GCTCATCGAG CTTCGAGAAT GAGAATTCTG     180
GACTACGACT GTGACGCCGA AGGAAGTGCT TACGAGTCAG CTATCAAACA ATGCTCGAGC     240
AATAAGTCTT CATCTGCTGA ATACGATGAA AACGTGTATG TTATCGACAA TACATATGAA     300
GATGAGGTTG ACCCTGCTTT AAAGGCCATC AGCTCGTGGA CAAGCCAGGC TTTCAACCTT     360
ACTCATGCAG AAGAAGGGAT TCCGTACCAG TGGAACGACA GCGTATCGGA TTTTGCCAAT     420
GTGGCTTGGG ATGCTCGTGA GAAGCTTGGA TGTGCAGTTG TTACGTGCGA CCAGGGAAAC     480
ACCACCCATG TAGTCTGCCA CTATGGACCG AAAGCAGCAA ACAAAACAGA ACCAATTTAC     540
AAGGTTGGCG TTCATGTTC AAACTGCACT GAATACACAC GTGGCGATGA AGAGAAAGTC     600
TTCTGTCACG CGGATGAGGG AGTCTGCGTT ATTAATCTGC GAGATCTTAA CAGTCATCTT     660
AATACGTCAC TCCGTTATCC ACCTATCTAA                                      690
```

(2) INFORMATION FOR SEQ ID NO: 125:

(i) SEQUENCE CHARACTERISTICS:
        (A) LENGTH:         229 AMINO ACIDS
        (B) TYPE:           AMINO ACID
        (D) TOPOLOGY:      LINEAR (ii) MOLECULE TYPE:       PEPTIDE (xi) SEQUENCE DESCRIPTION: SEQ ID NO: 125:

```
Asn Glu His Glu Pro Thr Cys Lys Gln Asn Asn Gly Ser Met Thr Asn
 1               5                  10                  15

Glu Leu Arg Arg Arg Phe Leu Arg Leu His Asn Gly Tyr Arg Ser Ile
            20                  25                  30

Leu Ala Leu Gly His Val Asn Ile Ser Glu Glu Ser Asn Glu Thr Phe
        35                  40                  45

Leu Tyr Ala His Arg Ala Ser Arg Met Arg Ile Leu Asp Tyr Asp Cys
    50                  55                  60

Asp Ala Glu Gly Ser Ala Tyr Glu Ser Ala Ile Lys Gln Cys Ser Ser
65                  70                  75                  80

Asn Lys Ser Ser Ser Ala Glu Tyr Asp Glu Asn Val Tyr Val Ile Asp
                85                  90                  95
```

```
Asn Thr Tyr Glu Asp Glu Val Asp Pro Ala Leu Lys Ala Ile Ser Ser
            100                 105                 110

Trp Thr Ser Gln Ala Phe Asn Leu Thr His Ala Glu Glu Gly Ile Pro
            115                 120                 125

Tyr Gln Trp Asn Asp Ser Val Ser Asp Phe Ala Asn Val Ala Trp Asp
            130                 135                 140

Ala Arg Glu Lys Leu Gly Cys Ala Val Val Thr Cys Asp Gln Gly Asn
145                 150                 155                 160

Thr Thr His Val Val Cys His Tyr Gly Pro Lys Ala Ala Asn Lys Thr
                165                 170                 175

Glu Pro Ile Tyr Lys Val Gly Val Pro Cys Ser Asn Cys Thr Glu Tyr
            180                 185                 190

Thr Arg Gly Asp Glu Glu Lys Val Phe Cys His Ala Asp Glu Gly Val
            195                 200                 205

Cys Val Ile Asn Leu Arg Asp Leu Asn Ser His Leu Asn Thr Ser Leu
210                 215                 220

Arg Tyr Pro Pro Ile
225

(2) INFORMATION FOR SEQ ID NO: 126:

(i) SEQUENCE CHARACTERISTICS:
        (A) LENGTH:            774 BASE PAIRS
        (B) TYPE:              NUCLEIC ACID
        (C) STRANDEDNESS:      SINGLE
        (D) TOPOLOGY:          LINEAR (ii) MOLECULE TYPE:        NUCLEIC (xi) SEQUENCE DESCRIPTION: SEQ ID NO: 126:

AACGAACACA ACCTGAGGTG CCCGCAGCAA GGAACAGAAA TGCCCGGTTT CCAAGACTCG      60

ATTAGGCTTC AATTTTTAGC AATGCACAAT GGTTACAGAT CAAAACTTGC GCTAGGTCAC     120

ATCAGCATAA CTGAAGAATC GAAAGTGAC GATGATGACG ATTTCGGTTT TTTACCCGAT      180

TTCGCTCCAA GGGCATCGAA AATGAGATAT CTGGAATATG ACTGTGAAGC TGAAAAAAGC     240

GCCTACATGT CGGCTAGACA ATGCTCGGAC AGTTCTTCTC CACCAGAGGG CTACGATGAA     300

AACAAGTATA TTTTCGAAAA CTCAAACCAG ATCAGTGAAG CTGCTCTGAA GGCCATGATC     360

TCGTGGGCAA AGAGGCTTT CAACCTACAG AAAACAAAAG AAGGAGAAGG AGTTCTGTAC      420

CGGTCGAACC ACGACATATC AAACTTCGCT AATCTGGCTT GGGACGCGCG TGAAAAGTTT     480

GGTTGCGCAG TTGTTAACTG CCCTTTGGGA GAAATCGATG ATGAAACCAA CCATGATGGA     540

GAAACCTATG CAACAACCAT CCATGTAGTC TGCCACTACC CGAAAATAAA CAAAACTGAA     600

GGACAGCCGA TTTACAAGGT AGGGACACCA TGCGACGATT GCAGTGAATA CACAAAAAAA     660

GCAGACAATA CCACGTCTGC GGATCCGGTG TGTATTCCGG ATGACGGAGT CTGCTTTATT     720

GGCTCGAAAG CCGATTACGA TAGCAAGGAG TTTTATCGAT TCCGAGAGTT ATAA           774

(2) INFORMATION FOR SEQ ID NO: 127:

(i) SEQUENCE CHARACTERISTICS:
        (A) LENGTH:            257 AMINO ACIDS
        (B) TYPE:              AMINO ACID
        (D) TOPOLOGY:          LINEAR (ii) MOLECULE TYPE:        PEPTIDE (xi) SEQUENCE DESCRIPTION: SEQ ID NO: 127:

Asn Glu His Asn Leu Arg Cys Pro Gln Gln Gly Thr Glu Met Pro Gly
```

```
                1               5                   10                  15
            Phe Gln Asp Ser Ile Arg Leu Gln Phe Leu Ala Met His Asn Gly Tyr
                            20                  25                  30

Arg Ser Lys Leu Ala Leu Gly His Ile Ser Ile Thr Glu Glu Ser Glu
                            35                  40                  45

Ser Asp Asp Asp Asp Phe Gly Phe Leu Pro Asp Phe Ala Pro Arg
                50                  55                  60

Ala Ser Lys Met Arg Tyr Leu Glu Tyr Asp Cys Glu Ala Glu Lys Ser
            65                  70                  75                  80

Ala Tyr Met Ser Ala Arg Gln Cys Ser Asp Ser Ser Pro Pro Glu
                            85                  90                  95

Gly Tyr Asp Glu Asn Lys Tyr Ile Phe Glu Asn Ser Asn Gln Ile Ser
                            100                 105                 110

Glu Ala Ala Leu Lys Ala Met Ile Ser Trp Ala Lys Glu Ala Phe Asn
                            115                 120                 125

Leu Gln Lys Thr Lys Glu Gly Glu Gly Val Leu Tyr Arg Ser Asn His
                130                 135                 140

Asp Ile Ser Asn Phe Ala Asn Leu Ala Trp Asp Ala Arg Glu Lys Phe
            145                 150                 155                 160

Gly Cys Ala Val Val Asn Cys Pro Leu Gly Glu Ile Asp Asp Glu Thr
                            165                 170                 175

Asn His Asp Gly Glu Thr Tyr Ala Thr Thr Ile His Val Val Cys His
                            180                 185                 190

Tyr Pro Lys Ile Asn Lys Thr Glu Gly Gln Pro Ile Tyr Lys Val Gly
                            195                 200                 205

Thr Pro Cys Asp Asp Cys Ser Glu Tyr Thr Lys Lys Ala Asp Asn Thr
                210                 215                 220

Thr Ser Ala Asp Pro Val Cys Ile Pro Asp Asp Gly Val Cys Phe Ile
            225                 230                 235                 240

Gly Ser Lys Ala Asp Tyr Asp Ser Lys Glu Phe Tyr Arg Phe Arg Glu
                            245                 250                 255

Leu (2) INFORMATION FOR SEQ ID NO: 128:

(i) SEQUENCE CHARACTERISTICS:
        (A) LENGTH:                774 BASE PAIRS
        (B) TYPE:                  NUCLEIC ACID
        (C) STRANDEDNESS:          SINGLE
        (D) TOPOLOGY:              LINEAR (ii) MOLECULE TYPE:            NUCLEIC (xi) SEQUENCE DESCRIPTION: SEQ ID NO: 128:

AACGAACACA ACCTGAGGTG CCCGCAGCAA GGAACAGAAA TGCCCGGTTT CCAAGACTCG      60

ATTAGGCTTC AATTTTTAGC AATGCACAAT GGTTACAGAT CAAAACTTGC GCTAGGTCAC     120

ATCAGCATAA CTGAAGAATC CGAAAGTGAC GATGATGACG ATTTCGGTTT TTTACCCGAT     180

TTCGCTCCAA GGGCATCGAA AATGAGATAT CTGGAATATG ACTGTGAAGC TGAAAAAAGC     240

GCCTACATGT CGGCTAGACA ATGCTCGGAC AGTTCTTCTC CACCAGAGGG CTACGATGAA     300

AACAAGTATA TTTTCGAAAA CTCAAACCAG ATCAGTGAAG CTGCTCTGAA GGCCATGATC     360

TCGTGGGCAA AGAGGCTTT CAACCTACAG AAAACAAAAG AAGGAGAAGG AGTTCTGTAC      420

CGGTCGAACC ACGACATATC AAACTTCGCT AATCTGGCTT GGGACGCGCG TGAAAAGTTT     480

GGTTGCGCAG TTGTTAATTG CCCTTTGGGA GAAATCGATG ATGAAACCAA CCATGATGGA     540
```

-continued

```
GAAACCTATG CAACAACCAT CCATGTAGTC TGCCACTACC CGAAAATACA GAAAACTGAA    600

GGACAGCCGA TTTACAAGGT AGGGACACCA TGCGACGATT GCAGTGAATA CACAAAAAAA    660

GCAGACCAAA CCACGTCTGC GGATCCGGTG TGTATTCCGG ATGACGGAGT CTGCTTTATT    720

GGCTCGAAAG CCGATTACGA TAGCAAGGAG TTTTATCGAT TCCGAGAGTT ATAA          774
```

(2) INFORMATION FOR SEQ ID NO: 129:

(i) SEQUENCE CHARACTERISTICS:
        (A) LENGTH:          257 AMINO ACIDS
        (B) TYPE:            AMINO ACID
        (D) TOPOLOGY:       LINEAR (ii) MOLECULE TYPE:        PEPTIDE (xi) SEQUENCE DESCRIPTION: SEQ ID NO: 129:

```
Asn Glu His Asn Leu Arg Cys Pro Gln Gln Gly Thr Glu Met Pro Gly
 1               5                  10                  15

Phe Gln Asp Ser Ile Arg Leu Gln Phe Leu Ala Met His Asn Gly Tyr
            20                  25                  30

Arg Ser Lys Leu Ala Leu Gly His Ile Ser Ile Thr Glu Glu Ser Glu
        35                  40                  45

Ser Asp Asp Asp Asp Asp Phe Gly Phe Leu Pro Asp Phe Ala Pro Arg
50                  55                  60

Ala Ser Lys Met Arg Tyr Leu Glu Tyr Asp Cys Glu Ala Glu Lys Ser
65                  70                  75                  80

Ala Tyr Met Ser Ala Arg Gln Cys Ser Asp Ser Ser Pro Pro Glu
                85                  90                  95

Gly Tyr Asp Glu Asn Lys Tyr Ile Phe Glu Asn Ser Asn Gln Ile Ser
            100                 105                 110

Glu Ala Ala Leu Lys Ala Met Ile Ser Trp Ala Lys Glu Ala Phe Asn
        115                 120                 125

Leu Gln Lys Thr Lys Glu Gly Glu Gly Val Leu Tyr Arg Ser Asn His
    130                 135                 140

Asp Ile Ser Asn Phe Ala Asn Leu Ala Trp Asp Ala Arg Glu Lys Phe
145                 150                 155                 160

Gly Cys Ala Val Val Asn Cys Pro Leu Gly Glu Ile Asp Asp Glu Thr
                165                 170                 175

Asn His Asp Gly Glu Thr Tyr Ala Thr Thr Ile His Val Val Cys His
            180                 185                 190

Tyr Pro Lys Ile Gln Lys Thr Glu Gly Gln Pro Ile Tyr Lys Val Gly
        195                 200                 205

Thr Pro Cys Asp Asp Cys Ser Glu Tyr Thr Lys Lys Ala Asp Gln Thr
    210                 215                 220

Thr Ser Ala Asp Pro Val Cys Ile Pro Asp Asp Gly Val Cys Phe Ile
225                 230                 235                 240

Gly Ser Lys Ala Asp Tyr Asp Ser Lys Glu Phe Tyr Arg Phe Arg Glu
                245                 250                 255

Leu
```

(2) INFORMATION FOR SEQ ID NO: 130:

(i) SEQUENCE CHARACTERISTICS:
        (A) LENGTH:          771 BASE PAIRS
        (B) TYPE:            NUCLEIC ACID
        (C) STRANDEDNESS:   SINGLE
        (D) TOPOLOGY:       LINEAR

-continued (ii) MOLECULE TYPE:           NUCLEIC (xi) SEQUENCE DESCRIPTION: SEQ ID NO: 130:

| | | | | | | |
|---|---|---|---|---|---|---|
| AATGAACACA | ACCTGAGGTG | CCCGCAGAAT | GGAACAGAAA | TGCCCGGTTT | CAACGACTCG | 60 |
| ATTAGGCTTC | AATTTTTAGC | AATGCACAAT | GGTTACAGAT | CAAAACTTGC | GCTAGGTCAC | 120 |
| ATCAGCATAA | CTGAAGAATC | CGAAAGTGAC | GATGATGACG | ATTTCGGTTT | TTTACCCGAT | 180 |
| TTCGCTCCAA | GGGCATCGAA | AATGAGATAT | CTGGAATATG | ACTGTGAAGC | TGAAAAAAGC | 240 |
| GCCTACATGT | CGGCTAGAAA | TTGCTCGGAC | AGTTCTTCTC | CACCAGAGGG | CTACGATGAA | 300 |
| AACAAGTATA | TTTTCGAAAA | CTCAAACAAT | ATCAGTGAAG | CTGCTCTGAA | GGCCATGATC | 360 |
| TCGTGGGCAA | AAGAGGCTTT | CAACCTAAAT | AAAACAAAAG | AAGGAGAAGG | AGTTCTGTAC | 420 |
| CGGTCGAACC | ACGACATATC | AAACTTCGCT | AATCTGGCTT | GGGACGCGCG | TGAAAAGTTT | 480 |
| GGTTGCGCAG | TTGTTAACTG | CCCTTTGGGA | GAAATCGATG | ATGAAACCAA | CCATGATGGA | 540 |
| GAAACCTATG | CAACAACCAT | CCATGTAGTC | TGCCACTACC | CGAAAATAAA | CAAAACTGAA | 600 |
| GGACAGCCGA | TTTACAAGGT | AGGGACACCA | TGCGACGATT | GCAGTGAATA | CACAAAAAAA | 660 |
| GCAGACAATA | CCACGTCTGC | GGATCCGGTG | TGTATTCCGG | ATGACGGAGT | CTGCTTTATT | 720 |
| GGCTCGAAAG | CCGATTACGA | TAGCAAGGAG | TTTTATCGAT | TCCGAGAGTT | A | 771 |

NEUTROPHIL INHIBITORS

CROSS REFERENCE TO RELATED APPLICATIONS

This application is a continuation-in-part of U.S. Ser. No. 08/060,433 filed May 11, 1993, now U.S. Pat No. 6,756,211, which is a continuation-in-part of U.S. Ser. No. 07/996,972 filed Dec. 24, 1992, now abandoned, which is a continuation-in-part of U.S. Ser. No. 07/881,721 filed May 11, 1992, now abandoned, the disclosures of which are incorporated herein by reference.

FIELD OF THE INVENTION

This invention relates to factors which inhibit granulocyte activity. These factors inhibit neutrophil activity, including inhibition of neutrophil activation and adhesion of neutrophils to vascular endothelial cells. These factors also inhibit eosinophil activity, including inhibition of eosinophil adhesion to vascular endothelial cells.

BACKGROUND OF THE INVENTION

Granulocytes are white blood cells (leukocytes) that contain an oddly shaped nucleus and a highly granulated cytoplasm. The granulocytes comprise neutrophils, eosinophils and basophils. Klein, J., *Immunology*, page 20, Blackwell Scientific Publications, Boston (1990).

Neutrophils are an essential component of the host defense system against microbial invasion. In response to soluble inflammatory mediators released by cells at the site of injury, neutrophils emigrate into tissue from the bloodstream by crossing the blood vessel wall. At the site of injury, activated neutrophils kill foreign cells by phagocytosis and by the release of cytotoxic compounds, such as oxidants, proteases and cytokines. Despite their importance in fighting infection, neutrophils themselves can promote tissue damage. During an abnormal inflammatory response, neutrophils can cause significant tissue damage by releasing toxic substances at the vascular wall or in uninjured tissue. Alternatively, neutrophils that stick to the capillary wall or clump in venules may produce tissue damage by ischemia. Such abnormal inflammatory responses have been implicated in the pathogenesis of a variety of clinical disorders including adult respiratory distress syndrome (ARDS); ischemia-reperfusion injury following myocardial infarction, shock, stroke, and organ transplantation; acute and chronic allograft rejection; vasculitis; sepsis; rheumatoid arthritis; and inflammatory skin diseases (Harlan et al., 1990 Immunol. Rev. 114, 5).

Neutrophil adhesion at the site of inflammation is believed to involve at least two discrete cell-cell interactive events. Initially, vascular endothelium adjacent to inflamed tissue becomes sticky for neutrophils; neutrophils interact with the endothelium via low affinity adhesive mechanisms in a process known as "rolling". In the second adhesive step, rolling neutrophils bind more tightly to vascular endothelial cells and migrate from the blood vessel into the tissue.

Neutrophil rolling along affected vascular segments and other initial low affinity contacts between neutrophils and the endothelium are reported to be mediated by a group of monomeric, integral membrane glycoproteins termed selectins. All three of the selectins so far identified, that is L-selectin (LECAM-1 or LAM-1) present on the surface of neutrophils, E-selectin (endothelial leukocyte adhesion molecule-1 or ELAM-1) present on endothelial cells and P-selectin (granule membrane protein-140, GMP-140, platelet activation-dependent granule-external membrane protein, PADGEM or CD62) expressed on endothelial cells, have been implicated in neutrophil adhesion to the vascular endothelium (Jutila et al., 1989 J. Immunol 143, 3318; Watson et al., 1991 Nature 349, 164; Mulligan et al., J. Clin. Invest. 88, 1396; Gundel et al., 1991 J. Clin. Invest. 88, 1407; Geng et al., 1990 Nature 343, 757; Patel et al., 1991 J. Cell Biol. 112, 749). The counter-receptor for E-selectin is reported to be the sialylated Lewis X antigen (sialyl-Lewis$^x$) that is present on cell-surface glycoproteins (Phillips et al., 1990 Science 250, 1130; Walz et al., 1990 Science 250, 1132; Tiemeyer et al., 1991 Proc. Natl. Acad. Sci. (USA) 88, 1138; Lowe et al., 1990 Cell 63, 475). Receptors for the other selectins are also thought to be carbohydrate in nature but remain to be elucidated.

The more stable secondary contacts between neutrophils and endothelial cells are reported to be mediated by a class of cell adhesion molecules known as integrins. Integrins comprise a broad range of evolutionarily conserved heterodimeric transmembrane glycoprotein complexes that are present on virtually all cell types. Members of the leukocyte-specific CD18 ($\beta_2$) family of integrins, which include CD11a/CD18 (LFA-1) and CD11b/CD18 (Mac-1, Mo-1 or CR3) have been reported to mediate neutrophil adhesion to the endothelium (See Larson and Springer, 1990 Immunol Rev. 114, 181). Endothelial cell counter-receptors for these integrins are the intercellular cell adhesion molecules ICAM-1 and ICAM-2 for CD11a/CD18 and ICAM-1 for CD11b/CD18, respectively (Rothlein et al., 1986 J. Immunol. 137, 1270; Staunton et al., 1988 Cell 52, 925; Staunton et al., 1989 Nature 339, 61). The ICAMs are monomeric transmembrane proteins that are members of the immunoglobulin superfamily.

The activation of endothelial cells and neutrophils is believed to represent an important component of neutrophil-mediated inflammation. Factors that induce cell activation are termed agonists. Endothelial cell agonists, which are believed to include small regulatory proteins such as tumor necrosis factor (TNFα) and interleukin-1α (IL-1α), are released by cells at the site of injury. Activation of endothelial cells has been reported to result in the increased surface expression of ICAM-1 (Staunton et al., 1988 Cell 52, 925) and ELAM-1 (Bevilacgua et al., 1987 Proc. Natl. Acad. Sci.(USA) 84, 9238). Raised levels of expression of these adhesive molecules on the surface of activated endothelial cells is believed to lead to the observed increased adhesivity of neutrophils for the vascular endothelium near sites of injury.

Activation of the neutrophil results in profound changes to its physiological state, including shape change, ability to phagocytose foreign bodies and release of cytotoxic substances from intracellular granules. Moreover, activation is believed to greatly increase the affinity of adhesive contacts between neutrophils and the vascular endothelium, perhaps through a conformational change in the CD11b/CD18 integrin complex on the neutrophil surface (Vedder and Harlan, 1988 J. Clin. Invest. 81, 676; Buyon et al., 1988 J. Immunol. 140, 3156). Factors that have been reported to induce neutrophil activation include IL-1α, GM-CSF, G-CSF, MIP-1, IL-8 (IL-8=interleukin-8, GM-CSF=granulocyte/monocyte-colony stimulating factor, G-CSF=granulocyte-colony stimulating factor), TNFα, the complement fragment C5a, the microbe-derived peptide formyl-Met-Leu-Phe and the lipid-like molecules leukotriene B4 (LTB$_4$) and platelet activating factor (Fuortes and Nathan, 1992, in *Molecular Basis of Oxidative Damage by Leukocytes* Eds Jesaitis, A. J. and Dratz, E. A. (CRC Press) pp. 81–90). In addition, phorbol esters (e.g., phorbol 12-myristate 13-acetate; PMA) have been proposed as a potent class of synthetic lipid-like neutrophil agonists. With the exception of PMA, these agonists are believed to activate neutrophils by binding receptors on their surface. Receptors that are occupied by agonist molecules are believed to initiate within the neutrophil a cascade of events that ultimately will result in the physiological changes that accompany neutrophil activation. This process is known as signal transduction. The lipid-like PMA is proposed to affect neutrophil activation by passing through the plasma membrane at the cell surface and directly interacting with intracellular components (i.e., protein kinase) of the signal transduction machinery.

There exist two general classes of compounds that have been reported to down regulate the function of neutrophils, and these compounds have been shown to mitigate inflammation. One group of anti-inflammatory compounds has been proposed to function as inhibitors of neutrophil activation, and presumably adhesion, by acting on components of the signal transduction machinery. A second class of anti-inflammatory compounds has been proposed to block neutrophil infiltration into inflammatory foci by acting as direct inhibitors of the adhesive receptors that mediate contact between neutrophils and the vascular endothelium.

Many of the anti-inflammatory compounds currently used as therapeutics, including prostaglandins, catecholamines, and a group of agents known as non-steroidal anti-inflammatory drugs (NSAIDs), are believed to fall into the first category (Showell and Williams, 1989, in *Immunopharmacology*, eds. Gilman, S. C. and Rogers, T. J. [Telford Press, NJ] pp 23–63). For example, the enhanced adhesiveness observed for TNFα-activated neutrophils has been reported as associated with decreased levels of a mediator of signal transduction, cyclic AMP (cAMP). (See Nathan and Sanchez, 1990 JCB 111, 2171). Exposure of neutrophils to prostaglandins and catecholamines has been correlated with elevated levels of intracellular cyclic AMP (Showell and Williams, 1989). While signal transduction inhibitors have been used extensively as anti-inflammatory therapeutic agents, they have been shown to have several disadvantages including poor efficacy in acute inflammatory conditions, lack of specificity and undesirable side-effects such as gastric or intestinal ulceration, disturbances in platelet and central nervous system function and changes in renal function (Insel, 1990 in *The Pharmacological Basis of Therapeutics*, eds. Gilman, A. G., Rall, T. W., Nies, A. S., and Taylor, P. [Pergamon, NY], 8th Ed., pp. 638–681).

Glucocorticoids have long been recognized for their anti-inflammatory properties. Steroid induced inhibition of neutrophils has been reported for several neutrophil functions, including adherence (Clark et al., 1979 Blood 53, 633–641; MacGregor, 1977 Ann. Intern. Med. 86, 35–39). The mechanisms by which glucocorticoids modulate neutrophil function are not well understood, but they are generally believed to involve the amplification or suppression of new proteins in treated neutrophils that play a key role in the inflammatory process (Knudsen et al., 1987 J. Immunol. 139, 4129). In particular, a group of proteins known as lipocortins, whose expression is induced in neutrophils by glucocorticoids, has been associated with anti-inflammatory properties (Flower, 1989 Br. J. Pharmacol. 94, 987–1015). Lipocortins may exert anti-neutrophil effects by interacting with sites on the neutrophil surface (Camussi et al., 1990 J. Exp. Med. 177, 913–927), but there is no evidence to suggest that the lipocortins act by directly blocking adhesive proteins on the neutrophil. Apart from their beneficial anti-inflammatory properties, glucocorticoids have been associated with significant side-effects. These include suppression of pituitary-adrenal function, fluid and electrolyte disturbances, hypertension, hyperglycemia, glycosuria, susceptibility to infection, ulcers, osteoporosis, myopathy, arrest of growth and behavioral disturbances (Insel, 1990).

A second class of anti-inflammatory compounds which are reported as direct inhibitors of neutrophil adhesion to the vascular endothelium are monoclonal antibodies. Monoclonal antibodies that recognize and block ligand-binding functions of some of these adhesive molecules have been reported to act as in vivo inhibitors of neutrophil-mediated inflammation. In particular, monoclonal antibodies to the CD18 subunit of the CD18 integrin complexes (i.e., CD11a/CD18, CD11b/CD18 and CD11c/CD18) on the surface of neutrophils have been reported to prevent a variety of neutrophil-mediated tissue injury in animal models, including pulmonary edema induced by reperfusion (Horgan et al, 1990 Am. J. Physiol. 259, L315–L319), organ injury induced by hemorrhagic shock (Mileski et al, 1990 Surgery 108, 206–212), myocardial damage following ischemia/reperfusion (Winquist et al, 1990 Circulation III-701), edema and tissue damage following ischemia/reperfusion of the ear (Vedder et al, 1990 Proc. Natl. Acad. Sci.(USA) 87, 2643–2646), brain edema and death produced by bacterial meningitis (Tuomanen et al, 1989 J. Exp. Med. 170, 959–968), vascular injury and death in endotoxic shock (Thomas et al, 1991 FASEB J. 5, A509) and indomethacin-induced gastric injury (Wallace et al, 1991 Gastroenterology 100, 878–883).

Monoclonal antibodies directed to the CD11b subunit have been reported by Todd, R. F. et al., U.S. Pat. No. 4,840,793 (Jun. 20, 1989), Todd, R. F. et al., U.S. Pat. No. 4,935,234 (Jun. 19, 1990), Schlossman, S. F. et al., U.S. Pat. No. 5,019,648 (May 28, 1991) and Rusche, J. R. et al., International Application No. WO 92/11870 (Jul. 23, 1992). Monoclonal antibodies directed to CD18 subunit have been reported by Arfors, K. E., U.S. Pat. No. 4,797,277 (Jan. 10, 1989), Wright, S. D. et al., European Patent Application No. 346,078 (Dec. 13, 1989), Law, M. et al., European Patent Application No. 438,312 (Jul. 24, 1991), Law, M. et al., European Patent Application No. 440,351 (Aug. 7, 1991), Wright, S. D. et al., U.S. Pat. No. 5,147,637 (Sep. 15, 1992) and Wegner, C. D. et al., European Patent Application No. 507,187 (Oct. 7, 1992).

Antibodies to other adhesive molecules have also been reported to have anti-inflammatory properties. Monoclonal antibodies that recognize the counter-receptor of CD11a/CD18 and CD11b/CD18, ICAM-1 have been reported to prolong cardiac allograft survival (Flavin et al, 1991 Transplant. Proc. 23, 533–534) and prevent chemically induced lung inflammation (Barton et al, 1989 J. Immunol. 143, 1278–1282). Furthermore, anti-selectin monoclonal antibodies have also been reported as active in animal models of neutrophil-mediated inflammation. Monoclonal antibodies to L-selectin have been reported to prevent neutrophil emigration into inflamed skin (Lewinshon et al., 1987 J. Immunol. 138, 4313) and inflamed ascites (Jutila et al., 1989 J. Immunol. 143, 3318; Watson et al., 1991 Nature 349, 164). Reports have also described inhibition of neutrophil influx into inflamed lung tissue by anti E-selectin monoclonal antibodies (Mulligan et al., 1991 J. Clin. Invest. 88, 1396; Gundel et al., 1991 J. Clin. Invest. 88, 1407). While monoclonal antibodies to adhesive proteins have demonstrated the feasibility of using neutrophil adhesion inhibitors as anti-inflammatory agents, their utility as therapeutics requires further evaluation.

Soluble adhesive receptors obtained by genetic engineering have been proposed as anti-inflammatory compounds.

Soluble receptors, in which the transmembrane and intracellular domains have been deleted by recombinant DNA technology, have been tested as inhibitors of neutrophil adhesion to endothelial cells. The functional use of recombinant soluble adhesive molecules has been reported using CD11b/CD18 (Dana et al., 1991 Proc. Natl. Acad. Sci. (USA) 88, 3106–3110) and L-selectin (Watson et al., 1991).

Recently, a new class of anti-leukocyte compounds collectively termed "leumedins" has been reported. These compounds have been reported to block the recruitment in vivo of T lymphocytes and neutrophils into inflammatory lesions. The mechanism of action of the leumedins is unclear, but there is evidence that they do not function by blocking neutrophil activation (Burch et al., 1991 Proc. Natl. Acad. Sci. (USA) 88, 355). It remains to be determined if leumedins block neutrophil infiltration by direct interference with adhesive molecules.

It has been suggested that parasites survive in their host by modulating host immunity and inflammatory response though the mechanisms by which this occurs remains unclear (Leid, W. S., 1987, Veterinary Parasitology, 25: 147). In this regard, parasite-induced immunosuppression in rodent models has been proposed (Soulsby et al., 1987, Immunol Lett. 16, 315–320). The various aspects of the modulation of host immunity by helminth parasites to evade immunological attack has recently been reviewed. See Maizels et al. (1993), Nature, 365:797–805.

Various parasites have been reported to have an affect on neutrophils of their host. For example, a protein isolated from the cestode, *Taenia taeniaeformis,* has been reported to inhibit chemotaxis and chemokinesis of equine neutrophils, as well as inhibit neutrophil aggregation (C. Suquet et al., 1984, Int'l J. Parasitol., 14: 165; Leid, R. W. et al., 1987, Parasite Immunology, 9: 195; and Leid, R. W. et al., 1987, Int'l J. Parasitol., 17: 1349). Peritoneal neutrophils from mice infected with the cestode, *Echinococcus multiocularis,* have been reported to lose their ability to migrate toward parasite antigens and nonspecific chemoattractants with increasing time of infection (Alkarmi, T. et al., Exptl. Parasitol., 1989, 69: 16). The nematode, *Trichinella spiralis,* has been reported to either excrete and/or secrete factors which inhibit chemotaxis and p-nitroblue tetrazolium reduction (i.e., release of oxidative metabolites) but enhance chemokinesis of human neutrophils (Bruschi, F. et al., 1989, Wiadomosci Parazytologiczne, 35: 391). The sera of humans infected with the nematode, *Trichinella spiralis,* has been reported to inhibit leukocyte chemotaxis and phagocytosis (Bruschi, F. et al., 1990, J. Parasitol., 76: 577). The saliva of the tick, *Ixodes dammini,* has been reported to inhibit neutrophil function (Ribeiro et al, 1990, Exp. Parasitol., 70, 382). A protein secreted by the cestode, *Echinococcus granulosus,* has been reported to inhibit human neutrophil chemotaxis (Shepard, J. C. et al., 1991, Mol. Biochem. Parasitol., 44: 81).

Another component of the host defense mechanism against invading pathogens are eosinophils. Functionally, eosinophils are similar to neutrophils in that both cell types have the ability to phagocytose and to release compounds that are either directly or indirectly toxic to pathogenic organisms. Eosinophils are distinguished from neutrophils by their morphologic features, constituents, products and associations with specific diseases. Although eosinophils have been reported to be capable of killing bacteria in vitro, this class of leukocyte alone is not believed sufficient to defend against bacterial. infections in vivo. Instead, it is thought that eosinophils afford primary defense against large organisms such as helminthic parasites (Butterworth A E, 1984; Adv. Parasitol. 23:143–235). Also, it is widely held that eosinophils can play a major role in certain inflammatory diseases. Specifically, substances released from eosinophils that are known collectively as cationic granule proteins, including major basic protein, eosinophil cationic protein and eosinophil-derived neurotoxin, have been implicated in asthma (Gleich G J and Adolphson, C R, 1986; Adv. Immunol. 39:177–253), inflammatory bowel disease (H ällren, R, 1989; Am. J. Med. 86:56–64) and atopic dermatitis (Tsuda, S, et al, 1992; J. Dermatol. 19:208–213). Moreover, other eosinophil products such as superoxide anions, hydroxyl radicals and singlet oxygen may also be involved in damage to host tissue in inflammatory disease states (Petreccia, D C et al, 1987, J. Leukoc. Biol. 41:283–288; Kanofsky, J R et al, 1988; J. Biol. Chem. 263:9692–9696).

An early step in eosinophil-mediated inflammatory disease is believed to be the movement of eosinophils from the vascular compartment to tissue. The first step in this extravasation process is reported to be the adherence of eosinophils to the luminal surface of the vascular endothelium. Although mechanisms of eosinophil-endothelial cell adhesion are not as well defined as those involving adhesion by neutrophils, it is reported that members of the CD11/CD18 family of integrins on the surface of the eosinophil are involved in eosinophil-endothelial adhesion (Lamas, A M, et al, 1988; J. Immunol. 140:1500; Walsh, G M, et al, 1990; Immunology 71:258), and it is reported that the endothelial cell counter-receptor is likely ICAM-1 (Wegner, CD, et al, 1990; Science 247:456–459). A second integrin known as VLA-4 (very late antigen-4, a4b1) that is present on eosinophils, lymphocytes and monocytes but not neutrophils, is thought to contribute to eosinophil adherence by binding to the VCAM-1 (vascular cell adhesion molecule-1) that is expressed on the surface of endothelial cells (Dobrina, A, et al, 1991, J. Clin. Invest. 88:20). IL-1 treatment of the endothelial cell monolayers has been reported to induce an increased adhesiveness for human basophils, eosinophils and neutrophils but treatment of these endothelial cells with an antibody directed to VACM-1 was reported to inhibit both basophil and eosinophil adhesion but not neutrophil adhesion. It has also been reported that monoclonal antibodies against VCAM-1 inhibit lymphocyte and monocyte cell adhesion to stimulated endothelium (Carlos et al. (1990), Blood, 76:965–970; Rice et al., J. Exp. Med. (1990), 171:1369–1374) but not to neutrophils.

Approaches to the treatment of eosinophil-mediated inflammation have been similar to those adopted for neutrophil-mediated disease. For example, potential therapeutics under investigation for eosinophil-mediated inflammation include glucocorticoids (Evans, P M, et al, 1993, J. Allergy Clin. Immunol. 91:643–650). As is the case for other agents that have been reported to modulate neutrophil function, these agents have been found to be sub-optimal in that they are relatively non-specific and toxic. A second approach to anti-eosinophil therapy has been the use of compounds that directly inhibit the adhesion of eosinophils to vascular endothelium. It has been reported that in animal models of asthma, monoclonal antibody against ICAM-1 blocks eosinophil infiltration into tissues. Wegner et al. (1990), Science, 247:456–459. ICAM-1 and functional derivatives thereof have been proposed as anti-inflammatory agents. Anderson et al., European Patent Application No. 314,863 (Apr. 29, 1988); Wegner et al., International Application No. WO 90/10453 (Sep. 20, 1990).

However, there remains a need for potent, highly specific inhibitors of neutrophil and eosinophil function, in particular, adhesion to vascular endothelium, as a treatment for abnormal granulocyte-mediated inflammation. The present invention describes potent and specific inhibitors of neutrophil and eosinophil activity, in particular the adhesion of these granulocytes to vascular endothelial cells, derived from hookworms (such as *Ancylostoma caninum*) and related species.

SUMMARY OF THE INVENTION

Among other factors, the present invention is based on our finding that the Neutrophil Inhibitory Factor of the present invention represents a pioneering step toward the development of a new generation of anti-inflammatory therapeutic products. This discovery will enable therapy for inflammatory disease based entirely on specific inhibition of the inflammatory response. The therapeutic advantages of this novel approach are realized through the specificity of Neutrophil Inhibitory Factor compared to current clinical treatment modalities such as steroids, catecholamines, prostaglandins, and nonsteroidal anti-inflammatory agents. The currently used therapeutic agents demonstrate poor efficacy and multiple adverse reactions due to generalized systemic effects that non-specifically target numerous biological processes in addition to the inflammatory process. Nonetheless, the existence of this extensive panel of anti-inflammatory agents, although suboptimal, and the total funds expended by the pharmaceutical industry in research in this area point to significant medical needs for effective anti-inflammatory agents and suggests that the novel and highly specific Neutrophil Inhibitory Factors of the present invention have important applications.

As noted in the Background, the inflammatory response may result in clinical syndromes ranging from debilitating arthritis and asthma to life threatening shock. In view of the severity of these disorders, the vast number of individuals afflicted therewith and the lack of suitable therapeutic intervention, the need for a breakthrough therapy represents a long felt need which has not been met. The Neutrophil Inhibitory Factor of the present invention is believed to meet this need by providing the potential for a lifesaving therapy which is currently being sought throughout the international medical and pharmaceutical research communities.

Further, in view of the myriad conditions associated with undesired and/or abnormal inflammatory conditions which appear to be associated with neutrophil activity, there remains a need for potent, highly specific inhibitors of neutrophil function, in particular, adhesion to vascular endothelium, as a treatment for abnormal neutrophil-mediated inflammation. The present invention is believed to fulfill this need by disclosing a potent and specific inhibitor of neutrophil activity, in particular the adhesion of neutrophils to vascular endothelial cells, derived from hookworms (such as *Ancylostoma caninum*) and related species.

The present invention is directed to a neutrophil inhibitory factor ("Neutrophil Inhibitory Factor" or "NIF") which may be isolated from natural sources or made by recombinant methods. Neutrophil Inhibitory Factor is a protein which is neither an antibody, a member of the integrin or selectin families nor a member of the immunoglobulin superfamily of adhesive proteins and which when isolated from a parasitic worm is a glycoprotein. Recombinant NIF produced by certain expression systems may or may not be glycosylated, or may be glycosylated to a variable degree. However, such NIFs whether glycosylated or not are considered to be within the scope of the present invention.

In one aspect, the present invention provides NIFs which contain, as part of their total amino acid sequence, an amino acid sequence selected from the group consisting of (a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gln, Lys or Arg; $X_3$ is Ala or Arg; $X_4$ is Leu or Met; Xs is Lys, Arg, Leu or Ile; $X_6$ is Val or Ile; and $X_7$ is Ser, Gly or Asn;

(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Al-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr,, Lys or Asn;

(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-Cys-$X_{28}$-$X_{29}$-Try (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe. Such NIFs exhibit neutrophil inhibitory activity.

In another aspect, the present invention provides mutant NIFs wherein certain asparagine residues are replaced with glutamine residues which is believed to result in the reduced glycosylation of these NIFs. The mutant NIFs contain, as part of their total amino acid sequence, an. amino acid sequence selected from the group consisting of peptides (a) to (f) hereinabove. Such NIFs exhibit neutrophil inhibitory activity.

In another aspect, the present invention provides NIFs which contain, as part of their total amino acid sequence, an amino acid sequence encoded by a nucleic acid sequence which is sufficiently complementary to hybridize to certain nucleic acid probes. Such NIFs exhibit neutrophil inhibitory activity. The present invention includes within its scope these nucleic acid probes.

In another aspect, the present invention provides nucleic acid molecules encoding for a NIF and which are isolated as described herein. Such isolated nucleic acid molecules include expression vectors containing a nucleic acid sequence encoding a NIF. The present invention also includes the host cells transformed by such expression vectors.

In another aspect, the present invention provides methods for making biologically active NIFs, wherein such NIFS are expressed and, optionally, secreted. The present invention also includes the NIFs made by these methods.

In another aspect, the present invention provides methods of making NIFS comprising preparing a cDNA library from a source suspected of having a NIF and hybridizing certain oligonucleotide probes of the present invention to the nucleic acid molecules from the source. Such NIFs exhibit neutrophil inhibitory activity. The present invention also includes the NIFs made by these methods.

In another aspect, the present invention provides methods of detecting in a sample the presence of a nucleic acid molecule encoding a NIF, which methods comprise the combining the sample thought to contain such nucleic acid molecule with a probe of the present invention and detecting the presence of hybridized probe.

In another aspect, the present invention provides monoclonal antibodies which bind to NIF. The present invention also includes the hybridoma cell lines which make such antibodies, a method of purifying NIF using such monoclonal antibodies and method of detecting in a sample the presence of NIF using such antibodies.

In another aspect, the present invention provides a. method for detecting in a sample NIF mimics which compete with NIFs for binding to the Mac-1 receptor, which methods comprise contacting a sample with the Mac-1 receptor. Such NIF mimics exhibit neutrophil inhibitory activity. The present invention also includes the NIF mimics detected by these methods.

In another aspect, the present invention provides methods for detecting in a sample a NIF antagonist which prevents NIF binding to the Mac-1 receptor, which methods comprise contacting such sample with the Mac-1 receptor. Such NIF antagonists do not exhibit neutrophil inhibitory activity themselves. The present invention also includes the NIF antagonists detected by these methods.

In another aspect, the present invention provides methods of using NIF to treat inflammatory conditions, especially to prevent or decrease inflammatory responses, which methods comprise. administering to a mammal a therapeutically effective amount of NIF.

Other features and advantages of the present invention will be apparent from the following descriptions of the preferred embodiments and from the claims.

Definitions

In accordance with the present invention and as used herein, the following terms are defined with the following meanings, unless explicitly stated otherwise.

The term "amino acid" refers to the natural L-amino acids. The natural amino acids shall be referred to by their names or may be abbreviated as shown below:

| L-amino acid | Abbreviation | |
|---|---|---|
| | Three letter | One Letter |
| alanine | Ala | A |
| arginine | Arg | R |
| asparagine | Asn | N |
| aspartic acid | Asp | D |
| cysteine | Cys | C |
| glutamic | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phynylalanine | Phe | F |
| proline | Pro | P |
| serine | Ser | S |
| threonine | Thr | T |
| tryptophan | Trp | W |
| tyrosine | Tyr | Y |
| valine | Val | V |

The term "amino acid residue" refers to —NH—CH(R)—CO—, wherein R is the side chain group distinguishing each amino acid. For cyclic amino acids, the residue is $$\underset{N}{\underset{|}{\diamondsuit}}\!\!\!\!\!\!-\!\!(CH_2)_x \atop -C(O)-,$$

wherein x is 1, 2 or 3 representing the azetidine-carboxylic acid, proline or pipecolic acid residues, respectively.

The term "isoform" refers to a family of related proteins from a single organism having homologous sequences of amino acid residues interspersed with variable sequences.

The term "nucleic acid" refers to polymers of either deoxynucleic acids or ribonucleic acids, either single-stranded or double-stranded.

The term "isolated nucleic acid" refers to nucleic acids which are isolated by biochemical or molecular biology techniques such as centrifugation, chromatography, electrophoresis, hybridization and the like.

The term "NIF mimic" refers to a small molecule, peptide, peptide analog or protein, which competes with NIF for binding to the Mac-1 receptor. A NIF mimic is also characterized as having neutrophil inhibitory activity, eosinophil inhibitory activity or both such activities.

The term "NIF antagonist" refers to a small molecule, peptide, peptide analog or protein, which prevents the binding of NIF to the Mac-1 receptor and does not possess any significant neutrophil inhibitory activity. A NIF antagonist prevents binding of NIF to the Mac-1 receptor by binding to a site on NIF which is required for binding to the receptor in effect sterically hindering binding, or alternatively, by binding to a site on NIF which results in a conformational change to the site needed for such binding which change substantially weakens or abolishes binding.

BRIEF DESCRIPTION OF THE DRAWINGS

FIG. 7 depicts the amino acid sequence of proteolytic fragments prepared from Neutrophil Inhibitory Factor isolated from canine hookworms [SEQ. ID. NOS. 61 to 79]. The fragments depicted are T-24 [SEQ. ID. NO. 61], T-20 [SEQ. ID. NO. 62], T-22-10 [SEQ. ID. NO. 63], T-13 [SEQ. ID. NO. 64]. T-15-6 [SEQ. ID. NO. 65], D-53 [SEQ. ID. NO. 66], D-54 [SEQ. ID. NO. 67], D-61 [SEQ. ID. NO. 68], D-67 [SEQ. ID. NO. 69], D-83 [SEQ. ID. NO. 70], D-85 [SEQ. ID. NO. 71], D-94 [SEQ. ID. NO. 72], D-96 [SEQ. ID. NO. 73], D-102 [SEQ. ID. NO. 74], K-34A [SEQ. ID. NO. 75], K-46B [SEQ. ID. NO. 76], K-48 [SEQ. ID. NO. 77], K-50A [SEQ. ID. NO. 78], AND K-58A [SEQ. ID. NO. 79].

FIG. 8 depicts the nucleotide sequence of the coding region of Neutrophil Inhibitory Factor cDNA (clone 1FL) (SEQ. ID. NO. 80) and its predicted amino acid sequence (SEQ. ID. NO. 81).

FIG. 9 depicts the alignment of the predicted amino acid sequences of several Neutrophil Inhibitory Factor isoform clones [SEQ. ID. NOS. 81 to 87]. The clones depicted are 1FL [SEQ. ID. NO. 81], 3P [SEQ. ID. NO. 82], 1P [SEQ. ID. NO. 83], 2FL [SEQ. ID. NO. 84], 3FL [SEQ. ID. NO. 85], 4FL [SEQ. ID. NO. 86], AND 6FL [SEQ. ID. NO. 87].

FIG. 15 depicts the nucleotide base sequence (SEQ. ID. NO. 88) of the two-cistron Met-NIF expression cassette of pMa5-NI1/3. The encoded methionyl-NIF and leader peptide are shown in the one-letter code (SEQ. ID. NO. 103). The following features are indicated: the −35 and −10 regions of the phage lambda PR promoter, the transcription initiation point, the Shine-Dalgarno elements preceding the leader cistron ($SD_{cro}$) and the Met-NIF gene (SD) and some restriction sites. The vector was obtained by ligation of the PCR amplified NIF-1FL coding region to the recipient vector which was cleaved by NcoI, treated with the Klenow fragment of DNA polymerase I and subsequently digested with HindIII (both ligation points are indicated). The construction scheme fuses the 5'-end of the NIF coding region to an ATG initiator codon.

Figure 16A:
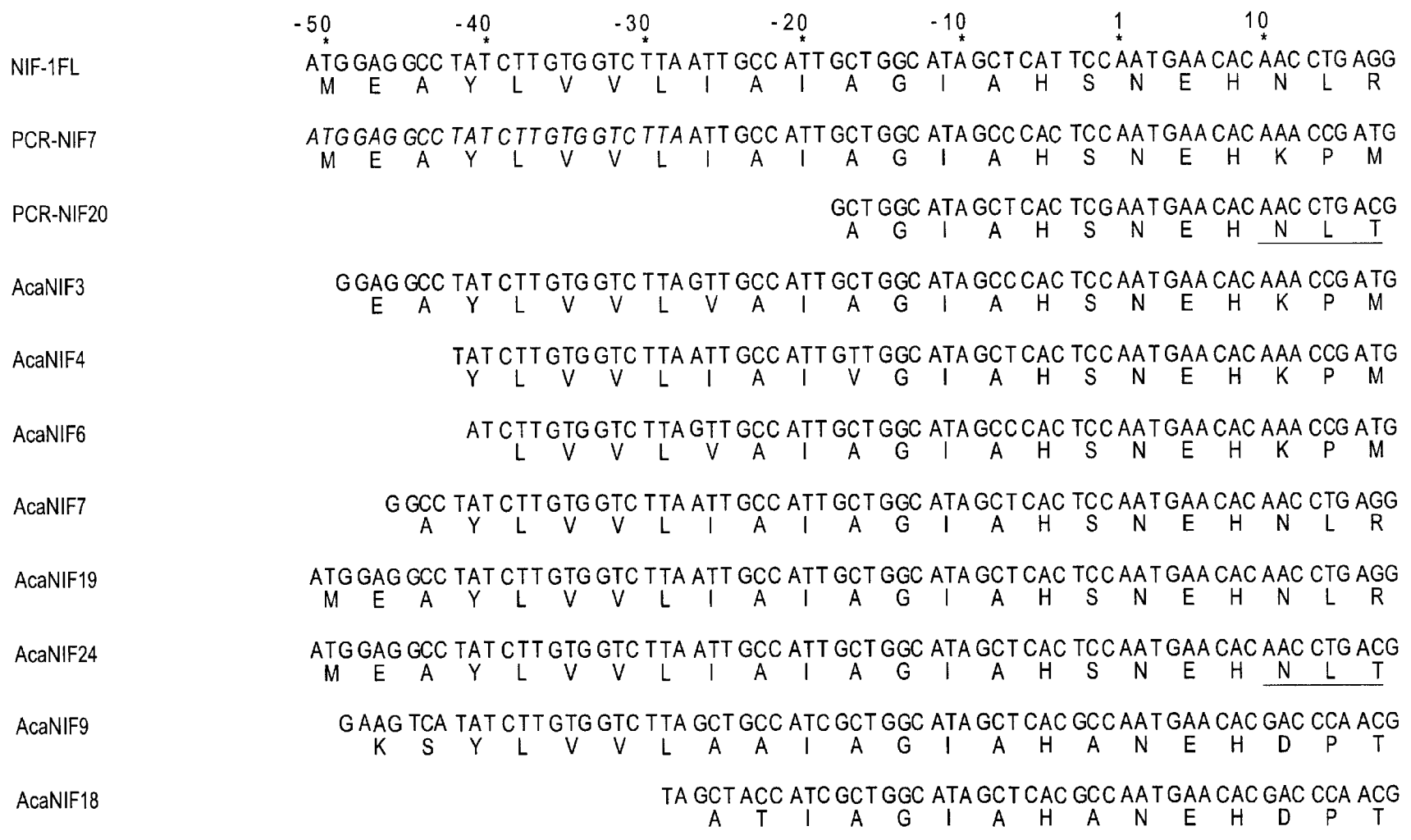
Figure 16B:
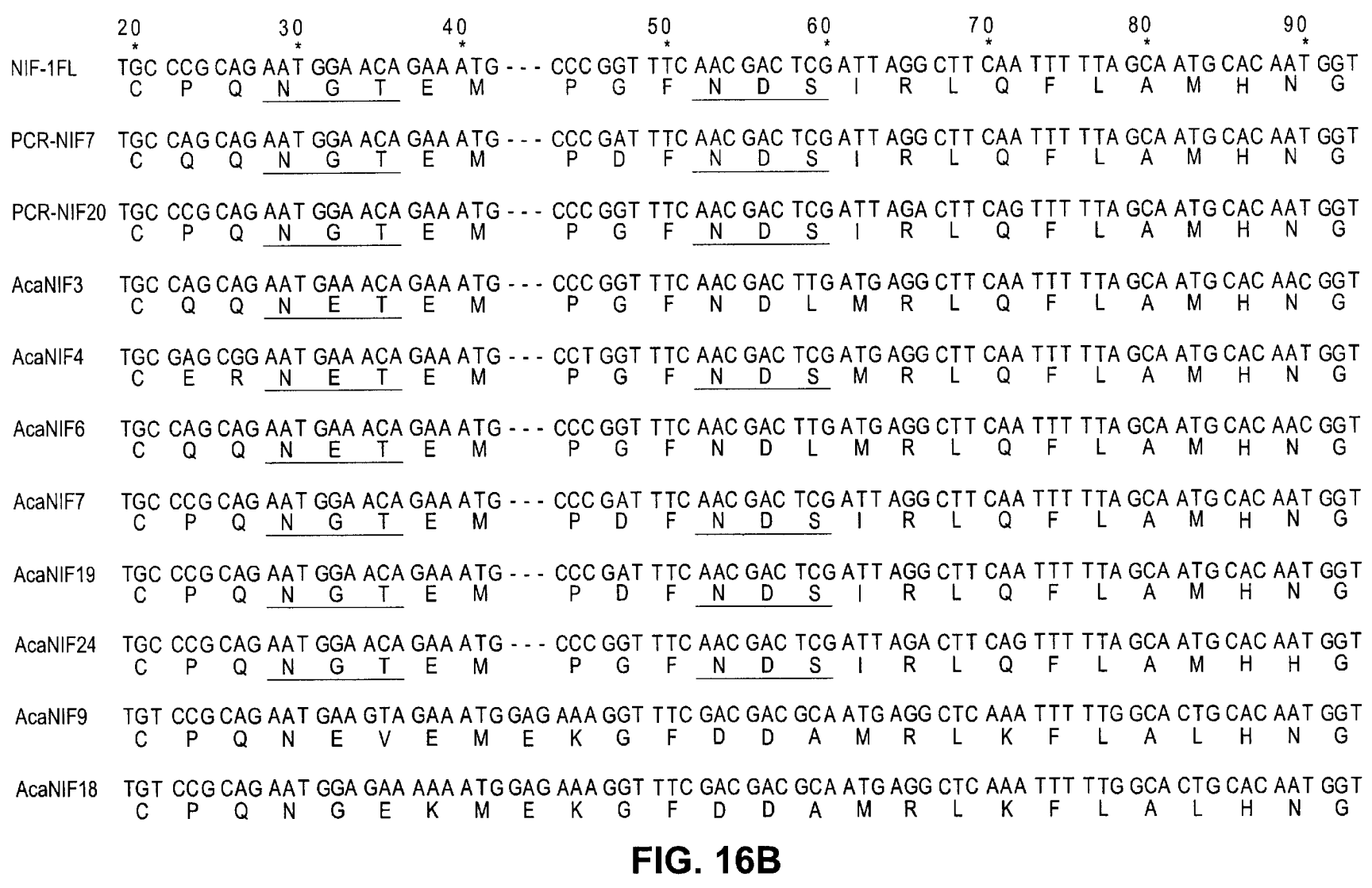
Figure 16D:
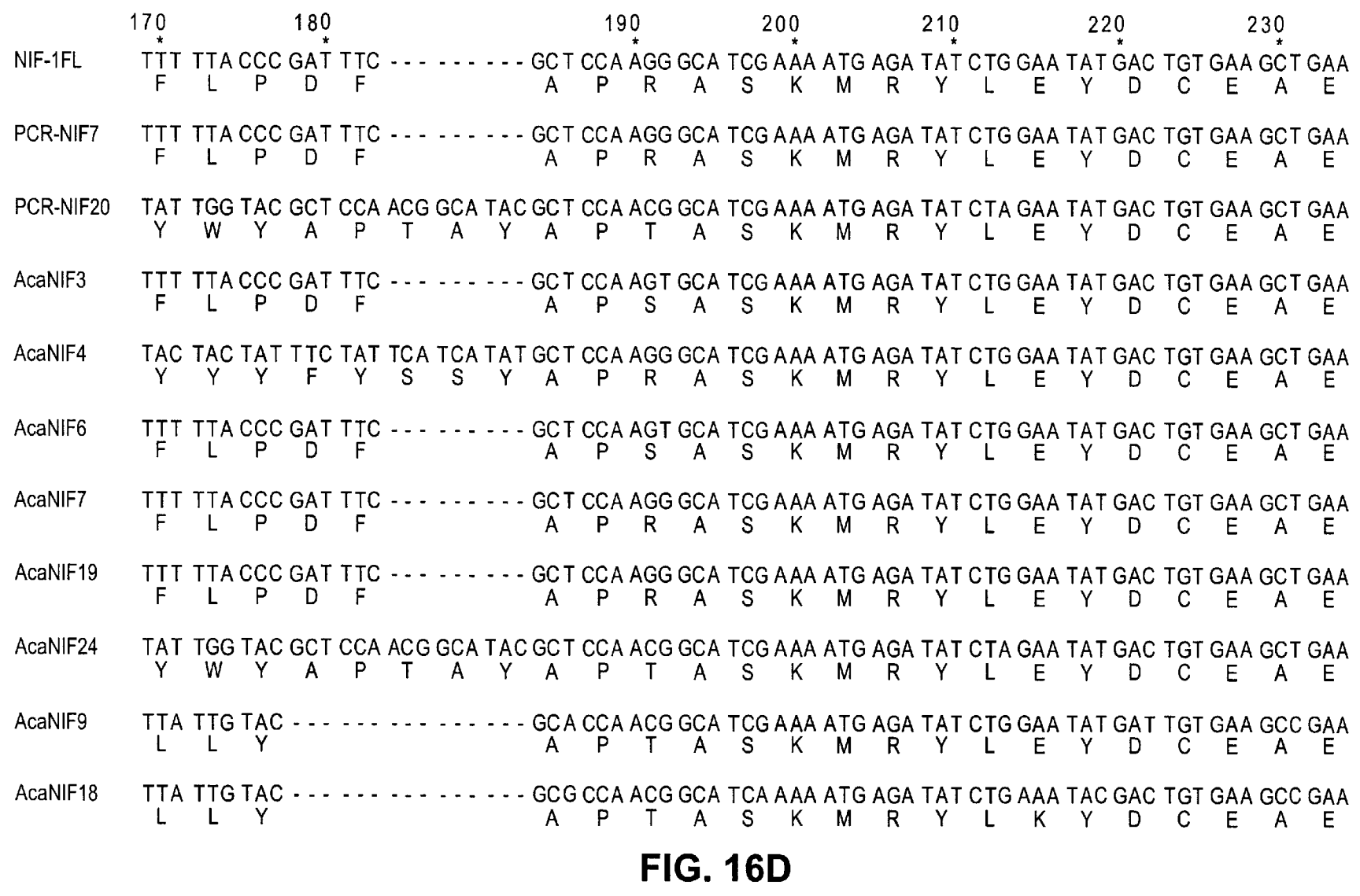
Figure 16G:
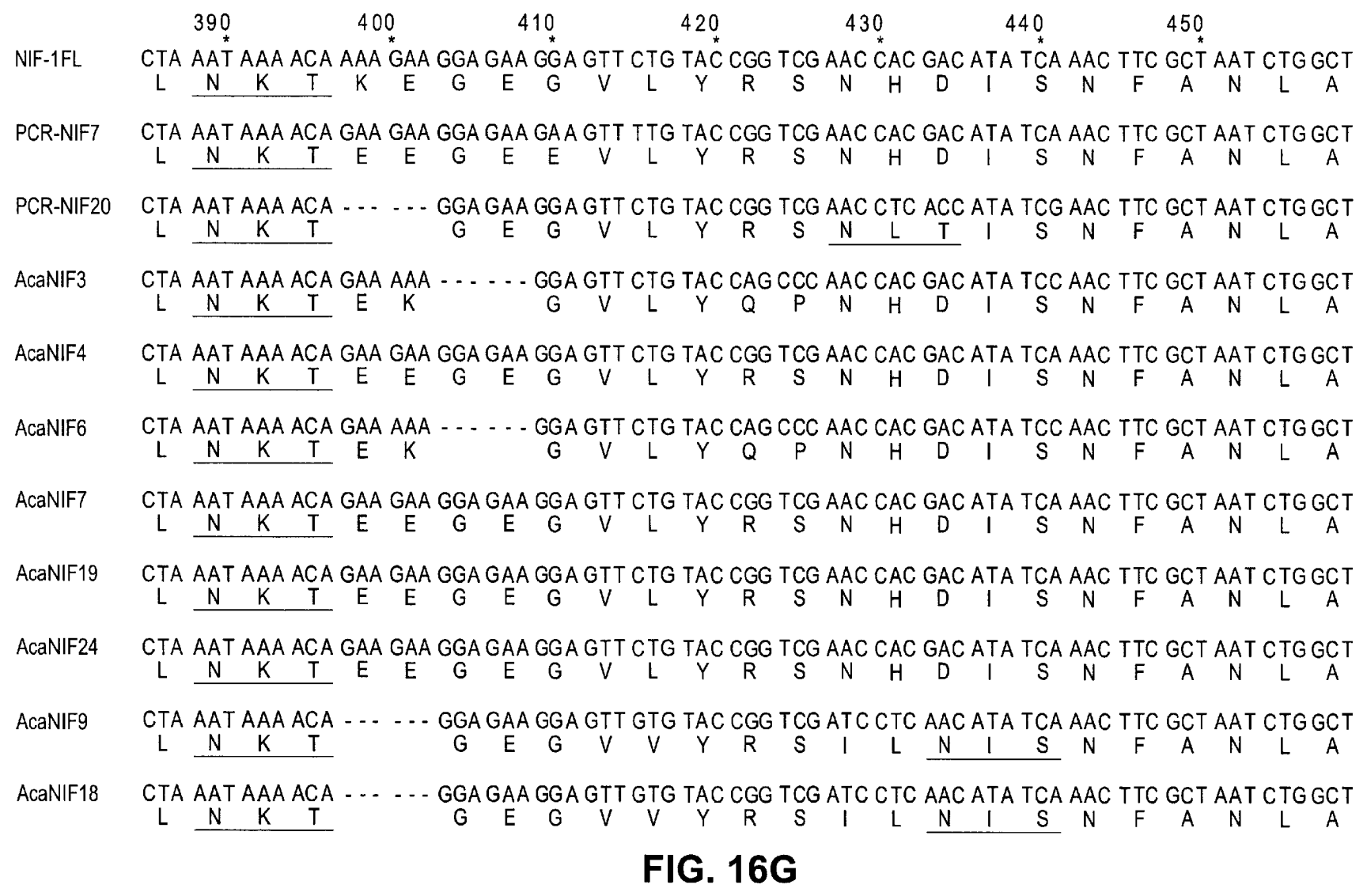
Figure 16I:
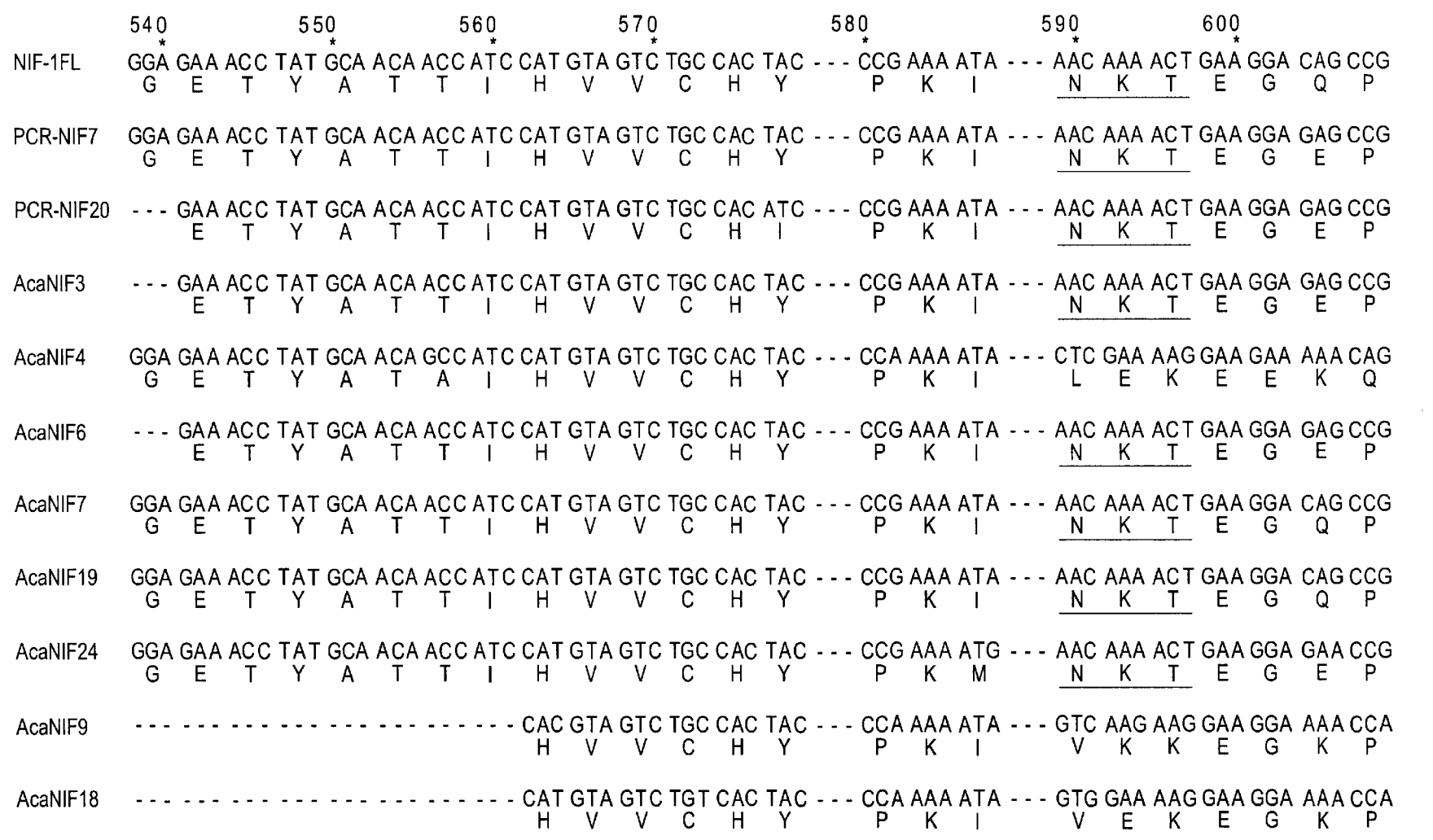
Figure 16J:
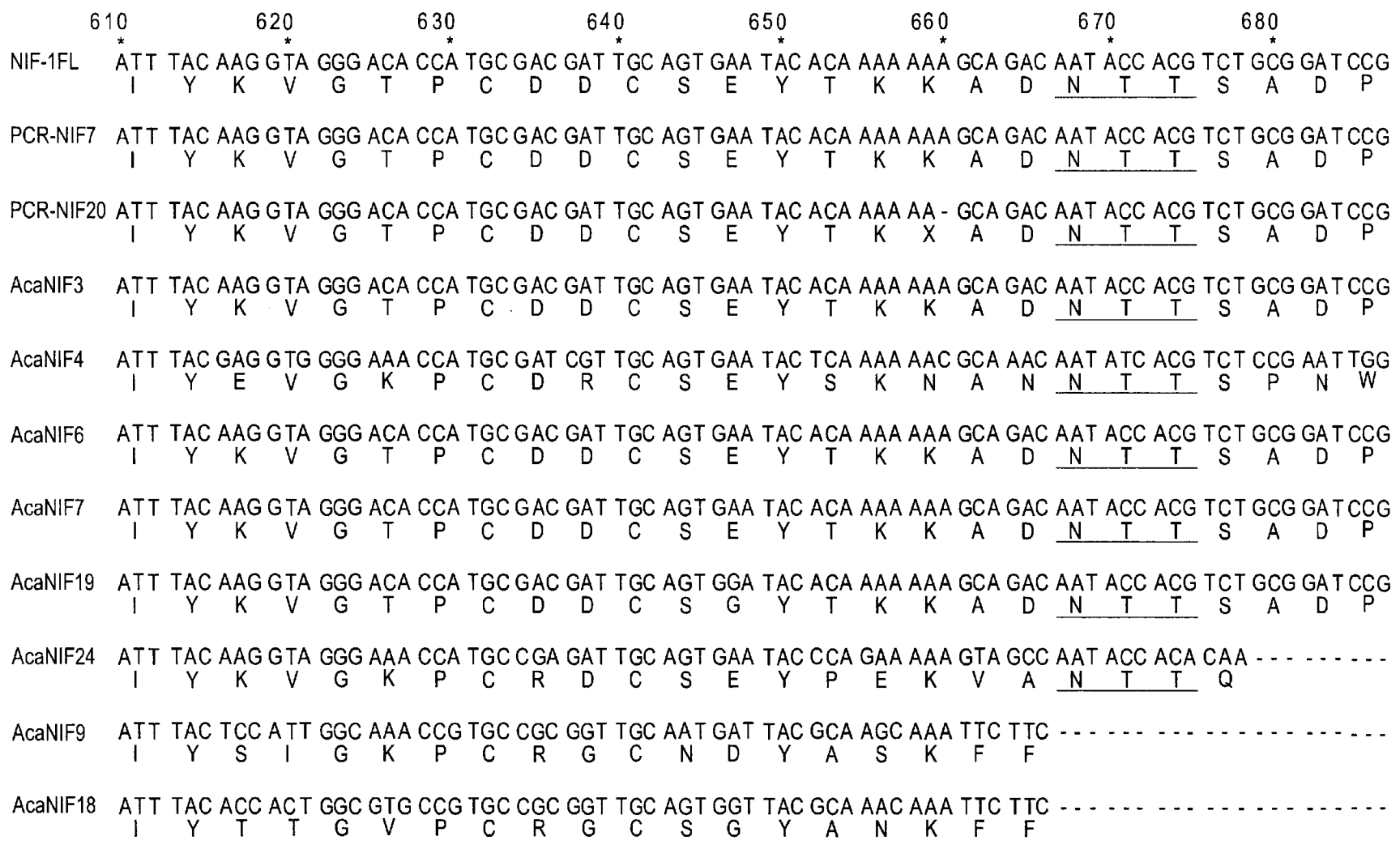

FIG. 16 depicts a comparison of the nucleotide (SEQ. ID. NOS. 89 to 99) and amino acid sequences of NIF proteins (SEQ. ID. NOS. 104 to 114) from hookworms. The sequences of NIF proteins depicted are NIF-1FL (SEQ. ID. NO. 104), PCR-NIF7 (SEQ. ID. NO. 105), PCR-NIF20 (SEQ. ID. NO. 106), AcaNIF3 (SEQ. ID. NO. 107), AcaNIF4 (SEQ. ID. NO. 108), AcaNIF6 (SEQ. ID. NO. 109), AcaNIF7 (SEQ. ID. NO. 110), AcaNIF19 (SEQ. ID. NO. 111), AcaNIF24 (SEQ. ID. NO. 112), AcaNIF9 (SEQ. ID. NO. 113), and AcaNIF18 (SEQ. ID. NO. 114). The NIF-1FL [SEQ. ID. NO. 89] nucleotide sequence is numbered; this numbering is also used to refer to positions in other genes. PCR-NIF7 [SEQ. ID. NO. 90] and PCR-NIF20 [SEQ. ID. NO. 91] were recovered by PCR-technology: the (regions matching with the) PCR-primers are italicized. AcaNIF7 (SEQ. ID. NOS. 95 and 114)and AcaNIF19 (SEQ. ID. NOS. 96 and 111) differ at only one position (G to E replacement; nucleotide-substitution located at position 647). The one remaining uncertainty in these sequences is at position 660 in PCR-NIF20 (SEQ. ID. NO. 91). No poly (A+) tail was found in NIF-1FL [SEQ. ID. NO. 89] sequence. Underlined sequences in the 3'-untranslated region (UAUAAA and AGUAAA) may serve as polyadenylation signals. Only the NIF-1FL [SEQ. ID. NO. 89], AcaNIF19 [SEQ. ID. NO. 96] and AcaNIF24 [SEQ. ID. NO. 97] cDNAs contain an entire secretion signal. The potential N-glycosylation sites (N-X-T/S) are underlined.

FIG. 19 depicts the nucleotide and amino acid sequence of a NIF protein from *A. ceylanicum* (AceNIF3) (SEQ. ID. NOS. 100 and 115). The underlined sequence (GAATTCCG) derives from the EcoRI linker that was added onto the cDNA. The sequence which may function as polyadenylation signal (AAUAAA) is also indicated. The encoded protein contains 10 potential N-glycosylation sites (N-X-T/S).

The NcoI and NotI restriction sites used for the cloning of the NIF-1FL coding region are indicated.

2) the bla gene which confers resistance to 100 μg/ml ampicillin or carbenicillin (bla/Ap$^R$).

3) the intergenic region, including the origin of replication, of filamentous phage M13 (M13-IR/ORI).

4) a ColE1-type plasmid borne origin of replication (ColE1-ORI).

In su$^{30}$ bacteria such as TG1, the pAN-NIF-1FL phagemid-vector codes for a NIF-1FL-pgIII fusion protein (pgIII; product of gIII) which becomes incorporated into filamentous virions upon infection of TG1 (pAN-NIF-1FL] cells with M13-VCS 'helper'-phage (Statagene). In su$^-$ strain WK6, pAN-NIF-1FL directs the synthesis of 'free' (not phage-attached) rNIF1which binds to the anti-NIF Mab 3D2 and to Mac-1.

TG1: Δ(lac-proAB), hsdΔ5 ($r_K^- m_K^-$), thi, supE/F' [traD36, lacI$^q$, lacZΔM15, proA$^+$B$^+$].

WK6: Δ(lac-proAB), galE, strA/F' (lacI, lacZΔM15, proA$^{B+}$].

Figure 22:
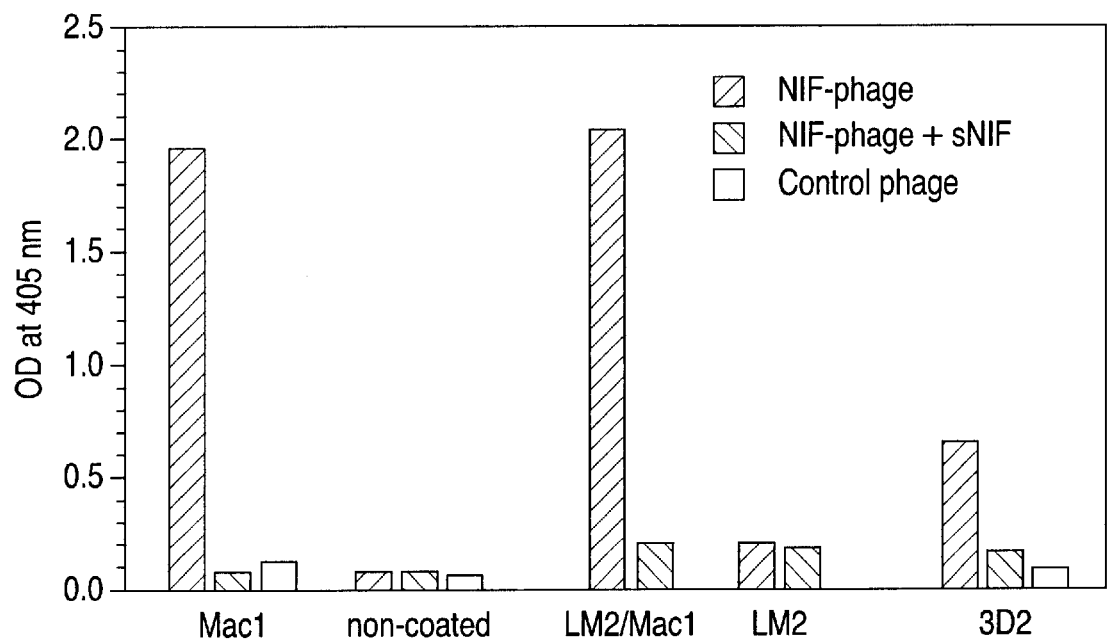

FIG. 22 depicts ELISAs with mature NIF-1FL-displaying phage (SEQ. ID. NO. 117). NIF-displaying phages (or non-displaying control phages, e.g. M13-VCS; in each experiment about 5×10$^9$ phage particles were added) were incubated in microtiter wells coated with Mac-1 (immunopurified on LM2-Sepharose), LM2/Mac-1, LM2 or the non-neutralizing anti-NIF MAb 3D2. In some experiments non-phage-attached 'soluble' NIF (sNIF) was allowed to react with the immobilized material (1 μM) 30 minutes prior to addition of the phages. Bound phages were detected with a rabbit anti-M13 serum and an alkaline phosphatase conjugated goat anti-rabbit serum.

Figure 23:
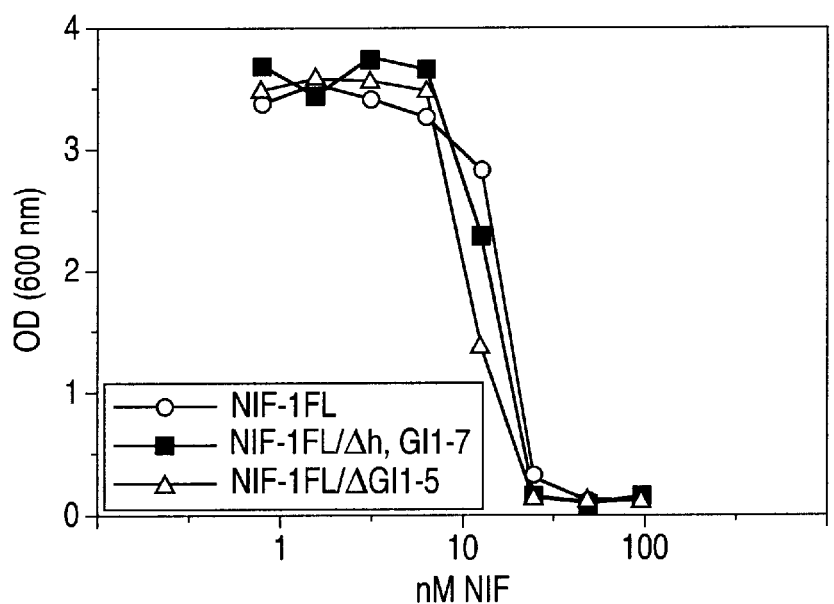
Figure 24A:
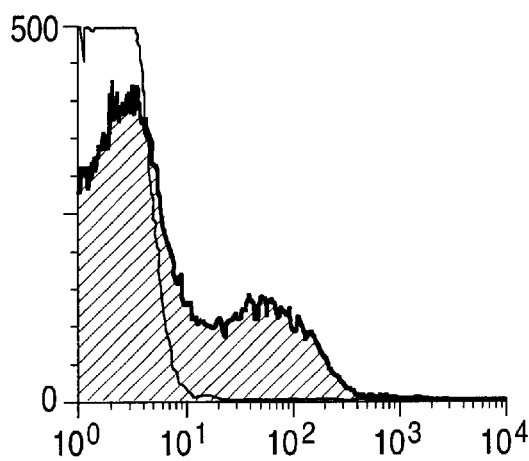
Figure 24D:
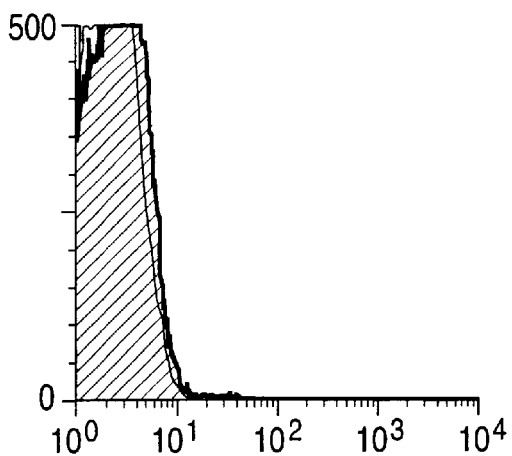
Figure 24B:
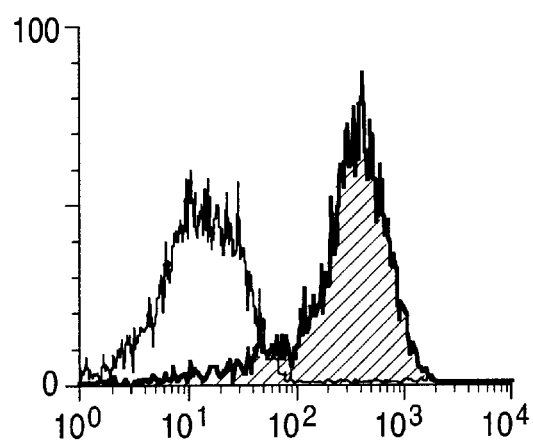
Figure 24E:
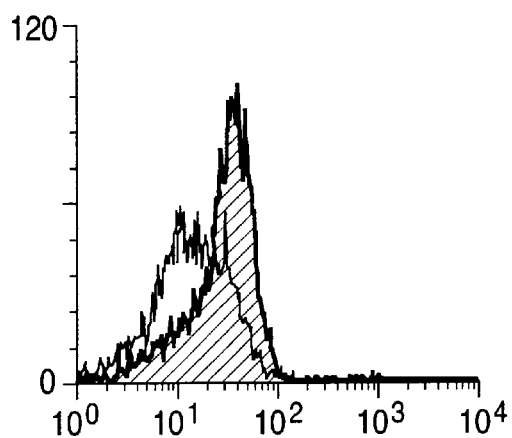
Figure 24C:
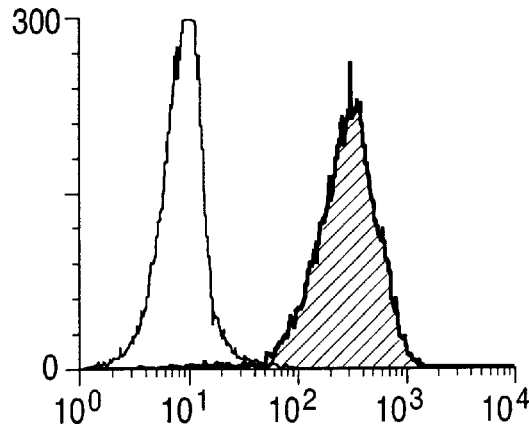
Figure 24F:
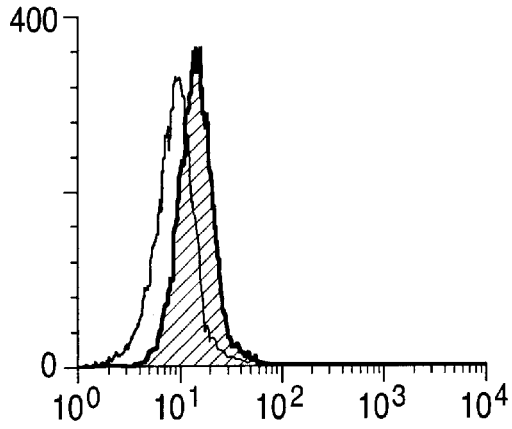

FIG. 23 depicts a comparison of the potency of AcaNIF1 (mature NIF-1FL) (SEQ. ID. NO. 117) with that of the mutants, AcaNIF1/Δh, Gl1–7 (SEQ. ID. NO. 129) and AcaNIF1/ΔGl1–5 (SEQ. ID. NO. 127), in a neutrophil-plastic adhesion assay of Example 1(C).

FIG. 24 depicts binding of rNIF-biotin to lymphocytes, monocytes and granulocytes as described in Example 30.

DETAILED DESCRIPTION OF THE INVENTION

1. Neutrophil Inhibitory Factor.

The present invention in its various aspects is directed to Neutrophil Inhibitory Factor ("NIF"), a protein that inhibits neutrophil activity and which is not an antibody, an integrin, a selectin or a member of the immunoglobulin superfamily of adhesive proteins and which, when isolated from a parasitic worm, is a glycoprotein. Recombinant NIFs produced by certain expression systems are not glycosylated. Such non-glycosylated NIFs are considered to be within the scope of the invention.

The inhibition of neutrophil activity by the NIFs of the present invention includes but is not limited to inhibition of one or more of the following activities by neutrophils: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis. Preferred assays include those where inhibition of neutrophil activity is demonstrated by an in vitro assay which determines adhesion of neutrophils to vascular endothelial cells, release of hydrogen peroxide from neutrophils, homotypic neutrophil aggregation or adhesion of neutrophils to plastic surfaces. Preferred NIFs would have an IC$_{50}$ of about 500 nM or less, more preferably less than 100 nM, as measured by one of these neutrophil activity assays. An IC$_{50}$ is that concentration of a NIF giving 50% inhibition of the measured activity (see Example 1).

The NIFs of the present invention are further characterized as also having the ability to bind to the Mac-1 receptor (see Example 14). A preferred assay for determining the binding of NIF to Mac-1 is described in Example 1(F)..

The NIFs of the present invention may be further characterized as having eosinophil inhibitory activity. A preferred assay for determining eosinophil inhibitory activity is the inhibition. of eosinophil activity demonstrated by an in vitro assay which determines adhesion of neutrophils to vascular endothelial cells as described in Example 29. A preferred NIF would have an IC$_{50}$ of about 500 nM or less, more preferably less than 100 nM, as measured by this eosinophil activity assay.

(a) Enriched Compositions.

In another aspect, the present invention is directed to compositions enriched for NIF, comprising NIF and which are a isolated by chromatographic or molecular biology methods, or a combination of both methods, from a parasitic worm, preferably a nematode.

Suitable parasitic worms include those selected from species of the phyla *Platyhelminthes, Nematoda, Nematomorpha* or *Acanthocephala*. An especially preferred source is endoparasitic hookworm species, such as those found to infect canines. It is believed that certain isoforms of NIF are produced by canine hookworm *Ancylostoma* species such as *Ancylostoma caninum*. Another suitable source is the endoparasitic worm species *Toxocara canis*. Substantially similar compounds may be isolated from other nematode species, as well as from other endoparasites of other phyla. Preferred sources for NIF include parasites, including parasitic worms, particularly endoparasitic nematodes and especially hookworm species, including *Ancylostoma braziliense, Ancylostoma caninum, Ancylostoma ceylanicum, Ancylostoma duodenale, Ancylostoma japonica, Ancylostoma malavanum, Ancylostoma tubaeforme, Bunostomum phlebotomum, Cyclodontostomum purvisi, Necator americanus, Necator argentinus, Necator suillus,* and *Uncinaria stenocephala*.

The enriched compositions may be enriched for NIF in one aspect by chromatographic methods, which methods may include chromatography on Concanavalin A Sepharose®, hydroxyapatite or an anion exchange column, gel filtration chromatography preferably using Superdex® 200, C4 reverse phase HPLC, isoelectric focusing or a combination of those methods or equivalent methods used for separating proteins or proteinaceous factors. For example, in place of Concanavalin A, other immobilized lectins may be used. In place of Superdex® 200, other acrylamide- or agarose-based gel filtration media which fractionate proteins in the appropriate molecular weight range may be used; these include those sold under the tradenames, Sephacryl® and Superose® (Pharmacia).

According to a preferred embodiment, the enriched composition is comprised of NIF. The NIF therein is a glycoprotein derived from or isolated from a parasitic worm, preferably a nematode, and more preferably a hookworm species, especially a canine hookworm species or, alternatively, a *Toxocara* species, or a compound, preferably a protein, which is substantially similar to said glycoprotein. It is believed that certain isoforms of said glycoprotein are produced by the canine hookworm *Ancylostoma caninum*.

By substantially similar is meant that the compound exhibits selective neutrophil inhibitory activity similar to that of the glycoprotein, and, preferably has an $IC_{50}$ of about 500 nM or less, more preferably less than 100 nM, as measured by neutrophil activity assays such as those described herein.

(B) Glycoprotein NIF and Isoforms.

In another aspect, the NIFs of the present invention comprise a purified glycoprotein. A NIF may be determined to be a glycoprotein by evaluating binding to Concanavalin A Sepharose (see Example 2(B)) and by positive testing as a glycoprotein in GlycoTrack™ diagnostic assay for the presence of carbohydrate groups (see Example 7).

One glycoprotein having neutrophil inhibitory activity which was isolated from canine hookworms has the following characteristics: This glycoprotein is acidic and exhibits an isoelectric point of about 4.5 as determined by isoelectric focusing (see Example 3). It has an observed molecular weight of about 41,000 daltons (±3,000) as determined by laser-desorption time-of-flight mass spectrometry (see Example 6). Its behavior when subjected to SDS-polyacrylamide gel electrophoresis indicated that it contained multiple disulfide bonds, since the reduced glycoprotein migrated on the gel at a significantly higher apparent molecular weight (see Example 5). The glycoprotein was demonstrated to specifically inhibit neutrophil activity and not to act as a general cytotoxin in another cell adhesion assay (see Example 13). This glycoprotein was demonstrated to inhibit neutrophil adhesion to vascular endothelial cells and homotypic neutrophil aggregation. One such enriched composition (see Example 2(D)) exhibited an $IC_{50}$ of about nM. An $IC_{50}$ is that concentration of inhibitor giving 50% inhibition of the measured activity (see Example 1). This glycoprotein was demonstrated to inhibit peritoneal inflammatory response when administered intraperitoneally or intravenously in an animal model of acute inflammation (see Example 16). This enriched composition was demonstrated to inhibit hydrogen peroxide release from neutrophils (see Example 1(E)) and neutrophil adhesion/spreading on plastic (see Example 1(C)). The Example 2(D) preparation had an $IC_{50}$ of about 10 nM. An enriched composition of the neutrophil function inhibitory factor was shown to have no inhibitory effect on platelet aggregation (see Example 13).

A second glycoprotein having neutrophil inhibitory activity has been isolated from *Toxocara canis*. This glycoprotein has an observed molecular weight of about 20,000 daltons as determined by molecular sieve chromatography. This glycoprotein was demonstrated to inhibit neutrophil adhesion to vascular endothelial cells and neutrophil adhesion/spreading on plastic.

In another aspect, the present invention is directed to methods for making enriched compositions comprising NIF, wherein such compositions are isolated from natural sources which may include but are not limited to the parasitic worms.

One preferred embodiment comprises isolating these enriched compositions by chromatographic methods, which methods would include chromatography on Concanavalin A-Sepharose®, hydroxyapatite or an anion exchange column, gel filtration chromatography preferably using Superdex® 200, C4 reverse phase HPLC, isoelectric focusing or a combination of those methods or equivalent methods used for separating proteins or proteinaceous factors. For example, in place of Concanavalin A-, other immobilized lectins may be used. In place of Superdex® 200, other acrylamide- or agarose-based gel filtration media which fractionate proteins in the appropriate molecular weight range may be used; these include those sold under the tradenames, Sephacryl® and Superose® (Pharmacia). Preferred methods of preparing enriched compositions comprising NIF are provided which comprise subjecting a lysate from a parasitic worm to the following isolation steps (a) chromatography on Concanavalin-A Sepharose, and (b) gel filtration on Superdex® 200, and (c) chromatography on ceramic hydroxyapatite. The enriched composition may be further enriched for NIF subjecting it to the further isolation step of reverse phase high performance liquid chromatography (HPLC) using a C4 column. Examples of methods of preparing the enriched compositions according to the present invention are described in Examples 2 to 5.

The enriched compositions comprising NIF isolated by chromatographic methods are at least about 50% pure, that is, they contain at least about 50% NIF. Preferably, the composition is enriched at least about 200-fold. According to another preferred embodiment, substantially pure Neutrophil Inhibitory Factor is prepared. By "substantially pure" is meant at least about 90 percent pure. More preferably the Neutrophil Inhibitory Factor so prepared is chromatographically pure.

It is believed that a NIF isolated from a particular source may include multiple isoforms. Accordingly such isoforms are considered to be scope of the present invention. Accordingly, in another aspect, the present invention is directed to a NIF which includes an amino acid sequence selected from the group consisting of (a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-X7-Ile [SEQ. ID. NO. 1], wherein X1 is Leu or Arg; $X_2$ is Gln, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;

(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala [SEQ. ID. NO. 2], wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys [SEQ. ID. NO. 3], wherein $X_{16}$ is Asn or Asp; $X_{17}$ is Val or Leu; $X_{18}$ is Ala or Thr; $X_{19}$, is Leu, Val or Phe; and $X_{20}$ is Thr, Lys or Asn;

(d) His-Val-Val-Cys-His-$X_{21}$-$X_{22}$-Pro-Lys [SEQ. ID. NO. 4], wherein $X_{21}$ is Tyr or Ile; and $X_{22}$ is Gly or no residue;

(e) Ile-Try-$X_{23}$-$X_24$-Gly-$X_{25}$-Pro-Cys-$X_{26}$-$X_{27}$-Cys-$X_{28}$-$X_{29}$-Tyr [SEQ. ID. NO. 5], wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile [SEQ. ID. NO. 6], wherein $X_{30}$ is His, Ile or Asn; $X_{31}$ is Ala, Pro or Asp; $X_{32}$ is Glu, Val, Asp or Ile; and $X_{33}$ is Ile, Val or Phe. The NIF may include from 1 to 6 of amino acid sequences (a) to (f) above. Preferably the NIF includes all of amino acid sequences (a) to (f). Preferably, the listed amino acid sequences appear in the following order in the protein (from amino terminal end to carboxy terminal end): (a), (b), (c), (d), (e), (f). Additional amino acid residues or peptide sequences may be interspersed between the above sequences or may be located at the amino terminal and/or carboxy terminal end of the protein (for example, see FIGS. 7 (SEQ. ID. NOS. 61 to 79) and 8 (SEQ. ID. NO. 81). The sequences depicted in FIG. 7 are T-24 [SEQ. ID. NO. 61], T-20 [SEQ. ID. NO. 62], T-22-10 [SEQ. ID. NO. 63], T-13 [SEQ. ID. NO. 64], T-15-6 [SEQ. ID. NO. 65], D-53 [SEQ. ID. NO. 60], D-54 [SEQ. ID. NO. 67), D-61 [SEQ. ID. NO. 68], D-67 [SEQ. ID. NO. 69], D-83 [SEQ. ID. NO. 70], D-85

[SEQ. ID. NO. 71], D-94 [SEQ. ID. NO. 72], D-96 [SEQ. ID. NO. 73], D-102 [SEQ. ID. NO. 74], K-34A (SEQ. ID. NO. 75], K-46B [SEQ. ID. NO. 76], K-48 [SEQ. ID. NO. 77], K-50A [SEQ. ID. NO. 78], and K-58A [SEQ. ID. NO. 79], and the sequences depicted in FIG. 8 are for clone 1FL, (SEQ. ID. NO. 81). The amino acid sequences of some of the NIF isoforms containing one or more of (a), (b), (c), (d), (e) or (f) are shown in FIG. 9 [SEQ. ID. NOS. 81 to 87] for canine hookworm NIF, in FIG. 16 for *Ancylostoma caninum* NIF (SEQ. ID. NOS. 104 to 114) and in FIG. 19 for *Ancylostoma ceylanicum* NIF (SEQ. ID. NO. 115). The isoform sequences depicted in FIG. 9 are 1FL [SEQ. ID. NO. 81], 3P [SEQ. ID. NO. 82], 1P [SEQ. ID. NO. 83], 2FL [SEQ. ID. NO. 84], 3FL [SEQ. ID. NO. 85], 4FL [SEQ. ID. NO. 86], and 6FL [SEQ. ID. NO. 87]. The sequences depicted in FIG. 16 are NIF-1FL (SEQ. ID. NO. 104), PCR-N1F7 (SEQ. ID. NO. 105), PCR-N1F20 (SEQ. ID. NO. 106), AcaNIF3 (SEQ. ID. NO. 107), AcaNIF4 (SEQ. ID. NO. 108), AcaNIF6 (SEQ. ID. NO. 109), AcaNIF7 (SEQ. ID. NO. 110), AcaNIF19 (SEQ. ID. NO. 111), AcaNIF24 (SEQ. ID. NO. 112), AcaNIF9 (SEQ. ID. NO. 113), and AcaNIF18 (SEQ. ID. NO. 114). FIG. 19 depicts the sequence for AceNIF3 (SEQ. ID. NO. 115). Preferred are NIFs comprising the amino acid sequence depicted in FIG. 8 (SEQ. ID. NO. 81).

According to the present invention, included are NIFs which have one or more of amino acid sequences (a), (b), (c), (d), (e) and (f) and exhibit neutrophil inhibitory activity in at least one of the in vitro assay. Suitable assays include those assays which determine adhesion of neutrophils to vascular endothelial cells, release of hydrogen peroxide from neutrophils, homotypic neutrophil aggregation and adhesion of neutrophils to plastic surfaces. Preferred are NIFs which have an $IC_{50}$ of about 500 nM or less, more preferably less than 100 nM, as measured by one these neutrophil activity assays and which do not substantially inhibit platelet aggregation at such neutrophil inhibitory concentrations. An $IC_{50}$ is that concentration of a NIF giving 50% inhibition of the measured activity (see Example 1).

The NIFs of the present invention are further characterized as also having the ability to bind to the Mac-1 receptor (see Example 14). A preferred assay for determining the binding of NIF to Mac-1 is described in Example 1(F).

The NIFs of the present invention are also further characterized as having eosinophil inhibitory activity. A preferred assay for determining eosinophil inhibitory activity is the inhibition of eosinophil activity demonstrated by an in vitro assay which determines adhesion of neutrophils to vascular endothelial cells as described in Example 29. Preferred are NIFs having an $IC_{50}$ of about 500 nM or less, more preferably less than 100 nM, as measured by this eosinophil activity assay.

(C) Recombinant NIFs.

In another aspect, the present invention is directed to NIFs made by methods comprising hybridizing the nucleic acid molecules from a source suspected to contain a NIF to certain oligonucleotide primers or cDNA made from such primers. Such NIFs exhibit neutrophil inhibitory activity. In yet another aspect, the present invention is directed to these methods of making NIFs.

In one preferred aspect, the present invention is directed to NIFs comprising an amino acid, sequence which is encoded by a nucleic acid sequence which is sufficiently complementary to hybridize to a primer derived from the amino acid sequence of a NIF. Preferred in the PCR cloning method are single stranded DNA primers of 20–100 nucleotides derived from the sequence of NIF from *Ancylostoma canium*. Preferred are primers having the following characteristics: limited degeneracy; adherence to codon usage preferences of the particular species from which the library is constructed and primers that target sequences which are conserved among the twelve *Ancylostoma caninum* NIF isoforms. Each PCR reaction utilizes two primers: a 5-primer that corresponds to the sense strand and a 3'-primer that corresponds to the antisense strand of the NIF coding sequence. Especially preferred are the primers 5-CTCGAATTCT(GATC)GC(ATC)AT(ATC)(CT)T (GATC)GG(ATC)TGGGC-3 [SEQ. ID. NO. 7] and 5'-CTCGAATTCTT(TC)TCTGG(GA)AA(GA)CG(GA)TC (GA)AA-3' [SEQ. ID. NO. 28]. The nucleotides within enclosing parentheses are redundant in that any one nucleotide may be used at the position enclosed by such parentheses.

The nucleic acid sequence of the DNA primers are preferably derived from the sequence of NIF from *Ancylostoma canium*. As described above, one example of NIF of the present invention comprises a glycoprotein which has been isolated in substantially pure form. Using procedures known in the art, one of ordinary skill in the art can use this protein to derive its amino acid sequence. For example, the protein may be analyzed to determine an N-terminal sequence, or fragments of the protein can be produced by enzymatic or other specific digestion procedures and the sequence of the terminal amino acids of those fragments determined. Such amino acid sequences, even if only between five and six contiguous amino acids in length, will provide sufficient information to determine potential DNA sequences of a gene encoding this protein.

If two or three such amino acid fragments are sequenced, a plurality of oligonucleotides can be synthesized using reported procedures, and such oligonucleotides can be used to probe a genomic or cDNA library from hookworm (or other source) to isolate the gene or fragments thereof encoding the sequenced protein. Those in the art will recognize that these oligonucleotides can be designed using standard parameters such that the oligonucleotide is chosen to encode the chosen amino acid sequence. For example, it is common to use a mixture of oligonucleotides as probes for any particular sequence of amino acids, with each oligonucleotide having the same nucleotide base sequence except at specific bases which are varied to take into account the redundancy of the codons that may code for any particular amino acid. It is of course desirable to select an amino acid sequence which is encoded by as few different oligonucleotides as possible. In addition, the various redundant codons may be specifically selected to represent those codons that are most preferred in, for example, hookworm nucleic acid.

In addition, the isolated pure NIF protein can be used to obtain antibodies using known procedures. Such antibodies may include monoclonal or polyclonal antibodies and can be used to screen bacteriophage lambda gt11 expression libraries containing other source (e.g., hookworm) DNA. In this manner, any particular clone which includes nucleic acid encoding a NIF can be readily identified using standard procedures.

Genomic DNA libraries of a hookworm, for example, can be formed using standard procedures to isolate the genomic DNA of the hookworm, fractionating that DNA using either a random procedure, such as sonication, or a specific procedure such as restriction endonuclease digestion and ligation of those fragments into an appropriate vector, such as a bacteriophage lambda, plasmid or cosmid vector. Such a library can be screened for useful clones by nucleic acid hybridization using the oligonucleotide mixtures described above. More preferably, however, a cDNA library can be constructed by isolation of total hookworm RNA, passage of that RNA over an oligo-dT column to purify the poly(A)-containing RNA (i.e., messenger RNA), and reverse transcription of such RNA to produce DNA fragments representative of the RNA (i.e., cDNA). These cDNA fragments can be inserted using standard procedures into any desired vector, for example, an expression vector such as a commercially available E. coli expression vector such as bacteriophage lambda-gt11 (for expression in E. coli), or into a plasmid pcDNA-1 which can be expressed in mammalian COS7 cells.

The biological activity of the protein expressed by individual clones of the plasmid expression library can be readily assayed using the neutrophil inhibitory activity assays described herein or other suitable assays. Alternatively, the antibodies described above can be used to probe for immunoreactive protein expressed from clones in the bacteriophage expression libraries (e.g., lambda-gt11). It is particularly preferred to screen various libraries in sub-pools, for example of 999 clones at a time, to determine which of those sub-pools includes a positive clone. When a positive clone is isolated a grid of the 999 colonies can be formed on a 33×33 plate and each of the 33 clones in each row and column in the plate assayed simultaneously (i.e., in 66 preparations) to identify the desired clone.

Once the desired clone is isolated, its structure is analyzed by standard procedures, for example, by DNA sequencing to determine whether it encodes the whole of the desired protein. If it does not, that clone can be used to screen further cDNA or genomic libraries for full-length clones, or the DNA can be used to hybrid select RNA present in the hookworm, or other source, and more selective cDNA libraries formed from that RNA using procedures described above.

In another preferred aspect, the present invention is directed to NIFs comprising an amino acid sequence which is encoded by a nucleic acid sequence which is sufficiently complementary to hybridize to cDNA probes derived from the amino acid sequence of a NIF. Preferred are probes having at least about 12 nucleotides which are complementary to a portion of the sequence of FIG. 8 [SEQ. ID. NO. 80].

It should be apparent to those skilled in the art that the oligonucleotide primers can be used in the polymerase chain reaction (PCR) to generate complementary DNA probes. These probes can be used to isolate NIF from other sources or isoforms from a single source. Preferred are animal, fungal, bacterial or viral sources. In the PCR cloning method, single stranded DNA primers of 20–100 nucleotides are derived from the sequence of NIF from Ancylostoma canium. Preferred primers have the following characteristics: limited.degeneracy; adherence to codon usage preferences of the particular species from which the library is constructed and primers that target sequences which are conserved among the twelve Ancylostoma NIF isoforms. Each PCR reaction utilizes two primers: a 5-primer that corresponds to the sense strand and a 3'-primer that corresponds to the antisense strand of the NIF coding sequence. Especially preferred are the primers 5-CTCGAATTCT(GATC)GC(ATC)AT(ATC)(CT)T(GATC)GG(ATC)TGGGC-3' [SEQ. ID. NO. 7] and 5'-CTCGAATTCTT(TC)TCTGG(GA)AA(GA)CG(GA)TC(GA)AA-3' [SEQ. ID. NO. 8]. The nucleotides within enclosing parentheses are redundant in that any one nucleotide may be used at the position enclosed by such parentheses.

Single stranded cDNA template is generated using poly (A)$^+$ or total RNA prepared from cells of the tissue or organism to be screened. RNA is primed with either random hexanucleotides or oligo d(T) and extended with reverse transcriptase. This reaction product is amplified using an appropriate DNA polymerase (e.g., Taq polymerase), with a sense and antisense primer, with an appropriate thermocycler.

A wide variety of polymerase chain reaction conditions may be employed, but initial experiments preferably involve relatively low stringency annealing and elongation steps. Preferred conditions are: cycles 1–3, denaturation at 94° C. for 1 minute, annealing at 37° C. for 1 minute and elongation at 72° C. for two minutes. The ramp time between annealing and elongation steps is extended to at least 2 minutes for these cycles; cycles 4–40, denaturation at 94° C. for 1 minute, annealing at 45° C. for 1 minute and elongation at 72° C. for two minutes. In subsequent experiments, annealing temperature is increased until a single product results from amplification with each primer pair.

Amplification products from individual amplification reactions are used as hybridization probes to screen genomic DNA or cDNA libraries constructed from the tissue from which PCR was effected. DNA or cDNA from any recombinant plaque or colony that hybridized to these amplification products is selected for further analyses.

NIF complementary DNAs isolated using the techniques described above are subjected to nucleotide sequence analysis using the procedure of dideoxy sequencing (Sanger et al, 1977, Proc. Natl. Acad. Sci USA 74:5463–5467).

NIF cDNA isolates containing open reading frames (i.e., initiating with a methionine and terminating with a TAA, TGA or TAG stop codon) are inserted into suitable vectors for protein expression in either bacterial, yeast, insect or mammalian cells. Expression systems comprise vectors designed to secrete recombinant protein (i.e., fusion of cDNA isolate open reading frame with a known secretion signal sequence for that cell type) into the culture medium. Vectors lacking a secretion signal sequence are also used for expression. Either conditioned media or cell lysate, depending on the expression system used, is tested for inhibitory activity using one or more of the following criteria for neutrophil activation: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis.

As discussed above and as described in Example 10, oligonucleotide primers derived from the peptide sequences of NIF (isolated from the hookworm, Ancylostoma caninum) were used in conjunction with the polymerase chain reaction to amplify NIF cDNA sequences. These NIF sequences were used in turn to probe a hookworm cDNA library. Ten full-length and six partial clone isoforms of NIF were isolated in addition to the protypical NIF-1FL full-length clone. This example illustrates the utility of this technique for isolation of sequences that are structurally related to NIF.

Applicants note that by using techniques such as those described above, as well as similar and equivalent techniques, DNA sequences which encode NIF from other animal, fungal, bacterial or viral source may be isolated and used to express recombinant NIF.

Should immunoreactive material be expressed from an expression library, the expression vectors described above, or derivatives thereof, can be used for expression of recombinant protein with biological activity. Such recombinant protein is useful in this invention.

Using one example of a NIF of the present invention, peptide fragments were produced and their amino acid sequences determined. This experiment is described in Example 9. The amino acid sequences obtained for the proteolytic fragments are set forth in FIG. 7 [SEQ. ID. NOS. 61 to 79). The fragments depicted in FIG. 7 are T-24 [SEQ. ID. NO. 61], T-20 [SEQ. ID. NO. 62], T-22-10 [SEQ. ID. NO. 63], T-13 [SEQ. ID. NO. 64], T-15-6 (SEQ. ID. NO. 65], T-53 [SEQ. ID. NO. 66], D-54 [SEQ. ID. NO. 67], D-61 [SEQ. ID. NO. 68], D-67 [SEQ. ID. NO. 69], D-83 [SEQ. ID. NO. 70], D-85 [SEQ. ID. NO. 71], D-94 [SEQ. ID. NO. 72], D-96 [SEQ. ID. NO. 73], D-102 [SEQ. ID. NO. 74], K-34A [SEQ. ID. NO. 75], K-46B [SEQ. ID. NO. 76], K-48 [SEQ. ID. NO. 77], K-50A [SEQ. ID. NO. 78], and K-58A [SEQ. ID. NO. 79].

An example of NIFs being cloned from a canine hookworm cDNA library as described in Examples 10 and 21. The nucleotide sequence for the cDNA of one of the isolated clones (clone 1FL) is depicted in FIG. 8 [SEQ. ID. NO. 80]. Deduced partial amino acid sequences for other isolated NIF isoform clones are depicted in FIGS. 9 [SEQ. ID. NOS. 81 to 87] and 16 (SEQ. ID. NOS. 104 to 114). The isoform sequences depicted in FIG. 9 are 1FL [SEQ. ID. NO. 81], 3P [SEQ. ID. NO. 82], 1P [SEQ. ID. NO. 83], 2FL [SEQ. ID. NO. 84], 3FL [SEQ. ID. NO. 85], 4FL [SEQ. ID. NO. 86], and 6FL [SEQ. ID. NO. 87). The sequences depicted in FIG. 16 are NIF-1FL (SEQ. ID. NO. 104), PCR-NIF7 (SEQ. ID. NO. 105), PCR-NIF20 (SEQ. ID. NO. 106), AcaNIF3 (SEQ. ID. NO. 107), AcaNIF4 (SEQ. ID. NO. 108), AcaNIF6 (SEQ. ID. NO. 109), AcaNIF7 (SEQ. ID. NO. 110), AcaNIF19 (SEQ. ID. NO. 111), AcaNIF24 (SEQ. ID. NO. 112), AcaNIF9 (SEQ. ID. NO. 113), and AcaNIF18.(SEQ. ID. NO. 114).

By using the techniques described herein and other techniques in the art, NIFs may be isolated from any source, whether, animal, bacterial, fungal, viral or other source suspected of having a NIF. Such NIFs and nucleic acid sequences encoding them may be isolated by methods such as probing a genomic or cDNA library from the source suspected of having a NIF using oligonucleotide probes sufficiently complementary to a nucleic acid sequence encoding a NIF such as those sequences depicted in FIG. 8, and then isolating and expressing those nucleic acid sequences which hybridize to the probes as described herein. Such probes have a sufficient number of nucleotides to describe a unique sequence. Typically such probes will have at least about 12 nucleotides. One preferred group of probes include those of the sequences: 5'-CTCGAATTCT(GATC)GC(ATC)AT(ATC)-(CT)T(GATC)GG(ATC)TGGG C-3' [SEQ. ID. NO. 7] and 5'-CTCGAATTCTT(TC)TC-TGG (GA)AA(GA)CG(GA)TC(GA)AA-3' (SEQ. ID. NO. 8]. The nucleotides within enclosing parentheses are redundant in that any one nucleotide may be used at the position enclosed by such parentheses.

Alternatively, NIF proteins and nucleic acids coding for such proteins may be isolated by probing a sample of nucleic acid from a source suspected of having a NIF with an oligonucleotide probe having at least about 12 nucleotides which is complementary to a nucleic acid sequence known to encode a NIF, such as the sequence depicted in FIG. 8 and isolating those nucleic acid sequences, such as a gene, which are sufficiently complementary to the oligonucleotide probe to hybridize thereto. The isolated nucleic acid sequence may then be cloned and expressed using art techniques.

(D) Isolated Nucleic Acid Molecules.

In another aspect, the present invention is directed to isolated nucleic acid molecules comprising a nucleic acid sequence encoding the amino acid sequence of NIF. The DNA isolate may also include additional sequences which do not code for portions of the finished protein, such as introns, and/or sequences which code for intervening amino acid residues or peptides in addition to the above peptide sequences. Preferred isolated nucleic acid molecules are those which encode a NIF comprising at least one amino acid sequence selected from the group consisting of (a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile [SEQ. ID. NO. 1], wherein $X_1$ is Leu or Arg; $X_2$ is Gln, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;

(b) Ala-$X_8$-$X_9$-Ala-Ser-X10-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala [SEQ. ID. NO. 2], wherein $X_8$ is His or Pro; $X_9$ is Thr, Arg or Ser; $X_{10}$ is Arg or Lys; $X_{11}$, is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cy5-Ala-Val-Val-$X_{20}$-Cys [SEQ. ID. NO. 3], wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;

(d) His-Val-Val-Cys-His-$X_{21}$-$X_{22}$-Pro-Lys [SEQ. ID. NO. 4], wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-CYS-$X_{28}$, $X_{29}$-Tyr [SEQ. ID. NO. 5], wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile [SEQ. ID. NO. 6], wherein $X_{30}$ is His, Ile or Asn; $X_{31}$ is Ala, Pro or Asp; $X_{32}$ is Glu, Val, Asp or Ile; and $X_{33}$ is Ile, Val or Phe. Especially preferred isolated nucleic acid molecules include those wherein its the coding region has the nucleotide sequence and/or codes for a protein having the deduced amino acid sequence set forth in FIG. 8 (SEQ. ID. NO. 81).

(E) Expression of NIF.

In another aspect, the present invention is directed to methods for making biologically active NIFs, wherein such NIFs are expressed intracellularly and are optionally secreted; expression vectors encoding NIF; and host cells transformed with these expression vectors which express and, optionally, secrete NIF.

The cDNA encoding NIF may be inserted into a replicable vector for expression, resulting in the synthesis of biologically active recombinant NIF. Many vectors are available for expression of heterologous proteins and selection of the appropriate vector will depend primarily on the desired properties of the host cell. Each of the available vectors contain various components specific to the host cell to be transformed. The vector components or control elements generally include, but are not limited to, one or more of the following: a signal sequence, an origin of replication, one or more marker genes, a promoter, an enhancer element and a transcription termination sequence. Once the expression vector containing the inhibitor is constructed, a suitable host cell is transfected or transformed with the expression vector, and recombinant NIF is purified either from the host cell itself or the host cell growth medium.

In general, the signal sequence may be a component of the vector, or it may be encoded by the NIF DNA that is inserted into the vector. If the native inhibitory factor is a secreted gene product (i.e., from the hookworm (or other source) cells), then the native pro-NIF from hookworm DNA may encode a signal sequence at the amino terminus of the polypeptide that is cleaved during post-translational processing of the polypeptide to form the mature NIF.

All vectors contain a nucleic acid sequence that enables the vector to replicate in one or more selected host cells.

Generally, in cloning vectors this sequence is one that enables the vector to replicate independently of the host chromosomal DNA, and includes origins of replication or autonomously replicating sequences. Such Sequences are well known for a variety of bacterial, yeast, insect and mammalian cells. The origin of replication from the plasmid pBR322 is suitable for most for most gram-negative bacteria, the 2 m plasmid origin is suitable for yeast, the baculovirus origin is suitable for some insect cells (e.g., Sf9 cells; ATCC# CRL1711) and various viral origins (e.g., SV40, adenovirus) are useful for cloning vectors in mammalian cells.

Expression vectors preferably contain a selection gene, also termed a selectable marker. This gene encodes a protein necessary for the survival or growth of transformed host cells grown in selective culture medium. Host cells not transformed with the vector containing the selection gene will not survive in the culture medium. Typical selection genes encode proteins that (a) confer resistance to antibiotics or other toxins, e.g., ampicillin, neomycin or methotrexate, (b) complement auxotrophic deficiencies, or (c) supply critical nutrients not available from complex media.

Expression vectors contain promoters that are recognized by the host organism. Promoters are untranslated sequences located upstream (5') to the start codon of a structural gene (generally within about 100 to 1000 base pairs) that control the transcription and translation of a particular nucleic acid sequence, such as hookworm NIF, to which they are operably linked. A large number of promoters recognized by a variety of potential host cells are well known. These promoters are operably linked to DNA encoding the NIF by inserting the latter into the vector in a way such that the 5' terminus of the NIF DNA is in close linear proximity to the promoter.

Transcription of a DNA encoding the NIFs of this invention by higher eukaryotes is often increased by inserting an enhancer sequence into the vector. (For example, see, Kriegler, M., 1991, *Gene Transfer and Expression,* pages 4–18, W. H. Freeman, New York). Enhancers are cis-acting elements of DNA, usually about 10–300 base pairs in length, that act on a promoter to increase its transcription. Enhancers are relatively orientation and position independent. Typically, one will use an enhancer from a eukaryotic cell virus for expression in mammalian cells. Examples include the SV40 enhancer, the cytomegalovirus early promoter enhancer and the adenovirus enhancers.

Expression vectors used in eukaryotic (i.e., non-bacterial) host cells will also contain sequences necessary for the termination of transcription and for stabilizing the mRNA. Such sequences are commonly available from the 5' end and, occasionally from the 3' untranslated regions of eukaryotic or viral DNAS.

Preferred expression vectors of the present invention include but are not limited to pHIL7SP-Nlc10, pSG5/NIF1FLCR1, pMa5-NI1/3, pAN-NIF-1FL, pYAM7SP-hNIF1/Δ, Gl1–5, pYAM7SP-hNIF1/Δ, Gl1–5, pYAMSP-AcaNIF4, pYAMSP-AcaNIF6, pYAMSP-AcaNIF9, pYANSP-AcaNIF24 and pAN-AceNIF3, the construction of which is described in the Examples.

Suitable host cells for the expression vectors described herein include bacterial, yeast, insect or mammalian cells. Preferred bacteria include *E. coli* strains, preferred yeast include *Saccharomyces cerevisiae* and *Pichia pastoris,* a preferred insect cell line is Sf9 (ATCC# CRL 1711); preferred mammalian cell lines are COS-7 (ATCC# CRL 1651), CHO dhfr⁻ (ATCC# CRL 9096), CHO-K1 (ATCC# CCL 61) and HeLa (ATCC# CCL 2). These examples of host cells are illustrative rather than limiting. Preferably the host cell should secrete animal amounts of proteolytic enzymes. Particularly suitable host cells for the expression of glycosylated NIF are derived from multicellular organisms. Such host cells are capable of complex post-translational processing and glycosylation of expressed proteins.

Host cells are transfected and preferably transformed with the above-described expression vectors of this invention and cultured in conventional nutrient media modified as appropriate for inducing promoters and selecting transformants. Transfection refers to the taking up of an expression vector by a host cell. Numerous methods of transfection are known to the ordinarily skilled artisan, for example, calcium phosphate coprecipitation, spheroplasting transformation and electroporation. Successful transfection is generally recognized when any indication of the operation of this vector occurs within the host cell. Transformation means introducing DNA into an organism so that the DNA is replicable, either as an extrachromosomal element or chromosomal integration. Depending on the host cell used, transformation is done using standard techniques appropriate to such cells (e.g., calcium chloride or electroporation for bacterial cells; spheroplasting or electroporation for yeast cells; calcium phosphate or electroporation for insect and mammalian cells).

The recombinant hookworm NIF preferably is recovered from the culture medium as secreted polypeptide, although it may also be recovered from host cell lysates when expressed intracellularly without a signal or secretory sequence. The expressed hookworm NIF may be purified from culture medium or from cell lysates by a variety of separation techniques including, but not limited to, gel filtration, affinity and ion exchange chromatography, hydroxyapatite chromatography, C4 reverse-phase HPLC and preparative isoelectric chromatography.

(F) Mutant NIFs.

In another aspect, the present invention is directed to mutant NIFs comprising the amino acid sequence shown in FIG. 8 (SEQ. ID. NO. 81) for mature NIF-1FL (SEQ. ID. NO. 117), wherein one or more of asparagine residues at positions 10, 18, 87, 110, 130, 197 or 223 is replaced by an glutamine residue.

Amino acid sequence variants of NIF may be prepared by introducing nucleotide changes into the DNA which encodes NIF, isolated as described above. Such variants include substitutions of residues within the amino acid sequence of the NIF. Any combination of substitutions can be made to arrive at the final construct, provided that the final construct possesses certain desired characteristics. The desired characteristics include, but are not limited to, an increased potency over the wild-type NIF and alteration of the amount of glycosylation of NIFs. Once variant NIF DNAs have been constructed, variant recombinant forms of NIF may be synthesized utilizing expression systems as described above. One possible method for preparing variants of NIF is mutagenesis with base-specific chemical mutagens as described in detail by Pine and Huang (1987, Methods Enzymol. 154, 415–430). Another approach is site-directed mutagenesis, for example, as described in Stanssens et al. (1989), Nucl. Acids Res., 17: 4441–4454. For example, Example 25 describes the substitution of certain asparagine residues in the amino acid sequence of a NIF referred to as mature NIF-1FL (SEQ. ID. NO. 117) (see FIG. 8 (SEQ. ID. NO. 81)) by site-specific mutagenesis.

The asparagine residues at positions 10, 18, 87, 110, 130, 197 and 223 of the amino acid sequence of NIF isoform, mature NIF-1FL (SEQ. ID. NO. 117), are believed to be sites associated with the potential N-linked glycosylation of this isoform. Using the stepwise site-directed procedure of Stanssens et al. and the five oligonucleotides described in Example 25 (SEQ. ID. NOS. 52 to 56), asparagine residues at positions 10, 18, 87, 110 and 130 of mature NIF-1FL (SEQ. ID. NO. 117) were replaced by glutamine residues to yield a mutant NIF. Subsequently, the cDNA encoding this mutant was further mutagenized by the same procedure using other oligonucleotides described to produce a mutant NIF, wherein the asparagine residues at positions 197 and 223 of the amino acid sequence of mature NIF-1FL (SEQ. ID. NO. 117) were also replaced with glutamine residues. In either case, the expressed mutant NIFs were found to have neutrophil inhibitory activity.

2. Peptide Fragments.

In another aspect, the present invention is directed to peptide fragments having neutrophil inhibitory activity which are prepared by proteolytic or chemical methods starting with the chromatographically pure NIF of the present invention.

Active peptide fragments, with or without sugar moieties, may be generated by using enzymatic or chemical techniques. Proteolytic cleavage can be accomplished by digestion of the inhibitor with one or more of the following enzymes: chymotrypsin, trypsin, leucine aminopeptidase, endoproteinase Glu-C, endoproteinase Lys-C, endoproteinase Arg-C, or endoproteinase Asp-N (Carrey, E. A., 1989 *Protein Structure. A Practical Approach*, pp. 117–143, T. E. Creighton, ed. IRL Press, New York). Chemical digestion of the inhibitor may be accomplished by cyanogen bromide, hydroxylamine, or 2-nitro-5-thiocyanobenzoate cleavage (Carrey, E. A., 1989, ibid.). Sugar moieties can be removed from either the peptide fragments or intact neutrophil inhibitory protein enzymatically with one or more of the following enzymes: glycopeptidase F, endoglycosidase H, endoglycosidase F, or endoglycosidase D as described by Keesey (Keesey, J., 1987 *Biochemica Information*, pp. 147–165, J. Keesey, ed., Boehringer Mannheim Biochemicals, Indianapolis). Alternatively, glycosylation of the intact inhibitor may be suppressed by expression of the protein in bacterial cells or by the inclusion of inhibitors of glycosylation in the eukaryotic cell culture growth medium. Inhibitors of glycosylation and their uses are described in the art (e.g., Keesey, J. 1987 *Biochemica Information*, pp. 135–141, J. Keesey, ed., Boehringer Mannheim Biochemicals, Indianapolis). Separation of active fragments from inactive fragments may be accomplished by conventional, low, medium, or high pressure chromatographic techniques known in the art.

3. Antibodies.

In another aspect, the present invention is directed to polyclonal and monoclonal antibodies which have the ability to bind to NIFs.

To prepare antibodies to NIF, any one of a number of conventional techniques which are known in the art can be employed. In one such technique, polyclonal antibodies are synthesized by injecting an animal (for example a rabbit) with one or more NIF of the present invention. After injection, the animal produces antibodies to these NIFs. When the antibody concentration (or titer) reaches a sufficient level, antibody-containing blood is then drawn from the animal, antiserum is prepared from the blood, and the compound-specific antibody is isolated from other antibodies in the serum by any one of a number of separation techniques (for example, affinity chromatography).

Monoclonal antibodies may be prepared using the techniques of Kohler and Milstein, Nature 256, 495–497 (1975) as well as other conventional techniques known to those skilled in the art. (See e.g., Harlow and Lane, *Antibodies. A Laboratory Manual* (Cold Spring Harbor Laboratory, 1988) the disclosures of which is incorporated herein by reference). Preferred monoclonal antibodies include those directed to the NIF isoform, 1FL, whose amino acid sequence is depicted in FIG. 8 and which are immunoglobulins of the IgG class. Especially preferred monoclonal antibodies are those which bind to the same epitope on this NIF as is bound by the monoclonal antibody, 3D2. The monoclonal antibody referred to as 3D2 is a preferred embodiment. The preparation of 3D2 is described in Example 26.

In another aspect, the present invention is directed to hybridomas which produce such monoclonal antibodies. These hybridomas are produced by conventional techniques such as those described by Harlow and Lane, Id., the disclosures of which is incorporated herein by reference. The preparation of a preferred hybridoma is described in Example 26.

In another aspect, the present invention is directed to methods of affinity purification of NIF from various sources and impure compositions of NIF derived from such sources using an antibody to NIF. Preferred method of isolating NIF would comprise the step of contacting a sample thought to contain a NIF with a monoclonal antibody which is capable of binding to said NIF. Preferred as the monoclonal antibody is either the monoclonal antibody, 3D2, or a monoclonal antibody binding to the same epitope on said NIF as is bound by the monoclonal antibody, 3D2. According to preferred methods of affinity purification the monoclonal antibody is covalently attached to a chromatographic resin. Especially preferred chromatographic resins include Emphaze™ Biosupport Medium (3M Corp.). Examples 27 and 28 describe preparation of a chromatographic resin coupled with the monoclonal antibody, 3D2, and its use to purify NIF from compositions comprising NIF.

In another aspect, the present invention is directed to immunoassays using the antibodies against NIF. Depending on the particular use for the immunoassay, an immunoassay format is selected. Some suitable immunoassays are described by Harlow and Lane, Id. (See especially pages 553 to 612), the disclosures of which are incorporated herein by reference.

Immunoassays utilizing the solid phase method or liquid phase method are well known to one skilled in the art of immunoassays. For example, monoclonal antibodies may be used to assay for drugs, hormones and proteins with such assays being in a solid phase or liquid phase format. The preferred methods of the present invention are solid phase assays.

The preferred methods of detecting NIF in a sample comprise contacting a sample thought to contain a NIF with a monoclonal antibody which is capable of binding to such NIF. According to a preferred embodiment, the monoclonal antibody is immobilized onto a plastic surface such polystyrene, polypropylene, polyethylene, nylon and the like. The plastic surface may be configured in the shape of test tube, microspheres, macroscopic beads, microtiter plates and the like. In this embodiment, monoclonal antibodies may be attached to the plastic surface by either covalent coupling or by passive absorption, preferably by passive absorption. Preferred as monoclonal antibodies are those which bind to the same epitope on a NIF as is bound by the monoclonal antibody, 3D2, or the monoclonal antibody, 3D2.

The monoclonal antibody may be contacted simultaneously with sample and a NIF which has been covalently linked to a detectable label. Alternatively, the monoclonal antibody may first be contacted with the sample, then with a NIF which has been covalently linked to a detectable label.

Preferred detectable labels are enzymes, fluorescent compounds or radioisotopes. Especially, preferred detectable labels are enzymes such as alkaline phosphatase, β-galactosidase or horseradish peroxidase, or radioisotopes such as iodine-125. The manner of covalently linking such enzymes and radioisotopes to monoclonal antibodies is well known to one skilled in the art of diagnostic assays.

4. Methods of Detecting NIF Mimics and NIF Antagonists.

In another aspect, the present invention is directed to a method of detecting in a sample the presence of a NIF mimic which competes with NIF for binding to Mac-1 receptor. In another aspect, the present invention is directed to a NIF antagonist which prevents NIF from binding to the Mac-1 receptor. The methods comprise contacting said sample with Mac-1 receptor. NIF mimics and NIF antagonists include but are not limited to small molecules, peptides, peptide analogs or proteins.

In preferred embodiments, NIF mimics or antagonists to be tested are preincubated in solution with neutrophils or immobilized Mac-1 receptor and the preincubated solution is then brought into contact with labeled NIF. The effect of test compound on the binding of NIF to neutrophils or of NIF to Mac-1 is then determined.

In one preferred embodiment, the assay method uses neutrophils which are free in solution. Here, NIF which has been linked to a detectable label, neutrophils and a sample thought to contain a NIF mimic or NIF antagonist are co-incubated in solution for a sufficient time to allow binding to occur. Unbound labeled NIF is removed from bound NIF by methods such as centrifugation, filtration or other suitable methods and bound NIF is determined by means of the detectable label.

In another preferred embodiment, neutrophils are immobilized on a plastic surface by passive absorption or chemical fixation such as by glutaraldehyde or similar chemicals. Labeled NIF is co-incubated with the immobilized neutrophils and a sample thought to contain a NIF mimic or NIF antagonist. Unbound labeled NIF is removed by washing and bound labeled NIF is then determined by means of the detectable label.

In an especially preferred embodiment, Mac-1 receptors from a detergent extract of human leukocytes are captured by anti-Mac-1 monoclonal antibody which is immobilized to a plastic surface. A NIF which is linked to a detectable label or a NIF which can be subsequently linked to a detectable label, and sample thought to contain a NIF mimic or NIF antagonist are co-incubated with the immobilized Mac-1 receptor. After the binding has occurred, unbound NIF is removed by washing. Detectable label is then added which links to NIF rendering it detectable (if the NIF was not originally linked to such label). Bound NIF is then determined by means of the detectable label.

Anti-Mac-1 antibody may be coupled to a plastic surface by covalent coupling or passive absorption, though passive absorption is preferred. Preferred plastic surfaces are polystyrene, polypropylene, polyethylene, nylon and the like, though polystyrene is preferred. The plastic surface may be configured in the shape of test tube, microspheres, macroscopic beads, microtiter plates and the like. A preferred anti-Mac-1 antibody is the monoclonal antibody referred as LM2.

NIF is linked to a detectable label or is capable of being linked to such label during a step of an assay method of the present invention. NIF is linked to a detectable label by covalent coupling using homobifunctional crosslinking reagents such as glutaraldehyde, disuccinimidyl suberate, dimethyl suberimidate and the like. NIF is made capable of being linked to a detectable label during a step of an assay method of the present invention by first linking biotin to NIF and avidin to the detectable label. Preferred detectable labels include enzymes, fluorophores or radioisotopes. Especially preferred detectable labels include alkaline phosphatase, β-galactosidase, horseradish peroxidase, or iodine-125.

A NIF mimic or NIF antagonist may be assayed for neutrophil inhibitory activity. Neutrophil inhibiting activity may be demonstrated by an assay such as those assays which determine adhesion of neutrophils to vascular endothelial cells, release of hydrogen peroxide from neutrophils, homotypic neutrophil aggregation and adhesion of neutrophils to plastic surfaces. NIF mimics are characterized as having an $IC_{50}$ for inhibiting neutrophil activity of about 500 nM or less, though an $IC_{50}$ is about 100 nM or less is preferred. NIF antagonists are characterized having such an $IC_{50}$ of about 1,000 nM to about 1 mM, although an $IC_{50}$ of about 5,000 nM to about 10 nM is preferred. An $IC_{50}$ is that concentration of a NIF mimic or NIF antagonist giving 50% inhibition of the measured activity (see Example 1).

Optionally a NIF mimic or NIF antagonist may be assayed for eosinophil inhibitory activity. Eosinophil inhibiting activity is demonstrated by an assay which determines adhesion of eosinophils to vascular endothelial cells. If assayed, NIF mimics are characterized as having an $IC_{50}$ for inhibiting eosinophil activity of about 500 nM or less, though a $IC_{50}$ is about 100 nM or less is preferred. If assayed, NIF antagonists are characterized having such an $IC_{50}$ of about 1,000 nM to about 1 mM, though an $IC_{50}$ of about 5,000 nM to about 10 mM is preferred. An $IC_{50}$ is that concentration of a NIF mimic or NIF antagonist giving 50% inhibition of the measured activity.

In another aspect, the present invention is directed to NIF mimics and NIF antagonists discovered by the above-disclosed methods of detection of this section.

5. Pharmaceutical Formulations and Methods of Treatment.

In another aspect, the present invention is directed to pharmaceutical compositions comprising NIF.

These pharmaceutical compositions may be formulated and used as tablets, capsules or elixirs for oral administration; suppositories for rectal administration; sterile solutions, suspensions for injectable administration and the like. The dose and method of administration can be tailored to achieve optimal efficacy but will depend on such factors as weight, diet, concurrent medication and other factors which those skilled in the medical arts will recognize. Generally, an amount between 0.01 mg/kg to 100 mg/kg body weight/day is administered dependent upon the potency of the composition used.

Preferred embodiments encompass pharmaceutical compositions prepared for storage and subsequent administration which comprise a therapeutically effective amount of NIF or an enriched composition of NIF, as described herein in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of phydroxybenzoic acid may be added as preservatives. In addition, antioxidants and suspending agents may be used.

In another aspect, the present invention is directed to methods of preventing in a mammal an inflammatory condition characterized by abnormal neutrophil activation or abnormal eosinophil activation comprising administering to said mammal a therapeutically effective amount of a NIF or their pharmaceutical compositions. In practicing the preferred methods, NIFs or their pharmaceutical compositions can be used alone or in combination with one another, or in combination with other therapeutic or diagnostic agents. These compositions can be utilized in vivo, ordinarily in a mammal, preferably in a human, or in vitro.

In employing NIFs or their pharmaceutical compositions in vivo, the compositions can be administered to the mammal in a variety of ways, including parenterally, intravenously, subcutaneously, intramuscularly, colonically, rectally, nasally or intraperitoneally, employing a variety of dosage forms. As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

The dosage for a NIF or its pharmaceutical compositions can range broadly depending upon the desired effects and the therapeutic indication. Typically, suitable dosages will be between about 0.01 mg and 100 mg/kg, preferably between about 0.01 and 10 mg/kg, body weight. Administration is preferably parenteral, such as intravenous on a daily or as-needed basis.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

6. Utility and Applications.

As noted previously, the NIFs of the present invention have potent neutrophil inhibitory activity and, thus, may be used as an- inhibitors of neutrophil activity, including neutrophil activation in vitro, as well as for preventing or treating in a mammal inflammatory conditions characterized by abnormal neutrophil activation.

Thus, NIF will be useful in the treatment of inflammation in which the abnormal activation of neutrophils plays a significant role. While applicants do not wish to be bound to any theory or mode of activity, it is believed that this compound will interfere with the inflammatory response which is set into action by neutrophil-endothelial cell interactions. Thus, where adhesion of neutrophils to the endothelium is prevented, the neutrophils will be unable to transmigrate to tissue to elicit a proinflammatory response with consequent tissue damage. Inhibition of neutrophil-neutrophil adhesion and/or aggregation by these NIFs should also prevent microvascular occlusion. Thus, these NIFs will be useful in treating a variety of clinical disorders, including shock, stroke, acute and chronic allograft rejection, vasculitis, autoimmune diabetes, rheumatoid arthritis, inflammatory skin diseases, inflammatory bowel disease, adult respiratory distress syndrome (ARDS), ischemia-reperfusion injury following myocardial infarction, in which neutrophil infiltration and activation has been implicated and acute inflammation caused by bacterial infection, such as sepsis or bacterial meningitis.

The ability of NIF to inhibit neutrophil activity makes it useful in inhibiting the physiological processes of inflammation, ischemia, and other neutrophil mediated tissue damage. The specific activities of NIFs in carrying out these related functions makes it particularly useful as therapeutic and/or diagnostic agents.

Antibodies, both monoclonal and polyclonal, directed to NIF are useful for diagnostic purposes and for the identification of concentration levels of the subject peptides in various biological fluids. Immunoassay utilizing these antibodies may be used as a diagnostic test, such as to detect infection of a mammalian host by a parasitic worm or to detect NIF from a parasitic worm in a tissue of the mammalian host. Also such immunoassays may be used in the detection and isolation of NIF from tissue homogenates, cloned cells and the like.

In another aspect of the present invention, NIFs can be used in a test method to screen other compounds to detect NIF mimics or to detect NIF antagonists for their ability to affect NIF binding to the Mac-1 receptor.

In yet another aspect of the present invention, NIF with suitable adjuvants can be used as a vaccine against parasitic worm infections in mammals. Immunization with NIF vaccine may be used in both the prophylaxis and therapy of parasitic infections. NIF fragments and synthetic polypeptides having the amino acid sequence of NIF may also be used as vaccines. Disease conditions caused by parasitic worms may be treated by administering to an animal infested with these parasites substances which antagonize NIF (such as NIF antagonists). Compounds may be screened for their anti-NIF effect according to the screening method described herein above. Examples of such antihelminthic agents include antibodies to NIF, both naturally occurring antibodies isolated from serum and polyclonal and monoclonal antibodies described above. Chemically synthesized compounds which act as inhibitors of NIF also are suitable antihelminthic agents.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Assays of Neutrophil Inhibitory Activity

The Neutrophil Inhibitory Factor of the present invention demonstrated activity in inhibiting neutrophil function as measured by neutrophil-HUVEC and neutrophil-plastic adhesion assays, homotypic neutrophil aggregation assay and hydrogen peroxide release assay. This inhibitory factor was isolated from hookworm tissue lysates as an enriched composition by a variety of methods including gel filtration chromatography, chromatography on hydroxyapatite and concanavalin A sepharose, C4 reverse-phase HPLC, Mono-Q ion exchange chromatography and preparative isoelectric focusing. The isolated factor appears to inhibit neutrophil adhesion to endothelial cell monolayers by inhibiting neutrophil activation.

(A) Cells and Reagents

Primary human umbilical vein endothelial cells (HUVEC), obtained from Clonetics (San Diego, Calif.), were maintained in EGM-UV medium (Clonetics) with 15% fetal bovine serum (PBS), in a 5% $CO_2$ atmosphere. HUVEC were passaged twice and used to seed fibronectin-coated 96 well microtiter plates (Collaborative Research, Bedford, Mass.) for adhesion assays.

The protease inhibitors E64, pepstatin A, chymostatin and APMSF were obtained from Calbiochem (La Jolla, Calif.).

Neutrophils were isolated using Mono-Poly resolving medium (ICN Biomedicals, Costa Mesa, Calif.) from either heparinized or citrated human blood following the instructions of the manufacturer. Neutrophils were resuspended in HSA buffer (RPMI1640 with 10 mM HEPES pH 7.4, 1.2 mM CaCl, 1.0 mM MgCl, 1% human serum albumin) at a concentration of $6.6 \times 10^6$ cells/ml and used within one hour after isolation.

Neutrophils were fluorescently labelled by the following procedure. The cells were washed once in Hank's balanced salt solution (HBSS) and resuspended at $1 \times 10^7$ cells/ml in HBSS containing 20 mg/ml calcein (Molecular Probes; Eugene, Oreg.). The calcein was initially solubilized in 50 ml dry dimethylsulfoxide prior to its addition to the HBSS. Cells were incubated at 37° C. with occasional mixing by inversion. After 45 minutes incubation the cells were chilled on ice for 5 minutes and then washed twice with ice-cold HSA buffer. Labelled neutrophils were resuspended in HSA buffer at $1.3 \times 10^7$ cells/ml for use in adhesion assays.

(1) Protein Concentration.

The molar protein concentration of purified NIF isoforms and mutants thereof was determined spectrophotometrically at 278 nm thereby using calculated extinction coefficients. The calculation is based on absorbance values of 5600 cm$^{-1}$ mol$^{-1}$ for tryptophan and 1420 cm$^{-1}$ mol$^{-1}$ for tyrosine residues.

|  | NIF-1FL | AcaNIF4 | AcaNIF6 | AcaNIF24 |
| --- | --- | --- | --- | --- |
| Trp-residues | 2 | 3 | 2 | 2 |
| Tyr-residues | 13 | 20 | 17 | 17 |
| $\epsilon_M$ | 29,660 | 45,200 | 35,320 | 40,920 |

(2) Preparation of 3D2-HRP Conjugate.

Two hundred fifty microliters glutaraldehyde (25% solution) was added to 1 ml of an 8 mg/ml solution of horseradish peroxidase (Sigma P8375; in phosphate buffered saline (PBS)). After 2 hours at room temperature the mixture was transferred to a dialysis bag (MW cut-off 12 kD) and dialysed against 1 liter PBS for 5 hours. Buffer was refreshed three times. After transfer of the solution to a test tube an equal volume of 3D2 purified MAb (see Example 26; dissolved in PBS at a concentration of 2 mg/ml) was added and further incubated overnight at room temperature. The reaction was stopped by adding glycine to a final concentration of 50 mM. Bovine serum albumin (BSA; Calbiochem) was added to a final concentration of 0.25% (w/v) and the solution was aliquoted and stored at −20° C.

(3) Preparation of Biotinylated *Pichia* NIF-1FL.

Purified recombinant NIF (mature NIF-1FL (SEQ. ID. NO. 117)) from *Pichia* was dialyzed against 100 mM acetate buffer pH 5.5 at a concentration of 1 mg/ml. An equal volume of cold 20 mM sodium-metaperiodate in 100 mM acetate buffer pH 5.5 was added. The oxidation reaction was allowed to proceed for 20 minutes in the dark on ice. The reaction was stopped by adding glycerol to reach a final concentration of 15 mM. The sample was desalted by ultrafiltration on Centricon 30. Biotin-LC hydrazide (Pierce) dissolved in dimethylsulfoxide was added to reach a final concentration of 5 mM and was then further incubated for 2 hrs at room temperature. The biotinylated sample was subsequently dialyzed against PBS using a Spectrapor membrane with a cut-off of 12,000.

(B) Neutrophil-HUVEC Adhesion Assays

Calcein-labelled neutrophils (175 ml at $1.32 \times 10^7$ cells/ml) were preincubated for 10 minutes at room temperature with 175 ml of test fraction (diluted in HSA buffer) in the presence of 169 nM phorbol 12-myristate 13-acetate (PMA; Sigma, St. Louis, Mo.). PMA is solubilized in dimethylsulfoxide at a stock concentration of 1.6 mM. A 96 well plate was used for this assay. One hundred microliters of this suspension was then aliquoted into each of three replicate wells that contained HUVEC monolayers. Neutrophils were incubated with the HUVEC monolayer for 30 minutes at 37° C. To remove non-adherent cells, wells were first filled with 250 ml HSA buffer, sealed with parafilm and then centrifuged inverted for 3 minutes at 75xg. Inverted plates were then placed on a rocking platform shaker for 5 minutes, after which contents were decanted off and wells were washed twice with 100 ml HSA buffer. Adherent neutrophils were lysed in 100 ml 0.1% (v/v) Triton X-100 (in 50 mM Tris HCl pH 7.4), and agitated for 10 minutes on a plate shaker. Twenty five microliters of the neutrophil/endothelial cell lysate was transferred to a 96 well microtiter plate that contained 100 ml of 50 mM Tris pH 7.4, and the wells were read at 530 nm (485 nm excitation) on a Cytofluor fluorometric plate reader (Millipore; Bedford, Mass.).

The hydroxyapatite pool preparation of hookworm Neutrophil Inhibitory Factor (see Example 1(D)) inhibited neutrophil adhesion to HUVEC monolayers with an $IC_{50}$ of about 10 nM.

(C) Neutrophil-Plastic Adhesion Assay (1) Protocol #1.

This assay was used in Examples 1 through 19, where it was applicable.

Neutrophils (20 ml at $6.6 \times 10^6$ cells/ml) were incubated with 5 ml PMA (0.8 mM) for 5 minutes at room temperature in a 0.5 ml polypropylene test tube. Twenty microliters of test fraction, diluted in HSA buffer, was added and the suspension was mixed gently. Aliquots of 10 ml of this suspension were added in triplicate to microtiter wells of 60-well HCA (Terasaki) plates (Nunc, Naperville, Ill.). Neutrophils were incubated 5 minutes at 37° C. and non-adherent cells were removed by submerging the plate 6 times in HBSS.

Adherent neutrophils were quantitated by counting under an inverted light microscope. Binding was quantitated visually. PHA-activated neutrophils spread and adhere tightly to polystyrene plastic. Non-activated neutrophils (i.e., in the absence of PMA) remain round and translucent and do not adhere tightly to plastic. Adherent neutrophils were larger, rhomboid in shape and more opaque, with a granular appearance. In the absence of Neutrophil Inhibitory Factor, greater than 80% of PHA-activated neutrophils rapidly and irreversibly bound plastic, underwent shape change and were not removed by the gentle wash procedure. Moreover, fractions containing the *Ancylostoma* Neutrophil Inhibitory Factor exhibited a profound inhibitory effect on plastic binding by activated neutrophils.

The hydroxyapatite pool preparation of hookworm Neutrophil Inhibitory Factor (see Example 1(D)) inhibited neutrophil adhesion to plastic in this assay with an $IC_{50}$ of about 10 nM.

(2) Protocol #2.

This assay was used in Examples 20 through 29, where it was applicable.

Neutrophils (60 µl at 8×10⁶cells/ml in HSA buffer) were incubated with 15 µl PMA (2.4 mM) and 5 µl CaCl2 0.05 M. After gently mixing 80 µl of the stimulated cell suspension were added to 96-well high binding polystyrene microtiter plates (Costar) containing 20 µl of the test sample diluted in HSA buffer. After 45 minutes incubation at 37° C., non-adherent cells were removed by submerging the plates 4 times in PBS. Adherent cells were loaded with dye by adding 100 µl of 0.5% (w/v) Crystal violet indicator (CAS 548-62-9) solution. After 10 min at room temperature plates were rinsed by submerging 4 times in PBS. Lysis of stained adherent cells was done by adding 100, µl of 1% (v/v) Triton X-100 solution. Absorbance was determined at 605nm with a Thermomax plate reader to quantitate adherent neutrophils.

(D) Homotypic Neutrophil Aggregation Neutrophil aggregation was performed at 37° C. in a Scienco dual channel aggregometer (Morrison, Colo.). Neutrophils (190 ml at 6.6×10⁶ cells) were preincubated with 200 ml test fraction (diluted in HSA Buffer) in a glass cuvette (Scienco) for 2 minutes at room temperature. Ten microliters of PHA were added to initiate aggregation (80 nM final). The inhibition of neutrophil aggregation was measured at the maximum aggregation response 5 minutes after the addition of PMA.

The hydroxyapatite pool preparation of Neutrophil Inhibitory Factor (see Example 1(D)) inhibited neutrophil adhesion with an $IC_{50}$ of about 10 nM.

(E) Hydrogen Peroxide Release Assay Neutrophils (6.6×10⁶ cells/ml) were incubated with test fractions in Release Assay Buffer (HBSS with 25 mM glucose, 10% PBS, 200 mg/ml phenol red, 32 mg/ml horseradish peroxidase) for 5 minutes at 37° C. Incubation vessels consisted of 1.5 ml plastic test tubes that were precoated with HBSS containing 50% FBS at 37° C. for 60 minutes; coated tubes were washed twice with 0.15 M NaCl before use. FMlP (Sigma; St. Louis, Mo.) at a final concentration of 250 mM was added and the neutrophil/test compound suspension was incubated at 37° C. for 60 minutes. Cells were pelleted by centrifugation at 8000×g for 3 minutes and 200 ml of supernatant was transferred to a 96 well microtiter plate. Ten microliters of 1 N NaOH was added to each well and absorbance was read at 610 nm with a Molecular Devices ThermoMax plate reader. Hydrogen peroxide concentrations were determined by using a standard curve. Data points were done in duplicate.

The hydroxyapatite pool preparation of hookworm Neutrophil Inhibitory Factor inhibited hydrogen peroxide release from neutrophils with an $IC_{50}$ of about 10 nM.

(F) Mac-1 Binding Assays

Microtiter polystyrene plates (Costar—high binding; 96 well) were coated with the Mac-1 binding, non-neutralizing mouse monoclonal antibody LM2 (50 µl of the purified LM2 MAb at a concentration of 10 µg/ml in 0.1 M NaHCO₃;pH 9.5; LM2 ATCC hybridoma #HB204) by overnight incubation at 4° C. After removal of the antibody, the wells were blocked with 200 µl PBS containing 1% (w/v) Skim-milk (Difco Laboratories) at room temperature. After 2 hours the blocking solution was removed and wells were washed 3 times with 200 µl of PBS.

The immobilized LM2 monoclonal antibody was used to immuno-capture the detergent solubilized Mac-1 receptor as follows. Neutrophils were isolated using Polymorphprep™ (Nycomed) from either citrated whole blood or from buffy-coat following the instructions of the manufacturer. The neutrophil pellet from a 50 ml buffy coat was resuspended in 40 ml RPMI and phorbol myristate acetate (PMA) to a final concentration of 0.8 µM was added. The suspension was gently rotated at room temperature for 20 minutes. The cells were spun down and resuspended in 5 ml 0.02 M Tris-HCl, 0.15 M NaCl, 0.001 M MgCl₂, 0.001 M CaCl₂. Cells were lysed by adding 5 ml buffer containing 2% Triton X-100 (Bio-Rad Laboratories), 0.02 M Tris pH 7.5, 0.15 M NaCl, 0.001 M MgCl₂, 0.001 M CaCl₂ and 0.02% thimerosal (Sigma T-5125). PMSF (Sigma) and iodoacetamide (Merck-Schuchardt) were added to final concentrations of 1 mM. After mixing, the suspension was stored on ice for 1 hour and vortexed periodically. After centrifugation at 30,000 g, the supernatant was diluted twofold with 0.02 M Tris-HCl, 0.15 M NaCl, 0.001 M MgCl₂, 0.001 M CaCl₂ and 2 ml of IgG-sepharose (Sigma) was added. After incubation for two hours in the cold, the resin was spinned down. The supernatant was removed and diluted 5-fold with 0.02 M Tris-HCl, 0.15 M NaCl, 0.001 M MgCl₂, 0.001 M CaCl₂. Fifty microliters of this neutrophil lysate was then added to LM2-coated wells and incubated for 2 hours at room temperature to capture the Mac-1 integrin. After washing with PBS, the plates were stored at −20° C.

In one type of assay, binding of NIF (NIF-1FL and isoforms or engineered variants)-to LM2/Mac-1 coated plates was detected with the 3D2-HRP conjugate. Samples containing NIF were diluted in PBS containing 0.1% (w/v) Skim-milk, 0.001 M MgCl₂, 0.001 M CaCl₂. After 2 hours incubation at room temperature, the wells were washed three times with 200 µl PBS containing 0.001 M MgCl₂, 0.001 M CaCl₂, 0.02% Tween-20 and 0.02% thimerosal. Then, 100 µl of an appropriate dilution (typically 2000-fold; in PBS containing 0.1% (w/v) skim-milk, 0.001 M MgCl₂, 0.001 M CaCl₂) of the 3D2-HRP conjugate was added. After 1 hour, the wells were washed three times with 200 µl PBS containing 0.001 M MgCl₂, 0.001 M CaCl₂, 0.02% thimerosal and 0.02% Tween 20. Substrate for HRP (100 µl; prepared by dissolving 2.3 mg ortho-phenylenediamine in 11.6 ml 50 mM citrate, 100 mM disodium phosphate buffer pH 5 and adding 2 µl of 35% H₂O₂) was then added to the wells. The reaction was stopped (typically after 20 minutes) by addition of 10 µl of a 4 M sulfuric acid solution; the absorbance was read at 605 nm with a Thermomax plate reader (Molecular Devices).

Alternatively, binding of NIF (NIF-1FL, other NIF proteins, and NIF mutants) to the LM2/Mac-1 complex was measured by competition with biotinylated recombinant NIF-1FL produced in *Pichia* (see Example 12). Samples containing a constant amount of biotinylated recombinant NIF-1FL and varying amounts of unlabeled recombinant NIF-1FL were prepared in PBS containing 0.001 M MgCl2, 0.001 M CaCl₂ and 0.1% (w/v) casein (Difco Laboratories). A 100 µl aliquot of each sample was added to individual LM2/Mac-1 coated wells and incubated for 2 hours at room temperature. Unbound material was removed by washing three times with 200 µl PBS containing 0.001 M CaCl₂, 0.001 M MgCl₂, 0.1% Tween 20 and 0.02% thimerosal. Retained biotinylated recombinant NIF-1FL was detected by incubating first with 100 µl of ExtrAvidin-phosphatase (Sigma) conjugate diluted in PBS containing 0.1% casein. After 1 hour incubation at room temperature, unbound conjugate was removed by washing three times with PBS containing 0.001 M CaCl₂, 0.001 M MgCl₂, 0.02% Tween 20 and 0.02% thimerosal. Substrate for alkaline phosphatase (100 µl of a solution containing 5 mg ortho-nitrophenylphosphate in 1.8 ml 0.01 M diethanolamine, 0.5 mM MgCl₂, pH 9.5) was added. After 30 minutes the wells were read at 405 nm with a Thermomax plate reader to quantitate bound biotinylated recombinant NIF-1FL.

Example 2
Isolation of Native Neutrophil Inhibitory Factor From Hookworm Lysate (A) Preparation of Hookworm Lysate Frozen canine hookworms were obtained from Antibody Systems (Bedford, Tex.). Hookworms were stored at −70° C. until used for homogenate.

Hookworms were homogenized on ice in homogenization buffer [0.02M Tris-HCl pH 7.4, 0.05 M NaCl, 0.001 M $MgCl_2$, 0.001 M $CaCl_2$, $1.0 \times 10^{-5}$M dithiothreitol, $1.0 \times 10^{-5}$M E-64 Protease Inhibitor (CAS 66701-25-5), $1.0 \times 10^{-6}$M pepstatin A (isovaleryl-Val-Val-4-amino-3-hydroxy-6-methyl-heptanoyl-Ala-4-amino-3-hydroxy-6-methyl-heptanoic acid, CAS 26305-03-3), $1.0 \times 10^{-5}$M chymostatin (CAS 9076-44-2), $2.0 \times 10^{-5}$M APMSF (amidinophenyl-methylsulfonyl fluoride-HCl), 5% (v/v) glycerol] using a Tekmar Tissuemizer homogenizer. The protease inhibitors E64, pepstatin A, chymostatin, and APMSP were obtained from Calbiochem (La Jolla, Calif.). Approximately 3–6 ml of homogenization buffer was used to homogenize each gram of frozen worms (approximately 500 worms). Insoluble material was pelleted by two sequential centrifugation steps: $40,000 \times g_{max}$ at 4° C. for 20 minutes followed by $105,000 \times g_{max}$ at 4° C. for 40 minutes. The supernatant solution was clarified by passage through a 0.2 mm cellulose acetate filter (CoStar).

(B) Concanavalin A Sepharose Chromatography of Hookworm Lysate

Hookworm lysate (79 ml) was adsorbed to 16 ml of Concanavalin A Sepharose (Pharmacia) pre-equilibrated with Con A buffer [0.02 M Tris-HCl, pH 7.4, 1 M NaCl, 0.001 M $CaCl_2$, 0.001 M $MnSO_4$, $1 \times 10^{-5}$ M dithiothreitol] by recycling it through a 1.6×8 cm column at a flow rate of 3 ml/min (90 cm/hour) for 2 hours. The column was at room temperature (24° C.) while the reservoir of lysate was maintained on ice throughout the procedure. The column was subsequently washed with 80 ml of Con A buffer. The Con A buffer in the column was displaced with buffer containing 0.5 M methyl-alpha-mannopyranoside and flow stopped for 30 minutes. Flow was then restarted at a flow rate of 0.5 ml/min (15 cm/hour). Material that had inhibitory activity in neutrophil function assays was eluted with approximately three column volumes of Con A buffer containing 0.5 M methyl-alpha-mannopyranoside (CAS 617-04-09). The yield of neutrophil adhesion inhibitory activity in this step was approximately 38%.

Figure 1:
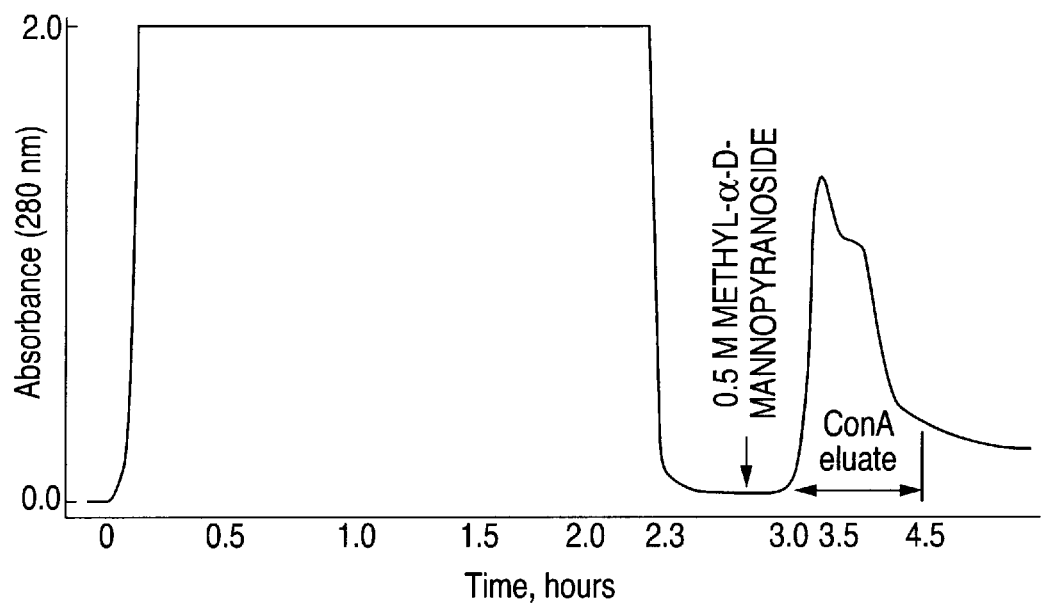
FIG. 1 depicts a chromatogram of hookworm lysate obtained as described in the Example 2(A) run on the Example 2(B) Concanavalin A Sepharose column.

FIG. 1 depicts Concanavalin A Sepharose chromatography of the hookworm lysate performed as described above. Absorbance at 280 nm was plotted as a function of time.

(C) Molecular Sieve Chromatography Using Superdex 200

Active fractions eluted from immobilized Concanavalin A (see step (B) above) and concentrated by ultrafiltration at 4° C. using an Amicon stirred cell equipped with a 10,000 dalton cut-off membrane (YM10), then 5–20 ml of the concentrate were loaded on a 2.6 cm×60 cm column of Superdex 200 prep (Pharmacia) attached in series with an identical column (combined dimensions of 2.6×120 cm). Both columns were pre-equilibrated with 0.01 M potassium phosphate, pH 7.35, 0.150 M NaCl, $1 \times 10^{-5}$ M dithiothreitol at 24° C. The chromatography was conducted at a flow rate of 1.5 ml/min; anti-adhesion activity typically eluted 395–410 ml into the run ($K_{av}$ of 0.46, see.FIG. 2). This elution volume would be expected for a globular protein with a molecular mass of 50,000. The yield of neutrophil function inhibitory activity in this step was typically 70–80%. If the ionic strength of the chromatography buffer employed was decreased to 0.01 M sodium phosphate, pH 7.00 and 10% (v/v) glycerol added, the activity eluted substantially earlier ($K_{av}$=0.34) suggesting that under such conditions the protein either aggregates or changes its conformation (assuming a larger Stoke's radius).

Figure 2:
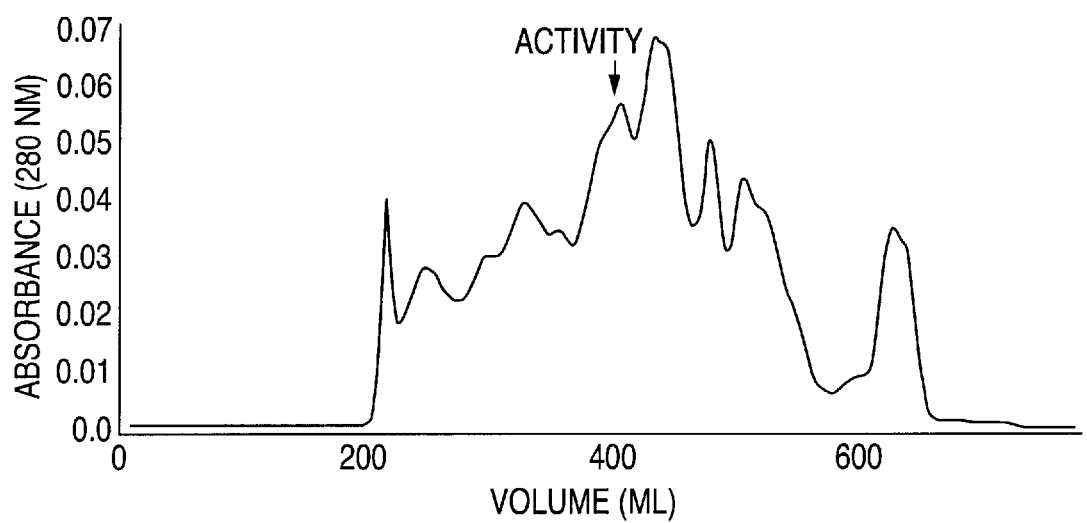
FIG. 2 depicts a chromatogram of Concanavalin A-purified hookworm lysate run on the Example 2(C) Superdex 200 column.

FIG. 2 depicts Superdex 200 Chromatography of Concanavalin A-Purified Hookworm Lysate. Absorbance at 280 nm is plotted versus elution volume. Active fractions eluted from immobilized Concanavalin A (see step (B) above) and concentrated by ultrafiltration at 4° C. using an Amicon stirred cell equipped with a 10,000 dalton cut-off membrane (YM10), then 5–20 ml of the concentrate were loaded on a 2.6 cm×60 cm column of Superdex 200 prep (Pharmacia) attached in series with an identical column (combined dimensions of 2.6×120 cm). Both columns were pre-equilibrated with 0.01 M potassium phosphate, pH 7.35, 0.150 M NaCl, $1 \times 10^{-5}$ M dithiothreitol at 24° C. The chromatography was conducted at a flow rate of 1.5 ml/min; activity eluted 395–410 ml into the run ($K_{av}$ of 0.46).

(D) Ceramic-Hydroxyapatite Chromatography

Material purified by molecular sieve chromatography was concentrated five-fold by ultrafiltration using an Amicon stirred cell equipped with a 10 kilodalton cut-off membrane at 4° C. and then diluted ten-fold with water. The desalted sample was loaded on a 0.8×10 cm column of ceramic hydroxyapatite ("HA") (Pentax, American International Chemical, Inc., Natick, Mass., 2 mm) equilibrated with 0.001 M potassium phosphate, pH 7.00, $1 \times 10^{-5}$ M $CaCl_2$, $1.0 \times 10^{-5}$ M dithiothreitol at 24° C. The loading was conducted at a flow rate of 0.8 ml/min (95.5 cm/hour). The column was developed with a 50 ml linear gradient of potassium phosphate ranging from 0.001 M to 0.0375 M at a flow rate of 0.5 ml/minute. Neutrophil inhibitory activity eluted sharply at 0.025 M potassium phosphate and then trailed to 0.0325 M potassium phosphate (fractions 37 to 48). The yield of activity in this step was approximately 48%.

Figure 3:
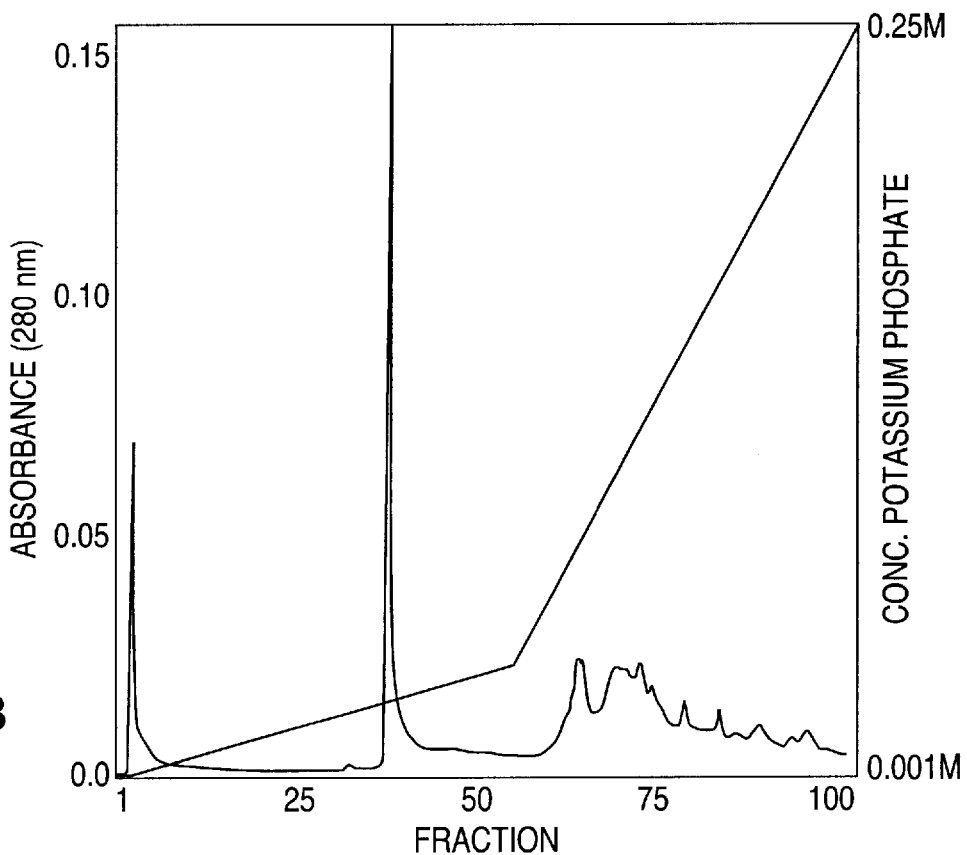
FIG. 3 depicts a chromatogram of the Concanavalin A Sepharose/Superdex purified hookworm lysate run on the Example 2(D) ceramic hydroxyapatite column.

FIG. 3 depicts Ceramic Hydroxylapatite chromatography of Superdex/Concanavalin A-Purified Hookworm lysate plotting absorbance at 280 nm and potassium phosphate concentration versus fraction number. Neutrophil inhibitory activity eluted in fractions 37 to 48.

(E) Reverse Phase HPLC

Hookworm lysate fractionated by chromatography on Concanavalin A Sepharose, Superdex, and ceramic hydroxylapatite (~100 mg) was loaded on to a 0.48×15 cm column of 300 angstrom C4 (Vydac) which was then developed with a linear gradient of 0–60% acetonitrile in 0.1% trifluoroacetic acid at 1 ml/minute with a rate of 1% change in acetonitrile/minute. Neutrophil inhibitory activity typically elutes between 41 and 45% acetonitrile, the activity corresponding with a broad peak.

Figure 4:
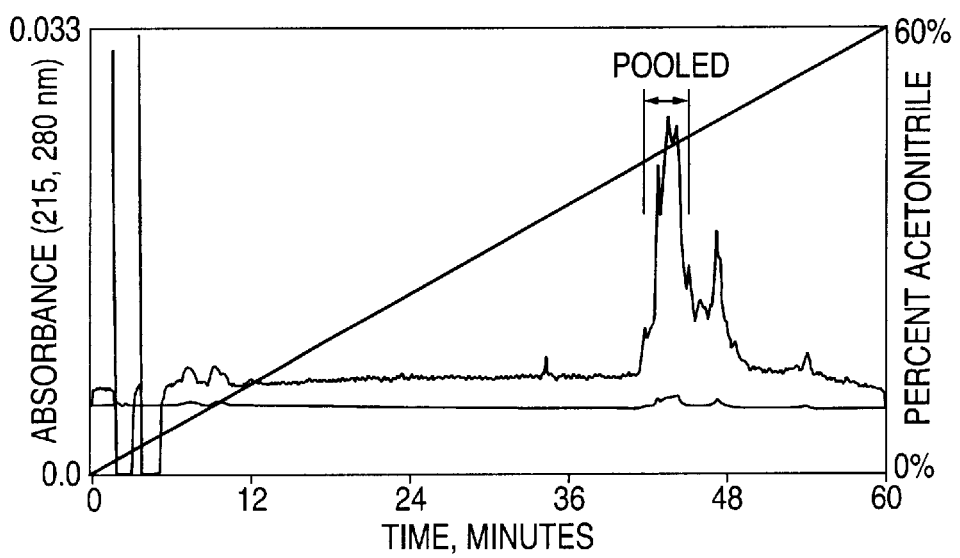
FIG. 4 depicts a chromatogram from reverse phase HPLC of hookworm lysate isolated by Concanavalin A Sepharose, Superdex 200 and hydroxyapatite chromatography as described in Example 1(E).

FIG. 4 depicts the results of reverse phase HPLC of the Neutrophil Inhibitory Factor. Inhibitory activity eluted between 43 and 45% acetonitrile, the activity corresponding with a broad peak at 43–45 minutes.

TABLE I

Summary of Example Purification

| FRACTIONATION STEP | PROTEIN (mg) | PERCENT ACTIVITY | SPECIFIC ACTIVITY | FOLD PURIF. |
|---|---|---|---|---|
| EXTRACTION | 528 | 100 | 0.2 | 1 |
| ConA ELUATE | 21.7 | 38 | 1.8 | 9 |

TABLE I-continued

Summary of Example Purification

| FRACTIONATION STEP | PROTEIN (mg) | PERCENT ACTIVITY | SPECIFIC ACTIVITY | FOLD PURIF. |
|---|---|---|---|---|
| SUPERDEX POOL | 1.5 | 25 | 16.7 | 88 |
| HYDROXYAPATITE POOL | 0.3 | 12 | 40.0 | 200 |

Example 3
Isolation of the Neutrophil Inhibitory Factor From Hookworm Lysate Using Preparative Isoelectric Focusing Hookworm lysate was partially fractionated and desalted by molecular sieve chromatography on a 2.6 cm×60 cm column of Superdex 200 prep (Pharmacia) attached in series with an identical column (combined dimensions of 2.6×120 cm). Both columns were pre-equilibrated with 0.01 M sodium phosphate, pH 7.00, 10% (v/v) glycerol at 24° C. Adhesion inhibiting fractions eluting at 350–370 ml were diluted to 55 ml by the addition of 1.4 ml of 40% Biolyte 3–10 ampholyte (BioRad) and 10% (v/v) glycerol. This mixture was focused with a constant power of 12 W for 5 hours at 40° C. in a Rotofor preparative isoelectric focusing prep cell (BioRad). Twenty fractions were harvested; inhibitory activity was detected in fractions 6–9, corresponding to an isoelectric point of 4.5. The overall yield of inhibitory activity for this step was approximately 30%.

Example 4
Ion Exchange Chromatography

Hookworm lysate fractionated by molecular sieve chromatography on Superdex 75 (Pharmacia) was mixed with an equal volume of Mono Q buffer [0.02 M Tris-HCl, pH 7.5) and loaded on to a 0.5×5.0 cm Mono Q anion exchange column (Pharmacia) equilibrated with Mono Q buffer at a flow rate of 1 ml/minute (306 cm/hour). The column was then developed with a linear gradient of 0–0.5 M NaCl in column buffer at 0.5 ml/minute (153 cm/hour). Neutrophil inhibitory activity consistently eluted at 0.4 M NaCl. he overall yield of inhibitory activity for this isolation was about 2–5%.

Example 5
SDS-Polyacrylamide Gel Electrophoresis

The protein composition of hookworm lysate and fractionated lysate was analyzed by sodium dodecyl sulfate polyacrylamide gel electrophoresis (SDS-PAGE) (Laemmli, U. K. 1970, Nature 227, 680) after silver staining (Morrisey, J. H. 1981, Anal. Biochem. 117, 307). Samples were mixed with an equal volume of 20% glycerol, 5% SDS, and 0.125 14 Tris-HCl, pH 6.8 and placed in a boiling water bath for 5 minutes. Samples were subsequently applied onto 10% SDS polyacrylamide slab gels of 0.75 mm thickness and subjected to electrophoresis for 2 hours at constant voltage (125 V).

Figure 5:
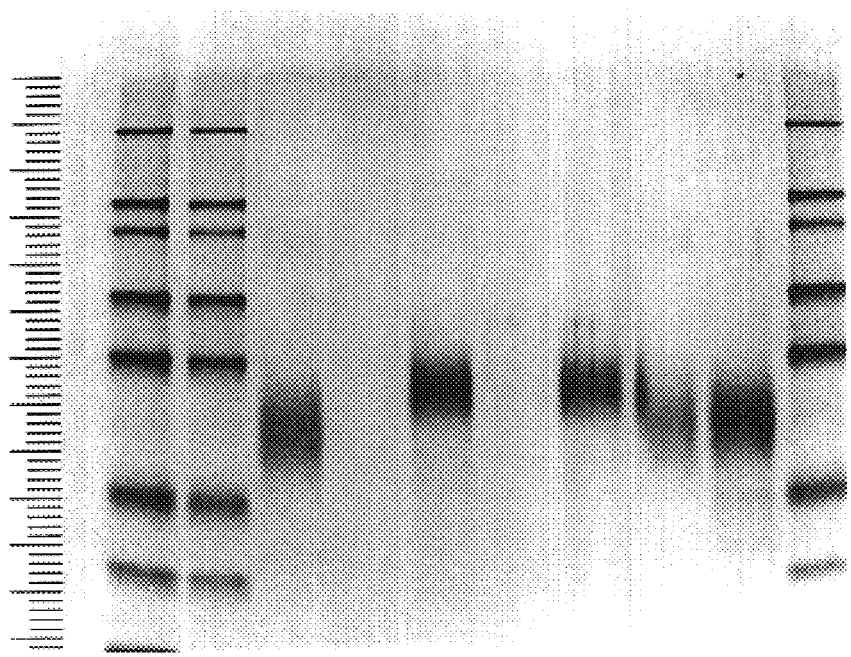
FIG. 5 depicts a gel pattern run using SDS-gel electrophoresis of the HPLC isolate and certain molecular weight standards.

FIG. 5 depicts the results of SDS polyacrylamide gel electrophoresis. Samples were applied to a 10% polyacrylamide slab gel (Novex, La Jolla, Calif.). Lanes 1–10, left to right, are (1) molecular weight standards; (2) molecular weight standards; (3) HPLC pool of HA fractions #37–41, non-reduced; (4) blank; (5) HPLC pool of HA fractions #37–41, reduced; (6) blank, (7) HPLC pool of HA fractions #37–41, reduced; (8) HPLC pool of HA fractions #37–41, non-reduced; (9) HPLC pool of HA trailing fractions #42–48, non-reduced, (10) molecular weight standards. The molecular weight standards used were: myosin, 200,000 (rabbit muscle); beta-galactosidase, 116,300 (*E. coli*); phosphorylase b, 97,400 (rabbit muscle); bovine serum albumin, 66,300; glutamic dehydrogenase, 55,400, (bovine liver); carbonic anhydrase, 1,000, (bovine erythrocyte); trypsin inhibitor, 21,500, (soybean).

Following the last step of the isolation procedure (reverse phase HPLC) only a single diffuse band with an apparent molecular weight ranging from 33,000 to 47,000 was observed upon SDS-PAGE (see FIG. 5). When 50 mM dithiothreitol was added to the sample prior to boiling, the diffuse band migrated with an estimated molecular weight of 43,000 to 54,000.

Example 6
Laser-Desorption Time-of-Flight Mass Spectrometry of the Isolated Neutrophil Inhibitory Factor The estimated mass for the NIF isolated as described in Example 2(E) was determined using laser-desorption time-of-flight mass spectrometry.

A 1 ml aliquot of the sample was diluted with an equal volume of a saturated solution of 3,5-dimethozy-4-hydroxycinnamic acid dissolved in 30% aqueous $CH_3CN$, 0.1% TFA. The diluted sample was spotted onto a copper sample stage and allowed to air dry. Mass analysis was performed using a Shimadzu LAMS-50KS laser desorption time of flight mass spectrometer (Shimadzu Corp., Kyoto, Japan). Ionization of the sample was accomplished by focusing 500 laser pulses (355 nm, pulse width <5 nsec) from a Nd-YAG laser (Spectra-Physics, Inc., Mt. View, Calif.) onto the sample stage. The resulting ions were accelerated into the mass spectrometer by a 5 kV potential. Calibration of the instrument was accomplished using standard proteins of known mass.

Figure 6:
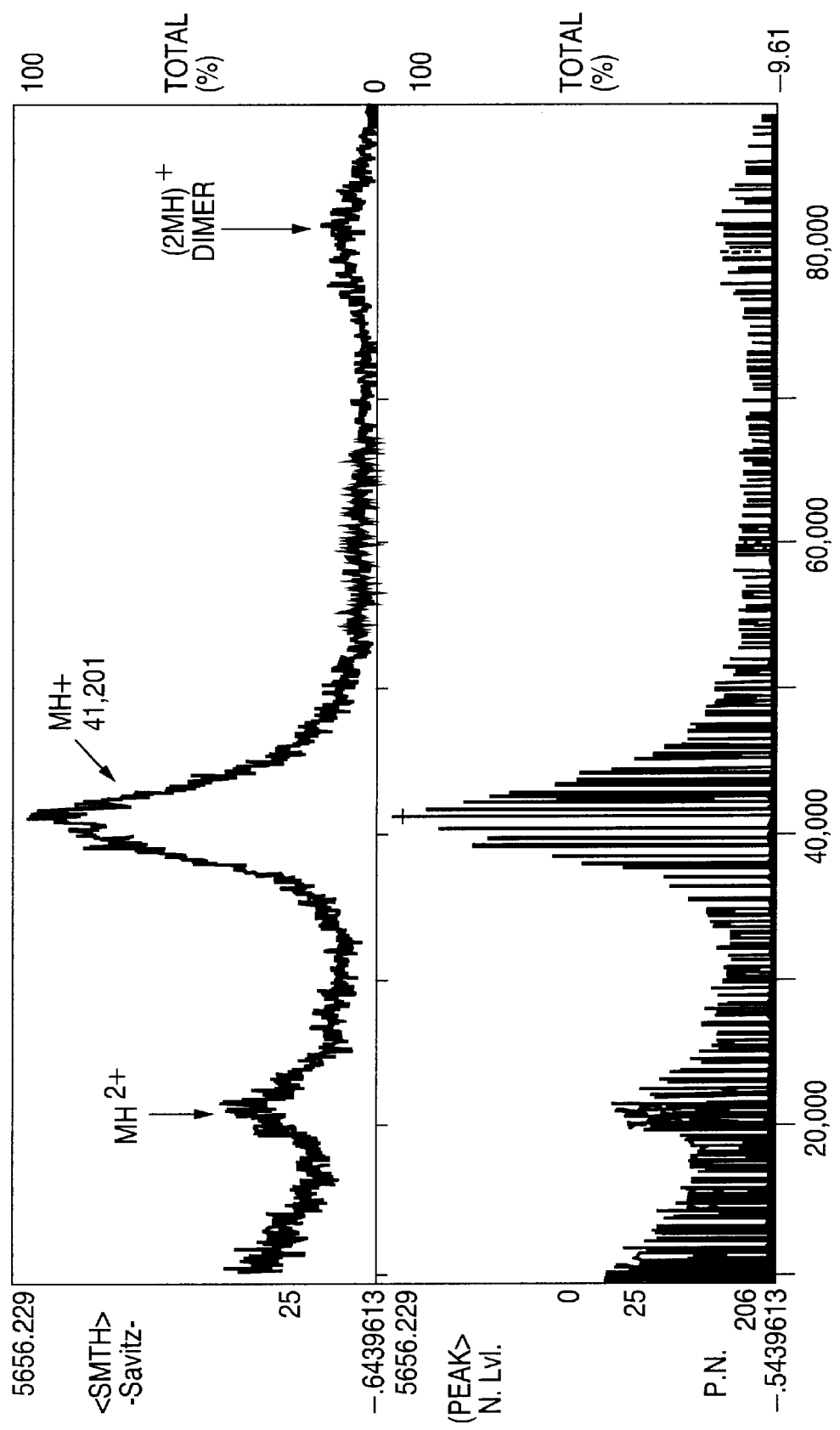
FIG. 6 depicts laser-desorption time-of-flight mass spectrometry of the purified Neutrophil Inhibitory Factor of the present invention.

FIG. 6 depicts the results of laser-desorption time-of-flight mass spectrometry of the isolated neutrophil adhesion inhibitor. Five picomoles of the purified neutrophil function inhibitor was analyzed with a laser desorption time-of-flight mass spectrometer. The estimated mass was determined as 41,200. A small fraction of the sample had a mass of 82,400; this was interpreted to be a diner.

Example 7
Neutrophil Inhibitory Factor is a Glycoprotein

Purified NIF (prepared according to Example 2(E)) (~2 mg) was electrophoresed in a 10% SDS polyacrylamide gel and the resolved protein transferred by Western blotting (Towbin, et al., 1919 Proc. Natl. Acad. Sci. (USA) 76, 4350–4354) to a Zeta-Probe® nitrocellulose membrane (BioRad, Emeryville, Calif.). The membrane was treated as described in the instructions to the GlycoTrack™ Kit (Oxford GlycoSystems, Rosedale, N.Y.) to oxidize carbohydrates to aldehydes which were then reacted with biotin-hydrazide leading to incorporation of biotin into any carbohydrate present. Biotinylated carbohydrate was subsequently detected by reaction with a streptavidin-alkaline phosphatase conjugate. Visualization was achieved using a substrate which reacts with alkaline phosphatase bound to glycoproteins on the membrane, forming a colored precipitate. Neutrophil Inhibitory Factor was stained using this method, demonstrating that it contained carbohydrate and is therefore a glycoprotein.

Example 8
Organic Extraction of the Hookworm Lysate

One milliliter of hookworm homogenate known to have inhibitory activity in the neutrophil-plastic adhesion assay was extracted by vortexing 1 minute with 1 ml of a chloroform/methanol (2:1) mixture in a 15 ml glass Corex test tube. The organic layer was removed and dried under a stream of nitrogen gas. Residual lipids were resuspended in 0.5 ml HSA assay buffer by sonication for 2 minutes (Branson Model 1200, Danbury, Conn.). Resuspended lipids had no inhibitory activity in the neutrophil-plastic adhesion assay when tested at a final dilution of 1:2.

Example 9
Production and Determination of the Amino Acid Sequence of Peptide Fragments of Neutrophil Inhibitory Factor Samples of NIF were obtained as described in Example 2. Two separate volumes, each containing approximately 10 mg NIF, were first degassed on a Speed Vac until the samples were frozen and then lyophilized. The dried samples were resuspended in 50 mM N-ethylmorpholine, pH 8.5, and digested with either endoproteinase AspN (Boehringer Mannheim, Indianapolis, Ind.), Lys C (Boehringer Mannheim, Indianapolis, Ind.) or trypsin (Worthington, Freehold, N.J.) at a substrate to enzyme ratio of 25:1. Incubation was at ambient temperature for 24 hours and a small amount of isopropanol was added to the digestion mix to prevent microbial contamination. At the end of the digestion, the samples were degassed on a Speed Vac and dried by lyophilizing. The digestion mixtures were resuspended in 6M guanidine/HCl for fractionation of peptides by reversed phase HPLC (RP HPLC). Peptides were isolated by RP HPLC on a ToyoSoda 120T C18 (4.5×250 mm) column using an LKB HPLC system with Kratos (ABI, Foster City, Calif.) detectors. The column was developed with a linear gradient of acetonitrile in 0.1% trifluoroacetic acid (TFA). The gradient was from 5 to 54% acetonitrile over 120 minutes at a flow rate of 0.5 ml/minute. Peptide peaks monitored by $A_{206}$ and $A_{280}$ were collected using an LKB SuperRac with calibrated peak detection. The collected fractions were neutralized with ammonium carbonate, 20 mg SDS was added, and the fractions dried under $N_2$ before sequencing. Peptides were sequenced on a 470A/120A/900A gas phase sequencer (ABI, Foster City, Calif.). Residue identification was performed manually by analysis of the HPLC chromatograms and quantification of the PTH residues was performed by online analysis on the 900A computer. Cysteine residues were not detected in this analysis because the protein had not been alkylated. In experiments in which the protein was digested with trypsin, the protein was alkylated with vinylpyridine before fragmentation, thereby permitting the detection of cysteine in the tryptic fragments. Aspartic acid and tryptophan residues were identified but not quantitated because background peaks overlapped the PTH residues in the HPLC elution. The initial yields ranged from 1 pmole to 10 pmole and the repetitive yield was usually between 92 and 95%. FIG. 7 depicts the amino acid sequences that were obtained from the proteolytic fragments [SEQ. ID. NOS. 61 to 79]. The fragments depicted in FIG. 7 are T-24 [SEQ. ID. NO. 61], T-20 [SEQ. ID. NO. 62], T-22-10 [SEQ. ID. NO. 63], T-13 [SEQ. ID. NO. 64], T-15-6 [SEQ. ID. NO. 65], D-53 [SEQ. ID. NO. 66], D-54 [SEQ. ID. NO. 67], D-61 [SEQ. ID. NO. 68], D-67 [SEQ. ID. NO. 69], D-83 [SEQ. ID. NO. 70], D-85 [SEQ. ID. NO. 71], D-94 [SEQ. ID. NO. 72], D-96 [SEQ. ID. NO. 73], D-102 [SEQ. ID. NO. 741, K-34A [SEQ. ID. NO. 75], K-46B (SEQ. ID. NO. 76], K-48 [SEQ. ID. NO. 77], K-50A (SEQ. ID. NO. 78], and K-58A [SEQ. ID. NO. 79]. In FIG. 7, positions enclosed in parentheses were not determined with absolute certainty.

Abbreviations for amino acids beginning with a capital letter were observed in higher yield and are preferred in these cases. The abbreviation Xxx indicates an undetermined amino acid at that position, since no specific amino acid was identified during Edman degradation of the peptide. See Scarborough et al. J. Biol. Chem. 266:9359, 1991.; Penn et al., J. Biol. Chem. 266:3877, 1991.

Example 10
Cloning and Sequencing of Neutrophil Inhibitory Factor from Hookworm

NIF was cloned from a canine hookworm cDNA library, constructed as follows: Total RNA was isolated from whole hookworms by guanidium thiocyanate extraction (McDonald et al., Meth. Enzymol. 152:219 (1987)). Poly (A)+ RNA was purified from 500 mg of total hookworm RNA using oligo d(T) cellulose affinity chromatography (PolyA Quik; Stratagene, La Jolla, Calif.). Double stranded cDNA was synthesized from poly(A)+ RNA using random hexamer primers and avian myoblastosis virus (AMV) reverse transcriptase (Amersham, Arlington Hills, Ill.). cDNA fragments larger than 1 kilobase pairs were purified on a 6% polyacrylamide gel and ligated to EcoRI linkers (Stratagene) using standard procedures. Linkered cDNA was ligated into lambda gt10 (Stratagene, La Jolla, Calif.) and packaged using Gigapack Gold II (Stratagene).

Double stranded cDNA probes for hookworm NIF were generated by polymerase chain reaction from hookworm RNA using primers derived from NIF peptide sequences. The sequences obtained for two NIF peptides (see FIG. 7), T-20 (Leu-Ala-Ile-Leu-Gly-Trp-Ala-Arg) [SEQ. ID. NO. 9] and T-22-10 (Leu-Phe-Asp-Arg-Phe-Pro-Glu-Lys) [SEQ. ID. NO. 10], were used to design primers 30.2 and 43.3.RC, respectively. The sequences of 30.2 and 43.3.RC were 5'-CTCGAATTCT(GATC)GC(ATC)AT(ATC)(CT)T (GATC)-GG(ATC)TGGG C-3' [SEQ. ID. NO. 7] and 5'-CTCGAATTCTT(TC)TCTGG(GA)AA-(GA)CG(GA) TC(GA)AA-3' [SEQ. ID. NO. 8], respectively. Bracketed positions represent redundant nucleotides. Single stranded cDNA was synthesized by priming 1 mg of hookworm poly(A)+ RNA (preparation described above) with random hexanucleotides and extending with AMV reverse transcriptase (Amersham, Arlington Hills, Ill.). One twentieth of the reaction product was amplified using the PCR GeneAmp kit (Perkin Elmer, Norwalk, Conn.), with 400 pmol of each of 30.1 and 43.RC (manufactured by Research Genetics, Huntsville, Ala.), on a Perkin Elmer DNA Thermal Cycler. PCR conditions were: cycles 1–2, denaturation at 94° C. for 2 minutes, annealing at 58° C. for 2 minutes and elongation at 72° C. for 2 minutes; cycles 3–42, denaturation at 94° C for 45 seconds, annealing at 58° C. for 45 seconds and elongation at 72° C. for 2 minutes. The ~430 base pair amplification product, referred to as the 30.2/43.3.RC fragment, was separated from reaction contaminants by electroelution from a 6% polyacrylamide gel (Novex, San Diego, Calif.). The 30.2/43.3.RC fragment was labelled with [$\alpha$-$^{32}$p]-dCTP (Amersham) using random primer labelling (Stratagene, La Jolla, Calif.); labelled DNA was separated from unincorporated nucleotides using a ChromaSpin-10 column (Clontech, Palo Alto, Calif.).

Prehybridization and hybridization conditions were 6×SSC (SSC: 150 mM NaCl, 15 mM trisodium citrate), 0.02 M sodium phosphate pH 6.5, 5×Denhardt's solution, 0.5% (w/v) SDS, 0.01 M EDTA, 100 mg/ml sheared, denatured salmon sperm DNA, 0.23% dextran sulfate, 50% formamide. Prehybridization and hybridization were at 42° C., and the filters were washed for 20 minutes with 0.2×SSC at 60° C. after two prewashes with 2×SSC for 15 minutes. The filters were exposed overnight to X-ray film with two intensifying screens at −70° C.

Approximately 300,000 recombinant phage of the random primed hookworm library (unamplified) were screened with the 30.2/43.3.RC NIF PCR fragment. About 120 recombinant phage hybridized to this probe, of which seven were isolated for nucleotide sequencing analysis. Double stranded sequencing was effected by subcloning the EcoRI cDNA fragments contained in these phage isolates into pBluescript II vector (Stratagene, La Jolla, Calif.). DNA was sequenced using the Sequenase version 2.0 kit (U.S. Biochemical, Cleveland, Ohio) and synthetic oligonucleotide primers.

The NIF phage isolates contained DNA that encoded polypeptides that bore striking resemblance to the amino acid sequences obtained for purified NIF (see FIG. 7 (SEQ. ID. NOS. 67 to 79)). FIG. 8 (SEQ. ID. NO. 80) depicts the nucleotide sequence of the coding region of Neutrophil Inhibitory Factor cDNA (clone 1FL) and its predicted amino acid sequence. A single isolate, NIF-1FL (SEQ. ID. NO. 81), encoded an open reading frame of 825 nt, initiating with a methionine and terminating with, a TGA stop codon (FIG. 8) (SEQ. ID. NO. 80). The NIF polypeptide encoded by NIF-1FL is 274 amino acid residues with a calculated molecular weight of 30,680 daltons. FIG. 9 depicts the alignment of the predicted amino acid sequences of several Neutrophil Inhibitory Factor isoform clones. Each line of sequence represents the corresponding sequence segments of the various clones isolated. Each segment is identified by its clone designation (e.g., 1FL (SEQ. ID. NO. 81), 3P (SEQ. ID. NO. 15 82), 2FL (SEQ. ID. NO. 84), 3FL (SEQ. ID. NO. 85), 4FL (SEQ. ID. NO. 86), 6FL (SEQ. ID. NO. 87) and 1P (SEQ. ID. NO. 83)). The complete amino acid sequence of clone 1FL is listed in standard three-letter amino acid code at the top of each sequence segment. Clones having the same amino acid in a given position as clone 1FL are denoted by ".". Amino acid substitutions are indicated by the appropriate three-letter code. "- - - " indicates a space inserted to maintain alignment of the sequences. The carboxy termini of the 1FL (SEQ. ID. NO. 81) and IP (SEQ. ID. NO. 83) sequences are denoted by an asterisk. The other six NIF phage isolates encoded partial NIF polypeptides; that is they did not contain either an N-terminal methionine residue or a C-terminal stop codon, as compared to the NIF-1FL polypeptide (FIG. 9). These partial NIF isolates comprised six predicted NIF isoforms that were significantly similar to, but not identical to the prototypical NIF-1FL polypeptide.

Example 11

Expression of Functional Recombinant Neutrophil Inhibitory Factor by Mammalian Cells (A) Transient Expression in COS-7 Cells.

The segment of DNA encoding the NIF-1FL isoform was amplified from the original λgt10 isolate DNA using unique. primers for the 5'- and 3'-ends of the coding region. The 5'-primer was composed of a restriction endonuclease site (EcoRl), a consensus ribosome binding site (Kozak, M., Cell 44: 283 (1986)), the ATG initiation codon of NIF and the succeeding 6 codons of the gene. The 3'-primer was composed of a unique nucleotide sequence to the 3'-side of the TGA termination codon of NIF and a restriction endonuclease site (EcoRl). The nucleotide sequences of the 5'- and 3'-primers were 5'-ACC-GAA-TTC-ACC-ATG-GAG-GCC-TAT-CTT-GTG-GTC [SEQ. ID. NO. 11] and 5'-CTG-GAA-TTC-TCG-CTT-ACG-TTG-CCT-TGG-C [SEQ. ID. NO. 12], respectively.

Five microliters of the lambda plaque suspended in 1 ml dilution buffer were used as template DNA. Amplification was accomplished using the PCR GeneAmp kit (Perkin Elmer, Norwalk, Conn.), with 400 pmol of each of the 5'- and 3'-primers (manufactured by Research Genetics), on a Perkin Elmer DNA Thermal Cycler. The PCR conditions were: cycle 1, denaturation at 97° C. for 1 minute, primer annealing for 1 minute at 37° C., ramp from 37° C. to 72° C. in 2 minutes, and amplification for 2 minutes at 72° C.; cycles 3 and 4, denaturation at 94° C. for 1 minute, primer annealing for 1 minute at 37° C., ramp from 37° C. to 72° C. in 2 minutes, and amplification for 2 minutes at 72° C.; cycles 5 through 34, denaturation at 94° C. for 1 minute, primer annealing for 1 minute at 45° C., and amplification for 2 minutes at 72° C.

The amplification product (887 bp) was separated from reaction contaminants using a ChromaSpin 400 column (Clontech Laboratories, Inc. Palo Alto , Calif.). The ends of the amplification product were trimmed with the restriction endonuclease EcoRi and the resulting fragment of DNA (875 bp) ligated into EcoRi-digested plasmid pSG5 (Stratagene, La Jolla, Calif.) using standard techniques. The resulting ligation mixture was used to transform SURE™ competent cells (Stratagene, La Jolla, Calif.).

An isolate containing the 875 bp insert in the proper orientation (5'-end of the coding region proximal to the pSG5 SV40 promoter) was grown in 250 ml Circle Grow™ (Biolo, San Diego, Calif.) with 50 mg/ml ampicillin and plasmid DNA was prepared using a Magic Maxi Prep™ DNA purification system (Promega, Madison, Wis.). Ten micrograms of purified plasmid DNA was transferred into $3.5 \times 10^6$ COS7 cells (ATCC No. CRL 1651) by electroporation (0.4 cm electroporation cell, 325 V, 250 F, infinite resistance, 0.5 ml cells at $7 \times 10^6$/ml in Hepes buffered saline, pH 7.0, 4° C.). After electroporation the cells were allowed to stand on ice for 2 to 3 minutes before dilution with 14 ml warm DMEM:RPMI 1640 (1 to 1 ratio) supplemented with 10% fetal bovine serum prewarmed to 37° C. The cells were placed in 100 mm cell culture dishes and incubated at 37° C. with 8% $CO_2$. Cell culture supernatant fluid was removed at 1, 2 and 3 days after plating and assayed for NIF activity.

(B) Detection and puantitation of Neutrophil Inhibitory Factor Activity in Cell Culture Medium.

15 ml of cell culture fluid was harvested from electroporated COS7 cells (pSG5/NIF1FLCR1). When assayed directly using the neutrophil-plastic adhesion assay (Example 1(C)), this fluid exhibited neutrophil inhibitory activity to dilutions as great as 1:8. An $IC_{50}$ at approximately 1:14 was determined using the hydrogen peroxide release assay (Example 1(E)). No activity was observed using cell culture fluid harvested from COS7 cells electroporated with a control expression plasmid (pCAT; Promega, Madison, Wis.).

(C) Stable Expression in CHO Cells (1) Preparation of Plasmid DNAs

The NIF-1FL insert in the pSG5 construct described above in section (A) was excised by digestion with the restriction endonuclease EcoRI. The 875 bp NIF-1FL fragment was gel purified (Magic PC Prep, Promega, Madison, Wis.) and ligated into EcoRI digested pBluescript II KS (Stratagene, La Jolla, Calif.) using standard techniques. The resulting ligation mixture was used to transform SURER competent cells as described by the supplier (Stratagene, La Jolla, Calif.). Transformed cells were plated on LB agar containing IPTG and X-gal (Sambrook, Fritsch, and Maniatis, Molecular Cloning, a Laboratory Manual, Cold Spring Harbor Laboratory Press, 1989, pp. 1.85 to 1.86). White colonies were screened for plasmids containing the NIF-1FL insert in the proper orientation by digesting plasmid DNA with BamHI; those colonies harboring a plasmid that yielded a 200 bp BamHI fragment were retained. Plasmid was prepared from one of these colonies (Magic Maxi Prep, ProMega, Madison, Wis.) and digested with HindIII and NotI to yield a NIF-1FL fragment with a HindIII overlap on the 5'-end and a NotI overlap on the 3'-end. This DNA fragment was gel purified and ligated into HindIII-NotI digested pRC/CMV (Invitrogen, San Diego, Calif.). The resulting ligation mixture was used to transform SURE™ competent cells. Milligram quantities of pRC/CMV-NIF-1FL were prepared using the Magic Maxi Prep kit.

The plasmid pLTRdHFR26 (Mol. Cell. Biol. 3:32–43 (1983), Nature 275:617–623 (1978)) in the *E. coli* strain RRI was purchased from the ATCC (American Type Culture Collection, Rockville, Md.). Plasmid DNA was purified from a chloramphenicol amplified culture (Sambrook, Fritsch, and Maniatis, Molecular Cloning, a Laboratory Manual, Cold Spring Harbor Laboratory Press, 1989, p. 1.33) using the Magic Maxi Prep kit.

(2) Transfection of CHO Cells

Chinese hamster ovary (CHO) cells harboring a defect in the dihydrofolate reductase gene (dhfr) were obtained from the ATCC (catalog number: CRL 9096) and grown in a 1:1 mixture of RPMI 1640 and DMEM media (Irvine Scientific, Santa Ana, Calif.) supplemented with 10% FBS, 10 mM HEPES, essential amino acids, nonessential amino acids, $5 \times 10^{-5}$ M β-mercaptoethanol, 10 mM sodium pyruvate, and 2 mM glutamine (combo medium). The CHO cells were transfected using the Calcium Phosphate Transfection System following the manufacturer's instructions (Gibco BRL, Gaithersburg, Md.) in 10 cm cell culture dishes at the following ratios: $1 \times 10^6$ cells, 20 g pRC/CMV-NIF1FL DNA and 5 g pLTRdHFR26 DNA. The cells were incubated for 12 hr at 37° C. in the presence of the co-precipitated DNAs.

(3) Selection and Amplification of CHO-NIF1FL Clones

The adhered cells were washed once with fresh combo medium and placed under combo medium containing 500 g/ml of the antibiotic G418 (Gibco BRL, Gaithersburg, N.Dak.) for two weeks at 37° C. to select for those clones exhibiting neomycin resistance. The G418 resistant cells were trypsinized from the culture dishes using standard techniques and washed once with fresh combo medium containing 500 g/ml G418. The washed cells were allowed to attach to 10 cm cell culture dishes ($1 \times 10^6$ per dish) and covered with combo medium containing 500 g/ml G418 and 10, 20, 40, 60, or 80 nM methotrexate (Sigma, St. Louis, Mo.). After two weeks incubation at 37° C., the dishes were examined for colonies and the culture supernatant fluids assayed for NIF activity using the calcein assay for neutrophil adhesion. The cells in dishes exhibiting NIF activity were trypsinized and washed as before and plated to obtain single colonies. One single cell isolate, designated 8F5, expressing NIF activity was chosen for further methotrexate amplification.

8F5 cells were grown to confluence in a 10 cm cell culture dish, detached with trypsin and washed as before. The cells were diluted with combo medium containing 500 g/ml G418 and $1 \times 10^6$ cells were placed in 10 cm culture dishes. The adhered cells were covered with combo medium containing 500 g/ml G418 and 40, 80, 160, 320, or 640 nM methotrexate. Again, after two weeks incubation at 37° C., the dishes were examined for colonies and supernatant fluids assayed for NIF activity. Cells were released from the plates by trypsin treatment as before. The pool of cells obtained from the 320 nM methotrexate dish was selected for further use and single cell isolates were obtained. Three successive rounds of single cell isolation were performed on each colony to ensure clonal purity. The final cell line, designated 8F5-1E6-8C11-1G8, produces NIF at greater than 50 g/m2L in the presence of 500 μg/ml G418 and 320 nM methotrexate.

(D) Fractionation of Neutrophil Inhibitory Factor Activity by Chromatography on Immobilized Concanavalin A.

Five ml of COS7(pSG5/NIF1FLCR1) cell culture fluid was mixed with an equal volume 0.02 M bis Tris-propane-HCl, pH 7.3, 1 M NaCl, 0.001 M $CaCl_2$, 0.001 M $MnSO_4$ and loaded onto a one ml column of Concanavalin A Sepharose (Pharmacia, Piscataway, N.J.) equilibrated with the same buffer. The sample was cycled through the column in a closed loop for 1 hour at 2 ml/minute at 20° C. The column was subsequently washed with 5 ml of 0.02 M bis Tris-propane-HCl, pH 7.3, 1 M NaCl, 0.001 M $CaCl_2$, 0.001 M $MnSO_4$. The buffer resident in the column was displaced with buffer containing 0.5 M methyl-alpha-mannopyranoside and flow stopped for 15 minutes. Flow was restarted at 1 ml/minute and approximately 11 ml of sugar-containing eluate collected. The eluate was dialyzed 18 hours against 1 liter 10 mM potassium phosphate, pH 7.35, 150 mM NaCl at 4° C. and concentrated to 1.1 ml using an Amicon centrifugal concentrator equipped with a 10,000 molecular weight cut-off membrane (CentriPrep 10, Amicon, Beverly, Mass.). When assayed by the neutrophil-plastic adhesion assay (Example 1(C)), this sample exhibited substantial activity at a dilution of 1:16, indicating that a significant portion of the neutrophil function inhibitor activity present in the cell culture fluid binds to immobilized Concanavalin A. This behavior is identical to that observed for crude extracts of *Ancylostoma caninum* (Example 2(B)) and is consistent with the inhibition resulting from the synthesis and secretion from transfected mammalian COS7 cells of a glycoprotein that acts as an inhibitor of neutrophil function.

As a control, 5 ml of COS7 cell culture medium from cells electroporated in the absence of DNA was chromatographed on Concanavalin A Sepharose in the same manner as described above. No activity was observed after Concanavalin A-Sepharose chromatography using the neutrophil-plastic adhesion assay (Example 1(C)).

(E) Fractionation of Neutrophil Inhibitory Factor Activity by Anion Exchange Chromatography using POROS II Q/M.

Five ml of COS7(pSG5/NIF1FLCR1) cell culture fluid was dialyzed 18 hours against one liter of 10 mM bis Tris-propane-HCl, pH 7.0 at 4° C. and loaded at 3 ml/minute onto a 0.46×10 cm column of Poros II Q/M (PerSeptive Biosystems, Inc., League City, Tex.) equilibrated with the same buffer. The column was washed with one column volume of equilibration buffer and developed with a linear gradient of sodium chloride from 0 to 0.5 M over 14.4 column volumes collecting 2 ml fractions. Significant activity in the neutrophil-plastic adhesion assay (Example 1(C) was detected in fractions 17 and 18, corresponding to about 0.45 M NaCl. When fractions were concentrated twenty-fold using centrifugal concentrators equipped with a 10,000 MWCO membrane (Amicon MicroCon 10, Beverly, Mass.), substantial activity was found in fractions 16–19.

Neutrophil inhibitory factor present in extracts from *Ancylostoma caninum* elutes likewise from an anion exchange column (Mono Q, Pharmacia, Piscataway N.J.) at 0.4 M NaCl (Example 4).

Example 12

Expression of Functional Recombinant Neutrophil Inhibitory Factor in *Pichia pastoris*

(A) Description of the *Pichia* Shuttle/Expression Vector.

The *Pichia* strain GTS115 (his4) (Stroman, D. W. et al., U.S. Pat. No. 4,855,231 (Aug. 8, 1989)) and the *E. coli-Pichia* shuttle vectors pHILS1 and pHILD5 referred to hereafter are part of the *Pichia* yeast expression system licensed from the Phillips Petroleum Company (Bartlesville, Okla.).

All of the *Pichia* manipulations were performed essentially as described for *Saccharomyces cerevesiae* in Gene Expression Technology, pp.231–471, Academic Press, New York, (D. V. Goeddel, edit. 1991) and in Stroman, D. W. et al., U.S. Pat. No. 4,855,231 (Aug. 8, 1989).

The pHIL7SP8 vector used to direct expression of NIF in *P. pastoris* was assembled from pHILS1 and pHILD5 and from synthetically generated fragments. The pHIL7SP8 plasmid contained the following elements cloned onto pBR322 sequences:

1) 5' AOX1, about 1000 bp segment of the *P. pastoris* alcohol oxidase 5' untranslated and promoter sequences (see Stroman, D. W. et al., U.S. Pat. No. 4,855,231 (Aug. 8, 1989) the disclosure of which is incorporated herein by reference)

2) The PHO1 *P. pastoris* secretion signal.

3) A 19-amino acid synthetic pro-sequence fused to the PHO1 signal. This pro-sequence represents one of the two 19-aa pro-sequences designed by Clements et al.,(1991. Gene, 106:267–272) on the basis of the yeast alpha-factor leader sequence.

4) A synthetic multi-cloning site.

5) 3' AOX1, about 0.256 bp segment of the aox1 terminating sequence (see Stroman, D. W. et al., U.S. Pat. No. 4,855,231 (Aug. 8, 1989) the disclosure of which is incorporated herein by reference).

6) *P. pastoris* histidinol dehydrogenase gene, his4, contained on a 2.4 kb fragment to complement the defective his4 gene in the host GTS115 (see Stroman, D. W. et al., U.S. Pat. No. 4,855,231 (Aug. 8, 1989) the disclosure of which is incorporated herein by reference).

7) Region of 3' AOX1 untranslated DNA sequence, which together with the 5' AOX1 region is necessary for site-directed integration (see Stroman, D. W. et al., U.S. Pat. No. 4,855,231 (Aug. 8, 1989) the disclosure of which is incorporated herein by reference).

(B) Construction of pHIL7SP-NIc1/pHIL7SP-Nic10 and expression in *Pichia*.

The segment of DNA encoding NIF was PCR-amplified from a sub-clone of NIF-1FL in BluescriptII (Stratagene, La Jolla, Calif.) using unique primers for the 5'- and 3'-ends of the coding region.

The 5'-primer contained no restriction endonuclease sites and corresponded to the region beginning at the 5'-end of proteolytically processed NIF and the succeeding 7 codons. The codon for the first residue of the mature NIF-1FL (SEQ. ID. NO. 117) was altered from AAT to AAC (both codons translate to asparagine). The 3'-primer was composed of 8 codons at the 3' end of the coding region, a TAA stop replacing the TGA stop of the natural gene, and three unique restriction endonuclease sites (HindIII, SpeI, and BglII). The sequences of the 5'- and 3'-primers used were 5'-AAC-GAA-CAC-AAC-CTG-AGG-TGC-CCG [SEQ. ID. NO. 13] and 5'-CCT-CCT-CCT-AGA-TCT-AAG-CTT-ACT-AGT-TTA-TAA-CTC-TCG-GAA-TCG-ATA-AAA-CTC [SEQ. ID. NO. 14], respectively.

Amplification was accomplished using 100 pmol of each primer, 2 units of Vent polymerase in 1×Vent buffer (New England Biolabs, Beverly, Mass.), and 0.2 mM of each of dATP, dCTP, dGTP, and dTTP. One hundred nanograms of BluescriptII-containing NIF-1FL (SEQ. ID. NO. 116) were used as template DNA. The PCR conditions were the same for all ten cycles: denaturation at 95° C. for 1 minute, primer annealing at 60° C. for 1 minute, and amplification for 1.5 minutes at 72° C. The amplification product was purified as described above and digested with BglII.

The amplification product was then ligated into StuI-BglII cleaved pHIL7SP8 using standard methods. The ligation mixture was used to transform *E. coli* WK6, and ampicillin resistant clones were obtained on ampicillin plates. Based on restriction and DNA sequence analysis, correct insert sequences in two of the resulting plasmid clones, pHIL7SP-NI1c1 and pHIL7SP-NI1c10, were selected to transform the *P. pastoris* yeast strain GTS115 (his4). These vectors were digested with either Not1 (targeting integration to the expression cassette in the AOX1 region) or Sal1 (targeting integration to the HIS4 locus).

The 4 restricted DNA preparations were introduced individually into *Pichia* by electroporation, essentially as described by Becker, D. and Guarente, L., Methods in Enzymology, vol. 194, pp. 182–189 (1991). Briefly, the cells were grown in YEPD medium at 30° C. to an $OD_{600}$ of 1.3 to 1.5. The cells were pelleted at 4° C. (1500×g for 5 minutes) and resuspended in 500 ml ice cold sterile distilled water. The cells were pelleted as above and resuspended in 250 ml ice cold distilled water. After the cells were pelleted again, they were resuspended in 20 ml ice cold 1 M sorbitol. After a final pelleting the cells were resuspended in 1 ml ice cold 1 M sorbitol. Forty µl cells in 1 M sorbitol were mixed with 5 µl of linearized DNA and the mixture transferred to an ice cold 0.2 cm gap electroporation cuvette. After 5 minutes on ice, the cells were pulsed at 50 uF, 1.5 kV/cm, and 200 Ω resistance. One ml of ice cold 1 M sorbitol was added to the cuvettes and 100 to 500 ul of the cell suspension were spread on minimal dextrose plates. The plates were incubated at 300 C until colonies appeared. The transformation mix was plated on minimal dextrose (MD) medium to select for His+transformants. Subsequent selection for NIF expression was performed in shake flask cultures in minimal medium containing methanol as described in Stroman, D. W. et al., U.S. Pat. No. 4,855,231 (Aug. 8, 1989)

(C) Detection and Quantitation of Neutrophil Inhibitory Activity in Cell Medium.

*Pichia* cell supernatant (pHIL7SP-N1c10) was obtained by centrifugation for 15 minutes at $1,800 \times g_{max}$ from cells 48 hours following methanol induction and filtered through a 0.22 µm cellulose acetate membrane. The filtered cell supernatant solution was concentrated about 3-fold using centrifugal concentrators equipped with a 10,000 MWCO membrane (Amicon MicroCon 10, Beverly, Mass.) and desalted by gel filtration using a 1×10 cm column of G-25 Sephadex Superfine (Pharmacia, Piscataway, N.J.). Using the neutrophil-plastic adhesion assay (Example 1(C)), the desalted supernatant solution (diluted 2× by gel filtration) exhibited neutrophil inhibitory activity to dilutions as great as 1:640. No activity was observed using cell supernatant solution similarly harvested and treated from *Pichia* cells expressing a recombinant anti-thrombotic protein devoid of neutrophil inhibitory activity.

(D) Purification of Neutrophil Inhibitory Factor from *Pichia*

Following methanol induction for 48 hours, 75 ml of *Pichia* cell supernatant (pHIL7SP-N1c10) 48 hours following methanol induction was obtained by centrifugation for 15 minutes at $1,800 \times g_{max}$, and filtered through a 0.22 µm cellulose acetate membrane. This was concentrated using an Amicon stirred UF cell equipped with a 10,000 molecular weight cut-off membrane (YM10) and then diluted with water (about 10-fold). This diafiltration process was repeated until the conductivity was reduced from 45 mS to 1 mS. The final volume of the concentrate was 25 ml.

This concentrate was dialyzed at 4° C. for 6 hours against one liter of 0.05 M bis Tris-propane-HCl, pH 7.0 to adjust the pH to neutrality, and then against two changes of one liter of 0.001 M potassium phosphate, pH 7.0.

Fifteen ml of the dialyzed cell supernatant was loaded onto a 0.8×15 cm column of ceramic hydroxyapatite (Pentax, 2 μm; American International Chemical, Inc., Natick, Mass.) equilibrated with 0.001 M potassium phosphate, pH 7.0 at a flow rate of 0.4 ml/min (48 cm/hour). The column was washed with one column volume of 0.001 M potassium phosphate, pH 7.0 and then developed with a linear gradient from 0.001 to 0.050 M potassium phosphate over 20 column volumes at a flow rate of 0.35 ml/min. Substantial neutrophil inhibitory activity eluted at approximately 0.02–0.035 M potassium phosphate in much the same fashion as observed for neutrophil inhibitory factor isolated from *Ancylostoma caninum* (Example 2(D)).

Fractions exhibiting substantial neutrophil inhibitory activity (assessed using the neutrophil-plastic adhesion assay (Example 1(C))) were combined and concentrated to about 3 ml using an Amicon centrifugal concentrator equipped with a 10,000 molecular weight cut-off membrane (CentriPrep 10, Amicon, Beverly, Mass.) and applied to a 1×25 cm C4 300 Å reverse phase column (5 μm particle size, Vydac, Hesperia, Calif.) equilibrated with 0.1% trifluoroacetic acid. The column was washed with four column volumes of equilibration buffer and then developed with a linear gradient of acetonitrile from 15 to 40% over column volumes at a flow rate of 5 ml/min. A major complex peak absorbing at 214, 254, and 280 nm eluted at about 36–38% acetonitrile.

Fractions including and bracketing this peak were dried using a centrifugal evaporator to remove solvent and trifluoroacetic acid and rehydrated with 0.065 M potassium phosphate, pH 7.0, 0.08 M NaCl. The rehydrated fractions possessed substantial neutrophil inhibitory activity as judged by the neutrophil-plastic adhesion assay (Example 1(C)) and the hydrogen peroxide release assay (Example 1(E)).

Fractions with substantial activity were combined and sequenced by Edman degradation using a 470A/120A/900A gas phase sequencer (ABI, Foster City, Calif.) (See Example 9) and yielded the following sequence:

Asn-Glu-His-Asn-Leu-Arg-Xxx-Pro-Gln-Xxx-Gly-Thr-Glu-Met-Pro-Gly-Phe-Xxx-Asp-Ser-Ile-Arg-Leu-Gln-Phe-Leu-Ala-Met-His-Asn-Gly-Tyr-Arg-Ser-Lys-Leu-Ala-Leu-Gly-His-Ile-Ser-Ile-Thr-Glu [SEQ. ID. NO. 15]. "Xxx" refers to an undetermined amino acid at that position, since no specific amino acid was identified during Edman degradation of the peptide.

This sequence matches the predicted N-terminal sequence of mature NIF-1FL (SEQ. ID. NO. 117), the NIF isoform used in this construction construct (pHIL7SP-N1c10; see FIG. 8 (SEQ. ID. NOS. 80 and 81)). The first position at which a residue was not detected is predicted to be a cysteine; cysteine residues could not be detected in this analysis because the protein had not been alkylated. The two other positions at which residues were not detected correspond to asparagine residues followed by either a serine or threonine one residue distant. This is a glycosylation consensus sequence [Asn-Xxx-(Ser/Thr)) and the fact that asparagine was not detected strongly suggests that these asparagines are glycosylated. The C4-purified preparation was estimated to have an $IC_{50}$ of about 5–10 nM in the hydrogen peroxide release assay (Example 1(E)).

Example 13

Determination of Specificity of the Neutrophil Inhibitory Factor

To test the specificity of the Neutrophil Inhibitory Factor of the present invention, and to confirm that it did not inhibit neutrophil activation by a general cytotoxic mechanism, the activity of the inhibitor was assessed in a non-neutrophil cell adhesion-based assay, platelet aggregation.

The effects of the hookworm Neutrophil Inhibitory Factor on blood platelet aggregation were examined. Platelet aggregation was performed with human platelet-rich plasma (PRP). PRP was stirred at 37° C. in an aggregometer (Scienco Model 247, Morrison, Colo.) and aggregation was initiated by the addition of 10 μM ADP (Sigma, St. Louis, Mo.). Aggregation was monitored as a change in light transmittance, and is expressed as the initial rate of aggregation. A concentration of Neutrophil Inhibitory Factor of approximately 150 nM, a concentration that completely blocked neutrophil function as assessed by neutrophil-HUVEC and neutrophil-plastic adhesion assays, homotypic neutrophil aggregation and hydrogen peroxide release by neutrophils, had no inhibitory effect on ADP-induced aggregation of human platelets.

Example 14

Mac-1 Integrin is a Primary Receptor for Neutrophil Inhibitory Factor from Hookworm (A) Immunopreciptation of $^{125}$I-Labelled NIF Using Monoclonal Antibodies to Mac-1 in the Presence of Neutrophil Extract.

NIF purified from *Ancylostoma caninum* was radiolabeled using the following method. Approximately 30 μg NIF was labeled with 2 mCi $Na^{125}I$ (carrier free; Amersham, Arlington Hills, Ill.) using Enzymobeads (BioRad, Hercules, Calif.). Briefly, to a 1.5 ml eppendorf test tube was added 360 μl of the Enzymobead suspension together with 180 μl of a 1% beta-D-glucose solution, NIF and $Na^{125}I$. This mixture was allowed to react at room temperature for 30 minutes. Labeled NIF was separated from unbound $^{125}$I-iodine by desalting on a PD10-DG column (BioRad, Hercules, Calif.) using phosphate buffered saline (0.1 M sodium phosphate pH 7.2, 0.15 M sodium chloride) containing 1% bovine serum albumin as elution buffer. Radioactive fractions containing NIF were pooled. The specific activity of the $^{125}$I-NIF was 13.9 μCi/μg.

Various leukocyte proteins were assessed for ability to capture NIF in immunoprecipitation experiments. Potential cellular receptors for NIF were selected from a detergent extract of leukocytes using specific monoclonal antibodies.

Leukocytes were prepared from human blood using Mono-poly (ICN, Biomedicals Inc., Costa Mesa, Calif.). The leukocyte cell pellet was resuspended in 1 ml resuspension buffer (20 mM Tris pH 7.5, 150 mM NaCl, 1 mM $CaCl_2$) followed by the addition of 1 ml extraction buffer (2% Triton X-100, 20 mM Tris pH 7.5, 150 mM NaCl, 1 mM $CaCl_2$). Cells were incubated on ice 30–60 minutes, vortexing briefly every 10 minutes. Cell debris was pelleted at 5000 g for 5 minutes at 4° C.

Monoclonal antibody-test protein complexes were formed by incubating 10 μg specific monoclonal antibody with 200 μl of leukocyte detergent extract at 4° C. for 4 hours. To this mixture was added 2.5 μl of the $^{125}$I-NIF and these reagents were incubated at 4° C. for 18 hours. Precipitation of the complex was effected by adding this mixture to a 1.5 ml eppendorf test tube containing 50 μl of protein G-sepharose (Pharmacia, Pistacaway N.J.; resuspended in TACTS 20 buffer (0.05% Tween 20, 20 mM Tris pH 8, 120 mM NaCl, 2 mM $CaCl_2$) with 1% bovine serum albumin) and gently agitating at 4° C. for 2 hours.

The protein G-sepharose beads were subsequently washed four times with TACTS 20 buffer. Fifty microliters of Laemmli sample buffer (Laemmli, U. K., 1970, Nature, 227:680–685) containing 5% β-mercaptoethanol was then added to the aspirated beads; this material was incubated at 100° C. for 10 minutes and loaded onto 4–12% gradient SDS-polyacrylamide gels (Novex, San Diego, Calif.). Gels were dried after running and visualized by exposure to X-Omat film (Kodak, Rochester, N.Y.) in the presence Quanta III screens (Dupont, Wilmington, Del.) at −70° C. Size standards were $^{14}$C-Rainbow markers (Amersham, Arlington Hills, Ill.).

When monoclonal antibodies (MAb) directed to the Mac-1 integrin complex (OKM-1, ATCC# CRL8026; LM-2, ATCC# HB204) were used in these experiments, $^{125}$I-NIF was precipitated as evidenced by a band that migrated with an apparent molecular weight of approximately 41,000 daltons upon autoradiography. Precipitation of $^{125}$I-NIF was dependent on the presence of these antibodies as well as the presence of leukocyte extract. Furthermore, the precipitation of $^{125}$I-NIF was not observed in the presence of a one hundred fold molar excess of cold NIF. $^{125}$I-NIF did not precipitate when MAbs to other leukocyte integrins were used including MAbs directed against the VLA-4 (L25.3; Becton Dickinson, Sunnyvale, Calif.) and p150,95 (SHCL-3; Becton Dickinson, Sunnyvale, Calif.) integrin complexes. A relatively minor amount of $^{125}$I-NIF was observed when a MAb directed against the LFA-1 (TS1/22; ATCC# HB202) integrin complex was used. This was likely due to cross-reactivity of the anti-LFA-1 antibody with the related integrin complex Mac-1. These results demonstrate that Mac-1 is a cell-surface receptor for *Ancylostoma caninum* NIF on leukocytes.

(B) Precipitation of $^{125}$I-Mac-1 Using Biotinylated NIF

As another approach to identify NIF receptors on leukocytes, biotin-labeled NIF was used to precipitate NIF-associating proteins from a detergent extract of surface iodinated leukocytes.

NIF was biotinylated by conjugation to its carbohydrate moieties. Approximately 8 µg of NIF purified from hookworm (*Ancylostoma caninum*) lysates (hydroxyapatite eluate; see Example 2(D)) was oxidized with 50 mM $NaIO_4$ in 1 ml 0.1 M sodium acetate, pH 5.5. After 20 minutes at 4° C. the reaction was terminated with the addition of 100 µl 165 mM glycerol. Oxidized NIF was separated from other reaction products using a Microcon 10 concentrator (Amicon, Beverly, Mass.), and diluted into 100 µl 0.1 M sodium acetate, pH 5.5. Biotinylation was effected by the addition of 400 µl 6.25 mM biotin-LC-hydrazide (Pierce, Skokie, Ill.). The reaction was allowed to proceed for 18 hours at 4° C. Biotinylated NIF was worked up by buffer exchange into phosphate buffered saline (PBS; 0.1 M sodium phosphate, 0.15 M sodium chloride, pH 7.2), using a Microcon 10 concentrator. To 250 µl of the concentrate was added an equal volume of glycerol, giving a final NIF-biotin concentration of approximately 16 µg/ml. This material was stored at −20° C.

The anti-CD18 integrin complex monoclonal antibodies LM-2 and OKM-1 (anti-Mac-1; ATCC #HB204 and CRL8026, respectively) and TS1/22 (anti-LFA-1; ATCC# HB202) were biotinylated using the protocol described above.

Cell surface iodination of human leukocytes was done using the following procedure. A total leukocyte fraction, prepared from 90 ml of fresh human blood using Mono-Poly density gradient separation (ICN Biomedical, Costa Mesa, Calif.), was suspended in 0.5 ml phosphate buffered saline. To the cell suspension was added 2 mCi $Na^{125}I$ (carrier free; Amersham; Arlington Heights, Ill.), 60 µl 0.03% hydrogen peroxide and 100 µl lactoperoxidase at 2 mg/ml (BioRad; Hercules, Calif.). The reaction was allowed to proceed for 30 minutes at room temperature, with gentle agitation every two minutes. The reaction was terminated by the addition of 25 mM KI in PBS, and the cells were washed two times with PBS. The leukocyte cell pellet was resuspended in 1 ml resuspension buffer and leukocyte extract was prepared as described above in Example 14(A).

Sixty microliters of NIF-biotin (16 µg/ml) was diluted with 40 µl resuspension buffer and incubated with 200 µl $^{125}$I-labeled leukocyte extract at room temperature for 6 hours. Precipitation of NIF-associating proteins from the leukocyte extract was effected by the addition of 100 µl streptavidin-agarose (Pharmacia; Piscataway, N.J.) to this mixture. Test tubes were agitated gently for 18 hours at 4° C. Beads were subsequently washed four times with 500 µl TACTS-20 buffer (0.05% Tween 20, 20 mM Tris pH 8, 120 mM NaCl, 2 mM $CaCl_2$), and associated proteins were solubilized with 50 µl sample buffer (5% β-mercaptoethanol) and analyzed by SDS-PAGE as described in Example 5. Control precipitations were performed in a similar manner with biotinylated monoclonal antibodies to Mac-1 and LFA-1.

Biotinylated NIF precipitated two $^{125}$I-labeled polypeptides that, when separated by 6% SDS-PAGE, had apparent molecular weights of about 170 kDa and about 95 kDa. These polypeptides comigrated on SDS-PAGE in this experiment with the two polypeptides that were precipitated by the anti-Mac-1 monoclonal antibodies LM-2 and OKM-1. This data strongly suggests that Mac-1 is a major receptor for NIF on leukocytes when considered with the results of the previous experiment (Example 14(A)), in which Mac-1 was shown to associate with NIF.

Example 15

Preparation Of Native Neutrophil Inhibitory Factor From *Toxocara canis*

(A) Preparation of *Toxocara* Lysate.

Frozen canine worms *Toxocara canis* were obtained from Antibody Systems (Bedford, Tex.) and were stored at −70° C. until homogenized. *Toxocara canis* were homogenized on ice in homogenization buffer (0.02 M Tris-HCl pH 7.4, 0.05 N NaCl, 0.001 M $MgCl_2$, 0.001 M CaCl2, $1.0 \times 10^{-5}$M E-64 Protease Inhibitor (CAS 66701-25-5), 1.0×10–6 M pepstatin A (isovaleryl-Val-Val-4-amino-3-hydroxy-6-methyl-heptanoyl-Ala-4-amino-3-hydroxy-6-methylheptanoic acid, CAS 26305-03-3), $1.0 \times 10^{-5}$M chymostatin (CAS 9076-44-2), $2.0 \times 10^{-5}$M APMSF (amidinophenylmethylsulfonyl fluoride-HCl), 5% (v/v) glycerol] using an Ultra-Tarrax homogenizer (Janke and Kunkel, Stanfen, Germany). The protease inhibitors E64, pepstatin A, chymostatin, and APMSF were obtained from Calbiochem (La Jolla, Calif.). Approximately 3–6 ml of homogenization buffer was used to homogenize each gram of frozen worm. Twenty-four grams of worms was used in total. Insoluble material was pelleted by two sequential centrifugation steps: $40,000 \times g_{max}$ at 4° C. for 25 minutes followed by $105,000 \times g_{max}$ at 4° C. for 1 hour. The supernatant solution was clarified by passage through glass wool and a 0.45 µm cellulose acetate filter (CoStar, Cambridge, Mass.).

(B) Concanavalin A Sepharose Chromatography of *Toxocara* Lysate

*Toxocara canis* lysate (68 ml) was absorbed to 26 ml of Concanavalin A Sepharose (Pharmacia, Piscataway, N.J.) pre-equilibrated with Con A buffer [0.02 M Tris-HCl, pH 7.4, 1 M NaCl, 0.001 M $CaCl_2$, 0.001 M $MnSO_4$] by recycling it through a 1.6×13 cm column at a flow rate of 4 ml/minute (119 cm/hour) for 2 hours. The column was at room temperature (24° C.) while the reservoir of lysate was maintained on ice throughout the procedure. The column was subsequently washed with 100 ml of Con A buffer. Material that had activity in anti-adhesion assays (see, Section (D) below) was eluted with approximately 3–5 column volumes of Con A buffer containing 0.5 methyl-alpha-mannopyranoside (CAS 617-04-09) at a flow rate of 1 ml/minute (30 cm/hour). The eluted material was concentrated to 5 ml using an Amicon stirred ultrafiltration vessel equipped with a 10,000 molecular weight cutoff membrane, then diluted to 50 ml with deionized water, and reconcentrated to 2.3 ml using a centrifugal ultrafiltration unit with a 10,000 molecular weight cut-off (Polysciences, Inc., Warrington, Pa.) Material used for molecular sieve chromatography with Superdex columns (1.5 ml) was additionally concentrated to 0.5 ml using centrifugal ultrafiltration units with a 10,000 molecular weight cut-off (Amicon, Inc., Beverly, Mass.).

(C) Molecular Sieve Chromatography Using Superdex 200 HR.

Material eluted from immobilized Concanavalin A (see step (B) above) and concentrated by ultrafiltration was loaded on a 1.0 cm×30 cm column of Superdex 200 HR (Pharmacia, Piscataway, N.J.). The column was pre-equilibrated with 0.01 M potassium phosphate, pH 7.35, and 0.15 H NaCl at 24° C. The chromatography was conducted at a flow rate of 0.25 ml/minute. Anti-adhesion activity eluted with an apparent molecular weight of approximately 20,000.

(D) Assay of Neutrophil Inhibitory Activity Isolated From *Toxocara canis*

Material eluted from Concanavalin A Sepharose with methyl alpha-mannopyranoside was assayed by the neutrophil-HUVEC adhesion assay (see Example 1(B)) and was found to inhibit the adhesion of neutrophils to endothelial cells. Adhesion inhibitory activity was also demonstrated using the neutrophil-plastic adhesion assay. (Example 1 (C)).

Material purified by chromatography on both Concanavalin A Sepharose and Superdex 200 HR inhibited neutrophil adhesion in the neutrophil-adhesion assay (see Example 1(C)).

Example 16
In Vivo Characterization Of Neutrophil Inhibitory Factor

Neutrophil Inhibitory Factor isolated from canine hookworms was tested in an animal model of acute inflammation.

Peritoneal inflammation was induced in 150–250 gram Sprague-Dawley rats by an intraperitoneal injection of nine ml of 2% oyster glycogen in $H_2O$ (see Baron et al., *Journal of Immunological Methods*, 49:305, 1982; McCarron et al., *Methods in Enzymology*, 108:274, 1984; Feldman et al., *Journal of Immunology*, 113:329, 1974; Rodrick et al., *Inflammation*, 6:1, 1982; and Kikkawa et al., *Laboratory Investigation*, 30:76, 1974).

Figure 10:
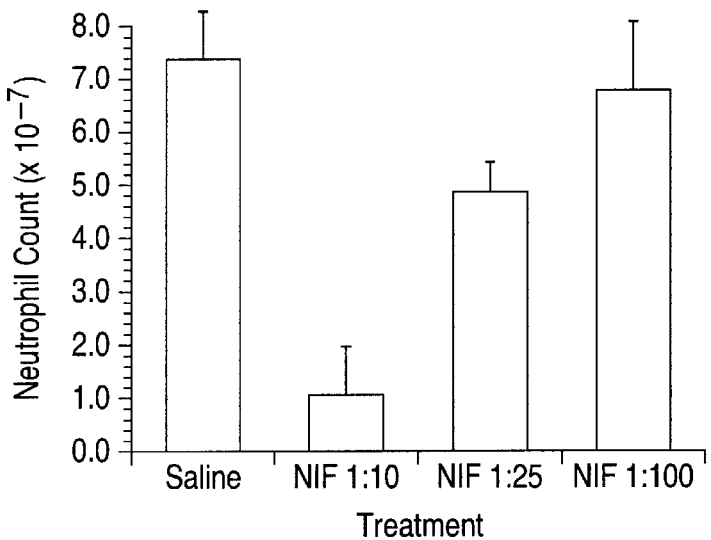
FIG. 10 depicts the anti-inflammatory effect of varied doses of Neutrophil Inhibitory Factor isolated from canine hookworms administered intraperitoneally in an animal model of inflammation.

NIF was prepared as described in Example 2. Lysate from approximately 20,000 hookworms (48.2 g wet weight) was prepared and chromatographed on ConA, Superdex, and hydroxyapatite (HA). The active fractions from two equivalent HA runs were combined to yield 41 ml of HA material. One ml of NIF solution (11 µg) was administered simultaneously with the glycogen by the intraperitoneal route or thirty minutes prior to glycogen administration by the intravenous route. Four hours later the peritoneal exudate was harvested by purging the peritoneal cavity with 30 ml of Hanks Balanced Salt Solution without $Ca^{++}$ or $Mg^{++}$, supplemented with 0.03% EDTA and blood cells were counted on a Celldyn 3000 (Abbott Laboratories, North Chicago, Ill.) automated multiparameter differential cell counting instrument. The major cellular component in the exudate was neutrophils. FIG. 10 depicts the effects of varying doses of Neutrophil Inhibitory Factor isolated from canine hookworms on neutrophil infiltration in peritoneal inflammation in rats induced by interperitoneal infusion with glycogen. Glycogen (9 ml) and Neutrophil Inhibitory Factor (1 ml) were injected simultaneously by intraperitoneal route.

FIG. 10 shows the results of six independent experiments. NIF caused a dose dependent inhibition of neutrophil infiltration to the rat peritoneal cavity in response to glycogen.

A second study was performed to determine if intravenous administration of NIF could prevent glycogen-induced rat peritoneal inflammation. In one set of rats, NIF and glycogen were administered by the intraperitoneal route as previously described. In a second group of rats, 1 µg of NIF was administered intravenously thirty minutes prior to the intraperitoneal infusion of glycogen. A third group of animals received glycogen and NIF treatment was replaced with saline. Four hours later the peritoneal exudate was collected and blood cells were counted.

Figure 11:
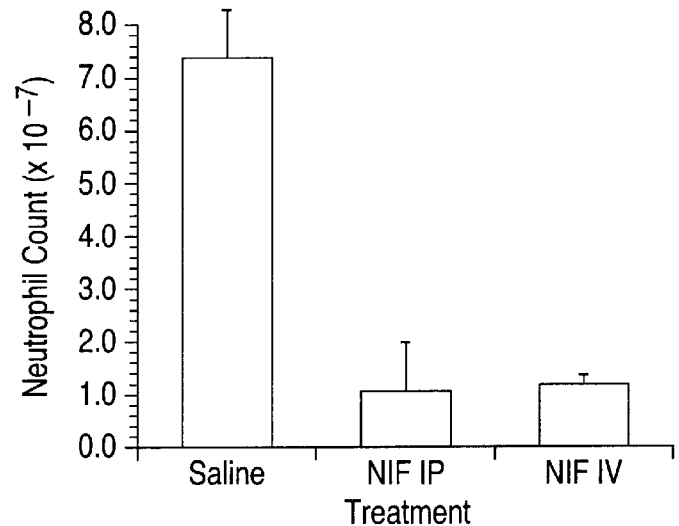
FIG. 11 depicts the anti-inflammatory effect of Neutrophil Inhibitory Factor isolated from canine hookworms administered either intraperitoneally or intravenously in an animal model of inflammation.

FIG. 11 depicts the effect of Neutrophil Inhibitory Factor isolated from canine hookworms on neutrophil infiltration in peritoneal inflammation in rats induced by intraperitoneal infusion of glycogen. Neutrophil Inhibitory Factor (1 ml) was injected by intraperitoneal route in conjunction with intraperitoneal infusion of glycogen, or by intravenous route thirty minutes prior to infusion of glycogen. FIG. 11 represents a summary of the six independent experiments for the intraperitoneal administration of NIF and the results of the single experiment for the intravenous administration of NIF. These results demonstrate that NIF, when administered by either the intraperitoneal or intravenous route, was effective in the prevention of peritoneal inflammatory response in glycogen-stimulated rats.

Example 17
Inhibition of Neutrophil-Mediated Inflammation In Vivo by Recombinant Neutrophil Inhibitory Factor The in vivo anti-inflammatory properties of recombinant NIF (rNIF) were tested in a rat ear inflammation assay (adapted from Young et al., 1984).

In this assay, inflammation was induced in the rat ear by topical administration of arachidonic acid. Sprague-Dawley rats (250 g) were anesthetized with pentobarbital (initial dose of 65 mg/kg intraperitoneal; Anpro Pharmaceutical, Arcadia, Calif.); rats were maintained at a surgical plane of anesthesia for the duration of the experiment (4 hours). A catheter was inserted into the femoral vein of the anesthetized rat. One hundred microliters of recombinant mature NIF (SEQ. ID. NO. 117) (produced in *Pichia pastoris;* see Example 12) at a concentration of 20 mg/ml in PBS was injected via the catheter. Control rats received 100 µl sterile 0.14 M NaCl. Five minutes after the IV administration of rNIF, arachidonic acid (Sigma, St. Louis, Miss.; diluted 1:1 with acetone to a final concentration of 500 mg/ml) was applied to the right ear in three 10 µl applications each to the inside and the outside of the ear. The right ear thus received a total dose of 30 mg arachidonic acid. The left ear, used as a background control, received a total of 60 µl acetone. Four hours after administration of arachidonic acid the rat was sacrificed with $CO_2$.

Neutrophil infiltration into the arachidonic acid-treated ear tissue was quantitated indirectly by determining myeloperoxidase activity. A tissue sample was obtained from the center of each ear using a 7 mm skin punch (Miltex; Lake Success, N.Y.). The tissue sample was cut into small pieces and added to a 16×100 mm test tube that contained 0.5 ml HTAB buffer (0.5% hexadecyltrimethylammonium bromide in 50 mM sodium phosphate, pH 6.4; HTAB was purchased from Sigma, St. Louis, Mo.). The ear tissue was homogenized for 20 seconds using an Ultra-Turrax (Janke and Kunkel; Staufen, Germany) at high speed. Insoluble matter was removed from the homogenate by centrifugation at 14,000×g for 10 minutes followed by filtration through Nytex gauze. Myeloperoxidase determinations were done in triplicate in 96 well polystyrene plates (Costar; Cambridge, Mass.). Twenty five microliters of HTAB-solubilized ear tissue was added to each well, and to this was added 100 µl of substrate solution. Substrate solution comprised two components: (1) 0.012% $H_2O_2$ in 0.1 M sodium acetate pH 4.5 and (2) 0.3 mg/ml 3,3',5,5'-tetramethylbenzidine in 10% HCl, combined immediately prior to use at a ratio of 0.125:1. After ten minutes the reaction was stopped by the addition of 125 µl 1 M $H_2SO_4$. Samples were quantitated colorimetrically at 450 nm and background was read at 650 nm. A standard curve was generated using human leukocyte myeloperoxidase (Sigma; St. Louis, Mo.).

Figure 12:
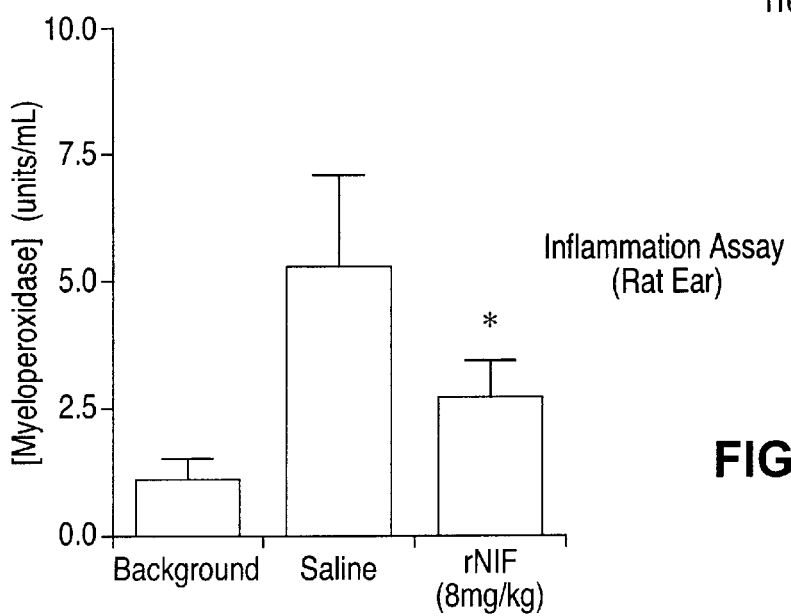
FIG. 12 depicts the anti-inflammatory effect of recombinant Neutrophil Inhibitory Factor produced in *Pichia pastoris* administered in vivo in an animal model of inflammation.

Recombinant NIF had a protective effect on arachidonic acid-induced neutrophil infiltration into ear tissue. FIG. 12 shows that ear tissue from rats that received rNIF had a mean of 1.6 myeloperoxidase units/ml (MU/ml) whereas ears from rats that received saline had a mean of 4.1 MU/ml, when background myeloperoxidase activity is subtracted (n=10 in each group). One myeloperoxidase unit will produce an increase in absorbance at 470 nm of 1.0 per minute at pH 7.0 and 25° C., calculated from the initial rate of reaction using guaiacol as substrate (Desser, R. K., et al., Arch. Biochem, Biophys. 148:452 (1972)). Neutrophil infiltration was thus reduced –60% in rats that received rNIF (8 mg/kg IV); there is a significant difference at the 95% confidence level between rats that received NIF and rats that received saline (Student's t test). These results are consistent with the demonstration that hookworm-derived NIF prevented neutrophil infiltration into the peritoneal cavity of rats in response to glycogen (see Example 16). These data further provide evidence that rNIF acts as a potent anti-inflammatory agent in vivo.

Example 18
The Use of Neutrophil Inhibitory Factor DNA Sequences to Isolate Neutrophil Inhibitory Factor-Related Proteins NIF cDNA sequences are used as probes to isolate DNA sequences that encode proteins that are functionally and structurally related to NIF.

Genomic DNA or cDNA libraries are formed using standard procedure (for example see Molecular Cloning. A Laboratory Manual. Sambrook, J., Fritsch, E F., and Maniatis, T. 2nd Ed. Cold Spring Harbor Laboratory Press, CSH, NY 1989). These libraries may be from any animal, fungal, bacterial or viral source, such as *Ancylostoma caninum*, other *Ancylostoma* species, other helminths and mammals including human placental tissue.

Such libraries are screened for useful clones by nucleic acid hybridization using NIF cDNA sequences isolated from *Ancylostoma* as probe. For example, NIF cDNA fragments of about 100–2000 base pairs labeled for detection by standard procedure (for example, see Molecular Cloning. A Laboratory Manual. Sambrook, J., Fritsch, E F., and Maniatis, T. 2nd Ed. Cold Spring Harbor Laboratory Press, CSH, NY 1989) is hybridized with a library from another tissue or another species under conditions of variable stringency. More preferably, however, reduced stringency hybridization conditions are utilized (e.g. 6×SSC [SSC is 150 mM NaCl, 15 mM trisodium citrate], 0.02 M sodium phosphate pH 6.5, 5×Denhardt's solution, 0.5% (w/v) SDS, 0.01 M EDTA, 100 µg/ml sheared, denatured salmon sperm DNA, 0.23% dextran sulfate, 20–30% formamide at 42° C. for 18 hours). Also, more preferably, reduced stringency conditions are used to wash filters after hybridization (0.5 to 2×SSC at 45–60° C. for 20 minutes after two prewashes with 2×SSC for 15 minutes).

NIF-related complementary DNAs isolated using the techniques described above are subjected to nucleotide sequence analysis using the procedure of dideoxy sequencing (Sanger et al, 1977, Proc. Natl. Acad. Sci. USA 74:5463–5467). Isolates containing open reading frames (i.e., initiating with a methionine and terminating with a TAA, TGA or TAG stop codon) are inserted into suitable vectors for protein expression in either bacterial, yeast, insect or mammalian cells. Expression systems comprise vectors designed to secrete recombinant protein (i.e., fusion of cDNA isolate open reading frame with a known secretion signal sequence for that cell type) into the culture medium. Vectors lacking a homologous secretion signal sequence are also used for expression. Either conditioned media or cell lysate, depending on the expression system used, is tested for inhibitory activity using one or more of the following criteria for neutrophil activation: release of hydrogen peroxide, release of superoxide anion, release of myeloperoxidase, release of elastase, homotypic neutrophil aggregation, adhesion to plastic surfaces, adhesion to vascular endothelial cells, chemotaxis, transmigration across a monolayer of endothelial cells and phagocytosis.

Proteins that are structurally related to NIF and that are inhibitory in one or more of these neutrophil function assays would be considered to belong to the NIF family of related molecules.

Example 19
Expression of Functional Recombinant NIF in *E. coli*

DNA for the NIF-1FL coding region (SEQ. ID. NO. 80), initiating at the codon that corresponds to the N-terminal methionine, is inserted into an *E. coli* expression vector. Examples of such vectors are given in Balbas, P. and. Bolivar, F., 1990 (Methods in Enzymology, 185:14–37). The DNA is inserted into the *E. coli* expression vector using methods similar to the methods of insertion of the NIF-1FL coding region into mammalian and yeast expression vectors described in Examples 11 and 12, respectively. PCR oligonucleotide primers are designed to generate an amplification product that contains the NIF-1FL coding region. As was described in connection for the methods for insertion of NIF-1FL into mammalian and yeast expression vectors (see Examples 11 and 12, respectively), primers are engineered so that this fragment contains 5' and 3' restriction sites that are compatible with insertion into the selected expression vector. The expression construct is preferably engineered so that the recombinant NIF will be secreted into the cytoplasm and not the periplasmic space. This may be accomplished by omitting an *E. coli* secretion signal from the construct.

*E. coli* cells are transformed with the NIF-1FL expression vector construct using standard methods. (See, e.g., Molecular Cloning A Laboratory Manual, Sambrook, J. Fritsch, E. F. and Maniatis, T., Second Edition, Cold Spring Harbor Laboratory Press, 1989, 1.74–1.84). Cells are grown in appropriate media (e.g. Luria Broth; see Molecular Cloning. A Laboratory Manual, Sambrook, J. Pritsch, E. P. and Maniatis, T., Second Edition, Cold Spring Harbor Laboratory Press, 1989, A.1) and harvested before they reach the stationary phase of growth.

The majority of the recombinant NIF should be present in the cytoplasm in the form of insoluble and functionally inactive aggregates. The solubilization and refolding of the recombinant protein present in these aggregates may be accomplished using known methods such as those reviewed in detail in Kohno et al., 1990 (Methods in Enzymology, 185:187–195). Refolded recombinant NIF may be separated from unfolded recombinant NIF and other reaction products using a number of standard chromatographic techniques, including C4 reverse phase HPLC (see, e.g., Example 2(E)). Refolded recombinant NIF is tested for functional activity using the neutrophil function assays described in Example 1.

This recombinant NIF is not glycosylated.

Example 20

Preparation of Functional Recombinant NIF by Refolding 'Insoluble' Methionyl-NIF Produced in the *E. coli* Cytoplasm (A) Description of the *E. coli* Expression Vector pMa5-NI1/3

PCR oligonucleotide primers were designed to generate an amplification product that contains the NIF-1FL coding region (SEQ. ID. NO. 116). The PCR product initiates at the first Asn-codon of mature NIF-1FL (SEQ. ID. NO. 117) which as a result of the amplification was changed from AAT to AAC. The 3'-primer replaces the TGA translational stop codon by a TAA triplet and introduces a SpeI, a HindIII and a BglII site downstream of the coding region. The PCR primers were as follows:

Pst414:
5'-CCTCCTCCTA-GATCTAAGCT-TACTAGTTTA-TAACTCTCGG-AATCGATAAA-ACTC [SEQ. ID. NO. 16] (54-mer; 3'-primer matching with the C-terminus)

Pst415:
5'-AACGAACACA-ACCTGAGGTG-CCCG [SEQ. ID. NO. 17] (24-mer; 5'-primer matching with the N-terminus)

Figure 14:
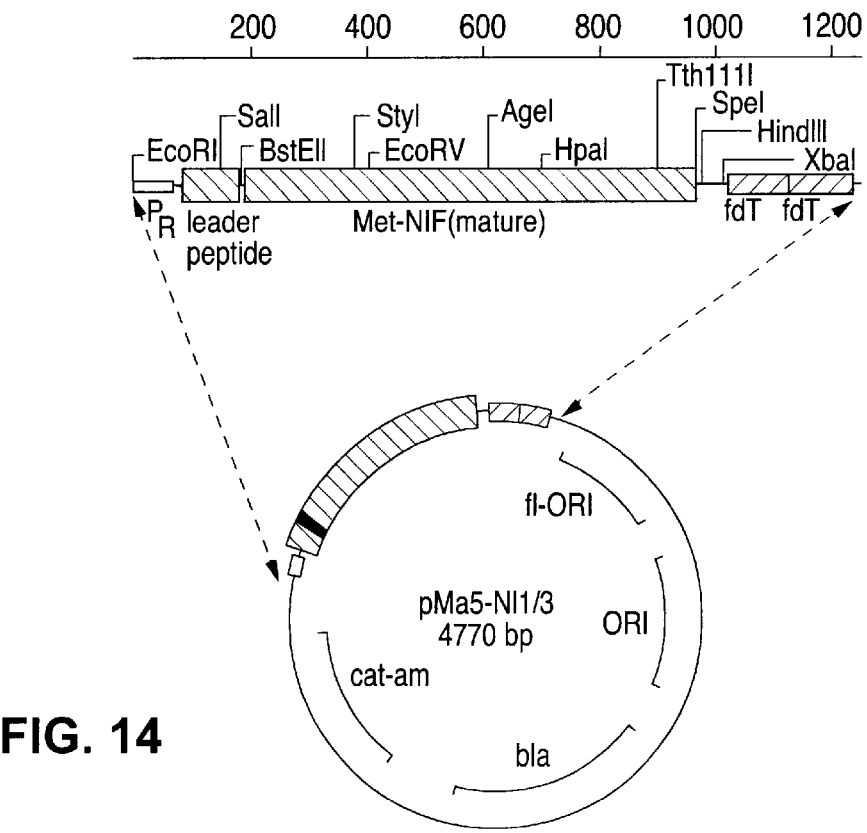
FIG. 14 depicts genetic map of the expression vector pMa5-NI1/3. The vector contains the following elements: (i) a ColE1 type origin of replication (ORI); (ii) the intercistronic region of filamentous phage f1 including the origin of replication (f1 ORI); (iii) the beta-lactamase gene which confers resistance to ampicillin (bla); (iv) the chloramphenicol acetyl transferase gene which contains an amber translational stop codon as the result of a single nucleotide substitution (cat-am); (v) the phage lambda $P_R$ promoter; (vi) a small leader cistron; (vii) the methionyl-NIF encoding region and (viii) two tandemly arranged copies of the central transcription terminator of phage fd (fdT). The sequence of the Met-NIF expression cassette (blown-up region) is shown in FIG. 15. The pMa/c family of vectors have been described. See Stanssens et al., Nuci. Acids Res. 17, 4441–4454, 1989.

After digestion with HindIII, the correctly sized PCR fragment was isolated from agarose-gel and inserted on an *E. coli* expression vector downstream of the phage lambda PR promoter. The recipient vector was opened with NcoI, treated with DNA polymerase I (Klenow fragment) and subsequently digested with HindIII. The resultant vector, designated pMa5-NI1/3, is schematically shown in FIG. 14; the sequence of the relevant part of the vector is shown in FIG. 15 (SEQ. ID. NO. 88). The NIF-1FL region present in this vector was entirely sequenced to rule out the presence of unwanted mutations. The expression module consists of the following elements: (1) The phage lambda PR promoter. (2) A small cistron which is present upstream of the Met-NIF-1FL region; this upstream cistron includes the first nine codons of the phage lambda cro gene and terminates at the TAA stop located in between the Shine Delgarno (SD)-box and the ATG initiator codon of Met-NIF-1FL (see FIGS. 14 and 15). The leader-cistron has the potential to code for a 31 residue polypeptide. Such a two-cistron arrangement, in addition to being found in a number of 'natural' operons, has been used successfully for improving the expression of heterologous genes whose level of expression is thought to be limited by the initiation of translation (Schoner et al., PNAS 81:5403–5407 (1984); Spanjaard et al., Gene 80:345–351 (1989); Makoff and Smallwood, NAR 18:1711–1718 (1990). (3) An open reading frame encoding Methionyl-NIF-1FL. The construction scheme is indeed such that the NIF-1FL 5'-end is correctly fused to an ATG initiator codon. Upstream of this ATG codon a SD-sequence (eg, GGAGGT; see FIGS. 14 and 15 (SEQ. ID. NO. 88)) is present. (4) Two copies of a phage fd derived transcription terminator (fdT) downstream of the Met-NIF-1FL coding region.

(B) Production of 'insoluble' methionyl-NIF.

To assess the effectiveness of pMa5-NI1/3 in expressing the NIF-1FL gene, the vector was introduced in W3110 cells harboring pcI857. The plasmid pcI857 specifies resistance to kanamycin (20 μg/ml), encodes a temperature sensitive repressor of the lambda PR promoter, and is compatible with the pMa5-NI1/3. Cultures were grown in LB medium at 28° C. to a density of about $2 \times 10^8$ cells/ml and then induced at 42° C. for 2–3 hours. Analysis of total cellular extracts of induced and non-induced cells by SDS-PAGE indicated that a new ~33 kDa protein (calculated molecular weight of NIF-1FL=~29 kDa) is synthesized upon thermo-induction of the promoter. In addition to total cellular extracts, we also analysed the pellet (insoluble) and supernatant (soluble) fraction obtained by opening the induced cells by sonication and clearing the lysate by centrifugation. The results indicated that the newly synthesized ~33 kDa protein precipitates intracellularly, i.e. forms so-called inclusion bodies. Following fractionation on an SDS-polyacrylamide gel, transfer onto ProBlott (ABI) and visualization by coomassie-staining, the ~33 kDa band was excised and its N-terminal amino acid sequence determined. The sequence obtained was: M-N-E-H . . . [SEQ. ID. NO. 101]. This result demonstrated that the initiator methionine was not removed from the primary translation product and clearly identified the 33 kDa band as recombinant NIF. It was estimated that the recombinant NIF protein accumulates to ~10 mg per liter and per $OD_{650}$ unit.

(C) Renaturation of NIF Protein Expressed in *E. coil*.

W3110 *E. coli* cells containing the plasmid pMa5-NI1/3 were grown in a shake flask incubator in six liter flasks each containing 1.5 liters of LB media at 28° C. until the optical density (OD) was in the range of 0.6–0.9 au at 550 nm. An additional 1.5 liters of LB media at 56° C. was added to each flask to induce expression of recombinant NIF, and the flasks were incubated at 42° C. with shaking. The OD was monitored and cells were harvested by centrifugation when the OD was within the range of 1.0–1.5. The cell pellets were frozen at −80° C. Each tube contained about 3.5 g cells.

Fifteen milliliters of TES buffer (0.05 N Tris, 0.05 M sodium ethylenediaminetetraacetate, 15% (w/v) sucrose, pH 8.0) was added to one tube, and the tube was sonicated to thaw and disperse the cell pellet. The suspension was then distributed into two 30 ml glass centrifuge tubes. An additional 2.5 ml of TES was used to wash the original tube and this wash solution was added to the glass tube. The suspensions in the glass tubes were sonicated (Branson Sonic Power Co., Danbury, Conn.) four times for 30 seconds each, with an ice incubation between sonications to maintain the temperature ≦10° C. throughout the procedure. The tubes were then centrifuged at 10,000 rpm for 20 minutes (12, 100×$g_{max}$) at 4° C. The supernatants were discarded. The pellets were resuspended in 15 ml of PSX buffer (0.02 M potassium phosphate, 1 M sodium chloride, 1% (v/v) Triton X-100, pH 7.2) per tube and sonicated at a low setting to break up the pellets followed by a 15 second sonication at medium power. The tubes were cooled on ice, resonicated at medium power for 15 seconds, and then centrifuged at 10,000 rpm for 20 minutes (12,100×$g_{max}$). The supernatant was discarded. The entire PSX resuspension/centrifugation process was repeated two additional times.

The pellets were resuspended in 15 ml of PBS buffer (0.01 M sodium phosphate, 0.15 M sodium chloride, pH 7.3) per tube, briefly sonicated, and centrifuged as before. The PBS resuspension was repeated one additional time.

The pellets were then resuspended in PBS by sonication, 12.5 ml per tube. The contents of both tubes were combined, and the volume was brought to 30 ml by the addition of further PBS. The protein concentration of the purified inclusion bodies was determined using the DC Protein Assay (Bio-Rad, Hercules, Calif.).

An aliquot of purified inclusion bodies containing 5 mg of protein was placed in each of several 1.7 ml plastic microcentrifuge tubes. The tubes were microcentrifuged for 10 minutes at 4° C. The supernatants were discarded. Each pellet was resuspended in 1 ml of 0.05 N Tris, 1% (w/v) Sarkosyl, pH 7.5 using sonication.

The tubes were vortexed at 37° C. for 48 hours using a Thermomixer vortexer (Eppendorf, Hamburg, Germany). Following this incubation, samples were submitted for NIF activity assays (see Example 1). Typically, activity corresponding to the activation (refolding) of 3% of the NIF present was found.

Example 21

Isolation and Characterization of NIF from *Ancylostoma caninum*

(A) Cloning and Sequencing of NIF sequences from *A. caninum*

Two new full-length coding regions that code for proteins related to NIF-1FL (see Example 10) were identified by PCR technology using single stranded oligonucleotide DNA primers that match with the NIF-1FL N- and C-terminal ends. These primers were as follows:

YG1:
5'-ATG-GAG-GCC-TAT-CTT-GTG-GTC-TTA [SEQ. ID. NO. 18] (5'-primer matching with the N-terminal region encoding: M-E-A-Y-L-V-V-L) [SEQ. ID. NO. 19]

YG2:
5'-TCA-TAA-CTC-TCG-GAA-TCG-ATA-AAA-CTC (SEQ. ID. NO. 20] (3'-primer matching with C-terminal sequence corresponding to: E-F-Y-R-F-R-E-L-stop codon [SEQ. ID. NO. 21])

The YG1/YG2 primer couple was found to yield a correctly sized PCR product when using a total RNA preparation of *A. caninum* (see Example 10) as template. First strand cDNA synthesis (First-Strand cDNA Synthesis Kit of Pharmacia, Uppsala, Sweden; 10 pmoles of the YG2 primer; ~15 µg of total RNA) and the subsequent amplification by PCR were carried out according to the manufacturer's specifications. The PCR was carried out with Taq DNA polymerase (Boehringer, Mannheim, Germany), 100 pmoles of both YG1 and YG2 and using 30 temperature cycles (1 minute denaturation step at 95° C.; 1 minute annealing period at 55° C.; 1.5 minute elongation step). The obtained PCR product was isolated from agarose gel and cloned onto a phagemid vector (allowing preparation of single stranded DNA). Three clones, designated PCR-NIF5, PCR-NIF7 and PCR-NIF20, were retained for sequence determination. PCR-NIF5 was found to be identical to NIF-1FL (SEQ. ID. NO. 81). PCR-NIF7 (SEQ. ID. NO. 90) and PCR-NIF20 (SEQ. ID. NO. 91), however, represent two new NIF sequences. Their sequences are shown in FIG. 16.

Additional full-length *A. caninum* NIF sequences were isolated by screening a cDNA library using as hybridization probe a radiolabeled PCR fragment obtained with primers that target sequences which are well conserved among the seven *A. caninum* NIF sequences described in Example 10 (1FL, 3P, 2FL, 3FL, 4FL, 6FL and 1P (SEQ. ID. NOS. 81 to 87)). The following primers were used:

YG3:
5'-CAC-AAT-GGT-TAC-AGA-TCG-AGA-CTT-GCG-CTA-GGT-CAC [SEQ. ID. NO. 22] the 5'-primer targeting the region which in NIF-1FL encodes the amino acid sequence H-N-G-Y-R-S-K-L-A-L-G-H [SEQ. ID. NO. 23])

YG4:
5'-T-TTT-TGG-GTA-GTG-GCA-GAC-TAC-ATG [SEQ. ID. NO. 24] the 3'-primer targeting the region which in NIF-1FL encodes H-V-V-C-H-Y-P-K-(I) [SEQ. ID. NO. 25]

Poly(A+) RNA was prepared from adult worms using the QuickPrep mRNA Purification Kit (Pharmacia, Uppsala, Sweden). Using this poly(A+) RNA preparation as template, an amplification product of about the expected length was obtained with the YG3/YG4 primer couple (the PCR conditions were as described above). The amplification product was shown by gel-electrophoretic analysis to be rather heterogeneous with respect to length. The YG3/YG4 primers were indeed designed to target sequences that flank that part of the coding region where the various NIF sequences display significant differences in length; the heterogeneous nature of the PCR product indicated that the primers are useful for the amplification of several different isoforms. The PCR product were gel-purified and subsequently radiolabeled by "random primer extension" (T7QuickPrime Kit™; Pharmacia, Uppsala, Sweden) for use as hybridization probe. A cDNA library was constructed using described procedures (Promega Protocols and Applications Guide 2nd Ed.; Promega Corp.). About 3 µg of mRNA was reverse transcribed using an oligo(dT)-NotI primer-adaptor (5'-TCGCGGCCGC(T)$_{15}$ [SEQ. ID. NO. 26]; Promega Corp., Madison, Wis.) and AMV (Avian Myeloblastosis Virus) reverse transcriptase (Boehringer, Mannheim, Germany). The enzymes used for double stranded cDNA synthesis were the following: *E. coli* DNA polymerase I and RNaseH from BRL Life Technologies (Gaithersburg, Md.) and T4 DNA polymerase from Pharmacia. The obtained cDNA was treated with EcoRI methylase (RiboClone EcoRI Linker Ligation System; Promega). The cDNAs were digested with NotI and EcoRI, size selected on a 1% agarose gel (fragments of between 1000–7000 base-pairs were eluted using the Geneclean protocol, BIO101 Inc., La Jolla, Calif.), and unidirectionally ligated into the EcoRI-NotI arms of the lambda gt11 Sfi-Not vector (Promega). After in vitro packaging (GigapackII-Gold, Stratagene, La Jolla, Calif.) recombinant phage were obtained by infecting strain Y1090 (Promega). The usefulness of the cDNA library was demonstrated by PCR analysis (Taq polymerase from Boehringer; 30 temperature cycles: 1 minute 95° C.; 1 minute 50° C.; 3 minutes 72° C.) of a number of randomly picked clones using the lambda gt11 primer #1218 (New England Biolabs, Beverly, Mass.) in combination with the above mentioned oligo(dT)-NotI primer adaptor. The majority of the clones was found to contain cDNA inserts of variable size.

Approximately $1 \times 10^6$ cDNA clones (duplicate plaque-lift filters were prepared using Hybond™-N; Amersham, Buckinghamshire, England) were screened with the radiolabeled YG3/YG4 PCR fragment using the following prehybridization and hybridization conditions: 5xSSC (SSC: 150 mM NaCl, 15 mM trisodium citrate), 5x Denhardt's solution, 0.5% SDS, 50% formamide, 100 µg/ml sonicated fish sperm DNA (Boehringer), overnight at 42° C. The filters were washed 4 times in 2xSSC, 0.1% SDS at 37° C. After overnight exposure to X-ray film, numerous plaques that hybridized to the probe were identified; it was estimated that about 0.1–0.2% of the clones scored positive. After a second hybridization round (24 positives were analyzed at lower plaque-density so as to isolate single pure clones), a number of phage clones were subjected to PCR analysis and those cDNA inserts which were found to be large enough to encompass the entire coding region were subcloned as SfiI-NotI fragments on pGEM-type phagemids (Promega). We have determined the sequence of eight of these NIF cDNAs (i.e., AcaNIF3 (SEQ. ID. NO. 92), AcaNIF4 (SEQ. ID. NO. 93), AcaNIF6 (SEQ. ID. NO. 94), AcaNIF7 (SEQ. ID. NO. 95), AcaNIF9 (SEQ. ID. NO. 98), AcaNIF18 (SEQ. ID. NO. 99), AcaNIF19, and AcaNIF24 (SEQ. ID. NO. 97)). The data are shown in FIG. 16.

(B) Expression of Functional NIF Proteins from *A. caninum* in *Pichia Pastoris*.

The segments of DNA encoding AcaNIF24 (SEQ. ID. NO. 97), AcaNIF6 (SEQ. ID. NO. 94), AcaNIF4 (SEQ. ID. NO. 93), and AcaNIF9 (SEQ. ID. NO. 98) were PCR amplified using pGEM-type vectors containing the respective cDNAs (see above) as template. The 5'-primers contained no restriction sites and matched with the 5'-end of that part of the coding regions corresponding to the mature protein. Also, the first codon was altered from AAT to AAC (both codons translate to asparagine). The sequences of the 5'-primers for the various NIF sequences were as follows:

AcaNIF24:
5'-AAC-GAA-CAC-AAC-CTG-ACG-TGC-CC [SEQ. ID. NO. 27]
AcaNIF6:
5'-AAC-GAA-CAC-AAA-CCG-ATG-TGC-CAG-C [SEQ. ID. NO. 28]
AcaNIF4:
5'-AAC-GAA-CAC-AAA-CCG-ATG-TGC-GAG [SEQ. ID. NO. 29]
AcaNIF9:
5'-AAC-GAA-CAC-GAC-CCA-ACG-TGT-CC [SEQ. ID. NO. 30]

The 3'-primers were composed of 8 codons at the 3' end of the coding region, a TAA stop replacing the TGA stop of the natural gene, and three unique restriction endonuclease sites (SpeI, HindIII, and BglII). The 3'-primers used were:

AcaNIF24:
5'-CCT-CCT-CCT-AGA-TCT-AAG-CTT-ACT-AGT-TTA-AAA-TCG-ATA-AAA-CTC-CTT-GCT-ATC [SEQ. ID. NO. 31]
AcaNIF6:
5'-CCT-CCT-CCT-AGA-TCT-AAG-CTT-ACT-AGT-TTA-TAA-CTC-TCG-GAA-TCG-ATA-AAA-CTC [SEQ. ID. NO. 32]
AcaNIF4:
5'-CCT-CCT-CCT-AGA-TCT-AAG-CTT-ACT-AGT-TTA-TAA-CTC-TCG-GAA-TCG-ATA-AAA-CTC [SEQ. ID. NO. 33]
AcaNIF9:
5'-CCT-CCT-CCT-AGA-TCT-AAG-CTT-ACT-AGT-TTA-TAG-CTC-TCG-AAA-CGG-ATA-AAA-ATA [SEQ. ID. NO. 34]

Amplification was accomplished using 100 pmoles of each primer, 2 units of Vent polymerase in 1× Vent buffer (New England Biolabs, Beverly, Mass.), 0.2 mM of each dNTP and 100 ng of template DNA. The PCR conditions were the same for all twenty cycles: denaturation at 95° C. for 1 minute, primer annealing at 60° C. for 1 minute, and amplification for 1.5 minutes at 72° C. The amplification product was gel-purified and digested with SpeI. The amplification product was ligated into StuI-SpeI cleaved pHIL7SP8 using standard methods. The ligation mixture was used to transform *E. coli* WK6 selecting for ampicillin resistant clones. In each case a correct clone was identified by restriction and DNA sequence analysis. These plasmids, designated pYAM7SP-AcaNIF24, pYAM7SP-AcaNIF6, pYAM7SP-AcaNIF4, and pYAM7SP-AcaNIF9, were used to transform the *P. pastoris* yeast strain GTS115(his4), as described in Example 12(B). Selection of His$^+$ transformants and subsequent selection for NIF expression were performed as described in Example 12(B). The accumulation of functional NIF protein in *Pichia* cell supernatant was detected and quantified using the LM2/Mac-1 based ELISA with 3D2-HRP detection (Example 1) in the case of AcaNIF24 (SEQ. ID. NO. 118), AcaNIF6 (SEQ. ID. NO. 119), and AcaNIF4 (SEQ. ID. NO. 120) and using the competitive assay for LM2/Mac-1 (Example 1) in the case of the AcaNIF9 (SEQ. ID. NO. 121).

(C) Purification and Characterization of NIF Proteins AcaNIF24, AcaNIF6, AcaNIF4, and AcaNIF9.

The functionally active recombinant AcaNIF24 (SEQ. ID. NO. 118), AcaNIF6 (SEQ. ID. NO. 119), and AcaNIF4 (SEQ. ID. NO. 120) proteins were purified and characterized in greater detail. Following methanol induction for 48 hours, *Pichia* cell supernatants were obtained by centrifugation for 15 minutes at 1,800×g.

In the case of the recombinant proteins AcaNIF24 (SEQ. ID. NO. 118) and AcaNIF6 (SEQ. ID. NO. 119), the 250 ml supernant was adjusted to pH 7.0 by adding Tris-HCl and kept overnight at 4° C. Precipitated material was removed by centrifugation. The cleared supernatant was loaded on a 3D2-immunoaffinity resin and bound material eluted with glycine-HCl pH 2.5 (Example 27). The eluted fractions were neutralized and concentrated by ultrafiltration. Both proteins were found to migrate as a single band on SDS-PAGE (4–20% gradient gel; Novex). Edman degradation confirmed that correctly processed proteins were produced. The following N-terminal amino acid sequences were found:

AcaNIF24: N-E-H-X-L-T-X-P-Q-N [SEQ. ID. NO. 35]

AcaNIF6: N-E-H-K-P-M-X-Q-Q-X-E-T-E-M-P [SEQ. ID. NO. 36]

where X represents an unidentified residue.

Figure 17A:
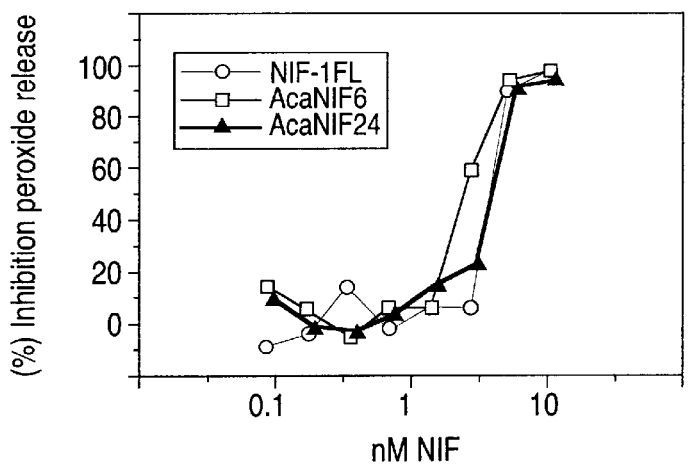
FIG. 17 depicts a comparison of the potency of recombinant mature NIF-1FL (SEQ. ID. NO. 117) with that of the recombinant proteins mature AcaNIF6 (SEQ. ID. NO. 119) and mature AcaNIF24 (SEQ. ID. NO. 118). The three purified proteins were tested in both the hydrogen peroxide release assay of Example 1(E) (panel A) and the neutrophil-plastic adhesion assay of Example 1(C) (panel B).
Figure 17B:
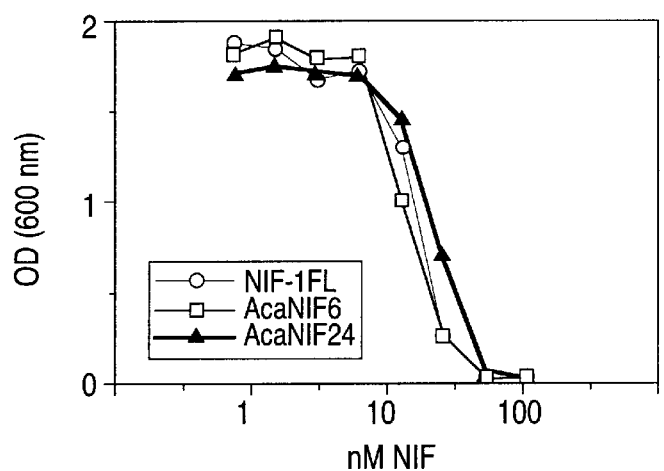

The concentrations were determined spectrophotometrically and the samples were assayed in the plastic adhesion and peroxide release assays (see Example 1). Both recombinant AcaNIF24 (SEQ. ID. NO. 118) and AcaNIF6 (SEQ. ID. NO. 119) proteins were found to be equally active as mature recombinant NIF-1FL (SEQ. ID. NO. 117) (FIG. 17).

Figure 18:
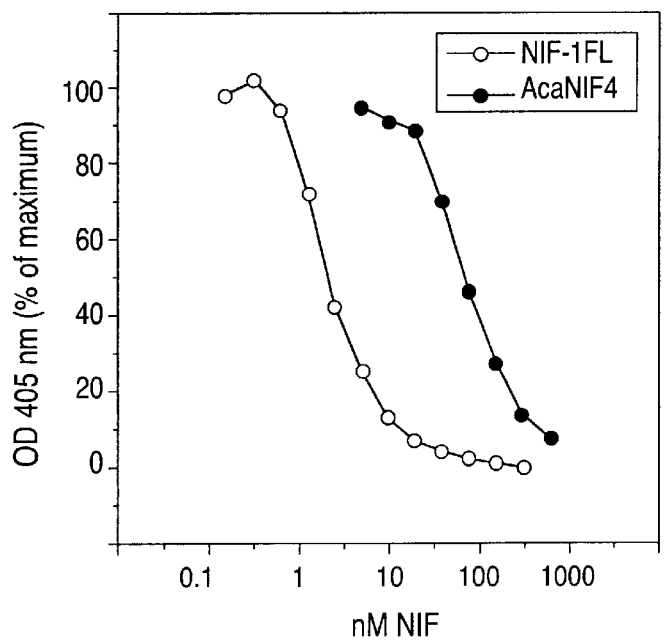
FIG. 18 depicts a comparison of recombinant mature NIF-1FL (SEQ. ID. NO. 117) with recombinant mature AcaNIF4 (SEQ. ID. NO. 120) in the competition binding assay of Example 1(F). Samples containing a fixed amount of biotinylated mature NIF-1FL (SEQ. ID. NO. 117) and varying amounts of either mature AcaNIF4 (SEQ. ID. NO. 120) or mature NIF-1FL (SEQ. ID. NO. 117), were assayed on immobilized LM2/Mac-1 complex. The amount of bound biotinylated NIF-1FL was detected with ExtrAvidin conjugated with alkaline phosphatase.

Recombinant AcaNIF4 (SEQ. ID. NO. 120) was purified by hydroxyapatite and reverse-phase chromatography essentially as described in Example 23, however, the gel filtration step on Superdex was omitted. The purified protein was found to migrate as a single band on SDS-PAGE (4–20% gradient gel; Novex). The concentration was determined spectrophotometrically. The results obtained in a competitive binding assay with biotinylated mature NIF-1FL (SEQ. ID. NO. 117) indicated that AcaNIF4 had a significantly lower affinity for the LM2/Mac1 complex than NIF-1FL (FIG. 18).

Recombinant AcaNIF9 (SEQ. ID. NO. 121) was partially purified by reverse-phase chromatography (see Example 23). Edman degradation revealed N-E-H-D-P [SEQ. ID. NO. 102] as N-terminal amino acid sequence confirming that correctly processed AcaNIF9 (SEQ. ID. NO. 121) protein was produced. This partially purified protein was found to have a considerably higher mobility on SDS-PAGE (4–20% gradient gel; Novex) than the *Pichia*-produced mature NIF-1FL protein (SEQ. ID. NO. 117) (30–35 kDa compared to 40–80 kDa) consistent with the presence of seven N-glycosylation sites in mature NIF-1FL (SEQ. ID. NO. 117) and of only two potential N-glycosylation sites in AcaNIF9 (SEQ. ID. NO. 121). The sample containing AcaNIF9 was tested in the competitive binding assay described in Example 1. The results demonstrated that binding of biotinylated recombinant NIF-1FL to the LM2/Mac1 complex can be prevented by recombinant AcaNIF9.

Example 22

Isolation and Characterization of a NIF Protein from *Ancylostoma ceylanicum*

(A) Cloning and Sequencing of NIF Sequences From *A. ceylanicum*.

A full-length *A. ceylanicum* NIF gene was isolated by screening a cDNA library using as hybridization probe a PCR fragment effected from the same species. The PCR fragment was obtained using primers that target sequences which are highly conserved among the seven *A. caninum* NIF isoforms described in Example 10 (1FL, 3P, 2FL, 3FL, 4FL, 6FL and 1P (SEQ. ID. NOS. 81 to 87)). These primers, designated YG3 (SEQ. ID. NO. 22) and YG4 (SEQ. ID. NO. 24), are described in Example 21.

Poly(A+) RNA was prepared from *A. ceylanicum* adult worms using the QuickPrep mRNA Purification Kit (Pharmacia, Uppsala, Sweden). Using this poly(A+) RNA preparation as template, an amplification product of about the expected length (i.e., about the same length as the PCR fragment seen with *A. caninum* RNA as template) was obtained with the YG3/YG4 primer couple. First strand cDNA synthesis (First-Strand cDNA Synthesis Kit; Pharmacia) and the subsequent amplification by PCR were carried out according to the manufacturer's specifications using 10 pmoles of the YG2 primer (SEQ. ID. NO. 20) (see Example 21) and 100 ng of *A. ceylanicum* mRNA. The PCR was carried out with Taq DNA polymerase (Boehringer, Mannheim, Germany), 100 pmoles of both YG3 and YG4 and using 30 temperature cycles (1 minute denaturation step at 95° C.; 1 minute annealing period at 55° C.; 1.5 minutes elongation step). The PCR product was gel-purified and subsequently radiolabeled by "random primer extension" ($^{T7}$Quickprime Kit™; Pharmacia) for use as hybridization probe.

An *A. ceylanicum* cDNA library was constructed in lambda gt11 using the procedures described in Example 21. The quality of the cDNA library was demonstrated by PCR analysis (Taq polymerase from Boehringer; 30 temperature cycles: 1 minute at 95° C.; 1 minute at 50° C.; 3 minutes at 72° C.) of a number of randomly picked clones using the lambda gt11 primer #1218 (New England Biolabs) in combination with an oligo(dT)-NotI primer adaptor (Promega). The majority of the clones were found to contain cDNA inserts of variable size.

About $5 \times 10^5$ lambda cDNA clones were screened with the radiolabeled YG3/YG4 PCR fragment using the hybridization conditions described in Example 21. Approximately 60 positives were identified. The cDNA insert of one positive clone, shown by PCR analysis (see above) to contain an insert of sufficient size to encompass the entire NIF coding region (~850 bp), was transferred to pGEM-9Zf(−) (Promega) as a SfiI-NotI fragment and its sequence determined. The sequence of the cDNA clone, designated AceNIF3, is shown in FIG. 19.

(B) Expression of a NIF like Protein from *A. ceylanicum* in a Phage-Attached Form.

The *A. ceylanicum* AceNIF3 region coding for the mature protein was cloned onto a phage display vector according to the procedures described for NIF-1FL in Example 23.

The N-terminal amino acid sequence of the authentic *A. ceylanicum* NIF protein is not known; it is, therefore, difficult to unambiguously locate the secretion signal processing site on the deduced amino acid sequence (FIG. 19). The following oligonucleotide primers were chosen to PCR amplify the AceNIF3 coding region:

YG16:
5'-GTCGCAACTG-CGGCCCAGCC-GG CCATGGCC-GCT<u>GACGAAC</u>-<u>CAACGTGCAA</u>-GCAG [SEQ. ID. NO. 37] (54-mer; 5'-primer; the NcoI site and AceNIF3 N-terminus are underlined); and YG15:
5'-GAGTTCTCGA-CTT<u>GCGGCCG</u>-CACCTCC <u>GAT</u>-<u>AGGTGGATAA</u>-CGGAGTGA [SEQ. ID. NO. 38] (48-mer; 3'-primer; the NotI site and AceNIF3 C-terminus are underlined).

Following NcoI/NotI digestion, the PCR product was gel-purified and cloned between the NcoI and NotI sites of the recipient vector. The resultant vector, designated pAN-AceNIF3, contains the intended in-frame fusion of the pelB, AceNIF3, and M13 gIII coding regions.

Figure 20:
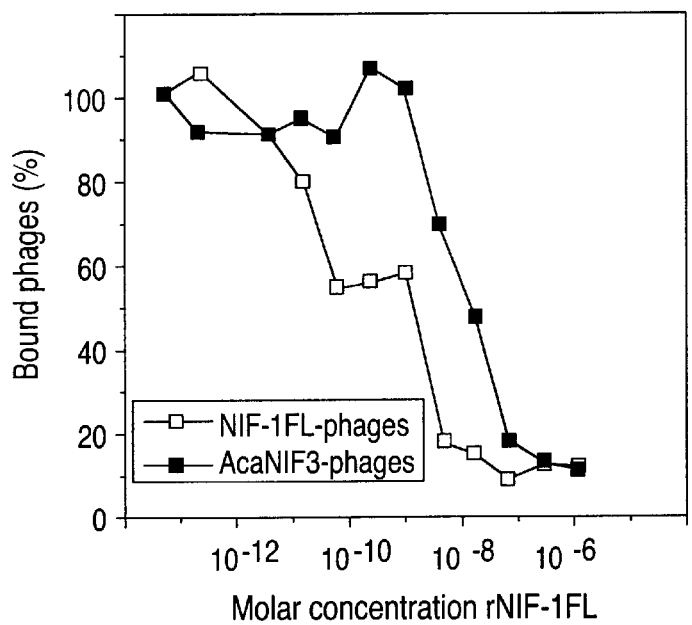
FIG. 20 depicts the binding of phages displaying a NIF protein from *A. ceylanicum* (AceNIF3) to Mac-1. Wells coated with LM2/Mac-1 complex were first incubated with varying amounts of *Pichia*-produced recombinant mature NIF-1FL (or buffer in the control experiment); after 30 minutes, $10^{10}$ virions displaying either recombinant mature NIF-1FL (SEQ. ID. NO. 117)or AceNIF3 (SEQ. ID. NO. 125) were added and the incubation continued for another 90 minutes. Retained phages were detected with rabbit anti-phage serum and goat anti-rabbit alkaline phosphatase conjugate. The various components were incubated in PBS containing 1 mM $MgCl_2$, 1 mM $CaCl_2$ and 0.1% skim-milk (phage samples contained 1% skim-milk). Unbound material was removed by washing with PBS containing 1 mM $CaCl_2$, 1 mM $MgCl_2$, 0.1% Tween 20 and 0.02% thimerosal. The relative amount of bound phages was calculated by taking the $OD_{405\ nm}$ reading obtained in the control experiment as 100%.

Phages displaying the AceNIF3 protein (SEQ. ID. NO. 123) were obtained by infecting TG1 (su+) bacteria harboring pAN-AceNIF3 with M13-VCS 'helper'-phage (see procedures described in Example 23). The rescued phages, resuspended in PBS, were assayed by an ELISA on immobilized LM2/Mac-1 complex (see FIG. 20). Phages displaying the *A. caninum* NIF-1FL isoform (Example 23) were used as positive control. Following a 30 minute incubation with varying amounts of *Pichia* produced recombinant mature NIF-1FL (SEQ. ID. NO. 117), $10^{10}$ virions displaying either recombinant mature NIF-1FL or recombinant AceNIF3 (SEQ. ID. NO. 123) were added to the LM2/Mac-1 coated wells. After a 90 minute incubation period, the amount of bound phages was detected with rabbit anti-phage serum and goat anti-rabbit alkaline phosphatase conjugate. Binding of phages to the immobilized receptor (see FIG. 20) clearly indicates that the AceNIF3 protein (SEQ. ID. NO. 123) must be displayed in a functionally active form on the phage surface. The data given in Example 23, show that phage binding occurs only when they display the NIF protein, i.e. non-displaying control phages do not bind to the LM2 monoclonal antibody nor do they bind to. the LM2/Mac-1 complex. Displacement of both NIF-1FL- and AceNIF3-displaying phages by an increasing amount of soluble *Pichia* produced recombinant mature NIF-1FL (SEQ. ID. NO. 117) demonstrates that both NIF proteins bind to the same site on the Mac-1 receptor with a comparable affinity. Phage display of the AceNIF3 protein (SEQ. ID. NO. 123) was also demonstrated by Western blot. After fractionation on an SDS-10% polyacrylamide gel, phage proteins were transferred onto ProBlott membrane (Applied Biosystems Inc.) and incubated consecutively with a rabbit anti-pgIII serum (GATC GmbH, Konstanz, Germany) and goat anti-rabbit alkaline phosphatase conjugate. Bands corresponding to the wild type phage pgIII protein and to the NIF-pgIII fusion product could be visualized.

(C) Construction of pYAM7SP-AceNIF3 and Expression in *Pichia*.

The segment of DNA encoding AceNIF3 (SEQ. ID. NO. 100) was PCR amplified from a subclone of AceNIF3 in pGEM-9Zf(−) (see above) using unique primers for the 5'- and 3'-ends of the coding region. The 5'-end of the proteolytically processed AceNIF3 being not unambiguously defined, a hybrid 5'-end was created based on sequence homology between AcaNIF9 (SEQ. ID. NO. 121) and AceNIF3 (SEQ. ID. NO. 115): the three N-terminal codons of proteolytically maturated AcaNIF9 (SEQ. ID. NO. 121) were used as 5'-end, followed by six codons originating from the AceNIF3 (SEQ. ID. NO. 115) sequence. The resulting N-terminal amino acid hybrid sequence was: N-E-H-E-P-T-C-K-Q [SEQ. ID. NO. 39], while the natural AcaNIF9 sequence was N-E-H-D-P-T-C-P-Q [SEQ. ID. NO. 40], and the natural AceNIF3 sequence was K-G-D-E-P-T-C-K-Q [SEQ. ID. NO. 41]. The sequence of the 5'-primer used was 5'-AAC-GAA-CAC-GAA-CCA-ACG-TGC-AAG CAG

[SEQ. ID. NO. 42]. The 3'-primer was composed of 8 codons at the 3'-end of the coding region, a TAA stop replacing the TGA stop of the natural gene, and three unique restriction endonuclease sites (SpeI, HindIII, and XbaI). The sequence of the 3'-primer used was 5'-CCT-CCT-CCT-TCT-AGA-AGC-TTA-CTA-GTT-TAG-ATA-GGT-GGA-TAA-CGG-AGT-GAC-G [SEQ. ID. NO. 43].

Amplification was accomplished using 100 pmoles of each primer, 2 units of Vent polymerase in 1× Vent buffer (New England Biolabs, Beverly, Mass.), and 0.2 mM of each of dATP, dCTP, dGTP, and dTTP. One hundred nanograms of pGEM-9Zf(−) containing AceNIF3 were used as template DNA. The PCR conditions were the same for all twenty cycles: denaturation at 95° C. for 1 minute, primer annealing at 60° C. for 1 minute, and amplification for 1.5 minutes at 72° C. The amplification product was gel-purified and digested with SpeI.

The amplification product was ligated into StuI-SpeI cleaved pHIL7SP8 using standard methods. The ligation mixture was used to transform E. coli WK6 selecting for ampicillin resistant clones. Based on restriction and DNA sequence analysis, a correct insert sequence in one of the resulting plasmid clones, pYAM7SP-AceNIF3, was selected to transform the P. pastoris yeast strain GTS115(his4), as described in Example 12(B). Selection of His$^+$ transformants and subsequent selection for AceNIF3 expression were performed as described in Example 12(B). The presence of AceNIF3 (SEQ. ID. NO. 125) in Pichia cell supernatant was detected and quantified in a competitive binding assay with biotinylated NIF1 (Example 1).

Following methanol induction for 48 hours, Pichia cell supernatant was obtained by centrifugation. The crude supernatant was shown to inhibit the adhesion of human neutrophils to plastic.

Example 23
Production by E. coli of Functionally Active NIF as Either a Bacteriophage-Attached Form or as 'Free' Soluble Protein
(A) Cloning of NIF-1FL on a phage display vector.

A phagemid-vector was assembled in which the NIF-1FL region coding for the mature protein is fused at its N-terminus to the secretion signal sequence derived from the pelb gene and at its C-terminal end to the filamentous phage M13 gene III (gIII). This gene fusion was placed under the transcriptional control of the Plac promoter. Some of the pelb codons were replaced by synonymous triplets so that the secretion signal contains an NcoI restriction site. An extra Ala-codon was introduced between the pelE and NIF-1FL regions such that the junction matches more closely the prokaryotic prototype signal sequence processing site. The NIF-1FL and pgIII (product of gIII) encoding regions are separated by (i) a linker sequence in which a NotI site is embedded and (ii) a TAG (amber) triplet which serves as a translational stop codon in a su$^-$ strain but is frequently read as a sense codon in su$^+$ bacterial cells.

Figure 21:
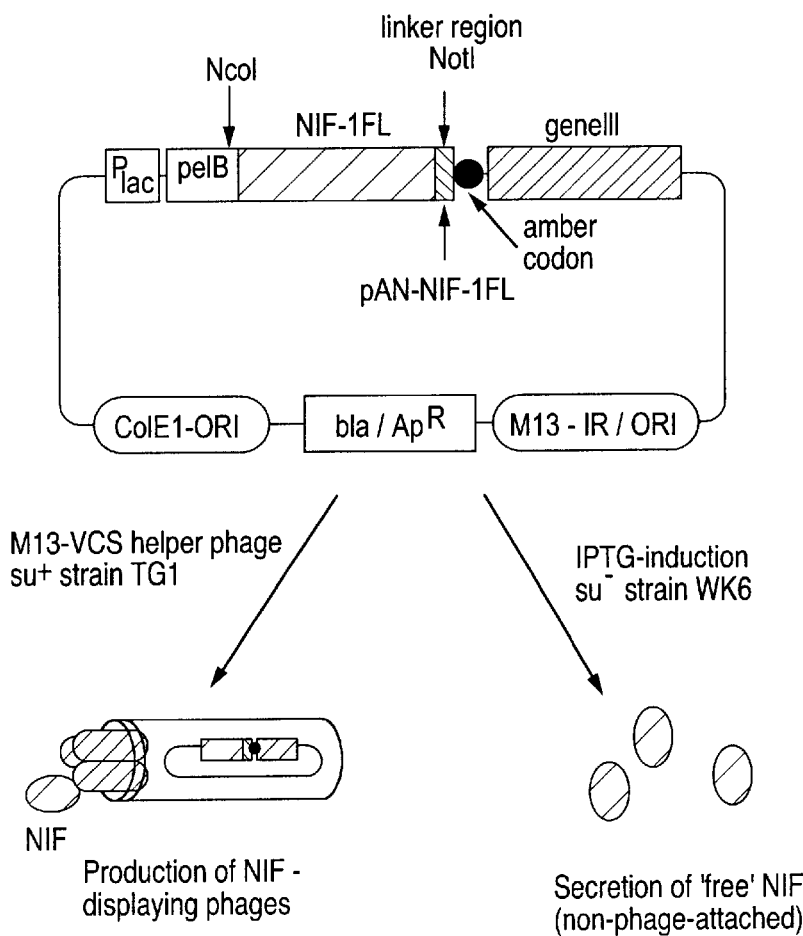
FIG. 21 depicts the synthesis of functional mature NIF-1FL (SEQ. ID. NO. 117) by pAN-NIF-1FL in either a phage-attached or 'soluble' form. The pAN-NIF-1FL vector contains the following elements:
1) a NIF-1FL containing gene fusion which is placed under the transcriptional control of the Plac promoter. The gene fusion consists of the pelB secretion signal, the NIF-1FL coding region, and the filamentous phage M13 geneIII (gIII). Between the NIF-1FL and the gIII sequences a TAG amber translational stop codon is present.

A schematic representation of the phagemid vector, designated pAN-NIF-1FL, is shown in FIG. 21. pAN-NIF-1FL was constructed by (i) PCR-amplification of the NIF-1FL coding region (SEQ. ID. NO. 130) with primers that contain 5'-extensions whose sequence is such that (ii) the NcoI/NotI directional cloning of the gel-purified PCR fragment in the recipient vector results in the intended in frame fusion of the pelB, NIF-1FL, and gIII coding elements.

The NIF-1FL coding region (SEQ. ID. NO. 130) was PCR-amplified making use of the following two oligonucleotide primers:
LJ045:
5'G-GTCGCAACTG-CGGCCCAGCC-GG
CCATGGCC-GCTAATGAAC-ACAACCTGAG-GTGC
[SEQ. ID. NO. 44] (54-mer; 5'-primer; The NcoI site and NIF-1FL N-terminus are underlined)
LJ046:
5'-GAGTTCTCGA-CTTGCGGCCG-CAGGTGG
TAA-CTCTCGGAAT-CGATAAAACT-C [SEQ. ID. NO. 45] (51-mer; 3'-primer; the NotI site and NIF-1FL C-terminus are underlined)

The NIF-1FL region (SEQ. ID. NO. 130) and flanking sequences present in pAN-NIF-1FL were entirely sequenced to rule out the presence of unwanted mutations.
(B) Display of Functional NIF by Filamentous Phages.

In su$^+$ bacteria such as TG1, the pAN-NIF-1FL phagemid-vector has the potential to code for a NIF-1FL-pgIII fusion protein. When the TG1 [pAN-NIF-1FL] host cells are infected with a so-called 'helper'-phage, this fusion protein can, during morphogenesis, become incorporated into filamentous virions (both 'helper'-phages and pseudo-virions which encapsidate one specific strand of the phagemid). Phage particles were rescued with M13-VCS 'helper'-phage (Stratagene) infection as follows. A 1 ml culture of TG1 [pAN-NIF-1FL] grown at 37° C. in 2×TY (2×TY: Tryptone 16 g/L; Yeast extract 10 g/L; NaCl 5 g/L) containing 100 µg/ml carbenicillin (or ampicillin) and 1% glucose to a density of $OD_{600}$~0.5–0.6 is infected with M13-VCS at a multiplicity of infection of ~20. The infected culture is incubated at 37° C. for 30 minutes without shaking, and then for another 30 minutes with shaking. A 10 ml prewarmed 2×TY aliquot containing both carbenicillin (100 µg/ml) and kanamycin (50 µg/ml) is inoculated with the 1 ml infected culture. The mixture is incubated with shaking first for 60 minutes at 37° C. and then overnight at −30° C. After removal of the infected cells by centrifugation 1:5 volume 20% polyethyleen glycol/2.5 M NaCl is added to the supernatant. Following a 60 minute incubation on ice, the precipitated phages are collected by centrifugation and resuspended in PBS ($Na_2HPO_4.2H_2O$ 1.14 g/L; $KH_2PO_4$ 0.2 g/L; NaCl 8.0 g/L; KCl 0.2 g/L; pH 7.3).

The rescued phages were shown to display functionally active NIF in several assays: (A) Western blot (After fractionation by SDS-10% PAGE, phage proteins were transferred onto ProBlott (Applied Biosystems Inc., Foster City, Calif.) membrane and incubated with rabbit anti-phage serum and goat anti-rabbit alkaline phosphatase conjugate. A band corresponding to the NIF-pgIII product could be visualized); (B) Mac-1-ELISA (see FIG. 22) (NIF-phage were then assayed for binding to Mac-1 (non-displaying phage were used as negative control). Mac-1-coated wells were prepared either by direct immobilization using 0.25 µg/ml immunopurified Mac-1 receptor (Diamond et al., 1990, J. Cell Biol., 111, 3129–3139), or by immuno-capture with monoclonal antibody LM2 .(ATCC number: HB 204). Binding of phages was detected with rabbit anti-phage antiserum and goat anti-rabbit alkaline phosphatase conjugate. Binding of phages to the immobilized receptor was shown to occur only when they display the NIF protein. It was also shown that NIF-phage are not able to bind to the LM2 monoclonal antibody nor to the Mac-1-coated wells after a pre-incubation with 1 mM Pichia-produced recombinant NIF-1FL for 30 minutes); (C) 3D2-ELISA (3D2 is a non-neutralizing mouse monoclonal antibody specific for NIF (see Example 26). In contrast to non-displaying control phages, NIF-phage were found to bind to 3D2-coated wells. NIF-phage binding could be eliminated by either blocking the 3D2-wells with 1 mM Pichia-produced recombinant mature NIF-1FL (SEQ. ID. NO. 117) or blocking the NIF-phages with 1 mM 3D2 monoclonal antibody); and (D) Panning against Mac-1 (pAN-NIF-1FL phage ($10^{10}$ virions)

were mixed with an equal amount of irrelevant non-displaying phage (fd-tet; $10^{10}$ virions), diluted in 100 µl Binding Buffer (PBS, 1 mM $CaCl_2$, 1 mM $MgCl_2$, 0.4% Tween-20 and 2% Skim-Milk) and incubated in a Mac-1-coated microtiter-well. After incubation for 120 minutes, and washing with PBS containing 1 mM $CaCl_2$ 1 mM $MgCl_2$ and 0.4% Tween-20 ten times, bound phage were eluted during a 10 minute incubation with glycine-HCl pH 2.0. Following neutralization with 1 M Tris-HCL pH 8.0, the number of tetracycline resistant (fd-tet) and ampicillin resistant (pAN-NIF-1FL) colony forming units was determined; pAN-NIF phage were 30-fold enriched over the non-displaying fd-tet phage).

The above experiments, e.g. functional display of NIF-1FL on filamentous phage and the specific enrichment of such NIF-phages by binding selection, show it is possible to use the phage technology for the identification of higher-affinity NIF variants (i.e., both naturally occurring isoforms or engineered mutants). Similar to what has been done in the immunoglobulin field, it should be possible to clone the vast majority of the *A. caninum* NIF protein repertoire on phage and then to select the highest affinity NIF isoform by subjecting the, phage library to several consecutive binding selection cycles (panning) using the Mac-1 receptor as target. Our sequence data show that the extent of conservation of the 5' and 3' termini of the region encoding mature NIF allows the design of (degenerate) oligonucleotide primers to rescue a substantial part of the NIF protein repertoire. For example, we generated PCR-amplification fragments of the expected length using a lambda. DNA preparation of the pooled *A. caninum* cDNA library as target with the following oligonucleotide primer sets:

5'-primer targeting the N-terminus: an equimolar mixture of three primers that contain at their 3'-end the following matching sequences:

AAT-GAA-CAC-AAC-cTG-ASG-TGC-3' [SEQ. ID. NO. 46]

AAT-GAA-CAC-GAC-CCA-ACG-TGT-3' [SEQ. ID. NO. 47]

AAT-GAA-CAC-AAA-CCG-ATR-TGC-3' [SEQ. ID. NO. 48]

where S=C or G and R=A or G; and

3'-primer targeting the C-terminus: an equimolar mixture of two primers that contain at their 3'-end the following matching sequences:

TAA-CTC-TCG-GAA-TCG-ATA-AAA-3' [SEQ. ID. NO. 49]

TAA-CTC-TCG-AAA-CSG-ATA-AAA-3' [SEQ. ID. NO. 50]

where S=C or G.

The PCR primers contain 5'-extensions which incorporate restriction sites allowing the facile unidirectional cloning of the amplification product in an appropriate display vector.
(C) Secretion of Soluble and Functionally Active NIF.

The phagemid display vector containing the NIF gene, pAN-NIF-1FL, is suitable for the production of NIF-1FL in both a phage-attached form and as 'free' soluble protein. In su bacteria such as WK6, the pAN-NIF-1FL phagemid-vector has the potential to direct the synthesis of the mature NIF-1FL protein (SEQ. ID. NO. 117) in a 'free' (i.e., not phage-attached) form.

Overnight induction of the Plac promoter by addition of isopropyl-β-D-thiogalactopyranoside (1 mM final concentration) to a WK6(pAN-NIF-1FL) culture was found to result in the accumulation of Mac-1-binding activity as shown by ELISA (on LM2/Mac-1 plates; detection was done with HRP-conjugated monoclonal antibody 3D2). The recombinant mature NIF-1FL protein (SEQ. ID. NO. 117) could be detected in both the supernatant of the induced culture and in a total cell lysate prepared by sonication of the induced cells followed by a clearing step. Comparison of the ELISA-signal with that generated by known amounts of *Pichia*-produced recombinant mature NIF-1FL (SEQ. ID. NO. 117) allowed us to estimate that the recombinant mature NIF-1FL protein accumulates to about 1 mg per liter of *E. coli* culture. The mature recombinant NIF-1FL protein was also immunopurified on a 3D2-Emphaze column (see Example 27) starting from a French-Press lysate of induced WK6[pAN-NIF-1FL] cells. Material eluted at low pH was still active as determined by the LM2/Mac-1 ELISA. The *E. coli* rNIF protein was shown to migrate as a sharp band on SDS-polyacrylamide gel and could be detected by rabbit anti-*Pichia*-recombinant mature NIF-1FL (SEQ. ID. NO. 117) serum in immuno-blot analysis.

Example 24

Alternative Purification Method For *Pichia* Produced NIF.

Cell-free supernatant was filtered (0.2 µm) and submitted to a diafiltration on a polyethersulfone omega membrane (30 kDa cut-off; 0.75 ft² Filtron) with 10 volumes of 50 mM citric acid pH 3.5 containing 1 mM EDTA. After adjustment to pH 7.4 by adding 1 M Tris-HCl, the solution was left on ice for at least one hour. Precipitated material was removed by filtration (0.2 µm). The cleared supernatant was submitted to a second dialfiltration (10 volumes 10 mM phosphate pH 7.4).

Afterwards calcium chloride was added to a final concentration of 0.3 mM. The solution was applied on a MacroPrep (40 µm) Hydroxyapatite (Bio-Rad Laboratories) column equilibrated with 10 mM phosphate pH 7.4 and containing 0.3 mM $CaCl_2$. After washing with 5 column volumes of the equilibration buffer, the recombinant NIF protein was eluted with 90 mM phosphate pH 7.4. Fractions containing recombinant NIF were identified by binding assays on LM2/Mac-1 plates and pooled. Subsequently, the protein present in the pooled fractions was further purified by reversed phase chromatography on a Poros R1/H (Perseptive Biosystems) column equilibrated with 10 mM ammonium formate pH 6.4 and 10% acetonitrile. Recombinant NIF was eluted by increasing the acetonitrile concentration. The fractions containing NIF were identified by gel-electrophoresis and were pooled. Acetonitrile present in this pool was removed in a rotavapor before freeze-drying. The dry protein was redissolved in PBS and applied on a Superdex 200 (Pharmacia) gel filtration column equilibrated in PBS. Fractions containing the NIF protein were pooled and concentrated by ultrafiltration on an omega membrane (10 kDa cut-off; Filtron). The recombinant NIF protein was stored at −80° C.

Example 25

Expression of Functional Derivatives of NIF-1FL in *Pichia pastoris*.

(A) pMa5-hNIF1 and pMc5-hNIF1 Expression Constructs.

The segment of DNA encoding NIF was PCR amplified from a subclone of NIF-1FL (SEQ. ID. NO. 116) in BluescriptII (Stratagene, La Jolla, Calif.) using unique primers for the 5'- and 3'-ends of the coding region.

The 5'-primer was composed of two restriction sites (EcoRI and HpaI) and the 23 first nucleotides of the region beginning at the 5'-end of proteolytically processed NIF and the succeeding 8 codons. The codon for the first residue of the mature NIF was altered from AAT to AAC (both codons translate to asparagine) and constitutes part of the HpaI restriction sites (GTT/AAC). The sequence of the 5'-primer used was 5'-CCG-GAA-TTC-GTT-AAC-GAA-CAC-AAC-CTG-AGG-TGC-CC [SEQ. ID. NO. 51]. The 3'-primer has been described in Example 12(B).

Amplification was accomplished using 100 pmol of each primer, 2 units of Vent polymerase in 1× Vent buffer (New England Biolabs, Beverly, Mass.), and 0.2 mM of each of dATP, dCTP, dGTP, and dTTP. One hundred nanograms of BluescriptII containing NIF-1FL were used as template DNA. The PCR conditions were the same for all twenty cycles: denaturation at 95° C. for 1 minute, primer annealing at 60° C. for 1 minute, and amplification for 1.5 minutes at 72° C. The amplification product was gel-purified and digested with EcoRI and HindIII.

The amplification product was then ligated into EcoRi-HindIII cleaved pMa5-8 and pMc5-8 respectively [Stanssens et al., Nucl. Acids Res. 17: 4441–4454 (1989)], using standard methods. The ligation mixtures were used to transform competent E. coli WK6 (Zell et al., (1987) EMBO J., 6: 1809–1815). Cells resistant to ampicillin and chloramphenicol, respectively, were selected and obtained on appropriate plates. Based on restriction and DNA sequence analysis, a correct insert sequence in each of the resulting plasmid clones, pMa5-hNIF1 and pMc5-hNIF1, were selected.

(B) Construction of pMa5-hNIF1/ΔGl1–5.

The NIF-1FL protein contains seven potential N (Asparagine)-glycosylation sites (consensus N-X-T/S amino acid sequence).

pMa5-hNIF1/ΔGl1–5 is a derivative of pMa5-hNIF1 (see above) in which five potential N-glycosylation sites of mature NIF-1FL have been modified by substituting glutamine residues for each of the asparagine residues in the corresponding consensus sequences. These residues are $Asn^{10}$, $Asn^{18}$, $Asn^{87}$, $Asn^{10}$, and $Asn^{30}$, where the number in superscript corresponds to the amino acid residue number of mature NIF-1FL (SEQ. ID. NO. 117) (see FIG. 8 (SEQ. ID. NO. 81)).

Stepwise site-directed mutagenesis was performed following the methodology described in Stanssens et al., (1989), Nucl. Acids Res. 17: 4441–4454, and using the following oligonucleotides:

(I) ΔGl1:dCCGGGCATTTCGGTACCTTGCTGCGGGCA CCTC [SEQ. ID. NO. 52], (II) ΔGl2:dCCTAATCGAGTCTTGGAACCCGGGCATTTC TGTTCC [SEQ. ID. NO. 53], (III) ΔGl3:dAACTGTCCGAGCATTGTCGTGCACTCATGT AGGCGCTTTTTTC [SEQ. ID. NO. 54], (IV) ΔGl4:dCAGAGCTTCAGAGATCTGGTTTGAGTTTTCG [SEQ. ID. NO. 55, and (V) AGl5:dCTCCTTCCTTTTGTTTTCTGCAGGTTGAAA GCCTC [SEQ. ID. NO. 56].

In the first mutagenesis round, the oligonucleotides I, IV and V were annealed together to the single strand DNA (ssDNA) template pMa5-hNIF1 to modify the corresponding glycosylation sites Gl1, Gl4 and Gl5. A resulting plasmid clone having the three intended sites altered was then used to prepare ssDNA template for the next mutagenesis round in order to modify the Gl2 and Gl3 remaining sites using the appropriate oligonucleotides (II and III).

(C) Construction of pMa5-NIF-1FL/Δh, Gl6–7.

The strategy outlined in (B) above was performed in parallel to construct another NIF-1FL derivative, pMa5-NIF-1FL/ΔhGl6–7, in which the potential N-glycosylation sites Gl6 and Gl7 of mature NIF-1FL (SEQ. ID. NO. 117) have been modified by substituting glutamine residues for each of the asparagine residues in the corresponding consensus sequences. These residues are $Asn^{19}$, and $Asn^{223}$. In addition, the HPaI restriction site (GTTAAC) present in the mature NIF-1FL (SEQ. ID. NO. 118) coding sequence was removed by introducing a silent mutation at the appropriate position: the AAC codon for $Asn^{166}$ was replaced by a AAT codon.

Stepwise site-directed mutagenesis was performed following the methodology described in Stanssens et al., (1989), Nucl. Acids Res. 17: 4441–4454, and using the following oligonucleotides:

(VI) ΔGl6:dCGGCTGTCCTTCAGTTTTCTGTATTTTCGGG TAGTGGC [SEQ. ID. NO. 57], (VII) ΔGl7:Dggatccgcagacgtcgtttggtctgcttttttg [SEQ. ID. NO. 58], and (VIII) Δh :dCTCCCAAAGGGCAATTAACAACTGCGC [SEQ. ID. NO. 59].

In the first mutagenesis round, the oligonucleotides VII and VIII were annealed together to the ssDNA template to modify the glycosylation site Gl7 and to remove the HpaI restriction site. A resulting plasmid clone harbouring the two intended sites altered was then used to prepare ssDNA template for the next mutagenesis round in order to modify the Gl6 remaining site using the appropriate oligonucleotide (VI).

(D) Construction of pMa5-hNIF1/Δh, Gl1–7.

The NIF-1FL derivative hNIF1/Δh, Gl1–7 (SEQ. ID. NO. 128) was constructed using standard methods by combining appropriate fragments prepared from the vectors pMa5-hNIF1/ΔGl1–5 (prepared as in (B) above) and pMa5-NIF-1FL/Δh, Gl6–7 (prepared as in (C) above). The 361 bp AgeI-HindIII fragment prepared from the vector pMa5-NIF-1FL/Δh, Gl6–7, and containing the three substitutions described in (C) above, was cloned into the large AgeI-HindIII. vector fragment prepared from the vector pMa5-hNIF1/ΔGl1–5, replacing the corresponding 361 bp AgeI-HindIII wild type NIF-1FL fragment of this vector.

The presence of the seven Asn/Gln substitutions as well as of the modified HpaI restriction site ($Asn^{166}$ codon modification) in the resulting plasmid, pMa5-hNIF1/Δh, Gl1–7, was confirmed by sequencing analysis of the complete NIF insert. A one base pair deletion in the NIF sequence (a missing G nucleotide in the $Gly^{201}$ GGA codon) revealed by this sequence analysis was corrected by site directed mutagenesis using the oligonucleotide dGTAAATCGGCTGTCCTTCAGTTTTCLG [SEQ. ID. NO. 60].

(E) Construction of pYAM7SP-hNIF1/ΔGl1–5 and Expression in Pichia pastoris.

The segment of DNA encoding hNIF1/ΔGl1–5 (SEQ. ID. NO. 126) was PCR-amplified from a subclone of pMa5-hNIF1/ΔGl1–5 following the methodology described in Example 12(B) and using the same set of primers. After purification, the amplification product was digested with SpeI and ligated into StuI-SpeI cleaved PHIL7SP8 using standard methods. The ligation mixture was used to transform E. coli WK6, and ampicillin resistant clones were obtained on ampicillin plates. Based on restriction and DNA sequence analysis, a correct insert sequence in one of the resulting plasmid clones, pYAM7SP-hNIF1/ΔGl1–5, was selected to transform the P. pastoris yeast strain GTS115 (his4), as described in Example 12(B). Selection of His+ transformants and subsequent selection for NIF-1FL/

ΔGl1–5 (SEQ. ID. NO. 127) expression were performed as described in Example 12(B). The presence of NIF-1FL/ΔGl1–5 (SEQ. ID. NO. 127) in *Pichia* cell supernatant was detected and quantified using the LM2/Mac1 based ELISA with 3D2-HRP detection (see Example 1).

(F) Construction of pYAM7SP-hNIF1/Δh, Gl1–7 and Expression in *Pichia pastoris*.

The HpaI-SpeI fragment of DNA encoding hNIF1/Δh, Gl1–7 was prepared from the vector pMa5-hNIF1/Δh, Gl1–7 (SEQ. ID. NO. 128) and ligated into StuI-SpeI cleaved pHIL7SP8 using standard methods. The ligation mixture was used to transform *E. coli* WK6, and ampicillin resistant clones were obtained on ampicillin plates. Based on restriction and DNA sequence analysis, a correct insert sequence in one of the resulting plasmid clones, pYAM7SP-hNIF1/Δh, Gl1–7, was selected to transform the *P. pastoris* yeast strain GTS115(his4), as described in Example 12(B). Selection of His+ transformants and subsequent selection for NIF-1FL/Δh, Gl1–7 (SEQ. ID. NO. 129) expression were performed as described in Example 12(B). The presence of NIF-1FL/Δh, Gl1–7 (SEQ. ID. NO. 129) in *Pichia* cell supernatant was detected and quantified using the LM2/Mac1 based ELISA with 3D2-HRP detection (see Example 1).

(G) Purification and Characterization of Recombinant NIF-1FL/ΔGl1–5 and Recombinant NIF-1FL/Δh, Gl1–7.

Following methanol induction for 48 hours, *Pichia* cell supernatants were obtained by centrifugation for 15 minutes at 1,800×g.

Recombinant NIF-1FL/ΔGl1–5 (SEQ. ID. NO. 127) was purified exactly as described in Example 23. The recombinant NIF-1FL mutant was found to migrate with an apparent molecular weight of 36–50 kDa on SDS-PAGE (4–20% gradient gel; Novex) under non-reducing conditions. The band is more discrete and has a significantly higher mobility than wild type mature NIF-1FL (SEQ. ID. NO. 117). produced in *Pichia*. Recombinant NIF-1FL/Δh, Gl1–7 (SEQ. ID. NO. 129) was purified by hydroxyapatite and reverse-phase chromatography (see Example 23; the gel filtration step on Superdex was omitted). Under non-reducing conditions, the purified protein was found to migrate as a single band on SDS-PAGE (4–20% gradient gel; Novex), with an apparent molecular weight of about 30 kDa. The observed higher mobility and apparent lesser heterogeneity of NIF-1FL/ΔGl1–5 (SEQ. ID. NO. 127) and NIF-1FL/Δh, Gl1–7 (SEQ. ID. NO. 129) compared to NIF-1FL (SEQ. ID. NO. 117) is likely due to the relatively decreased extent of glycosylation of these mutants compared to the wild-type protein.

Both mutants were evaluated in the plastic adhesion assay (see FIG. 23). The results indicate that elimination of part or all of the seven potential N-glycosylation sites does not affect the potency of the mature NIF-1FL (SEQ. ID. NO. 117) molecule as measured in this in vitro assay.

Example 26
Preparation of Monoclonal Antibodies to NIF

Hybridomas producing MAbs that bind to NIF were prepared from mice immunized with *Pichia*-produced recombinant mature NIF-1FL (SEQ. ID. NO. 117) by previously described methods (H. R. Soule, E. Linder, T. S. Edgington, Proc. Natl. Acad. Sci. USA 80:1332 (1983); G. Kohler and C. Milstein, Nature (London) 256:495 (1975)). One monoclonal antibody designated 3D2 was shown to bind both hookworm-derived NIF and *Pichia*-produced mature recombinant NIF-1FL (SEQ. ID. NO. 117) by antigen capture assay (E. Harlow and D. P. Lane, Antibodies: A Laboratory Manual (Cold Spring Harbor Laboratory, Cold Spring Harbor, N.Y., 1988), pp. 192–193).

Example 27
Coupling of 3D2 Murine Monoclonal Antibody to 3M Emphaze Biosupport Medium (A) Single Step Method.

Twenty eight milligrams of 3D2 antibody was concentrated to 0.5 ml and 4.5 ml of 0.6 N sodium carbonate, 0.1 N sodium citrate, pH 9.0 was added. Three hundred fifteen milligrams of dry Emphaze Biosupport Medium (3M, St. Paul, Minn.) was added to the antibody solution, and mixed end-over-end for one hour. The Emphaze slurry was collected over a plastic frit, draining the remaining antibody solution. The resin was washed with 20 ml of 10 mM sodium phosphate, 0.15 M sodium chloride, pH 7.3. The collected resin was then mixed end-over-end with 3.0 M ethanolamine, pH 9.0 for 2.5 hours. The resin was again collected on a frit, and washed with 10 mM sodium phosphate, 0.15 M sodium chloride, pH 7.3 until the solution flowing through the frit was pH 7.3. The resin was stored in 10 mM sodium phosphate, 0.15 N sodium chloride, 0.05% sodium azide, pH 7.3, until use. Two milliliters of 3D2/Emphaze resin coupled using this procedure was found to bind 1.4 mg of purified NIF protein.

(B) Two Step Method.

Thirty milligrams of 3D2 antibody was dialyzed into 0.5 M Tris-HCl, pH 4.0, concentrated to a volume of 5.0 ml (6 mg/ml), and chilled to 4° C. Three hundred fifteen milligrams of Emphaze Biosupport Medium was added to the antibody solution and mixed end-over-end for 10 minutes at 4° C. Sodium sulfate was added to a concentration of 0.8 M (563 mg) and the Emphaze slurry was mixed end-over-end for an additional 10 minutes at 4° C. The pH was raised to 9.0 by dropwise addition of 1M NaOH. The coupling reaction was allowed to proceed for 60 minutes at 4° C. with end-over-end mixing. The Emphaze slurry was collected over a plastic frit, and remaining antibody solution was drained. The resin was washed with 20 ml of 10 mM sodium phosphate, 0.15 N sodium chloride, pH 7.3. The reaction was quenched by the addition of 6 ml of 1.0 N ethanolamine, pH 9.3, and the resin in ethanolamine was mixed end-over-end for 2.5 hours at 4° C. The resin was again collected over a frit, and washed with 0.2 N sodium phosphate, 0.5 N sodium chloride, pH 7.3 until the solution flowing through the frit was pH 7.3. The resin was suspended in 0.01 M sodium phosphate, 0.15 N sodium chloride, 0.05% (w/v) sodium azide, pH 7.3, until use. A 2 ml 3D2/Emphaze column coupled using this method typically bound 1.5 mg of purified NIF protein.

(C) Scale-Up of Coupling Reactions.

Twenty milliliters of resin has been made using both coupling methods by simply scaling up all volumes and amounts 10 fold. Both methods yielded resin capable of binding NIF protein. A 20 ml portion of 3D2/Emphaze resin coupled by the Two Step Method bound 10 fold more NIF protein than did 2 ml columns (15–19 mg versus 1.5 mg), whereas 20 ml of 3D2/Emphaze resin coupled using the Single Step Method did not scale linearly (typically 5–8 mg NIF protein bound). Thus, the Two Step Coupling Method was used for larger couplings.

A 150 ml Two Step coupling was performed in which 2.25 g of 3D2 antibody in 450 ml of 0.5 N Tris-HC1, pH 4.0 at 4° C. was mixed with 19 g of Emphaze Biosupport Medium in a 1000 ml microcarrier spinner flask (Bellco Glass Inc., Vineland, N.J.) for 10 minutes at 4° C. Forty two grams of sodium sulfate was added to the Emphaze slurry and this was stirred for an additional 10 minutes at 4° C. The pH was raised to 9.0 by dropwise addition of 1 M NaOH through the arms of the spinner flask. The reaction was allowed to proceed for 60 minutes at 4° C. with stirring. The Emphaze slurry was collected over a 90 mm, 0.45 micron filter (Corning Glass Works, Corning, N.Y.), and remaining antibody solution was drained. The resin was washed with 1 liter of 0.01 M sodium phosphate, 0.15 M sodium chloride, pH 7.3. The reaction was quenched by the addition of 500 ml of 1.0 M ethanolamine, pH 9.3 to the resin. The quenching reaction was allowed to continue 2.5 hours at 4° C. with stirring. The resin was again collected over a 90mm, 0.45 micron cellulose acetate filter, and washed with 0.2 N sodium phosphate, 0.5 N sodium chloride, pH 7.3 until the solution flowing through the filter was pH 7.3. The resin was suspended in 0.01 M sodium phosphate, 0.15 M sodium chloride, 0.05% sodium azide, pH 7.3, until use. A 2 ml portion of resin from this coupling bound 1.5 mg of NIF protein, the same amount of NIF protein bound by resin coupled in a 2 ml reaction.

Example 28
Purification of Recombinant NIF Protein Using 3D2/Emphaze Immunoaffinity Chromatography Column Cell supernatant containing recombinant NIF protein was filtered through a Sartobran PH 0.07 micron dead-end filter (Sartorius North America, Bohemia, N.Y.), and then concentrated 10–50 fold by tangential flow filtration using a Mini Crossflow System containing 10 kDa Minisart polysulfone membrane modules (Sartorius). The concentrate was then diafiltered against five volumes of 0.01 M sodium phosphate, 0.15 M sodium chloride, pH 7.3 in the Mini Crossflow apparatus. Immediately before application to the 3D2/Emphaze column, the concentrate was filtered through a 90mm, 0.22 micron cellulose acetate filter (Corning). Approximately 150 mg of NIF protein was applied to a 400 ml 3D2/Emphaze column at 20 ml/min. The concentrate was washed from the column with 400 ml of 0.1 M sodium phosphate, 0.15 M sodium chloride, pH 7.3 at 20 ml/min. The column flowthrough was collected and retained. The column was then washed with 400 ml of 1 M NaCl and the wash was discarded. The recombinant NIF protein bound to the column was eluted by applying 800 ml of 0.1 N glycine, pH 2.5. After elution, the purified NIF protein from the column was brought to neutral pH by the dropwise addition of 1 M Tris base. The column was then re-equilibrated to loading conditions by passing 800 ml of 0.1 M sodium phosphate, 0.15 M sodium chloride, pH 7.3, through it until the pH of solution exiting the column was pH 7.3.

When approximately 1 g of NIF protein had been purified by the 3D2/Emphaze column, the protein was pooled and then concentrated using an Easyflow 20 kDA polysulfone concentration apparatus (Sartorius). The concentrated protein was then applied at a flow rate of 10 ml/min. to a 60 cm×600 cm Superdex 200 prep gel filtration column (Pharmacia, Piscataway, N.J.) equilibrated in 0.01 H sodium phosphate, 0.15 M sodium chloride, pH 7.3. The only peak observed during elution (870–1050 ml) corresponds to NIF protein.

Example 29
Neutrophil Inhibitory Factor is an Inhibitor of Eosinophil Adhesion to Vascular Endothelial Cells NIF was assayed for effect on adhesion of human eosinophils to cytokine-stimulated endothelial cells. Eosinophils were isolated from normal individuals as described by Moser et al (1992a) (J. Immunol. 149:1432–1438]. Isolated eosinophils were cultured in the presence of 10 pM GM-CSF and 10 pM IL-3 for 24 hours following the procedure of Moser et al (1992a). Endothelial cells were harvested from umbilical cord veins, seeded in tissue culture flasks and transferred to 24-well plates as described by Moser et al (1992a). The adhesion assay was carried out following the procedure described by Moser et al (1992a). Briefly, human umbilical vein endothelial, cell (HUVEC) monolayers were washed with Hank's balanced salt solution (HBSS) and preincubated with 500 μl of TNFα at a final concentration of 10 ng/ml for 4 hours at 37° C. Immediately before use in adhesion assays, HUVEC monolayers were washed. Next, $2.5 \times 10^5$ eosinophils in 500 μl of HBSS containing 5 mg/ml of purified human albumin were layered onto the washed HUVEC monolayers. After incubation for 30 minutes at 37° C. and saturated humidity/5% $CO_2$, the 24-well plate was submerged three times in a bath of 300 ml PBS to remove loosely adherent eosinophils. Plates were dried at 4° C. and the number of adherent neutrophils was quantitated by measuring peroxidase activity, as described in Moser et al, 1992b [Blood 79:2937].

Figure 13:
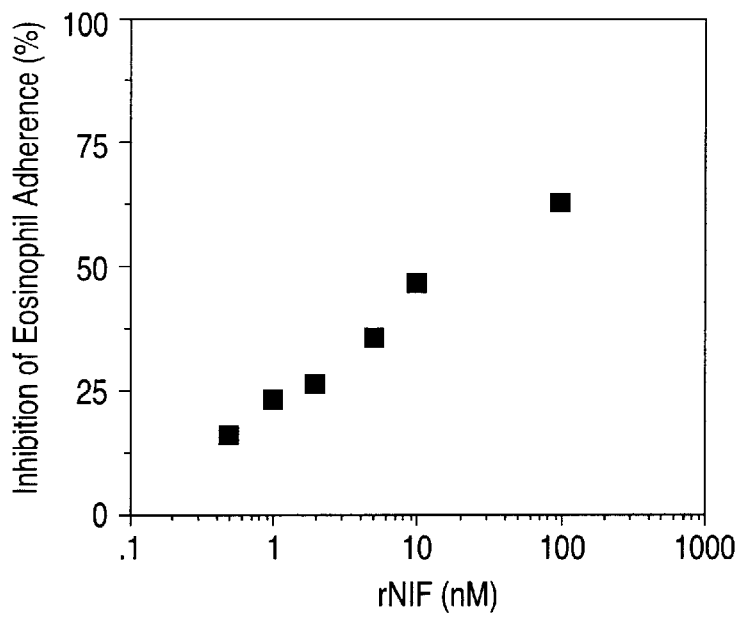
FIG. 13 depicts the effect of recombinant NIF on the inhibition of eosinophil adherence to TNF-stimulated HUVEC monolayers. Data points are means of triple determinations of one experiment.

Recombinant NIF (rNIF) inhibited adhesion of GM-CSF/IL-3 primed human neutrophils to TNF-activated HUVEC monolayers, to a maximum of approximately 63% inhibition at 100 nM rNTF. About 50% inhibition of adhesion was obtained in the presence of approximately 10 nM rNIF (see FIG. 13).

Example 30
Binding of NIF to Leukocytes

The interaction of NIF with leukocytes was assessed by flow-assisted cell sorting (FACS) using biotinylated recombinant mature NIF-1FL (SEQ. ID. NO. 117). This NIF was produced by the Pichia pastoris expression system (see Example 12(D). Biotinylation was by conjugation to carbohydrate moieties present on the NIF glycoprotein, using the procedure described in Example 14(B), with the following modifications. Two hundred micrograms recombinant mature NIF-1FL was oxidized in 50 nM $NaIO_4$ in 1 ml 0.1 M sodium acetate, pH 5.5. Following oxidation and buffer exchange, the recombinant mature NIF-1FL was reacted with biotin-LC-hydrazide (final concentration of 5 mM) in a total volume of 500 μl. Following derivatization, concentration, buffer exchange, recombinant mature NIF-1FL—biotin was at a final concentration of ~1 mg/ml in phosphate buffered saline.

FACS analysis was done with freshly drawn heparinized human whole blood. Biotinylated recombinant mature NIF-1FL (rNIF-biotin) was incubated with 100 μl blood at a final concentration of ~0.3 μg/ml for 20 minutes at room temperature. Red blood cells were then lysed with 3 ml of a 150 mM ammonium chloride solution that contained 0.02% sodium azide, for 5 minutes at room temperature. The cell pellet was resuspended in 75 μl wash buffer containing 3 μg/ml streptavidin-phycoerythrin (Pharmingen, San Diego, Calif.). After 15 minutes at 4° C. the cells were washed and resuspended in 0.5 ml wash buffer. Flow cytometry was performed with a FACScan® apparatus (Becton-Dickinson), using Lysys II software (Becton-Dickinson). Leukocyte populations (i.e., lymphocytes, monocytes, granulocytes) were electronically gated using cytograms of forward versus right angle light scatter.

Greater than 95% of the gated monocytes and granulocytes were shown to bind recombinant NIF-biotin relative to the BSA-biotin control (FIG. 1). Thirty percent. of the gated lymphocytes bound rNIF-biotin (FIG. 1). When blood cells were incubated with rNIF-biotin in the presence of 15 μg/ml non-derivatized recombinant mature NIF-1FL the staining of these cell populations by rNIF-biotin was abolished. These data suggest that in each of these leukocyte populations there exist cells that specifically bind rNIF.

FIG. 24 depicts binding of rNIF-biotin (0.3 μg/ml) to lymphocytes (panels A, D), monocytes (panels B, E), and granulocytes (panels C, F). In panels D, E and F cells were co-incubated with 15 μl/ml rNIF and 0.3 μg/ml rNIF-biotin. Histograms are shown after FACScan® analysis of human leukocytes. Fluorescence intensity is shown in a logarithmic scale, on x axis, cell number in a linear scale on the y axis.

What is claimed is:

1. A DNA probe consisting of the sequence of 5'-CTCGAATTCT(GATC)GC(ATC)AT(ATC) (CT)T(GATC)GG ATC)TGGGC-3' (SEQ. ID. NO. 7).

2. A DNA probe consisting of the sequence of 5'-CTCGAATTCTT(TC)TCTGG(GA)AA(GA)CG(GA)TC (GA)AA-3' (SEQ. ID. NO. 8).

3. An isolated nucleic acid molecule comprising a nucleic acid sequence encoding an amino acid sequence for a Neutrophil Inhibitory Factor wherein said Neutrophil Inhibitory Factor has neutrophil inhibitory activity and comprises an amino acid sequence which occurs in or is obtainable from an *Ancylostoma* species and which is selected from the group consisting of (a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gln, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;

(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;

(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

4. An isolated nucleic acid molecule according to claim 3 wherein said neutrophil inhibitory activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

5. An isolated nucleic acid molecule according to claim 4 wherein said Neutrophil Inhibitory Factor is further characterized as having an $IC_{50}$ for inhibiting neutrophil activity of about 500 nM or less.

6. An isolated nucleic acid molecule according to claim 5 wherein said Neutrophil Inhibitory Factor is further characterized by its ability to. bind to the integrin complex, Mac-1.

7. An isolated nucleic acid molecule according to claim 3 wherein said Neutrophil Inhibitory Factor is further characterized as having eosinophil inhibiting activity.

8. An isolated nucleic acid molecule according to claim 7 wherein said eosinophil inhibiting activity is demonstrated by an assay which determines adhesion of eosinophils to vascular endothelial cells.

9. An isolated nucleic acid molecule according to claim 8 wherein Neutrophil Inhibitory Factor is further characterized as having an $IC_{50}$ for inhibiting eosinophil activity of about 500 nM or less.

10. An isolated nucleic acid molecule according to claim 3 wherein said Neutrophil Inhibitory Factor comprises an amino acid sequence which is encoded by a nucleic acid sequence which is sufficiently complementary to hybridize to a probe having a sequence selected from the group consisting of 5-CTCGAATTCT(GATC)GC(ATC)AT(ATC)-(CT)T(GATC)GG(ATC)TGCGC-3' (SEQ. ID. NO. 7) and 5'-CTCGAATTCTT(TC)TCTGG(GA)AA(GA)CG(GA)TC (GA)AA-3' (SEQ. ID. NO. 8).

11. An isolated nucleic acid molecule according to claim 10 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

12. An isolated nucleic acid molecule according to claim 11 wherein said Neutrophil Inhibitory Factor is further characterized as having an $IC_{50}$ for inhibiting neutrophil activity of about 500 nM or less.

13. An isolated nucleic acid molecule according to claim 12 wherein said Neutrophil Inhibitory Factor is further characterized by its ability to bind to the integrin complex, Mac-1.

14. An isolated nucleic acid molecule according to claim 10 wherein said Neutrophil Inhibitory Factor is further characterized as having eosinophil inhibiting activity.

15. An isolated nucleic acid molecule according to claim 14 wherein said eosinophil inhibiting activity is demonstrated by an assay which determines adhesion of eosinophils to vascular endothelial cells.

16. An isolated nucleic acid molecule according to claim 15 wherein said a Neutrophil Inhibitory Factor is further characterized as having an $IC_{50}$ for inhibiting eosinophil activity of about 500 nM or less.

17. An isolated nucleic acid molecule according to claim 3 wherein said Neutrophil Inhibitory Factor comprises an amino acid sequence which is encoded by a nucleic acid sequence which is sufficiently complementary to hybridize to a probe having at least about 12 nucleotides which is complementary to a portion of the sequence of FIG. 8 (SEQ. ID. NO. 80).

18. An isolated nucleic acid molecule according to claim 17 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

19. An isolated nucleic acid molecule according to claim 18 wherein said Neutrophil Inhibitory Factor is further characterized as having an $IC_{50}$ for inhibiting neutrophil activity of about 500 nM or less.

20. An isolated nucleic acid molecule according to claim 19 wherein said Neutrophil Inhibitory Factor is further characterized by its ability to bind to the integrin complex, Mac-1.

21. An isolated nucleic acid molecule according to claim 17 wherein said Neutrophil Inhibitory Factor is further characterized as having eosinophil inhibiting activity.

22. An isolated nucleic acid molecule according to claim 21 wherein said eosinophil inhibiting activity is demonstrated by an assay which determines adhesion of eosinophils to vascular endothelial cells.

23. An isolated nucleic acid molecule according to claim 22 wherein said Neutrophil Inhibitory Factor is further characterized as having an $IC_{50}$ for inhibiting eosinophil activity of about 500 nM or less.

24. An isolated nucleic acid molecule comprising a nucleic acid sequence encoding an amino acid sequence for a Neutrophil Inhibitory Factor wherein said Neutrophil Inhibitory Factor has neutrophil inhibitory activity and wherein said Neutrophil Inhibitory Factor is a mutant Neutrophil Inhibitory Factor comprising the amino acid sequence shown in FIG. 8 (SEQ. ID. NO. 81), wherein one or more of asparagine residues at positions 10, 18, 87, 110, 130, 197 or 223 is replaced by a glutamine residue.

25. An isolated nucleic acid molecule according to claim 24 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

26. An isolated nucleic acid molecule according to claim 25 wherein said mutant Neutrophil Inhibitory Factor is further characterized as having an $IC_{50}$ for inhibiting neutrophil activity of about 500 nM or less.

27. An isolated nucleic acid molecule according to claim 26 wherein said mutant Neutrophil Inhibitory Factor is further characterized by its ability to bind to the integrin complex, Mac-1.

28. An isolated nucleic acid molecule according to claim 24 wherein said mutant Neutrophil Inhibitory Factor is further characterized as having eosinophil inhibiting activity.

29. An isolated nucleic acid molecule according to claim 28 wherein said eosinophil inhibiting activity is demonstrated by an assay which determines adhesion of eosinophils to vascular endothelial cells.

30. An isolated nucleic acid molecule according to claim 29 wherein said mutant Neutrophil Inhibitory Factor is further characterized as having an $IC_{50}$ for inhibiting eosinophil activity of about 500 nM or less.

31. An expression vector comprising an isolated nucleic acid molecule of any of claims 3, 4, 5, 6, 7, 8, 9, 10, 11, 12, 13, 14, 15, 16, 17, 18, 19, 20, 21, 22, 23, 24, 25, 26, 27, 28, 29, or 30 operably linked to control sequences recognized by a host cell transformed with the vector.

32. An expression vector of claim 31 selected from the group consisting of pHIL7SP-Nlc10, pSG5/NIF1FLCR1, pMa5-NI1/3, pAN-NIF-1FL, pYAM7SP-hNIF/ΔGl1–5, pYAM7SP-hNIF1/Δh, Gl1–7, pYAM7SP-AcaNIF4, pYAM7SP-AcaNIF6, pYAM7SP-AcaNIF9, pYAM7SP-AcaNIF24, pAN-AceNIF3 and pYAM7SP-AceNIF3.

33. A host cell transformed with an expression vector of claim 32.

34. An isolated nucleic acid molecule comprising a nucleic acid sequence encoding an amino acid sequence for a Neutrophil Inhibitory Factor wherein said Neutrophil Inhibitory Factor has neutrophil inhibitory activity and comprises the amino acid sequence shown in FIG. 8 (SEQ. ID. NO. 81).

35. An isolated nucleic acid molecule comprising a nucleic acid sequence encoding an amino acid sequence for a Neutrophil Inhibitory Factor wherein said Neutrophil Inhibitory Factor has neutrophil inhibitory activity and comprises an amino acid sequence selected from the group consisting of the amino acid sequences shown in FIG. 9 for 3P (SEQ. ID. NO. 82), 1P (SEQ. ID. NO. 83), 2FL (SEQ. ID. NO. 84). 3FL (SEQ. ID. NO. 85), 4FL (SEQ. ID. NO. 86) and 6FL (SEQ. ID. NO. 87).

36. An isolated nucleic acid molecule comprising a nucleic acid sequence encoding an amino acid sequence for a Neutrophil Inhibitory Factor wherein said Neutrophil Inhibitory Factor has neutrophil inhibitory activity and comprises an amino acid sequence selected from the group consisting of the amino acid sequences shown in FIG. 16 for PCR-NIF#7 (SEQ. ID. NO. 105), AcaNIF19 (SEQ. ID. NO. 111) and AcaNIF24 (SEQ. ID. NO. 112).

37. An isolated nucleic acid molecule comprising a nucleic acid sequence encoding an amino acid sequence for a Neutrophil Inhibitory Factor wherein said Neutrophil Inhibitory Factor has neutrophil inhibitory activity and comprises an amino acid sequence selected from the group consisting of the amino acid sequences shown in FIG. 16 for PCR-NIF#20 (SEQ. ID. NO. 106), AcaNIF4 (SEQ. ID. NO. 108), AcaNIF6 (SEQ. ID. No. 109), AcaNIF7 (SEQ. ID. NO. 110), AcaNIF9 (SEQ. ID. NO. 113) and AcaNIF18 (SEQ. ID. NO. 114).

38. A method of making biologically active Neutrophil Inhibitory Factor comprising the steps of culturing host cells having an expression vector which comprises an isolated nucleic acid molecule which encodes a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence which occurs in or is obtainable from an *Ancylostoma* species and which is selected from the group consisting of (a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gln, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;

(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;

(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

39. A method according to claim 38 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

40. A method according to claim 39 wherein said Neutrophil Inhibitory Factor is further characterized as having an $IC_{50}$ for inhibiting neutrophil activity of about 500 mM or less.

41. A method according to claim 40 wherein said Neutrophil Inhibitory Factor is further characterized by its ability to bind to the integrin complex, Mac-1.

42. A method according to claim 38 wherein said Neutrophil Inhibitory Factor is further characterized as having eosinophil inhibiting activity.

43. A method according to claim 42 wherein said eosinophil inhibiting activity is demonstrated by an assay which determines adhesion of eosinophils to vascular endothelial cells.

44. A method according to claim 43 wherein said Neutrophil Inhibitory Factor is further characterized as having an $IC_{50}$ for inhibiting eosinophil activity of about 500 mM or less.

45. A method of claim 38, wherein said *Ancylostoma* species is a canine hookworm.

46. A method of claim 38, wherein said *Ancylostoma* species is *Ancylostoma ceylanicum*.

47. A method of claim 38, wherein said host cell is selected from the group consisting of bacterial cell, yeast cell, mammalian cell and insect cell.

48. A method of claim 47, wherein said host cell is a bacterial cell.

49. A method of claim 47, wherein said host cell is a yeast cell.

50. A method of claim 49, wherein said yeast cell is *Saccharomyces cerevisiae*.

51. A method of claim 47, wherein said host cell is a mammalian cell.

52. A method of claim 51, wherein said mammalian cell is COS-7.

53. A method of any of claim 38 or 39 to 44 wherein said host cell is *E. coli* WK6.

54. A method of any claim 38 or 39 to 44 wherein said host cell is *Pichia pastoris*.

55. A method of any claim 38 or 39 to 44 wherein the host cell is CHO-X1.

56. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises the amino acid sequence shown in FIG. 8 (SEQ. ID. NO. 81).

57. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence selected from the group consisting of the amino acid sequences shown in FIG. 16 for PCR-NIF#7 (SEQ. ID. NO. 105), AcaNIF19 (SEQ. ID. NO. 111), and AcaNIF24 (SEQ. ID. NO. 112).

58. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence selected from the group consisting of the amino acid sequences shown in FIG. 16 for PCR-NIF#20 (SEQ. ID. NO. 106), AcaNIF4 (SEQ. ID. NO. 108), AcaNIF6 (SEQ. ID. NO. 109) AcaNIF7 (SEQ. ID. No. 110), AcaNIF9 (SEQ. ID. NO. 113), and AcaNIF18 (SEQ. ID. NO. 114).

59. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a mutant Neutrophil Inhibitory Factor which has neutrophil inhibitory activity and comprises the amino acid sequence shown in FIG. 8 (SEQ. ID. NO. 81), wherein one or more asparagine residues at positions 10, 18, 87, 110, 130, 197 or 223 is replaced by a glutamine residue.

60. A method according to claim 59 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

61. A method according to claim 60 wherein said mutant Neutrophil Inhibitory Factor is further characterized as having an $IC_{50}$ for inhibiting neutrophil activity of about 500 nM or less.

62. A method according to claim 61 wherein said mutant Neutrophil Inhibitory Factor is further characterized by its ability to bind to the integrin complex, Mac-1.

63. A method according to claim 59 wherein said mutant Neutrophil Inhibitory Factor is further characterized as having eosinophil inhibiting activity.

64. A method according to claim 63 wherein said eosinophil inhibiting activity is demonstrated by an assay which determines adhesion of eosinophils to vascular endothelial cells.

65. A method according to claim 64 wherein said mutant Neutrophil Inhibitory Factor is further characterized as having an $IC_{50}$ for inhibiting eosinophil activity of about 500 mM or less.

66. A method of making Neutrophil Inhibitory Factor comprising the step of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is secreted, wherein said isolated nucleic acid molecule encodes a Neutrophil Inhibitory Factor which has neutrophil inhibitory activity and comprises an amino acid sequence which occurs in or is obtainable from an *Ancylostoma* species and which is selected from the group consisting of
   (a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gln, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;
   (b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;
   (c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;
   (d) His-Val-Val-Cys-His-$X_{21}$-$X_{22}$-Pro-Lys (SEQ. ID. No. 4), wherein $X_{21}$ is Tyr or Ile; and $X_{22}$ is Gly or no residue;
   (e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and
   (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

67. A method according to claim 66 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

68. A method according to claim 67 wherein said Neutrophil Inhibitory Factor is further characterized as having an $IC_{50}$ for inhibiting neutrophil activity of about 500 nM or less.

69. A method according to claim 68 wherein said Neutrophil Inhibitory Factor is further characterized by its ability to bind to the integrin complex, Mac-1.

70. A method according to claim 66 wherein said Neutrophil Inhibitory Factor is further characterized as having eosinophil inhibiting activity.

71. A method according to claim 70 wherein said eosinophil inhibiting activity is demonstrated by an assay which determines adhesion of eosinophils to vascular endothelial cells.

72. A method according to claim 71 wherein said Neutrophil Inhibitory Factor is further characterized as having an $IC_{50}$ for inhibiting eosinophil activity of about 500 nM or less.

73. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises the amino acid sequence shown in FIG. 8 (SEQ. ID. NO. 81).

74. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises an amino acid sequence selected from the group consisting of the amino acid sequences shown in FIG. 16 for PCR-NIF#7 (SEQ. ID. NO. 105), AcaNIF19 (SEQ. ID. NO. 111) and AcaNIF24 (SEQ. ID. NO. 112).

75. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises an amino acid sequence selected from the group consisting of the amino acid sequences shown in FIG. 16 for PCR-NIF#20 (SEQ. ID. NO. 106), AcaNIF4 (SEQ. ID. NO. 108), AcaNIF6 (SEQ. ID. NO. 109), AcaNIF7 (SEQ. ID. NO. 110), AcaNIF9 (SEQ. ID. NO. 113), and AcaNIF18 (SEQ. ID. NO. 114).

76. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory factor is expressed and said Neutrophil Inhibitory Factor is secreted and isolating the Neutrophil Inhibitory Factor secreted by the host cells, wherein said isolated nucleic acid molecule encodes a mutant Neutrophil Inhibitory Factor which has neutrophil inhibitory activity and comprises the amino acid sequence shown in FIG. 8 (SEQ. ID. NO. 81), wherein one or more of asparagine residues at positions 10, 18, 87, 110, 130, 197 or 223 is replaced by an glutamine residue.

77. A method according to claim 76 wherein said neutrophil inhibiting activity is demonstrated by an assay selected from the group consisting of assays which determine adhesion of neutrophils to vascular endothelial cells, release of hydrogen peroxide from neutrophils, homotypic neutrophil aggregation and adhesion of neutrophils to plastic surfaces.

78. A method according to claim 77 wherein said mutant Neutrophil Inhibitory Factor is further characterized as having an $IC_{50}$ for inhibiting neutrophil activity of about 500 nM or less.

79. A method according to claim 78 wherein said mutant Neutrophil Inhibitory Factor is further characterized by its ability to bind to the integrin complex, Mac-1.

80. A method according to claim 76 wherein said mutant Neutrophil Inhibitory Factor is further characterized as having eosinophil inhibiting activity.

81. A method according to claim 80 wherein said eosinophil inhibiting activity is demonstrated by an assay which determines adhesion of eosinophils to vascular endothelial cells.

82. A method according to claim 81 wherein said mutant Neutrophil Inhibitory Factor is further characterized as having an $IC_{50}$ for inhibiting eosinophil activity of about 500 nM or less.

83. An isolated nucleic acid molecule comprising a nucleic acid sequence encoding an amino acid sequence for a Neutrophil Inhibitory Factor wherein said Neutrophil Inhibitory Factor has neutrophil inhibitory activity and comprises the amino acid sequence shown in FIG. 19 for AceNIF3 (SEQ. ID. NO. 115).

84. An expression vector comprising an isolated nucleic acid molecule of any of claims 24, 34, 35, 36, 37, or 83 operably linked to control sequences recognized by a host cell transformed with the vector.

85. An expression vector of claim 84 selected from the group consisting of pHIL7SP-N1c10, pSGS/NIF1FLCR1, pMa5-NI1/3, pAN-NIF-1FL, pYAN7SP-hNIF1/ΔGl1–5, pYAM7SP-hNIF1/Δh, Gl1–7, pYAN7SP-AcaNIF4, pYAM7SP-AcaNIF6, pYAM7SP-AcaNIF9, pYAN7SP-AcaNIF24, pAN-AceNIF3 and pYAM7SP-AceNIF3.

86. A host cell transformed with an expression vector of claim 85.

87. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating the Neutrophil Inhibitory Factor from the host cells, wherein said isolated nucleic acid molecule encodes a Neutrophil Inhibitory Factor which has neutrophil inhibitory activity and comprises the amino acid sequence shown in FIG. 19 for AceNIF3 (SEQ. ID. NO. 115).

88. A method of any of claims 56, 57 to 59, 60 to 65, or 87 wherein said host cell is *E. coli* WK6.

89. A method of any of claims 56, 57 to 59, 60 to 65, or 87 wherein said host cell is *Pichia pastoris*.

90. A method of any of claims 56, 57 to 59, 60 to 65, or 87 wherein said host cell is CHO-K1.

91. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises the amino acid sequence shown in FIG. 19 for AceNIF3 (SEQ. ID. NO. 115).

92. A method of any of claims 73, 74 to 76, 77 to 82, or 91 wherein said host cell is *E. coli* WK6.

93. A method of any of claims 73, 74 to 76, 77 to 82, or 91 wherein said host cell is *Pichia pastoris*.

94. A method of any of claims 73, 74 to 76, 77 to 82, or 91 wherein said host cell is CHO-K1.

95. An isolated nucleic acid molecule comprising a nucleic acid sequence encoding an amino acid sequence for a Neutrophil Inhibitory Factor wherein said Neutrophil Inhibitory Factor (i) is isolated from an *Ancylostoma* species of parasitic worm or is obtainable from an *Ancylostoma* species of parasitic worm, (ii) has neutrophil inhibitory activity, and (iii) comprises an amino acid sequence selected from the group consisting of:

(a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Glu; Lys or Arg; $X_3$ is Ala or Arg; $X_4$ is Leu or Met; $X_5$ is Lys, Arg, Leu or Ile; $X_6$ is Val or Ile; and $X_7$ is Ser, Gly, Asn;

(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lye or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;

(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

96. An expression vector comprising an isolated nucleic acid molecule of claim 95 operably linked to control sequences recognized by a host cell transformed with the vector.

97. An expression vector of claim 96 selected from the group consisting of pHIL7SP-N1c10, pSG5/NIF1FLCR1, pMa5-NI1/3, pAN-NI1/3, pAN-NIF-1FL, pYAM7SP-hNIF1/ΔGl1–5, pYAM7SP-hNIF1/Δh, Gl1–7, pYAM7SP-AcaNIF4, pYAM7SP-AcaNIF6, pYAM7SP-AcaNIF9, pYAM7SP-AcaNIF24, pAN-AceNIF3 and pYAM7SP-AceNIF3.

98. A host cell transformed with an expression vector of claim 97.

99. An isolated nucleic acid molecule comprising a nucleic acid sequence encoding an amino acid sequence for a Neutrophil Inhibitory Factor which occurs in or is obtainable from an *Ancylostoma* species and wherein said Neutrophil Inhibitory Factor (i) has neutrophil inhibitory activity and (ii) comprises amino acid sequences (a) to (f), wherein sequences (a) to (f) are:

(a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Glu; Lys or Arg; $X_3$ is Ala or Arg; $X_4$ is Leu or Met; $X_5$ is Lys, Arg, Leu or Ile; $X_6$ is Val or Ile; and $X_7$ is Ser, Gly, Asn;

(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$, is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;

(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;

(d) His-Val-Val-Cys-His-$X_{21}$-$X_{22}$-Pro-Lys (SEQ. ID. NO. 4) wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, LYE or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

100. An isolated nucleic acid molecule according to claim 99 wherein amino acid sequences (a) to (f) appear in order from amino terminal end to carboxy terminal end of (a), (b), (c), (d), (e) and (f).

101. An isolated nucleic acid molecule according to claim 100 which comprises a nucleotide sequence encoding an amino acid sequence selected from the group consisting of SEQ. ID. NOS. 81, 103 to 115, 117 to 121, 123, 125, 127 and 129.

102. An isolated nucleic acid molecule according to claim 101 which comprises a nucleotide sequence encoding an amino acid sequence selected from the group consisting of SEQ. ID. NOS. 117 to 121, 125, 127 and 129.

103. An isolated nucleic acid molecule which comprises a nucleotide sequence encoding a Neutrophil Inhibitory Factor comprising the amino acid sequence of SEQ. ID. NO. 117.

104. An isolated nucleic acid molecule which encodes a Neutrophil Inhibitory Factor comprising an amino acid sequence selected from the group consisting of SEQ. ID. NOS. 118, 119, 120 and 121.

105. An isolated nucleic acid molecule which comprises a nucleotide sequence encoding a Neutrophil Inhibitory Factor comprising the amino acid sequence of SEQ. ID. NO. 125.

106. An isolated nucleic acid molecule which comprises a nucleotide sequence encoding a Neutrophil Inhibitory Factor comprising an amino acid sequence selected from the group consisting of SEQ. ID. NOS. 127 and 129.

107. A method of making a Neutrophil Inhibitory Factor comprising the steps of culturing host cells having an expression vector which comprises a nucleic acid molecule of any of claims 95 to 106 inserted in said cells under cell culture conditions whereby Neutrophil Inhibitory Factor is expressed and isolating Neutrophil Inhibitory Factor from the host cells.

108. A method of claim 107 wherein said host cell is *E. coli* WK6.

109. A method of claim 107 wherein said host cell is *Pichia pastoris*.

110. A method of claim 107 wherein said host cell is CHO-K1.

111. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence SEQ. ID. NO. 117.

112. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence selected from the group consisting of the amino acid sequences SEQ. ID. NOS. 118, 119, 120 and 121.

113. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence SEQ. ID. NO. 125.

114. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a Neutrophil Inhibitory Factor which has neutrophil inhibitory activity and comprises an amino acid sequence selected from the group consisting of the amino acid sequences SEQ. ID. NOS. 127 and 129.

115. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises the amino acid sequence SEQ. ID. NO. 117.

116. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises an amino acid sequence selected from the group consisting of the amino acid sequences SEQ. ID. NOS. 118, 119, 120 and 121.

117. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises an amino acid sequence SEQ. ID. NO. 125.

118. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory Factor is expressed and said Neutrophil Inhibitory Factor is secreted and isolating the Neutrophil Inhibitory Factor secreted by the host cells, wherein said isolated nucleic acid molecule encodes a Neutrophil Inhibitory Factor which has neutrophil inhibitory activity and comprises an amino acid sequence selected from the group consisting of the amino acid sequences SEQ. ID. NOS. 127 and 129.

119. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions, whereby the Neutrophil Inhibitory factor is expressed and said Neutrophil Inhibitory Factor is secreted and isolating the Neutrophil Inhibitory Factor secreted by the host cells, wherein said isolated nucleic acid molecule encodes a mutant Neutrophil Inhibitory Factor which has neutrophil inhibitory activity and comprises the amino acid sequence SEQ. ID. NO. 117, wherein one or more of asparagine residues at positions 10, 18, 87, 110, 130, 197 or 223 is replaced by an glutamine residue.

120. A method of any of claims 111 to 119 wherein said host cell is *E. coli* WK6.

121. A method of any of claims 111 to 119 wherein said host cell is *Pichia pastoris*.

122. A method of any of claims 111 to 119 wherein said host cell is CHO-K1.

123. An isolated nucleic acid molecule encoding a Neutrophil Inhibitory Factor comprising a nucleotide sequence selected from the group consisting of SEQ. ID. NOS. 116 and 130.

124. An isolated nucleic acid molecule according to claim 123 comprising SEQ. ID. NO. 116.

125. An isolated nucleic acid molecule encoding a Neutrophil Inhibitory Factor comprising a nucleotide sequence selected from the group consisting of SEQ. ID. NOS. 122 and 124.

126. An isolated nucleic acid molecule encoding a Neutrophil Inhibitory Factor comprising a nucleotide sequence selected from the group consisting of SEQ. ID. NOS. 126 and 128.

127. An isolated nucleic acid molecule encoding a Neutrophil Inhibitory Factor comprising an amino acid sequence for mature NIF-1FL (SEQ. ID. NO. 117) wherein one or more of asparagine residues at positions 10, 18, 87, 110, 130, 197 or 223 is replaced by a glutamine residue.

128. An expression vector comprising an isolated nucleic acid molecule of any of claims 99 to 106 or 123 to 127 operably linked to control sequences recognized by a host cell transformed with the vector.

129. A host cell transformed with an expression vector of claim 128.

130. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule encodes a mutant Neutrophil Inhibitory Factor which has neutrophil inhibitory activity and comprises the amino acid sequence (SEQ. ID. NO. 117), wherein one or more of asparagine residues at positions 10, 18, 87, 110, 130, 197 or 223 is replaced by a glutamine residue.

131. An isolated nucleic acid molecule encoding an amino acid sequence for a Neutrophil Inhibitory Factor (NIF) wherein said NIF:
   (a) occurs in an *Ancylostoma* species or is obtainable from a NIF which occurs in an *Ancylostoma* species;
   (b) has neutrophil inhibitory activity; and
   (c) comprises an amino acid sequence selected from the group consisting of SEQ. ID. NO.s 1, 2, 3, 4, 5, and 6.

132. An isolated nucleic acid molecule which encodes an amino acid sequence for a Neutrophil Inhibitory Factor (NIF) where said NIF:
   (a) has neutrophil inhibitory activity; and
   (b) comprises an amino acid sequence selected from the group consisting of SEQ. ID. NO.s 1, 2, 3, 4, 5, and 6 which occurs in an *Ancylostoma* species.

133. An isolated nucleic acid molecule which encodes an amino acid sequence for a Neutrophil Inhibitory Factor (NIF) where said NIF:
(a) has neutrophil inhibitory activity; and
(b) comprises SEQ. ID. NO.s 1 to 6 which occur in an *Ancylostoma* species.

134. An isolated nucleic acid molecule which encodes an amino acid sequence for Neutrophil Inhibitory Factor (NIF) wherein said NIF:
(i) has neutrophil inhibitory activity;
(ii) has an amino acid sequence obtainable from an *Ancylostoma* species; and
(iii) comprises an amino acid sequence selected from the group consisting of
(a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gin, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;
(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;
(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;
(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;
(e) Ile-Tyr-$X_{22}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and
(f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

135. An isolated nucleic acid molecule which encodes a Neutrophil Inhibitory Factor (NIF) wherein said NIF:
(i) has neutrophil inhibitory activity;
(ii) includes an amino acid sequence selected from the group consisting of
(a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gin, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;
(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;
(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{26}$ is Asn or Asp; $X_{17}$ is Val or Leu; $X_{18}$ is Ala or Thr; $X_{19}$ is Leu, Val or Phe; and $X_{20}$ is Thr, Lys or Asn;
(d) His-Val-Val-Cys-His-$X_{21}$-$X_{22}$-Pro-Lys (SEQ. ID. NO. 4), wherein $X_{21}$ in Tyr or Ile; and $X_{22}$ is Gly or no residue;
(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and
(f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe; which sequence is obtainable from an *Ancylostoma* species.

136. An isolated nucleic acid molecule which encodes an amino acid sequence for Neutrophil Inhibitory Factor (NIF) wherein said NIF:
(i) has neutrophil inhibitory activity; and
(ii) comprises the following amino acid sequences
(a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gin, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;
(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;
(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID. NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;
(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;
(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and
(f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe; which sequence is obtainable from an *Ancylostoma* species.

137. An isolated nucleic acid molecule which encodes an amino acid sequence for Neutrophil Inhibitory Factor (NIF) wherein said NIF has neutrophil inhibitory activity; and wherein said isolated nucleic acid molecule comprises a nucleotide sequence obtainable from an *Ancylostoma* species which encodes an amino acid sequence selected from the group consisting of
(a) Arg-$X_1$-$X_2$-Phe-Leu-$X_3$-$X_4$-His-Asn-Gly-Tyr-Arg-Ser-$X_5$-Leu-Ala-Leu-Gly-His-$X_6$-$X_7$-Ile (SEQ. ID. NO. 1), wherein $X_1$ is Leu or Arg; $X_2$ is Gin, Lys or Arg; $X_3$ is Ala or Arg; $X_4$ is Leu or Met; $X_5$ is Lys, Arg, Leu or Ile; $X_6$ is Val or Ile; and $X_7$ is Ser, Gly or Asn;
(b) Ala-$X_8$-$X_9$-Ala-Ser-$X_{10}$-Met-Arg-$X_{11}$-Leu-$X_{12}$-Tyr-Asp-Cys-$X_{13}$-Ala-Glu-$X_{14}$-Ser-Ala-Tyr-$X_{15}$-Ser-Ala (SEQ. ID. NO. 2), wherein $X_8$ is His or Pro; $X_9$ is Thr, Arg or Ser; $X_{10}$ is Arg or Lys; $X_{11}$ is Ile or Tyr; $X_{12}$ is Asp, Lys or Glu; $X_{13}$ is Asp or Glu; $X_{14}$ is Gly, Lys or Arg; and $X_{15}$ is Glu, Met, Thr or Val;
(c) Ser-$X_{16}$-Phe-Ala-Asn-$X_{17}$-Ala-Trp-Asp-$X_{18}$-Arg-Glu-Lys-$X_{19}$-Gly-Cys-Ala-Val-Val-$X_{20}$-Cys (SEQ. ID.

NO. 3), wherein $X_{16}$ is Asn or Asp; $X_{17}$ is Val or Leu; $X_{18}$ is Ala or Thr; $X_{19}$ is Leu, Val or Phe; and $X_{20}$ is Thr, Lys or Asn;

(d) His-Val-Val-Cys-His-$X_{21}$-$X_{22}$-Pro-Lys (SEQ. ID. NO. 4), wherein $X_{21}$ is Tyr or Ile; and $X_{22}$ is Gly or no residue;

(e) Ile-Tyr-$X_{23}$-$X_{24}$-Gly-$X_{25}$-Pro-Cys-$X_{26}$-$X_{27}$-Cys-$X_{28}$-$X_{29}$-Tyr (SEQ. ID. NO. 5), wherein $X_{23}$ is Thr, Ser, Lys or Glu; $X_{24}$ is Thr, Val or Ile; $X_{25}$ is Val, Lys or Thr; $X_{26}$ is Arg, Ser or Asp; $X_{27}$ is Asn, Gly, Asp or Arg; $X_{28}$ is Asn, Ser or Thr; and $X_{29}$ is Gly, Glu or Asp; and (f) Cys-$X_{30}$-$X_{31}$-Asp-$X_{32}$-Gly-Val-Cys-$X_{33}$-Ile (SEQ. ID. NO. 6), wherein $X_{30}$ is His, Ile or Asn; $X_{31}$ is Ala, Pro or Asp; $X_{32}$ is Glu, Val, Asp or Ile; and $X_{33}$ is Ile, Val or Phe.

138. An expression vector comprising an isolated nucleic acid molecule of any of claims 131 to 136 and 137 operably linked to control sequences recognized by a host cell transformed with the vector.

139. expression vector of claim 138 selected from the group consisting of pHIL7SP-N1c10, pSG5S/NIF1FLCR1, pMa5-NI1/3, pAN-NIF-1FL, pYAM7SP-hNIF/ΔGl1–5, pYAM7SP-hNIF1/Δh, Gl1–7, pYAM7SP-AcaNIF4, pYAM7SP-AcaNIF6, pYAM7SP-AcaNIF9, pYAM7SP-AcaNIF24, pAN-AceNIF3 and pYAM7SP-AceNIF3.

140. A host cell transformed with an expression vector of claim 139.

141. A method of making Neutrophil Inhibitory Factor comprising the steps of culturing host cells having an expression vector which comprise an isolated nucleic acid molecule which encodes an amino acid sequence for a Neutrophil Inhibitory Factor inserted in said cells under cell culture conditions whereby said Neutrophil Inhibitory Factor is expressed and isolating Neutrophil Inhibitory Factor from the host cells, wherein said isolated nucleic acid molecule is selected from the isolated nucleic acid molecules of claims 131 to 136 or 137.

142. A method of making Neutrophil Inhibitory Factor comprising the steps of culturing host cells having an expression vector which comprises an isolated nucleic acid molecule which encodes an amino acid sequence for a Neutrophil Inhibitory Factor inserted in said cells under cell culture conditions whereby the Neutrophil Inhibitory Factor is expressed and said Neutrophil Inhibitory Factor is secreted and isolating the Neutrophil Inhibitory Factor secreted by the host cells, wherein said isolated nucleic acid molecule is selected from the isolated nucleic acid molecules of claims 131 to 136 or 137.

* * * * *

UNITED STATES PATENT AND TRADEMARK OFFICE
CERTIFICATE OF CORRECTION

PATENT NO. : 6,962,795 B2  Page 1 of 1
APPLICATION NO. : 08/151064
DATED : November 8, 2005
INVENTOR(S) : Moyle et al.

It is certified that error appears in the above-identified patent and that said Letters Patent is hereby corrected as shown below:

In the Claims:
In claim 3, column 189 at line 46, replace "Gin" with --Gln--.
In claim 10, column 190 at line 65, replace "(CT)T(GATC)GG(ATC)TGCGC-3'" with --(CT)T(GATC)GG(ATC)TGGGC-3'--.
In claim 41, column 206 at line 5, replace "comprise" with --comprises--.
In claim 53, column 194 at line 22, replace "claim" with --claims--.
In claim 54, column 194 at line 24, replace "claim" with --claims--.
In claim 55, column 194 at line 26, replace "claim" with --claims--.
In claim 55, column 194 at line 27, replace "–X1" with -- –K1 --.
In claim 66, column 196 at line 6, replace "$-X_{22}$" with -- $-X_{32}$ --.
In claim 95, column 198 at line 56, replace "Lye" with --Lys--.
In claim 99, column 199 at line 36, replace "$X_{11}$," with --$X_{11}$--.
In claim 99, column 199 at line 49, replace "LYE" with --Lys--.
In claim 134, column 203 at line 17, replace "Gin" with --Gln--.
In claim 135, column 203 at line 50, replace "Gin" with --Gln--.
In claim 135, column 203, at line 62, replace "$-X_{26}$" with ---$X_{16}$--.
In claim 136, column 204 at line 19, replace "Gin" with --Gln--.
In claim 137, column 204 at line 57, replace "Gin" with --Gln--.
In claim 139, column 205 at line 21, replace "pSG5S/" with -- pSG5/--.

Signed and Sealed this

Fifth Day of September, 2006

JON W. DUDAS
*Director of the United States Patent and Trademark Office*